US011945877B2

(12) United States Patent
Wang et al.

(10) Patent No.: US 11,945,877 B2
(45) Date of Patent: Apr. 2, 2024

(54) ANTI-HER2 ANTIBODIES

(71) Applicant: Agency for Science, Technology and Research, Singapore (SG)

(72) Inventors: Cheng-I Wang, Singapore (SG); Lionel Jianrong Low, Singapore (SG); Angeline Goh, Singapore (SG); Sandy Wen-Hsin Lee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 157 days.

(21) Appl. No.: 16/969,119

(22) PCT Filed: Feb. 12, 2019

(86) PCT No.: PCT/SG2019/050077
§ 371 (c)(1),
(2) Date: Aug. 11, 2020

(87) PCT Pub. No.: WO2019/160501
PCT Pub. Date: Aug. 22, 2019

(65) Prior Publication Data

US 2021/0139605 A1 May 13, 2021

(30) Foreign Application Priority Data

Feb. 13, 2018 (SG) ........................... 10201801219V

(51) Int. Cl.
*C07K 16/32* (2006.01)
*A61K 39/00* (2006.01)
*A61P 35/00* (2006.01)

(52) U.S. Cl.
CPC .............. *C07K 16/32* (2013.01); *A61P 35/00* (2018.01); *A61K 2039/505* (2013.01); *C07K 2317/33* (2013.01); *C07K 2317/73* (2013.01); *C07K 2317/92* (2013.01)

(58) Field of Classification Search
CPC ............... C07K 16/32; C07K 2317/33; C07K 2317/73; A61K 2039/505
See application file for complete search history.

(56) References Cited

U.S. PATENT DOCUMENTS

| | | | | |
|---|---|---|---|---|
| 10,716,818 | B2 * | 7/2020 | Suzuki .................. | A61K 35/17 |
| 2009/0304590 | A1 | 12/2009 | Gill et al. | |
| 2012/0309942 | A1 | 12/2012 | Li et al. | |
| 2015/0322162 | A1 | 11/2015 | Cho et al. | |
| 2016/0361401 | A1 | 12/2016 | Shahabi et al. | |
| 2017/0283507 | A1 | 10/2017 | Wels et al. | |

FOREIGN PATENT DOCUMENTS

| | | | |
|---|---|---|---|
| CN | 106831987 | | 6/2017 |
| CN | 106831987 | A | 6/2017 |
| CN | 107488636 | A | 12/2017 |
| EP | 1106183 | A2 | 6/2001 |
| KR | 10-2015-0130893 | A | 11/2015 |
| WO | WO-1997/20858 | A1 | 6/1997 |
| WO | WO-2009/055074 | A2 | 4/2009 |
| WO | WO-2009/117277 | A2 | 9/2009 |
| WO | WO-2009/123894 | A2 | 10/2009 |
| WO | WO-2010/060939 | A2 | 6/2010 |
| WO | WO-2015/157592 | A1 | 10/2015 |
| WO | WO-2015/184002 | A1 | 12/2015 |
| WO | WO-2015/195904 | A1 | 12/2015 |
| WO | WO-2015/195917 | A1 | 12/2015 |
| WO | WO-2016/135239 | A1 | 9/2016 |
| WO | WO-2016/149665 | A1 | 9/2016 |
| WO | WO-2017/079694 | A2 | 5/2017 |
| WO | WO-2017/191327 | A2 | 11/2017 |

OTHER PUBLICATIONS

Janeway et al., The structure of a typical antibody molecule, Immunobiology: The Immune System in Health and Disease.5th edition. New York: Garland Science; 2001 (Year: 2001).*
Cho et al., Biochanin-A induces apoptosis and suppresses migration in FaDu human pharynx squamous carcinoma cells, Oncology Reports, 38: 2985-2992, Publication Date: Sep. 13, 2017 (Year: 2017).*
Parakh et al., Evolution of anti-HER2 therapies for cancer treatment, Cancer Treatment Reviews 59 (2017) 1-21, Publication Date: Jul. 15, 2017 (Year: 2017).*
Brodowicz, T. et al., Anti-Her-2/neu antibody induces apoptosis in Her-2/neu overexpressing breast cancer cells independently from p53 status, Brit. Jrnl. Canc., 85(11):1764-1770 (2001).
International Preliminary Report on Patentability for PCT/SG2019/050077, 53 pages (dated Feb. 24, 2020).
International Search Report for PCT/SG2019/050077, 6 pages (dated May 8, 2019).
Kim, A. Y. et al., Novel murine anti-HER2 monoclonal antibodies to induce apoptosis and regulate miR-21 in breast cancer cell, Jrnl. Clin. Onco., Abstract, 31(15):3081 (2013).
Liu, X. et al., Affinity-Tuned ErbB2 or EGFR Chimeric Antigen Receptor T Cells Exhibit an Increased Therapeutic Index against Tumors in Mice, Canc. Res., 75(17):3596-3607 (2015).
Mineo, J-F et al., Recombinant humanised anti-HER2/neu antibody (Herceptin) induces cellular death of glioblastomas, Brit. Jrnl. Canc., 91:1195-1199 (2004).
Morgan, R. A. et al., Case Report of a Serious Adverse Event Following the Administration of T Cells Transduced With a Chimeric Antigen Receptor Recognizing ERBB2, Mol. Thera., 18(4):843-851 (2010).

(Continued)

*Primary Examiner* — Peter J Reddig
*Assistant Examiner* — Cheng Lu
(74) *Attorney, Agent, or Firm* — Polsinelli PC

(57) ABSTRACT

Antibodies, antigen-binding fragments and polypeptides that bind to HER2 are disclosed, as well as nucleic acids and vectors encoding the same. Also provided are cells comprising the antibodies, antigen-binding fragments, polypeptides, nucleic acids and vectors, methods of making such molecules, and the use of such molecules for therapeutic applications.

17 Claims, 16 Drawing Sheets

Specification includes a Sequence Listing.

(56) References Cited

OTHER PUBLICATIONS

Written Opinion for PCT/SG2019/050077, 7 pages (dated May 8, 2019).
Han, Y. et al., Antitumor effects and persistence of a novel HER2 CAR T cells directed to gastric cancer in preclinical models, Am. J. Cancer Res., 8(1):106-119 (2018).
Liu, X. et al., Driving better and safer HER2-specific CARs for cancer therapy, Oncotarget, 8(37):62730-62741 (2017).
Lu, Q. et al., An anti-ErbB2 fully human antibody circumvents trastuzumab resistance, Oncotarget, 7(41):67129-67141 (2016).
Zhang, A. et al., Anti-HER-2 engineering antibody ChA21 inhibits growth and induces apoptosis of SK-OV-3 cells, Jrnl. Experi. Clin. Cancer Res., 29:23, 9 pages (2010).

* cited by examiner

SEQ ID NO:1

P1A3 (lambda)

QAVVTQEPSL SVSPGGTVTL TCGLSSGSVS TGHYASWYQQ TPGQAPRTLF YNTNTRSSGV
PDRFSGSIVG NKAALTITGA QADDESDYYC VLYVGDGIWV FGGGTKLTVL GQPKAAPSVT
LFPPSSEELQ ANKATLVCLI SDFYPGAVTV AWKADSSPVK AGVETTTPSK QSNNKYAASS
YLSLTPEQWK SHKSYSCQVT HEGSTVEKTV APTECS

Figure 1A

SEQ ID NO:2

P1C5 (lambda)

QTVVTQEPSF SVSPGGTVTL TCGLSSGSVS TGYYPSWYQQ TPGQAPRTLI YSTNSRSSGV
PDRFSGSILG NKAALTITGA QADDESDYYC VLYMGSGISV FGGGTKLTVL GQPKAAPSVT
LFPPSSEELQ ANKATLVCLI SDFYPGAVTV AWKADSSPVK AGVETTTPSK QSNNKYAASS
YLSLTPEQWK SHKSYSCQVT HEGSTVEKTV APTECS

Figure 1B

SEQ ID NO:3

P1E4 (lambda)

QTVVTQEPSF SVSPGGTVTL TCGLSSGSVS TSYYPSWYQQ IPGQAPRTLI YTTNIRSSGV
PDRFGGSILG NKAALTITGA QAEDESDYYC MLYMGSGIWV FGGGTKLTVL GQPKTAPSVT
LFPPSSEELQ ANKATLVCLI SDFYPGAVTV AWKADSSPVK AGVETTTPSK QSNNKYAASS
YLSLTPEQWK SHKSYSCQVT HEGSTVEKTV APAECS

Figure 1C

SEQ ID NO:4

P1F1 (lambda)

QTVVTQEPSF SVSPGGTVTL TCGLSSGSVS TSYYPSWYQQ TPGQAPRTLI YSTNTRSSGV
PDRFSGSILG NKAALTITGA QADDESDYYC VLYMGSGIWV FGGGTKLTVL GQPKAAPSVT
LFPPSSEELQ ANKATLVCLI SDFYPGAVTV AWKADSSPVK AGVETTTPSK QSNNKYAASS
YLSLTPEQWK SHKSYSCQVT HEGSTVEKTV APTECS

Figure 1D

SEQ ID NO:5

P1A3

EVQLVQSGTE VKKPGASVRV SCKSSGYTFT SYYIHWVRQA PGQGLEWMAI INPGNGDTNY AQRFQGRVTM TRDTSTSTVY MELRSLRSDD TAVYFCAREI ASYSGSYYDY WGQGTLVTVS S

Figure 2A

SEQ ID NO:6

P1C5

QVQLQESGPG LVKPSETLSL TCTVSGGSIS SSSYYWGWIR QPPGKGLEWI GSIYYSGSTY YNPSLKSRVT ISVDTSKNQF SLKLSSVTAA DTAVYYCARY APDSSGYLVA FDIWGQGTMV TVSS

Figure 2B

SEQ ID NO:7

P1E4

QVQLQQWGAG LLKPSETLSL TCAVYGGSFS GYYWSWIRQP PGKGLEWIGE INHSGSTNYN PSLKSRVTIS VDTSKNQFSL KLSSVTTADT AVYYCARMGI NSGGYLYGMD VWGQGTTVTV SS

Figure 2C

SEQ ID NO:8

P1F1

QVQLVESGPG LVKPSGTLSL TCAVSGGSIS SSNWWSWVRQ PPGKGLEWIG EIYHSGSTNY NPSLKSRVTI SVDTSKNQFS LKLSSVTAAD TAVYYCARMG ANSGGYLYGM DVWGQGTTVT VSS

Figure 2D

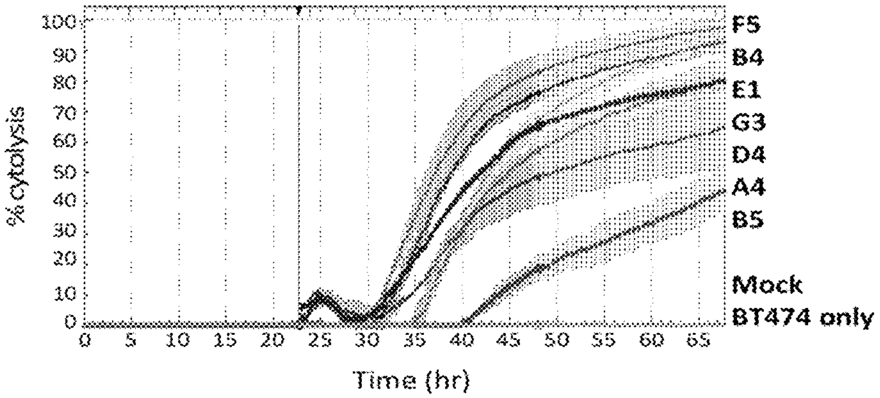
Figure 18A
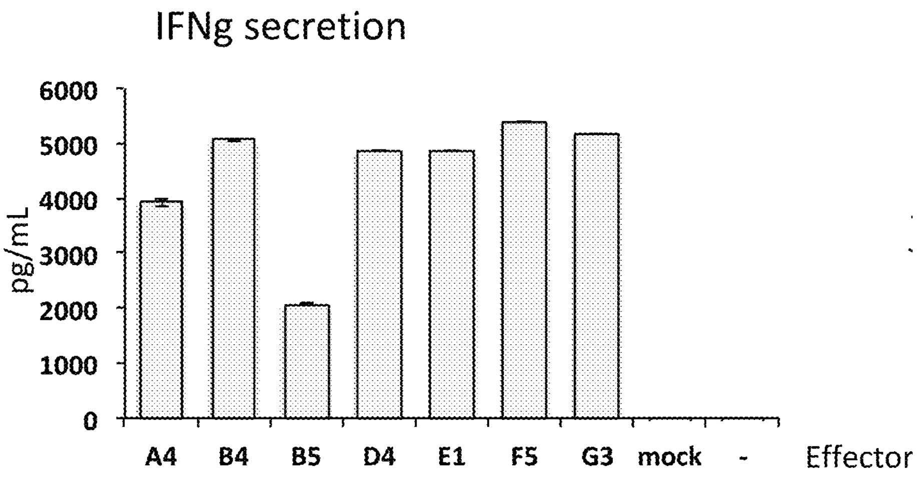
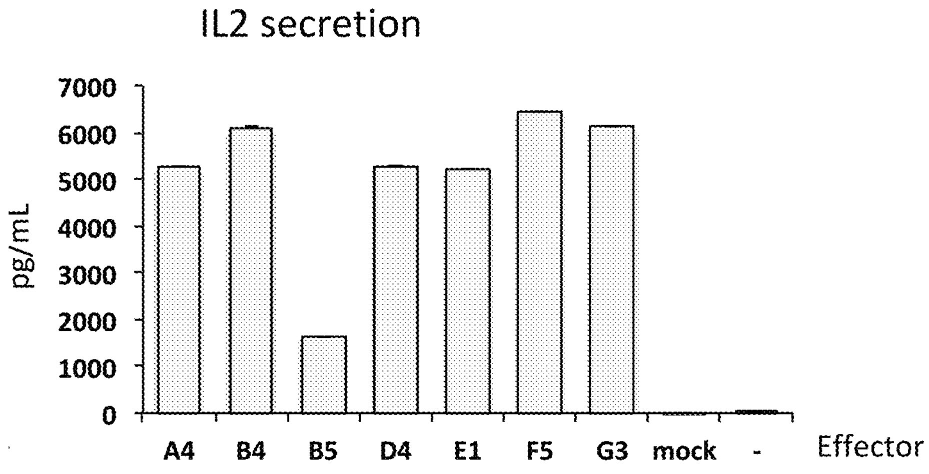
Figure 18B

ANTI-HER2 ANTIBODIES

This application is a National Stage of International Application No. PCT/SG2019/050077 which claims priority from SG10201801219V filed 13 Feb. 2018, the contents and elements of each of which are herein incorporated by reference for all purposes.

SEQUENCE LISTING

This application contains a Sequence Listing that has been submitted in .txt format via EFS-Web and is hereby incorporated by reference in its entirety. The .txt file is named "P611291US01 0910404-744364 Second Amended SL.txt", created on Sep. 25, 2023, and is 220 KB in size.

FIELD OF THE INVENTION

The present invention relates to antibodies that bind to the HER2 protein.

BACKGROUND TO THE INVENTION

Breast cancer is the most common cause of cancer deaths in females with more than 400,000 deaths per year globally. In Singapore, it is the most frequent cancer in women; affecting more than 8,000 women in Singapore from 2007-2011, representing about 30% of cancer cases in Singaporean females and being the leading cause of cancer deaths in Singaporean women (Singapore Cancer Registry, Interim Annual Registry Report, Trends in Cancer Incidence in Singapore).

A turning point in breast cancer treatment has been reached with the introduction of the monoclonal antibody, trastuzumab (Herceptin®) targeting the Epidermal Growth Factor Receptor 2 (HER2/HER-2) positive cancers, i.e. ~20-30% of breast cancers and the most aggressive ones. HER2 is a member of the epidermal growth factor receptor family including epidermal growth factor receptor (EGFR/HER1), HER3 and HER4. Either homo- or hetero-dimerization of these receptor tyrosine kinases results in the phosphorylation of intracellular domain residues, triggering a downstream signalling cascade including the RAS/Raf and Akt pathways. Dimerization of HER2 is known to result in increased cell survival, proliferation and resistance to apoptosis.

Trastuzumab is a humanised antibody approved for the treatment of HER2-positive breast cancer by FDA in 1998. Trastuzumab binds to domain IV of HER2, and while the mechanism of action of the antibody is still not well understood, several effects had been observed, including cell cycle arrest, immune-mediated cytolysis and inhibition of angiogenesis. However, response rates to trastuzumab treatment are still low, ranging from 15-30%. While the use of trastuzumab in combination with chemotherapy prolongs response duration, a majority of responders develop resistance within a year.

The mechanism of resistance has been studied intensively, but has not been validated clinically. Possible causes of resistance include reduced trastuzumab binding, e.g., the masking of trastuzumab binding sites by MUC4 glycoprotein upon association with HER2, signalling through alternative HER22 independent pathways, e.g., Insulin-like growth factor-I receptor (IGF-IR), and constitutive HER2 signalling as a result of mutations in downstream signalling molecules such as PTEN and PI3K.

In addition, there is evidence for an important role of HER3/HER2 heterodimers in breast cancer development, and the inability of trastuzumab to inhibit such heterodimer formation could be a contributing factor in the resistance to treatment.

To address this, pertuzumab (Perjeta®), a second generation HER2 humanised monoclonal antibody was developed. It binds to HER2 domain II, an epitope which hinders the receptor's dimerization. A phase III clinical study comparing the use of pertuzumab in combination with trastuzumab, and an anti-mitotic drug docetaxel (Taxotere®) in HER2-positive patients, showed significant improvements in overall survival with the new regimen, prompting the FDA to approve the combination therapy for treatment of HER2-positive metastatic breast cancer patients in 2012.

The prevalence of HER2-related cancers and the high risk of resistance to current therapies highlights the importance of developing new therapeutics to treat such cancers.

SUMMARY OF THE INVENTION

The present invention is concerned with antibodies, or antigen binding fragments, that bind to HER2. Heavy and light chain polypeptides are also disclosed. The antibodies, antigen binding fragments and polypeptides may be provided in isolated and/or purified form and may be formulated into compositions suitable for use in research, therapy and diagnosis.

In one aspect of the present invention an antibody, or antigen binding fragment, is provided, the amino acid sequence of the antibody or antigen binding fragment may comprise the amino acid sequences i) to iii), or the amino acid sequences iv) to vi), or preferably the amino acid sequences i) to vi):

i) LC-CDR1: (SEQ ID NO: 9)
$GLSSGSVSTX_1X_2YX_3S$;

ii) LC-CDR2: (SEQ ID NO: 10)
$X_4TNX_5RSS$;

iii) LC-CDR3: (SEQ ID NO: 11)
$X_6LYX_7GX_8GIX_9V$;

iv) HC-CDR1: (SEQ ID NO: 12)
$X_{10}X_{11}X_{12}X_{13}X_{14}X_{15}X_{16}$;

v) HC-CDR2: (SEQ ID NO: 13)
$X_{17}X_{18}X_{19}X_{20}X_{21}X_{22}GX_{23}TX_{24}YX_{25}X_{26}X_{27}X_{28}X_{29}X_{30}$;

vi) HC-CDR3: (SEQ ID NO: 14)
$X_{31}X_{32}X_{33}X_{34}X_{35}SX_{36}X_{37}YX_{38}X_{39}X_{40}X_{41}X_{42}X_{43}$;

or a variant thereof in which one or two or three amino acids in one or more of the sequences (i) to (vi) are replaced with another amino acid, where $X_1$=G or S; $X_2$=H or Y; $X_3$=A or P; $X_4$=N, S or T; $X_5$=T, S or I; $X_6$=V or M; $X_7$=V or M; $X_8$=D or S; $X_9$=W or S; $X_{10}$=S or absent; $X_{11}$=S or absent; $X_{12}$=S or G; $X_{13}$=Y or N; $X_{14}$=Y or W; $X_{15}$=I or W; $X_{16}$=H, G or S; $X_{17}$=I or absent; $X_{18}$=I, S or E; $X_{19}$=N or I; $X_{20}$=P, Y or N; $X_{21}$=G, Y or H; $X_{22}$=N or S; $X_{23}$=D or S; $X_{24}$=N or Y; $X_{25}$=A or N; $X_{26}$=Q or P, $X_{27}$=R or S, $X_{28}$=F or L; $X_{29}$=Q or K; $X_{30}$=G or S; $X_{31}$=E or absent; $X_{32}$=Y or M; $X_{33}$=A or G; $X_{34}$=S, P, I or A, $X_{35}$=Y. D or N;

$X_{36}$=G or S; $X_{37}$=G or S; $X_{38}$=L or absent; $X_{39}$=V or Y; $X_{40}$=A, or G; $X_{41}$=F, M or Y; $X_{42}$=D or absent; and $X_{43}$=I, V or absent.

In some embodiments LC-CDR1 is one of (SEQ ID NO: 15)
GLSSGSVSTGHYAS, (SEQ ID NO: 21)
GLSSGSVSTGYYPS,
or (SEQ ID NO: 27)
GLSSGSVSTSYYPS.

In some embodiments LC-CDR2 is one of (SEQ ID NO: 16)
NTNTRSS, (SEQ ID NO: 22)
STNSRSS, (SEQ ID NO: 28)
TTNIRSS,
or (SEQ ID NO: 33)
STNTRSS.

In some embodiments LC-CDR3 is one of (SEQ ID NO: 17)
VLYVGDGIWV, (SEQ ID NO: 23)
VLYMGSGISV;

(SEQ ID NO: 29)
MLYMGSGIWV,
or (SEQ ID NO: 34)
VLYMGSGIWV.

In some embodiments HC-CDR1 is one of (SEQ ID NO: 18)
SYYIH, (SEQ ID NO: 24)
SSSYYWG, (SEQ ID NO: 30)
GYYWS,
or (SEQ ID NO: 35)
SSNWWS.

In some embodiments HC-CDR2 is one of (SEQ ID NO: 19)
IINPGNGDTNYAQRFQG, (SEQ ID NO: 25)
SIYYSGSTYYNPSLKS, (SEQ ID NO: 31)
EINHSGSTNYNPSLKS,
or (SEQ ID NO: 36)
EIYHSGSTNYNPSLKS.

In some embodiments HC-CDR3 is one of (SEQ ID NO: 20)
EIASYSGSYYDY, (SEQ ID NO: 26)
YAPDSSGYLVAFDI, -continued (SEQ ID NO: 32)
MGINSGGYLYGMDV,
or (SEQ ID NO: 37)
MGANSGGYLYGMDV.

In some embodiments the antibody, or antigen binding fragment, may comprise at least one light chain variable region incorporating the following CDRs:

LC-CDR1:
(SEQ ID NO: 9)
GLSSGSVST$X_1X_2$Y$X_3$S;

LC-CDR2:
(SEQ ID NO: 10)
$X_4$TN$X_5$RSS;

LC-CDR3:
(SEQ ID NO: 11)
$X_6$LY$X_7$G$X_8$GI$X_9$V;

where $X_1$=G or S; $X_2$=H or Y; $X_3$=A or P; $X_4$=N, S or T; $X_5$=T, S or I; $X_6$=V or M; $X_7$=V or M; $X_8$=D or S; and $X_9$=W or S.

In some embodiments the antibody, or antigen binding fragment, may comprise at least one light chain variable region incorporating the following CDRs:

LC-CDR1:
(SEQ ID NO: 15)
GLSSGSVSTGHYAS

LC-CDR2:
(SEQ ID NO: 16)
NTNTRSS

LC-CDR3:
(SEQ ID NO: 17)
VLYVGDGIWV.

In some embodiments the antibody, or antigen binding fragment, may comprise at least one light chain variable region incorporating the following CDRs:

LC-CDR1:
(SEQ ID NO: 21)
GLSSGSVSTGYYPS

LC-CDR2:
(SEQ ID NO: 22)
STNSRSS

LC-CDR3:
(SEQ ID NO: 23)
VLYMGSGISV.

In some embodiments the antibody, or antigen binding fragment, may comprise at least one light chain variable region incorporating the following CDRs:

LC-CDR1:
(SEQ ID NO: 27)
GLSSGSVSTSYYPS

LC-CDR2:
(SEQ ID NO: 28)
TTNIRSS

-continued

LC-CDR3: (SEQ ID NO: 29)
MLYMGSGIWV.

In some embodiments the antibody, or antigen binding fragment, may comprise at least one light chain variable region incorporating the following CDRs:

LC-CDR1: (SEQ ID NO: 27)
GLSSGSVSTSYYPS

LC-CDR2: (SEQ ID NO: 33)
STNTRSS

LC-CDR3: (SEQ ID NO: 34)
VLYMGSGIWV.

In some embodiments the antibody, or antigen binding fragment, may comprise at least one heavy chain variable region incorporating the following CDRs:

HC-CDR1: (SEQ ID NO: 12)
$X_{10}X_{11}X_{12}X_{13}X_{14}X_{15}X_{16}$;

HC-CDR2: (SEQ ID NO: 13)
$X_{17}X_{18}X_{19}X_{20}X_{21}X_{22}GX_{23}TX_{24}YX_{25}X_{26}X_{27}X_{28}X_{29}X_{30}$;

HC-CDR3: (SEQ ID NO: 14)
$X_{31}X_{32}X_{33}X_{34}X_{35}SX_{36}X_{37}YX_{38}X_{39}X_{40}X_{41}X_{42}X_{43}$;

where $X_{10}$=S or absent; $X_{11}$=S or absent; $X_{12}$=S or G; $X_{13}$=Y or N; $X_{14}$=Y or W; $X_{15}$=I or W; $X_{16}$=H, G or S; $X_{17}$=I or absent; $X_{18}$=I, S or E; $X_{19}$=N or I; $X_{20}$=P, Y or N; $X_{21}$=G, Y or H; $X_{22}$=N or S; $X_{23}$=D or S; $X_{24}$=N or Y; $X_{25}$=A or N; $X_{26}$=Q or P, $X_{27}$=R or S, $X_{28}$=F or L; $X_{29}$=Q or K; $X_{30}$=G or S; $X_{31}$=E or absent; $X_{32}$=1, Y or M; $X_{33}$=A or G; $X_{34}$=S, P, I or A, $X_{35}$=Y, D or N; $X_{35}$=G or S; $X_{37}$=G or S; $X_{38}$=L or absent; $X_{39}$=V or Y; $X_{40}$=A, D or G; $X_{41}$=F, M or Y; $X_{42}$=D or absent; and $X_{43}$=I, V or absent.

In some embodiments the antibody, or antigen binding fragment, may comprise at least one heavy chain variable region incorporating the following CDRs:

HC-CDR1: (SEQ ID NO: 18)
SYYIH

HC-CDR2: (SEQ ID NO: 19)
IINPGNGDTNYAQRFQG

HC-CDR3: (SEQ ID NO: 20)
EIASYSGSYYDY.

In some embodiments the antibody, or antigen binding fragment, may comprise at least one heavy chain variable region incorporating the following CDRs:

HC-CDR1: (SEQ ID NO: 24)
SSSYYWG

-continued

HC-CDR2: (SEQ ID NO: 25)
SIYYSGSTYYNPSLKS

HC-CDR3: (SEQ ID NO: 26)
YAPDSSGYLVAFDI.

In some embodiments the antibody, or antigen binding fragment, may comprise at least one heavy chain variable region incorporating the following CDRs:

HC-CDR1: (SEQ ID NO: 30)
GYYWS

HC-CDR2: (SEQ ID NO: 31)
EINHSGSTNYNPSLKS

HC-CDR3: (SEQ ID NO: 32)
MGINSGGYLYGMDV.

In some embodiments the antibody, or antigen binding fragment, may comprise at least one heavy chain variable region incorporating the following CDRs:

HC-CDR1: (SEQ ID NO: 35)
SSNWWS

HC-CDR2: (SEQ ID NO: 36)
EIYHSGSTNYNPSLKS

HC-CDR3: (SEQ ID NO: 37)
MGANSGGYLYGMDV.

The antibody may comprise at least one light chain variable region ($V_L$) comprising the amino acid sequence of one of SEQ ID NOs 1, 15, 16, 17; or 2, 21, 22, 23; or 3, 27, 28, 29; or 4, 33, 34, 35, or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to SEQ ID NOs 1, 15, 16, 17; or 2, 21, 22, 23; or 3, 27, 28, 29; or 4, 33, 34, 35.

The antibody may comprise at least one heavy chain variable region ($V_H$) comprising the amino acid sequence of one of SEQ ID NOs 5, 18, 19, 20; or 6, 24, 25, 26; or 7, 30, 31, 32; or 8, 36, 37, 38, or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to SEQ ID NOs 5, 18, 19, 20; or 6, 24, 25, 26; or 7, 30, 31, 32; or 8, 36, 37, 38.

The antibody may comprise at least one light chain variable region ($V_L$) comprising the amino acid sequence of one of SEQ ID NOs 1, 15, 16, 17; or 2, 21, 22, 23; or 3, 27, 28, 29; or 4, 33, 34, 35, or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to SEQ ID NOs 1, 15, 16, 17; or 2, 21, 22, 23; or 3, 27, 28, 29; or 4, 33, 34, 35, and at least one heavy chain variable region ($V_H$) comprising the amino acid sequence of one of SEQ ID NOs 5, 18, 19, 20; or 6, 24, 25, 26; or 7, 30, 31, 32; or 8, 36, 37, 38, or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to SEQ ID NOs 5, 18, 19, 20; or 6, 24, 25, 26; or 7, 30, 31, 32; or 8, 36, 37, 38.

An antibody, antigen binding fragment or polypeptide provided herein, may optionally bind HER2, optionally human or murine HER2. The antibody, antigen binding fragment, polypeptide may bind specifically to human, rhesus macaque and/or murine HER2. The antibody, antigen binding fragment or polypeptide may optionally have amino acid sequence components as described above. The antibody, antigen binding fragment or polypeptide may be an IgG or derived from an IgG. The antibody, antigen binding fragment or polypeptide may have a molecular weight of about 140 to 160 kDa, preferably about 150 kDa. In one embodiment an in vitro complex, optionally isolated, comprising an antibody, antigen binding fragment, or polypeptide as described herein, bound to HER2 is provided.

In one aspect of the present invention an isolated light chain variable region polypeptide is provided, the light chain variable region polypeptide comprising the following CDRs:

LC-CDR1:
(SEQ ID NO: 9)
$GLSSGSVSTX_1X_2YX_3S$

LC-CDR2:
(SEQ ID NO: 10)
$X_4TNX_5RSS$

LC-CDR3:
(SEQ ID NO: 11)
$X_6LYX_7GX_8GIX_9V$;

where $X_1$=G or S; $X_2$=H or Y; $X_3$=A or P; $X_4$=N, S or T; $X_5$=T, S or I; $X_6$=V or M; $X_7$=V or M; $X_8$=D or S; and $X_9$=W or S.

In some embodiments the isolated light chain variable region polypeptide is provided in combination with a heavy chain variable region polypeptide as described herein.

In some embodiments LC-CDR1 is one of GLSSGSVSTGHYAS (SEQ ID NO:15), GLSSGSVSTGYYPS (SEQ ID NO:21), or GLSSGSVSTSYYPS (SEQ ID NO:27). In some embodiments LC-CDR2 is one of NTNTRSS (SEQ ID NO:16), STNSRSS (SEQ ID NO:22), TTNIRSS (SEQ ID NO:28), or STNTRSS (SEQ ID NO:33). In some embodiments LC-CDR3 is one of VLYVGDGIWV (SEQ ID NO:17), VLYMGSGISV (SEQ ID NO:23); MLYMGSGIWV (SEQ ID NO:29), or VLYMGSGIWV (SEQ ID NO:34). In some embodiments the isolated light chain variable region polypeptide is capable of binding to HER2.

In one aspect of the present invention an light chain variable region polypeptide is provided, comprising an amino acid sequence having at least 85% sequence identity to the light chain sequence: SEQ ID NO:1, 2, 3, or 4 (FIG. 1A to 1D). In some embodiments the isolated light chain variable region polypeptide is capable of binding to HER2.

In one aspect of the present invention an isolated heavy chain variable region polypeptide is provided, the heavy chain variable region polypeptide comprising the following CDRs:

HC-CDR1:
(SEQ ID NO: 12)
$X_{10}X_{11}X_{12}X_{13}X_{14}X_{15}X_{16}$;

HC-CDR2:
(SEQ ID NO: 13)
$X_{17}X_{18}X_{19}X_{20}X_{21}X_{22}GX_{23}TX_{24}YX_{25}X_{26}X_{27}X_{28}X_{29}X_{30}$;

HC-CDR3:
(SEQ ID NO: 14)
$X_{31}X_{32}X_{33}X_{34}X_{35}SX_{36}X_{37}YX_{38}X_{39}X_{40}X_{41}X_{42}X_{43}$;

where $X_{10}$=S or absent; $X_{11}$=S or absent; $X_{12}$=S or G; $X_{13}$=Y or N; $X_{14}$=Y or W; $X_{15}$=I or W; $X_{16}$=H, G or S; $X_{17}$=I or absent; $X_{18}$=I, S or E; $X_{19}$=N or I; $X_{20}$=P, Y or N; $X_{21}$=G, Y or H; $X_{22}$=N or S; $X_{23}$=D or S; $X_{24}$=N or Y; $X_{25}$=A or N; $X_{26}$=Q or P, $X_{27}$=R or S, $X_{28}$=F or L; $X_{29}$=Q or K; $X_{30}$=G or S; $X_{21}$=E or absent; $X_{32}$=I, Y or M; $X_{33}$=A or G; $X_{34}$=S, P, I or A, $X_{35}$=Y, or N; $X_{38}$=G or S; $X_{37}$=G or S; $X_{38}$=L or absent; $X_{39}$=V or Y; $X_{49}$=A. D or G; $X_{41}$=F, M or Y; $X_{42}$=D or absent; and $X_{43}$=I, V or absent.

In some embodiments the isolated heavy chain variable region polypeptide is provided in combination with a light chain variable region polypeptide as described herein.

In some embodiments HC-CDR1 is one of SYYIH (SEQ ID NO:18), SSSYYWG (SEQ ID NO:24), GYYWS (SEQ ID NO:30), or SSNWWS (SEQ ID NO:35). In some embodiments HC-CDR2 is one of IINPGNGDTNYAQRFQG (SEQ ID NO:19), SIYYSGSTYYNPSLKS (SEQ ID NO:25), EINHSGSTNYNPSLKS (SEQ ID NO:31), or EIYHSGSTNYNPSLKS (SEQ ID NO:36). In some embodiments HC-CDR3 is one of EIASYSGSYYDY (SEQ ID NO:20), YAPDSSGYLVAFDI (SEQ ID NO:26), MGINSGGYLYGMDV (SEQ ID NO:32), or MGANSGGYLYGMDV (SEQ ID NO:37). In some embodiments the isolated heavy chain variable region polypeptide is capable of binding to HER2.

In one aspect of the present invention an isolated heavy chain variable region polypeptide is provided, comprising an amino acid sequence having at least 85% sequence identity to the heavy chain sequence of SEQ ID NO:5, 6, 7, or 8 (FIG. 2A to 2D). In some embodiments the isolated heavy chain variable region polypeptide is capable of binding to HER2.

In one aspect of the present invention an antibody, or antigen binding fragment, is provided, the antibody, or antigen binding fragment, comprising a heavy chain and a light chain variable region sequence, wherein: the light chain comprises a LC-CDR1, LC-CDR2, LC-CDR3, having at least 85% overall sequence identity to LC-CDR1: one of $GLSSGSVSTX_1X_2YX_3S$ (SEQ ID NO:9), GLSSGSVSTGHYAS (SEQ ID NO:15), GLSSGSVSTGYYPS (SEQ ID NO:21), or GLSSGSVSTSYYPS (SEQ ID NO:27), LC-CDR2: one of $X_4TNX_5RSS$ (SEQ ID NO:10), NTNTRSS (SEQ ID NO:16), STNSRSS (SEQ ID NO:22), TTNIRSS (SEQ ID NO:28), or STNTRSS (SEQ ID NO:33), and LC-CDR3: one of $X_6LYX_7GX_8GIX_9V$ (SEQ ID NO:11), VLYVGDGIWV (SEQ ID NO:17), VLYMGSGISV (SEQ ID NO:23); MLYMGSGIWV (SEQ ID NO:29), or VLYMGSGIWV (SEQ ID NO:34), respectively, where $X_1$=G or S; $X_2$=H or Y; $X_3$=A or P; $X_4$=N, S or T; $X_5$=T, S or I; $X_6$=V or M; $X_7$=V or M; $X_8$=D or S; and $X_9$=W or S, and;

the heavy chain comprises a HC-CDR1, HC-CDR2, HC-CDR3, having at least 85% overall sequence identity to HC-CDR1: one of $X_{10}X_{11}X_{12}X_{13}X_{14}X_{15}X_{16}$ (SEQ ID NO:12), SYYIH (SEQ ID NO:18), SSSYYWG (SEQ ID NO:24), GYYWS (SEQ ID NO:30), or SSNWWS (SEQ ID NO:35), HC-CDR2: one of $X_{17}X_{18}X_{19}X_{20}X_{21}X_{22}GX_{23}TX_{24}YX_{25}X_{26}X_{27}X_{28}X_{29}X_{30}$ (SEQ ID NO:13), IINPGNGDTNYAQRFQG (SEQ ID NO:19), SIYYSGSTYYNPSLKS (SEQ ID NO:25), EINHSGSTNYNPSLKS (SEQ ID NO:31), or EIYHSG-STNYNPSLKS (SEQ ID NO:36), and HC-CDR3: one of $X_{30}X_{32}X_{33}X_{34}X_{35}SX_{36}X_{37}YX_{38}X_{39}X_{40}X_{41}X_{42}X_{43}$ (SEQ ID NO:14), EIASYSGSYYDY (SEQ ID NO:20), YAP-DSSGYLVAFDI (SEQ ID NO:26), MGINSGGYLYGMDV (SEQ ID NO:32), or MGANSGGYLYGMDV (SEQ ID NO:37), respectively, where $X_{10}$=S or absent; $X_{11}$=S or absent; $X_{12}$=S or G; $X_{13}$=Y or N; $X_{14}$=Y or W; $X_{15}$=I or W; $X_{16}$=H, G or S; $X_{17}$=I or absent; $X_{18}$=I, S or E; $X_{19}$=N or I; $X_{20}$=P, Y or N; $X_{21}$=G, Y or H; $X_{22}$=N or S; $X_{23}$=D or S; $X_{24}$=N or Y; $X_{25}$=A or N; $X_{26}$=Q or P, $X_{27}$=R or S, $X_{28}$=F or L; $X_{29}$=Q or K; $X_{30}$=G or S; $X_{31}$=E or absent; $X_{32=1}$, Y or M; $X_{33}$=A or G, $X_{34}$=S, P, I or A, $X_{35}$=Y, or N; $X_{36}$=G or S; $X_{37}$=G or S; $X_{38}$=L or absent; $X_{39}$=V or Y; $X_{40}$=A, D or G; $X_{41}$=F, M or Y; $X_{42}$=D or absent; and $X_{43}$=I, V or absent.

In some embodiments the degree of sequence identity may be one of 86%, 87%, 88%, 89%, 90%, 91%, 92%, 93%, 94%, 95%, 96%, 97%, 98%, 99%, or 100%.

In another aspect of the present invention an antibody or antigen binding fragment which is capable of binding to HER2, optionally isolated, is provided comprising a heavy chain and a light chain variable region sequence, wherein: the light chain sequence has at least 85% sequence identity to the light chain sequence of SEQ ID NO:1, 2, 3, or 4 (FIG. 1A to 1D), and;

the heavy chain sequence has at least 85% sequence identity to the heavy chain sequence of SEQ ID NO:5, 6, 7, or 8 (FIG. 2A to 2D).

In some embodiments the degree of sequence identity may be one of 86%, 87%, 88%, 89%, 90%, 91%, 92%, 93%, 94%, 95%, 96%, 97%, 98%, 99%, or 100%.

In another aspect of the present invention an antibody, antigen binding fragment or polypeptide which is capable of binding to HER2, optionally isolated, is provided having the amino acid sequences i) to iii), or the amino acid sequences iv) to vi), or preferably the amino acid sequences i) to vi):

i)
LC-CDR1: one of
(SEQ ID NO: 74)
RSSQSLLHSNGFNYLD,
(SEQ ID NO: 84)
RSSQSLLHSDGNKYLD,
(SEQ ID NO: 93)
RSSQSLVYSDGNTYLN,
(SEQ ID NO: 102)
RSSQSLLHSNGYNYLD,
(SEQ ID NO: 110)
RSSQSLLHSNGNTYLD,
(SEQ ID NO: 120)
RASQSVRNNLA,
(SEQ ID NO: 138)
GSTTGAVTSGHYPS, -continued
(SEQ ID NO: 161)
RASQSVSSSYLA,
(SEQ ID NO: 170)
RSSQSLQHSNGYQYLD,
(SEQ ID NO: 186)
TGRSANIGGFDVQ,
(SEQ ID NO: 194)
ALTSGSVSTSYYPS,
(SEQ ID NO: 211)
TSSQSLVYSDGNTYLN,
(SEQ ID NO: 217)
RSSQSLLRSDGYNFVD,
(SEQ ID NO: 226)
RASQGISSWLA,
(SEQ ID NO: 247)
RASRSVGKYLA,
(SEQ ID NO: 255)
GLSSGSVSTTYYPS,
(SEQ ID NO: 261)
TLRSGINVGTYRIY,
(SEQ ID NO: 270)
RASQSVSSYLA,
(SEQ ID NO: 279)
GLTSGAVSSSYYPS,
(SEQ ID NO: 287)
TGNNNNVGFAGAA;

ii)
LC-CDR2: one of
(SEQ ID NO: 75)
LGSNRAS,
(SEQ ID NO: 94)
KVSNRDS,
(SEQ ID NO: 111)
SGSNRAS;
(SEQ ID NO: 121)
YASTRAT,
(SEQ ID NO: 139)
STSNKHS,
(SEQ ID NO: 146)
LGSHRAS,
(SEQ ID NO: 155)
LGSNRAP,
(SEQ ID NO: 162)
GASSRAT,
(SEQ ID NO: 171)
LGSFRAS,
(SEQ ID NO: 187)
DNSNRPS,
(SEQ ID NO: 195)
STNLRSS,
(SEQ ID NO: 204)
KVSDRDS,
(SEQ ID NO: 212)
KVSKRDS, -continued (SEQ ID NO: 218)
LGSDRAS, (SEQ ID NO: 227)
AASSLQS, (SEQ ID NO: 262)
YKSDSDKQQGS, (SEQ ID NO: 248)
DASTRAS, (SEQ ID NO: 33)
STNTRSS, (SEQ ID NO: 271)
DASNRAT, (SEQ ID NO: 230)
NTDIRFS, (SEQ ID NO: 288)
RNNDRPS;

iii)
LC-CDR3: one of (SEQ ID NO: 76)
MQGLQTPYT, (SEQ ID NO: 85)
MLGTHWPPMYI, (SEQ ID NO: 95)
MQGTHWPLT, (SEQ ID NO: 103)
MQALQTPWT, (SEQ ID NO: 112)
MQGTHWPPT, (SEQ ID NO: 122)
QHYGSSRT, (SEQ ID NO: 130)
MAGLQTPRLT, (SEQ ID NO: 140)
LLYYGGARV, (SEQ ID NO: 147)
MQALQTPLT, (SEQ ID NO: 163)
QQYGSSPRT, (SEQ ID NO: 172)
MHALSTPPWT, (SEQ ID NO: 180)
MQGTHWPGT, (SEQ ID NO: 188)
GTWDSYLNIWV, (SEQ ID NO: 196)
ELYMGSGISV, (SEQ ID NO: 205)
MQGTHWPQT, (SEQ ID NO: 219)
MQALQTPRT, (SEQ ID NO: 228)
QQANSFPPT, (SEQ ID NO: 233)
QQYGSSSA, -continued (SEQ ID NO: 263)
MIWHSSAWV, (SEQ ID NO: 249)
QHYGTSPPFI, (SEQ ID NO: 256)
VLYMGNGISV, (SEQ ID NO: 272)
QQRSNWPLT, (SEQ ID NO: 23)
VLYMGSGISV, (SEQ ID NO: 289)
SAWDSSLKVQV;

iv)
HC-CDR1: one of (SEQ ID NO: 77)
SYGMH, (SEQ ID NO: 86)
SAAAAWN, (SEQ ID NO: 96)
SYAMH, (SEQ ID NO: 113)
SFAMN, (SEQ ID NO: 123)
SYGIS, (SEQ ID NO: 131)
SYAMS, (SEQ ID NO: 148)
SYAIS, (SEQ ID NO: 173)
TYTMH, (SEQ ID NO: 30)
GYYWS, (SEQ ID NO: 197)
SYWIG, (SEQ ID NO: 234)
NYGMH, (SEQ ID NO: 241)
SYAIH, (SEQ ID NO: 24)
SSSYYWG, (SEQ ID NO: 281)
DYYIH;

v)
HC-CDR2: one of (SEQ ID NO: 78)
VISYDGSNKYYADSVKG, (SEQ ID NO: 87)
RTYYRSKWYSEYAVSVKS, (SEQ ID NO: 104)
WINAGNGNTKYSQKFQG, (SEQ ID NO: 114)
TIGGSGDSTFYADPVKG, (SEQ ID NO: 124)
WISAYNGNTNYAQKLQG, (SEQ ID NO: 132)
AISGSGGSTYYADSVKG, -continued

GIIPIFGTANYAQKFQG, (SEQ ID NO: 149)

GINWNGGSTGYADSVKG, (SEQ ID NO: 164)

WITPGNGNTHYSQNFQG, (SEQ ID NO: 174)

EINFISGSTNYNPSLKS, (SEQ ID NO: 31)

IIYPGDSDTRYSPSFQG, (SEQ ID NO: 198)

AISSNGGSTYYADSVKG, (SEQ ID NO: 206)

VISYDESNKYYADSVKG, (SEQ ID NO: 220)

FISYDGTNKYYADSVKG, (SEQ ID NO: 235)

SIYYSGSTYYNPSLKS, (SEQ ID NO: 25)

VIWYDGSNKYYADSVKG, (SEQ ID NO: 264)

SISSSSSYIYYADSVKG, (SEQ ID NO: 273)

WVSAYNGDINYAQKFQG; (SEQ ID NO: 282)

vi)
HC-CDR3: one of

DLFAVVGYYYYYGMDV, (SEQ ID NO: 79)

GSIFDV, (SEQ ID NO: 88)

SRGYYGMDV, (SEQ ID NO: 97)

GGYLVGY, (SEQ ID NO: 105)

AYGSGGHYFFAY, (SEQ ID NO: 115)

DWGSSWSDY, (SEQ ID NO: 125)

TYYDEWSGRVGAFDI, (SEQ ID NO: 133)

DRGYYGMDV, (SEQ ID NO: 141)

GRGSGYPDTWFWFDP, (SEQ ID NO: 150)

SYGSGSYRSHAFDI, (SEQ ID NO: 156)

GLVPAASMDV, (SEQ ID NO: 165)

SRVGALDY, (SEQ ID NO: 175)

SRGYSGYDN, (SEQ ID NO: 181)

GLPYYYFDY, (SEQ ID NO: 189)

-continued

LGYGVPLPEYFDL, (SEQ ID NO: 199)

EPSGSWSYLYYYYGMDV, (SEQ ID NO: 221)

HYGDYYYYGMDV, (SEQ ID NO: 236)

VYGYGLHYYGMDV, (SEQ ID NO: 242)

SYDSSGYYYFDY, (SEQ ID NO: 250)

YAPDSSGYLVAFDI, (SEQ ID NO: 26)

MTTEDY, (SEQ ID NO: 265)

DGSAWSRPY, (SEQ ID NO: 274)

EIASYSGSYYDY, (SEQ ID NO: 20)

GADWNSDY; (SEQ ID NO: 290)

or a variant thereof in which one or two or three amino acids in one or more of the sequences (i) to (vi) are replaced with another amino acid.

In another aspect of the present invention an antibody, antigen binding fragment, or polypeptide which is capable of binding to HER2, optionally isolated, is provided comprising a heavy chain and a light chain variable region sequence, wherein:

the light chain comprises a LC-CDR1, LC-CDR2, LC-CDR3, having at least 85% overall sequence identity to LC-CDR1; one of

RSSQSLLHSNGFNYLD, (SEQ ID NO: 74)

RSSQSLLHSDGNKYLD, (SEQ ID NO: 34)

RSSQSLVYSDGNTYLN, (SEQ ID NO: 93)

RSSQSLLHSNGYNYLD, (SEQ ID NO: 102)

RSSQSLLHSNGNTYLD, (SEQ ID NO: 110)

RASQSVRNNLA, (SEQ ID NO: 120)

GSTTGAVTSGHYPS, (SEQ ID NO: 133)

RASQSVSSSYLA; (SEQ ID NO: 161)

RSSQSLQHSNGYQYLD, (SEQ ID NO: 170)

TGRSANIGGFDVQ, (SEQ ID NO: 186)

ALTSGSVSTSYYPS, (SEQ ID NO: 194)

TSSQSLVYSDGNTYLN, (SEQ ID NO: 211)

-continued (SEQ ID NO: 217)
RSSQSLLRSDGYNFVD, (SEQ ID NO: 226)
RASQGISSVVLA, (SEQ ID NO: 247)
RASRSVGKYLA, (SEQ ID NO: 255)
GLSSGSVSTTYYPS, (SEQ ID NO: 261)
TLRSGINVGTYRIY, (SEQ ID NO: 270)
RASQSVSSYLA, (SEQ ID NO: 279)
GLTSGAVSSSYYPS, (SEQ ID NO: 287)
TGNNNNVGFAGAA;

LC-CDR2: one of (SEQ ID NO: 75)
LGSNRAS, (SEQ ID NO: 94)
KVSNRDS, (SEQ ID NO: 111)
SGSNRAS, (SEQ ID NO: 121)
YASTRAT, (SEQ ID NO: 139)
STSNKHS, (SEQ ID NO: 146)
LGSHRAS, (SEQ ID NO: 155)
LGSNRAP, (SEQ ID NO: 162)
GASSRAT, (SEQ ID NO: 171)
LGSFRAS, (SEQ ID NO: 187)
DNSNRPS, (SEQ ID NO: 195)
STNLRSS, (SEQ ID NO: 204)
KVSDRDS, (SEQ ID NO: 212)
KVSKRDS, (SEQ ID NO: 218)
LGSDRAS, (SEQ ID NO: 227)
AASSLQS, (SEQ ID NO: 262)
YKSDSDKQQGS, (SEQ ID NO: 248)
DASTRAS, (SEQ ID NO: 33)
STNTRSS, (SEQ ID NO: 271)
DASNRAT, -continued (SEQ ID NO: 280)
NTDIRFS, (SEQ ID NO: 288)
RNNDRPS;

LC-CDR3: one of (SEQ ID NO: 76)
MQGLQTPYT, (SEQ ID NO: 85)
MLGTHWPPMYI, (SEQ ID NO: 95)
MQGTHWPLT, (SEQ ID NO: 103)
MQALQTPWT, (SEQ ID NO: 112)
MQGTHWPFT, (SEQ ID NO: 122)
QHYGSSRT, (SEQ ID NO: 130)
MAGLQTPRLT, (SEQ ID NO: 140)
LLYYGGARV, (SEQ ID NO: 147)
MQALQTPLT, (SEQ ID NO: 163)
QQYGSSPRT, (SEQ ID NO: 172)
MHALSTFPWT, (SEQ ID NO: 180)
MQGTHWPGT, (SEQ ID NO: 188)
GTWDSYLNIWV, (SEQ ID NO: 196)
ELYMGSGISV, (SEQ ID NO: 205)
MQGTHWPQT, (SEQ ID NO: 219)
MQALQTPRT, (SEQ ID NO: 228)
QQANSFPFT, (SEQ ID NO: 233)
QQYGSSSA, (SEQ ID NO: 263)
MIWHSSAWV, (SEQ ID NO: 249)
QHYGTSPPFI, (SEQ ID NO: 256)
VLYMGNGISV, (SEQ ID NO: 272)
QQRSNWPLT, -continued (SEQ ID NO: 23)
VLYMGSGISV, (SEQ ID NO: 289)
SAWDSSLKVQV,
and;

the heavy chain comprises a HC-CDR1, HC-CDR2, HC-CDR3, having at least 85% overal sequence identity to HC-CDR1: one of (SEQ ID NO: 77)
SYGMH, (SEQ ID NO: 86)
SAAAAWN, (SEQ ID NO: 96)
SYAMH, (SEQ ID NO: 113)
SFAMN, (SEQ ID NO: 123)
SYGIS, (SEQ ID NO: 131)
SYAMS, (SEQ ID NO: 148)
SYAIS, (SEQ ID NO: 173)
TYTMH, (SEQ ID NO: 30)
GYYWS, (SEQ ID NO: 197)
SYWIG, (SEQ ID NO: 234)
NYGMH, (SEQ ID NO: 241)
SYAIH, (SEQ ID NO: 24)
SSSYYWG, (SEQ ID NO: 281)
DYYIH;

HC-CDR2: one of (SEQ ID NO: 78)
VISYDGSNKYYADSVKG, (SEQ ID NO: 87)
RTYYRSKWYSEYAVSVKS, (SEQ ID NO: 104)
WINAGNGNIKYSOKFQG, (SEQ ID NO: 114)
TIGGSGDSTFYADPVKG, (SEQ ID NO: 124)
WISAYNGNINYAQKLQG, (SEQ ID NO: 132)
AISGSGGSTYYADSVKG, (SEQ ID NO: 149)
GIIPIFGTANYAQKFQG, (SEQ ID NO: 164)
GINWNGGSTGYADSVKG, (SEQ ID NO: 174)
WITPGNGNTHYSQNFQG, -continued (SEQ ID NO: 31)
EINHSGSTNYNPSLKS, (SEQ ID NO: 198)
IIYPGDSDTRYSPSFQG, (SEQ ID NO: 206)
AISSNGGSTYYADSVKG, (SEQ ID NO: 220)
VISYDESNKYYADSVKG, (SEQ ID NO: 235)
FISYDGTNKYYADSVKG, (SEQ ID NO: 25)
SIYYSGSTYYNPSLKS, (SEQ ID NO: 264)
VIWYDGSNKYYADSVKG, (SEQ ID NO: 273)
SISSSSSYIYYADSVKG, (SEQ ID NO: 282)
WVSAYNGDTNYAQKFQG;

HC-CDR3: one of (SEQ ID NO: 79)
DLFAVVGYYYYYGMDV, (SEQ ID NO: 38)
GSIFDV, (SEQ ID NO: 97)
SRGYYGMDV, (SEQ ID NO: 105)
GGYLVGY, (SEQ ID NO: 115)
AYGSGGHYFFAY, (SEQ ID NO: 125)
DWGSSWSDY, (SEQ ID NO: 133)
TYYDFWSGRVGAFDI, (SEQ ID NO: 141)
DRGYYGMDV, (SEQ ID NO: 150)
GRGSGYPDTWFWFDP, (SEQ ID NO: 156)
SYGSGSYRSHAFDI, (SEQ ID NO: 165)
GLVPAASMDV, (SEQ ID NO: 175)
SRVGALDY, (SEQ ID NO: 181)
SRGYSGYDN, (SEQ ID NO: 189)
GLPYYYFDY, (SEQ ID NO: 199)
LGYGVPLPEYFDL, (SEQ ID NO: 221)
EPSGSWSYLYYYYYGMDV, (SEQ ID NO: 236)
HYGDYYYYYGMDV, (SEQ ID NO: 242)
VYGYGLHYYGMDV, -continued (SEQ ID NO: 250)
SYDSSGYYYFDY, (SEQ ID NO: 26)
YAPDSSGYLVAFDI, (SEQ ID NO: 265)
MTTEDY, (SEQ ID NO: 274)
DGSAWSRPY, (SEQ ID NO: 20)
EIASYSGSYYDY, (SEQ ID NO: 290)
GADWNSDY.

In some embodiments the degree of sequence identity may be one of 86%, 87%, 88%, 89%, 90%, 91%, 92%, 93%, 94%, 95%, 96%, 97%, 98%, 99%, or 100%.

In some embodiments the antibody, antigen binding fragment or polypeptide has at least one light chain variable region incorporating the following CDRs: LC-CDR1: RSSQSLLHSNGFNYLD (SEQ ID NO:74), LC-CDR2: LGSNRAS (SEQ ID NO:75), LC-CDR3: MQGLQTPYT (SEQ ID NO:76). In some embodiments the antibody, antigen binding fragment or polypeptide has at least one heavy chain variable region incorporating the following CDRs: HC-CDR1: SYGMH (SEQ ID NO:77), HC-CDR2: VISYDGSNKYYADSVKG (SEQ ID NO:78), HC-CDR3: DLFAVVGYYYYYGMDV (SEQ ID NO:79). In some embodiments the antibody, antigen binding fragment or polypeptide has at least one light chain variable region incorporating the following CDRs: LC-CDR1: RSSQSLLHSNGFNYLD (SEQ ID NO:74), LC-CDR2: LGSNRAS (SEQ ID NO:75), LC-CDR3: MQGLQTPYT (SEQ ID NO:76), and at least one heavy chain variable region incorporating the following CDRs: HC-CDR1: SYGMH (SEQ ID NO:77), HC-CDR2: VISYDGSNKYYADSVKG (SEQ ID NO:78), HC-CDR3: DLFAVVGYYYYYGMDV (SEQ ID NO:79).

In some embodiments the antibody, antigen binding fragment or polypeptide has at least one light chain variable region incorporating the following CDRs: LC-CDR1: RSSQSLLHSDGNKYLD (SEQ ID NO:84), LC-CDR2: LGSNRAS (SEQ ID NO:75), LC-CDR3: MLGTHWPPMYI (SEQ ID NO:85). In some embodiments the antibody, antigen binding fragment or polypeptide has at least one heavy chain variable region incorporating the following CDRs: HC-CDR1: SAAAAWN (SEQ ID NO:86), HC-CDR2: RTYYRSKWYSEYAVSVKS (SEQ ID NO:87), HC-CDR3: GSIFDV (SEQ ID NO:88). In some embodiments the antibody, antigen binding fragment or polypeptide has at least one light chain variable region incorporating the following CDRs: LC-CDR1: RSSQSLLHSDGNKYLD (SEQ ID NO:84), LC-CDR2: LGSNRAS (SEQ ID NO:75), LC-CDR3: MLGTHWPPMYI (SEQ ID NO:85), and at least one heavy chain variable region incorporating the following CDRs: HC-CDR1: SAAAAWN (SEQ ID NO:86), HC-CDR2: RTYYRSKWYSEYAVSVKS (SEQ ID NO:87), HC-CDR3: GSIFDV (SEQ ID NO:88).

In some embodiments the antibody, antigen binding fragment or polypeptide has at least one light chain variable region incorporating the following CDRs: LC-CDR1: RSSQSLVYSDGNTYLN (SEQ ID NO:93), LC-CDR2: KVSNRDS (SEQ ID NO:94), LC-CDR3: MQGTHWPLT (SEQ ID NO:95). In some embodiments the antibody, antigen binding fragment or polypeptide has at least one heavy chain variable region incorporating the following CDRs: HC-CDR1: SYAMH (SEQ ID NO:96), HC-CDR2: VISYDGSNKYYADSVKG (SEQ ID NO:78), HC-CDR3: SRGYYGMDV (SEQ ID NO:97). In some embodiments the antibody, antigen binding fragment or polypeptide has at least one light chain variable region incorporating the following CDRs: LC-CDR1: RSSQSLVYSDGNTYLN (SEQ ID NO:93), LC-CDR2: KVSNRDS (SEQ ID NO:94), LC-CDR3: MQGTHWPLT (SEQ ID NO:95), and at least one heavy chain variable region incorporating the following CDRs: HC-CDR1: SYAMH (SEQ ID NO:96), HC-CDR2: VISYDGSNKYYADSVKG (SEQ ID NO:78), HC-CDR3: SRGYYGMDV (SEQ ID NO:97).

In some embodiments the antibody, antigen binding fragment, or polypeptide has at least one light chain variable region incorporating the following CDRs: LC-CDR1: RSSQSLLHSNGYNYLD (SEQ ID NO:102), LC-CDR2: LGSNRAS (SEQ ID NO:75), LC-CDR3: MQALQTPWT (SEQ ID NO:103). In some embodiments the antibody, antigen binding fragment, or polypeptide has at least one heavy chain variable region incorporating the following CDRs: HC-CDR1: SYAMH (SEQ ID NO:96), HC-CDR2: WINAGNGNTKYSQKFQG (SEQ ID NO:104), HC-CDR3: GGYLVGY (SEQ ID NO:105), In some embodiments the antibody, antigen binding fragment, or polypeptide has at least one light chain variable region incorporating the following CDRs: LC-CDR1: RSSQSLLHSNGYNYLD (SEQ ID NO:102), LC-CDR2: LGSNRAS (SEQ ID NO:75), LC-CDR3: MQALQTPWT (SEQ ID NO:103), and at least one heavy chain variable region incorporating the following CDRs: HC-CDR1: SYAMH (SEQ ID NO:96), HC-CDR2: WINAGNGNTKYSQKFQG (SEQ ID NO:104), HC-CDR3: GGYLVGY (SEQ ID NO:105).

In some embodiments the antibody, antigen binding fragment, or polypeptide has at least one light chain variable region incorporating the following CDRs: LC-CDR1: RSSQSLLHSNGNTYLD (SEQ ID NO:110), LC-CDR2: SGSNRAS (SEQ ID NO:111), LC-CDR3: MQGTHWPPT (SEQ ID NO:112). In some embodiments the antibody, antigen binding fragment, or polypeptide has at least one heavy chain variable region incorporating the following CDRs: HC-CDR1: SFAMN (SEQ ID NO:113), HC-CDR2: TIGGSGDSTFYADPVKG (SEQ ID NO:114), HC-CDR3: AYGSGGHYFFAY (SEQ ID NO:115). In some embodiments the antibody, antigen binding fragment, or polypeptide has at least one light chain variable region incorporating the following CDRs: LC-CDR1: RSSQSLLHSNGNTYLD (SEQ ID NO:110), LC-CDR2: SGSNRAS (SEQ ID NO:111), LC-CDR3: MQGTHWPPT (SEQ ID NO:112), and at least one heavy chain variable region incorporating the following CDRs: HC-CDR1: SFAMN (SEQ ID NO:113), HC-CDR2: TIGGSGDSTFYADPVKG (SEQ ID NO:114), HC-CDR3: AYGSGGHYFFAY (SEQ ID NO:115).

In some embodiments the antibody, antigen binding fragment, or polypeptide has at least one light chain variable region incorporating the following CDRs: LC-CDR1: RASQSVRNNLA (SEQ ID NO:120), LC-CDR2: YASTRAT (SEQ ID NO:121), LC-CDR3: QHYGSSRT (SEQ ID NO:122), In some embodiments the antibody, antigen binding fragment, or polypeptide has at least one heavy chain variable region incorporating the following CDRs: HC-CDR1: SYGIS (SEQ ID NO:123), HC-CDR2: WISAYNGNTNYAQKLQG (SEQ ID NO:124), HC-CDR3: DWGSSWSDY (SEQ ID NO:125). In some embodiments the antibody, antigen binding fragment, or polypeptide has at least one light chain variable region incorporating the following CDRs: LC-CDR1: RASQSVRNNLA (SEQ ID NO:120), LC-CDR2: YASTRAT (SEQ ID NO:121), LC-CDR3: QHYGSSRT (SEQ ID NO:122), and at least one heavy chain variable region incorporating the following CDRs: HC-CDR1: SYGIS (SEQ ID NO:123), HC-CDR2: WISAYNGNTNYAQKLQG (SEQ ID NO:124), HC-CDR3: DWGSSWSDY (SEQ ID NO:125).

In some embodiments the antibody, antigen binding fragment, or polypeptide has at least one light chain variable region incorporating the following CDRs: LC-CDR1: RSSQSLLHSNGYNYLD (SEQ ID NO:102), LC-CDR2: LGSNRAS (SEQ ID NO:75), LC-CDR3: MAGLQTPRLT (SEQ ID NO:130), In some embodiments the antibody, antigen binding fragment, or polypeptide has at least one heavy chain variable region incorporating the following CDRs: HC-CDR1: SYAMS (SEQ ID NO:131), HC-CDR2: AISGSGGSTYYADSVKG (SEQ ID NO:132), HC-CDR3: TYYDFWSGRVGAFDI (SEQ ID NO:133). In some embodiments the antibody, antigen binding fragment, or polypeptide has at least one light chain variable region incorporating the following CDRs: LC-CDR1: RSSQSLLHSNGYNYLD (SEQ ID NO:102), LC-CDR2: LGSNRAS (SEQ ID NO:75), LC-CDR3: MAGLQTPRLT (SEQ ID NO:130), and at least one heavy chain variable region incorporating the following CDRs: HC-CDR1: SYAMS (SEQ ID NO:131), HC-CDR2: AISGSGGSTYYADSVKG (SEQ ID NO:132), HC-CDR3: TYYDFWSGRVGAFDI (SEQ ID NO:133).

In some embodiments the antibody, antigen binding fragment, or polypeptide has at least one light chain variable region incorporating the following CDRs: LC-CDR1: GSTTGAVTSGHYPS (SEQ ID NO:138), LC-CDR2: STSNKHS (SEQ ID NO:139), LC-CDR3: LLYYGGARV (SEQ ID NO:140). In some embodiments the antibody, antigen binding fragment, or polypeptide has at least one heavy chain variable region incorporating the following CDRs: HC-CDR1: SYGMH (SEQ ID NO:77), HC-CDR2: VISYDGSNKYYADSVKG (SEQ ID NO:78), HC-CDR3: DRGYYGMDV (SEQ ID NO:141). In some embodiments the antibody, antigen binding fragment, or polypeptide has at least one light chain variable region incorporating the following CDRs: LC-CDR1: GSTTGAVTSGHYPS (SEQ ID NO:138), LC-CDR2: STSNKHS (SEQ ID NO:139), LC-CDR3: LLYYGGARV (SEQ ID NO:140), and at least one heavy chain variable region incorporating the following CDRs: HC-CDR1: SYGMH (SEQ ID NO:77), HC-CDR2: VISYDGSNKYYADSVKG (SEQ ID NO:78), HC-CDR3: DRGYYGMDV (SEQ ID NO:141).

In some embodiments the antibody, antigen binding fragment, or polypeptide has at least one light chain variable region incorporating the following CDRs: LC-CDR1: RSSQSLLHSNGYNYLD (SEQ ID NO:102), LC-CDR2: LGSHRAS (SEQ ID NO:146), LC-CDR3: MQALQTPLT (SEQ ID NO:147). In some embodiments the antibody, antigen binding fragment, or polypeptide has at least one heavy chain variable region incorporating the following CDRs: HC-CDR1: SYAIS (SEQ ID NO:148), HC-CDR2: GIIPIFGTANYAQKFQG (SEQ ID NO:149), HC-CDR3: GRGSGYPDTWFWFDP (SEQ ID NO:150). In some embodiments the antibody, antigen binding fragment, or polypeptide has at least one light chain variable region incorporating the following CDRs: LC-CDR1: RSSQSLLHSNGYNYLD (SEQ ID NO:102), LC-CDR2: LGSHRAS (SEQ ID NO:146), LC-CDR3: MQALQTPLT (SEQ ID NO:147), and at least one heavy chain variable region incorporating the following CDRs: HC-CDR1: SYAIS (SEQ ID NO:148), HC-CDR2: GIIPIFGTANYAQKFQG (SEQ ID NO:149), HC-CDR3: GRGSGYPDTWFWFDP (SEQ ID NO:150).

In some embodiments the antibody, antigen binding fragment, or polypeptide has at least one light chain variable region incorporating the following CDRs: LC-CDR1: RSSQSLLHSNGYNYLD (SEQ ID NO:102), LC-CDR2: LGSNRAP (SEQ ID NO:155), LC-CDR3: MQGTHWPLT (SEQ ID NO:95). In some embodiments the antibody, antigen binding fragment, or polypeptide has at least one heavy chain variable region incorporating the following CDRs: HC-CDR1: SYAMH (SEQ ID NO:96), HC-CDR2: VISYDGSNKYYADSVKG (SEQ ID NO:78), HC-CDR3: SYGSGSYRSHAFDI (SEQ ID NO:156). In some embodiments the antibody, antigen binding fragment, or polypeptide has at least one light chain variable region incorporating the following CDRs: LC-CDR1: RSSQSLLHSNGYNYLD (SEQ ID NO:102), LC-CDR2: LGSNRAP (SEQ ID NO:155), LC-CDR3: MQGTHWPLT (SEQ ID NO:95), and has at least one heavy chain variable region incorporating the following CDRs: HC-CDR1: SYAMH (SEQ ID NO:96), HC-CDR2: VISYDGSNKYYADSVKG (SEQ ID NO:78), HC-CDR3: SYGSGSYRSHAFDI (SEQ ID NO:156).

In some embodiments the antibody, antigen binding fragment, or polypeptide has at least one light chain variable region incorporating the following CDRs: LC-CDR1: RASQSVSSSYLA (SEQ ID NO:161), LC-CDR2: GASSRAT (SEQ ID NO:162), LC-CDR3: QQYGSSPRT (SEQ ID NO:163), In some embodiments the antibody, antigen binding fragment, or polypeptide has at least one heavy chain variable region incorporating the following CDRs: HC-CDR1: SYAMS (SEQ ID NO:131), HC-CDR2: GINWNGGSTGYADSVKG (SEQ ID NO:164), HC-CDR3: GLVPAASMDV (SEQ ID NO:165). In some embodiments the antibody, antigen binding fragment, or polypeptide has at least one light chain variable region incorporating the following CDRs: LC-CDR1: RASQSVSSSYLA (SEQ ID NO:161), LC-CDR2: GASSRAT (SEQ ID NO:162), LC-CDR3: QQYGSSPRT (SEQ ID NO:163), and has at least one heavy chain variable region incorporating the following CDRs: HC-CDR1: SYAMS (SEQ ID NO:131), HC-CDR2: GINWNGGSTGYADSVKG (SEQ ID NO:164), HC-CDR3: GLVPAASMDV (SEQ ID NO:165).

In some embodiments the antibody, antigen binding fragment, or polypeptide has at least one light chain variable region incorporating the following CDRs: LC-CDR1: RSSQSLQHSNGYQYLD (SEQ ID NO:170), LC-CDR2: LGSFRAS (SEQ ID NO:171), LC-CDR3: MHALSTPPWT (SEQ ID NO:172), In some embodiments the antibody, antigen binding fragment, or polypeptide has at least one heavy chain variable region incorporating the following CDRs: HC-CDR1: TYTMH (SEQ ID NO:173), HC-CDR2: WTPGNGNTHYSQNFQG (SEQ ID NO:174), HC-CDR3: SRVGALDY (SEQ ID NO:175). In some embodiments the antibody, antigen binding fragment, or polypeptide has at least one light chain variable region incorporating the following CDRs: LC-CDR1: RSSQSLQHSNGYQYLD (SEQ ID NO:170), LC-CDR2: LGSFRAS (SEQ ID NO:171), LC-CDR3: MHALSTPPWT (SEQ ID NO:172), and has at least one heavy chain variable region incorporating the following CDRs: HC-CDR1: TYTMH (SEQ ID NO:173), HC-CDR2: WITPGNGNTHYSQNFQG (SEQ ID NO:174), HC-CDR3: SRVGALDY (SEQ ID NO:175).

In some embodiments the antibody, antigen binding fragment or polypeptide has at least one light chain variable region incorporating the following CDRs: LC-CDR1:

RSSQSLVYSDGNTYLN (SEQ ID NO:93), LC-CDR2: KVSNRDS (SEQ ID NO:94), LC-CDR3: MQGTHWPGT (SEQ ID NO:180), In some embodiments the antibody, antigen binding fragment, or polypeptide has at least one heavy chain variable region incorporating the following CDRs: HC-CDR1: SYGMH (SEQ ID NO:77), HC-CDR2: VISYDGSNKYYADSVKG (SEQ ID NO:78), HC-CDR3: SRGYSGYDN (SEQ ID NO:181). In some embodiments the antibody, antigen binding fragment, or polypeptide has at least one light chain variable region incorporating the following CDRs: LC-CDR1: RSSQSLVYSDGNTYLN (SEQ ID NO:93), LC-CDR2: KVSNRDS (SEQ ID NO:94), LC-CDR3: MQGTHWPGT (SEQ ID NO:180), and has at least one heavy chain variable region incorporating the following CDRs: HC-CDR1: SYGMH (SEQ ID NO:77), HC-CDR2: VISYDGSNKYYADSVKG (SEQ ID NO:78), HC-CDR3: SRGYSGYDN (SEQ ID NO:181).

In some embodiments the antibody, antigen binding fragment, or polypeptide has at least one light chain variable region incorporating the following CDRs: LC-CDR1: TGRSANIGGFDVQ (SEQ ID NO:186), LC-CDR2: DNSNRPS (SEQ ID NO:187), LC-CDR3: GTWDSYLNIWV (SEQ ID NO:188). In some embodiments the antibody, antigen binding fragment, or polypeptide has at least one heavy chain variable region incorporating the following CDRs: HC-CDR1: GYYWS (SEQ ID NO:30), HC-CDR2: EINHSGSTNYNPSLKS (SEQ ID NO:31), HC-CDR3: GLPYYYFDY (SEQ ID NO:189). In some embodiments the antibody, antigen binding fragment, or polypeptide has at least one light chain variable region incorporating the following CDRs: LC-CDR1: TGRSANIGGFDVQ (SEQ ID NO:186), LC-CDR2; DNSNRPS (SEQ ID NO:187), LC-CDR3: GTWDSYLNIWV (SEQ ID NO:188), and has at least one heavy chain variable region incorporating the following CDRs: HC-CDR1: GYYWS (SEQ ID NO:30), HC-CDR2: EINHSGSTNYNPSLKS (SEQ ID NO:31), HC-CDR3: GLPYYYFDY (SEQ ID NO:189).

In some embodiments the antibody, antigen binding fragment, or polypeptide has at least one light chain variable region incorporating the following CDRs: LC-CDR1: ALTSGSVSTSYYPS (SEQ ID NO:194), LC-CDR2: STNLRSS (SEQ ID NO:195), LC-CDR3: ELYMGSGISV (SEQ ID NO:196). In some embodiments the antibody, antigen binding fragment, or polypeptide has at least one heavy chain variable region incorporating the following CDRs: HC-CDR1: SYWIG (SEQ ID NO:197), HC-CDR2: IIYPGDSDTRYSPSFQG (SEQ ID NO:198), HC-CDR3; LGYGVPLPEYFDL (SEQ ID NO:199). In some embodiments the antibody, antigen binding fragment, or polypeptide has at least one light chain variable region incorporating the following CDRs: LC-CDR1: ALTSGSVSTSYYPS (SEQ ID NO:194), LC-CDR2: STNLRSS (SEQ ID NO:195), LC-CDR3: ELYMGSGISV (SEQ ID NO:196), and at least one heavy chain variable region incorporating the following CDRs: HC-CDR1: SYWIG (SEQ ID NO:197), HC-CDR2: IIYPGDSDTRYSPSFQG (SEQ ID NO:198), HC-CDR3; LGYGVPLPEYFDL (SEQ ID NO:199).

In some embodiments the antibody, antigen binding fragment, or polypeptide has at least one light chain variable region incorporating the following CDRs: LC-CDR1: RSSQSLVYSDGNTYLN (SEQ ID NO:93), LC-CDR2: KVSDRDS (SEQ ID NO:204), LC-CDR3: MQGTHWPQT (SEQ ID NO:205). In some embodiments the antibody, antigen binding fragment, or polypeptide has at least one heavy chain variable region incorporating the following CDRs: HC-CDR1; SYAMH (SEQ ID NO:96), HC-CDR2: AISSNGGSTYYADSVKG (SEQ ID NO:206), HC-CDR3: SRGYYGMDV (SEQ ID NO:97). In some embodiments the antibody, antigen binding fragment, or polypeptide has at least one light chain variable region incorporating the following CDRs: LC-CDR1: RSSQSLVYSDGNTYLN (SEQ ID NO:93), LC-CDR2: KVSDRDS (SEQ ID NO:204), LC-CDR3: MQGTHWPQT (SEQ ID NO:205), and has at least one heavy chain variable region incorporating the following CDRs: HC-CDR1: SYAMH (SEQ ID NO:96), HC-CDR2: AISSNGGSTYYADSVKG (SEQ ID NO:206), HC-CDR3: SRGYYGMDV (SEQ ID NO:97).

In some embodiments the antibody, antigen binding fragment, or polypeptide has at least one light chain variable region incorporating the following CDRs: LC-CDR1: TSSQSLVYSDGNTYLN (SEQ ID NO:211), LC-CDR2: KVSKRDS (SEQ ID NO:212), LC-CDR3: MQGTHWPLT (SEQ ID NO:95). In some embodiments the antibody, antigen binding fragment, or polypeptide has at least one heavy chain variable region incorporating the following CDRs: HC-CDR1: SYAMH (SEQ ID NO:96), HC-CDR2: VISYDGSNKYYADSVKG (SEQ ID NO:78), HC-CDR3: SRGYYGMDV (SEQ ID NO:97). In some embodiments the antibody, antigen binding fragment, or polypeptide has at least one light chain variable region incorporating the following CDRs: LC-CDR1: TSSQSLVYSDGNTYLN (SEQ ID NO:211), LC-CDR2: KVSKRDS (SEQ ID NO:212), LC-CDR3: MQGTHWPLT (SEQ ID NO:95), and has at least one heavy chain variable region incorporating the following CDRs: HC-CDR1: SYAMH (SEQ ID NO:96), HC-CDR2: VISYDGSNKYYADSVKG (SEQ ID NO:78), HC-CDR3: SRGYYGMDV (SEQ ID NO:97).

In some embodiments the antibody, antigen binding fragment, or polypeptide has at least one light chain variable region incorporating the following CDRs: LC-CDR1: RSSQSLLRSDGYNFVD (SEQ ID NO:217), LC-CDR2: LGSDRAS (SEQ ID NO:218), LC-CDR3: MQALQTPRT (SEQ ID NO:219). In some embodiments the antibody, antigen binding fragment, or polypeptide has at least one heavy chain variable region incorporating the following CDRs: HC-CDR1: SYAMH (SEQ ID NO:96), HC-CDR2: VISYDESNKYYADSVKG (SEQ ID NO:220), HC-CDR3: EPSGSWSYLYYYYYGMDV (SEQ ID NO:221). In some embodiments the antibody, antigen binding fragment, or polypeptide has at least one light chain variable region incorporating the following CDRs: LC-CDR1: RSSQSLLRSDGYNFVD (SEQ ID NO:217), LC-CDR2: LGSDRAS (SEQ ID NO:218), LC-CDR3: MQALQTPRT (SEQ ID NO:219), and has at least one heavy Chain variable region incorporating the following CDRs: HC-CDR1: SYAMH (SEQ ID NO:96), HC-CDR2: VISYDESNKYYADSVKG (SEQ ID NO:220), HC-CDR3: EPSGSWSYLYYYYYGMDV (SEQ ID NO:221).

In some embodiments the antibody, antigen binding fragment, or polypeptide has at least one light chain variable region incorporating the following CDRs: LC-CDR1: RASQGISSWLA (SEQ ID NO:226), LC-CDR2: AASSLQS (SEQ ID NO:227), LC-CDR3: QQANSFPPT (SEQ ID NO:228). In some embodiments the antibody, antigen binding fragment, or polypeptide has at least one heavy chain variable region incorporating the following CDRs: HC-CDR1: SYAMH (SEQ ID NO:96), HC-CDR2: VISYDGSNKYYADSVKG (SEQ ID NO:78), HC-CDR3: SRGYYGMDV (SEQ ID NO:97). In some embodiments the antibody, antigen binding fragment, or polypeptide has at least one light chain variable region incorporating the following CDRs: LC-CDR1: RASQGISSWLA (SEQ ID NO:226), LC-CDR2: AASSLQS (SEQ ID NO:227), LC- CDR3: QQANSFPPT (SEQ ID NO:228), and has at least one heavy chain variable region incorporating the following CDRs: HC-CDR1: SYAMH (SEQ ID NO:96), HC-CDR2. VISYDGSNKYYADSVKG (SEQ ID NO:78), HC-CDR3. SRGYYGMDV (SEQ ID NO:97).

In some embodiments the antibody, antigen binding fragment, or polypeptide has at least one light chain variable region incorporating the following CDRs: LC-CDR1: RASQSVSSSYLA (SEQ ID NO:161), LC-CDR2: GASSRAT (SEQ ID NO:162), LC-CDR3: QQYGSSSA (SEQ ID NO:233). In some embodiments the antibody, antigen binding fragment, or polypeptide has at least one heavy chain variable region incorporating the following CDRs: HC-CDR1: NYGMH (SEQ ID NO:234), HC-CDR2: FISYDGTNKYYADSVKG (SEQ ID NO:235), HC-CDR3: HYGDYYYYYGMDV (SEQ ID NO:236). In some embodiments the antibody, antigen binding fragment, or polypeptide has at least one light chain variable region incorporating the following CDRs: LC-CDR1: RASQSVSSSYLA (SEQ ID NO:161), LC-CDR2: GASSRAT (SEQ ID NO:162), LC-CDR3: QQYGSSSA (SEQ ID NO:233), and has at least one heavy chain variable region incorporating the following CDRs: HC-CDR1: NYGMH (SEQ ID NO:234), HC-CDR2: FISYDGTNKYYADSVKG (SEQ ID NO:235), HC-CDR3: HYGDYYYYYGMDV (SEQ ID NO:236).

In some embodiments the antibody, antigen binding fragment, or polypeptide has at least one light chain variable region incorporating the following CDRs: LC-CDR1: RSSQSLLHSNGYNYLD (SEQ ID NO:102), LC-CDR2: LGSNRAS (SEQ ID NO:75), LC-CDR3: MQGTHWPGT (SEQ ID NO:180). In some embodiments the antibody, antigen binding fragment, or polypeptide has at least one heavy chain variable region incorporating the following CDRs: HC-CDR1: SYAIH (SEQ ID NO:241), HC-CDR2: AISSNGGSTYYADSVKG (SEQ ID NO:206), HC-CDR3: VYGYGLHYYGMDV (SEQ ID NO:242). In some embodiments the antibody, antigen binding fragment, or polypeptide has at least one light chain variable region incorporating the following CDRs: LC-CDR1: RSSQSLLHSNGYNYLD (SEQ ID NO:102), LC-CDR2: LGSNRAS (SEQ ID NO:75), LC-CDR3: MQGTHWPGT (SEQ ID NO:180), and has at least one heavy chain variable region incorporating the following CDRs: HC-CDR1: SYAIH (SEQ ID NO:241), HC-CDR2: AISSNGGSTYYADSVKG (SEQ ID NO:206), HC-CDR3: VYGYGLHYYGMDV (SEQ ID NO:242).

In some embodiments the antibody, antigen binding fragment, or polypeptide has at least one light chain variable region incorporating the following CDRs: LC-CDR1: RASRSVGKYLA (SEQ ID NO:247), LC-CDR2: DASTRAS (SEQ ID NO:248), LC-CDR3: QHYGTSPPFI (SEQ ID NO:249). In some embodiments the antibody, antigen binding fragment, or polypeptide has at least one heavy chain variable region incorporating the following CDRs: HC-CDR1: SYAIS (SEQ ID NO:148), HC-CDR2: GIIPIFGTANYAQKFQG (SEQ ID NO:149), HC-CDR3: SYDSSGYYYFDY (SEQ ID NO:250). In some embodiments the antibody, antigen binding fragment, or polypeptide has at least one light chain variable region incorporating the following CDRs: LC-CDR1: RASRSVGKYLA (SEQ ID NO:247), LC-CDR2: DASTRAS (SEQ ID NO:248), LC-CDR3: QHYGTSPPFI (SEQ ID NO:249), and has at least one heavy chain variable region incorporating the following CDRs: HC-CDR1: SYAIS (SEQ ID NO:148), HC-CDR2: GIIPIFGTANYAQKFQG (SEQ ID NO:149), HC-CDR3: SYDSSGYYYFDY (SEQ ID NO:250).

In some embodiments the antibody, antigen binding fragment, or polypeptide has at least one light chain variable region incorporating the following CDRs: LC-CDR1: GLSSGSVSTTYYPS (SEQ ID NO:255), LC-CDR2: STNTRSS (SEQ ID NO:33), LC-CDR3: VLYMGNGISV (SEQ ID NO:256). In some embodiments the antibody, antigen binding fragment, or polypeptide has at least one heavy chain variable region incorporating the following CDRs: HC-CDR1: SSSYYWG (SEQ ID NO:24), HC-CDR2: SIYYSGSTYYNPSLKS (SEQ ID NO:25), HC-CDR3: YAPDSSGYLVAFDI (SEQ ID NO:26). In some embodiments the antibody, antigen binding fragment, or polypeptide has at least one light chain variable region incorporating the following CDRs: LC-CDR1: GLSSGSVSTTYYPS (SEQ ID NO:255), LC-CDR2: STNTRSS (SEQ ID NO:33), LC-CDR3: VLYMGNGISV (SEQ ID NO:256), and has at least one heavy chain variable region incorporating the following CDRs: HC-CDR1: SSSYYWG (SEQ ID NO:24), HC-CDR2: SIYYSGSTYYNPSLKS (SEQ ID NO:25), HC-CDR3: YAPDSSGYLVAFDI (SEQ ID NO:26).

In some embodiments the antibody, antigen binding fragment, or polypeptide has at least one light chain variable region incorporating the following CDRs: LC-CDR1: TLRSGINVGTYRIY (SEQ ID NO:261), LC-CDR2: YKSDSDKQQGS (SEQ ID NO:262), LC-CDR3: MIWHSSAWV (SEQ ID NO:263). In some embodiments the antibody, antigen binding fragment, or polypeptide has at least one heavy chain variable region incorporating the following CDRs: HC-CDR1: SYGMH (SEQ ID NO:77), HC-CDR2: VIWYDGSNKYYADSVKG (SEQ ID NO:264), HC-CDR3: MTTEDY (SEQ ID NO:265). In some embodiments the antibody, antigen binding fragment, or polypeptide has at least one light chain variable region incorporating the following CDRs: LC-CDR1: LC-CDR1: TLRSGINVGTYRIY (SEQ ID NO:261), LC-CDR2: YKSDSDKQQGS (SEQ ID NO:262), LC-CDR3: MIWHSSAWV (SEQ ID NO:263), and has at least one heavy chain variable region incorporating the following CDRs: HC-CDR1: SYGMH (SEQ ID NO:77), HC-CDR2: VIWYDGSNKYYADSVKG (SEQ ID NO:264), HC-CDR3: MTTEDY (SEQ ID NO:265).

In some embodiments the antibody, antigen binding fragment, or polypeptide has at least one light chain variable region incorporating the following CDRs: LC-CDR1: RASQSVSSYLA (SEQ ID NO:270), LC-CDR2: DASNRAT (SEQ ID NO:271), LC-CDR3: QQRSNWPLT (SEQ ID NO:272). In some embodiments the antibody, antigen binding fragment, or polypeptide has at least one heavy chain variable region incorporating the following CDRs: HC-CDR1; SYAMS (SEQ ID NO:131), HC-CDR2: SISSSSSYIYYADSVKG (SEQ ID NO:273), HC-CDR3: DGSAWSRPY (SEQ ID NO:274). In some embodiments the antibody, antigen binding fragment, or polypeptide has at least one light chain variable region incorporating the following CDRs: LC-CDR1: RASQSVSSYLA (SEQ ID NO:270), LC-CDR2: DASNRAT (SEQ ID NO:271), LC-CDR3: QQRSNWPLT (SEQ ID NO:272), and has at least one heavy chain variable region incorporating the following CDRs: HC-CDR1: SYAMS (SEQ ID NO:131), HC-CDR2: SISSSSSYIYYADSVKG (SEQ ID NO:273), HC-CDR3: DGSAWSRPY (SEQ ID NO:274).

In some embodiments the antibody, antigen binding fragment, or polypeptide has at least one light chain variable region incorporating the following CDRs: LC-CDR1: GLTSGAVSSSYYPS (SEQ ID NO:279), LC-CDR2: NTDIRFS (SEQ ID NO:280), LC-CDR3: VLYMGSGISV (SEQ ID NO:23). In some embodiments the antibody, antigen binding fragment, or polypeptide has at least one heavy chain variable region incorporating the following CDRs: HC-CDR1: DYYIH (SEQ ID NO:281), HC-CDR2: WVSAYNGDTNYAQKFQG (SEQ ID NO:282), HC-CDR3: EIASYSGSYYDY (SEQ ID NO:20). In some embodiments the antibody, antigen binding fragment, or polypeptide has at least one light chain variable region incorporating the following CDRs: LC-CDR1: GLTSGAVSSSYYPS (SEQ ID NO:279), LC-CDR2: NTDIRFS (SEQ ID NO:280), LC-CDR3: VLYMGSGISV (SEQ ID NO:23), and has at least one heavy chain variable region incorporating the following CDRs: HC-CDR1: DYYIH (SEQ ID NO:281), HC-CDR2: WVSAYNGDTNYAQKFQG (SEQ ID NO:282), HC-CDR3: EIASYSGSYYDY (SEQ ID NO:20).

In some embodiments the antibody, antigen binding fragment, or polypeptide has at least one light chain variable region incorporating the following CDRs: LC-CDR1: TGNNNNVGFAGAA (SEQ ID NO:287), LC-CDR2: RNNDRPS (SEQ ID NO:238), LC-CDR3: SAWDSSLKVQV (SEQ ID NO:289). In some embodiments the antibody, antigen binding fragment, or polypeptide has at least one heavy chain variable region incorporating the following CDRs: HC-CDR1: SYAIS (SEQ ID NO:148), HC-CDR2: GIIPIFGTANYAQKFQG (SEQ ID NO:149), HC-CDR3: GADWNSDY (SEQ ID NO:290). In some embodiments the antibody, antigen binding fragment, or polypeptide has at least one light chain variable region incorporating the following CDRs: LC-CDR1: TGNNNNVGFAGAA (SEQ ID NO:287), LC-CDR2: RNNDRPS (SEQ ID NO:288), LC-CDR3: SAWDSSLKVQV (SEQ ID NO:289), and has at least one heavy chain variable region incorporating the following CDRs: HC-CDR1: SYAIS (SEQ ID NO:148), HC-CDR2: GIIPIFGTANYAQKFQG (SEQ ID NO:149), HC-CDR3: GADWNSDY (SEQ ID NO:290).

In some embodiments the antibody, antigen binding fragment, or polypeptide has at least one light chain variable region incorporating the following CDRs: LC-CDR1: RSSQSLLHSNGYNYLD (SEQ ID NO:102), LC-CDR2: LGSNRAP (SEQ ID NO:155), LC-CDR3: MQGTHWPLT (SEQ ID NO:95). In some embodiments the antibody, antigen binding fragment, or polypeptide has at least one heavy chain variable region incorporating the following CDRs: HC-CDR1; SYAMH (SEQ ID NO:96), HC-CDR2: VISYDGSNKYYADSVKG (SEQ ID NO:78), HC-CDR3: SYGSGSYRSHAFDI (SEQ ID NO:156). In some embodiments the antibody, antigen binding fragment, or polypeptide has at least one light chain variable region incorporating the following CDRs: LC-CDR1: RSSQSLLHSNGYNYLD (SEQ ID NO:102), LC-CDR2: LGSNRAP (SEQ ID NO:155), LC-CDR3: MQGTHWPLT (SEQ ID NO:95), and has at least one heavy chain variable region incorporating the following CDRs: HC-CDR1: SYAMH (SEQ ID NO:96), HC-CDR2: VISYDGSNKYYADSVKG (SEQ ID NO:78), HC-CDR3: SYGSGSYRSHAFDI (SEQ ID NO:156).

In another aspect of the present invention an antibody, antigen binding fragment, or polypeptide which is capable of binding to HER2, optionally isolated, is provided comprising a heavy chain and a light chain variable region sequence, wherein;

the light chain sequence has at least 85% sequence identity to the light chain sequence of SEQ ID NO: 72, 82, 91, 100, 108, 118, 128, 136, 144, 153, 159, 168, 178, 184, 192, 202, 209, 215, 224, 231, 239, 245, 253, 259, 268, 277, 285, or 293, and;

the heavy chain sequence has at least 85% sequence identity to the heavy chain sequence of SEQ ID NO:73, 83, 92, 101, 109, 119, 129, 137, 145, 154, 160, 169, 179, 185, 193, 203, 210, 216, 225, 232, 240, 246, 254, 260, 269, 278, 286, or 294.

In some embodiments the degree of sequence identity may be one of 86%, 87%, 88%, 89%, 90%, 91%, 92%, 93%, 94%, 95%, 96%, 97%, 98%, 99%, or 100%.

In some embodiments an isolated light chain variable region polypeptide is provided comprising the following CDRs:

LC-CDR1: one of

RSSQSLLHSNGFNYLD, (SEQ ID NO: 74)

RSSQSLLHSDGNKYLD, (SEQ ID NO: 84)

RSSQSLVYSDGNTYLN, (SEQ ID NO: 93)

RSSQSLLHSNGYNYLD, (SEQ ID NO: 102)

RSSQSLLHSNGNTYLD, (SEQ ID NO: 110)

RASQSVRNNLA, (SEQ ID NO: 120)

GSTTGAVTSGHYPS, (SEQ ID NO: 138)

RASQSVSSSYLA, (SEQ ID NO: 161)

RSSQSLQHSNGYQYLD, (SEQ ID NO: 170)

TGRSANIGGFDVQ, (SEQ ID NO: 186)

ALTSGSVSTSYYPS, (SEQ ID NO: 194)

TSSQSLVYSDGNTYLN, (SEQ ID NO: 211)

RSSQSLLRSDGYNFVD, (SEQ ID NO: 217)

RASQGISSWLA, (SEQ ID NO: 226)

RASRSVGKYLA, (SEQ ID NO: 247)

GLSSGSVSTTYYPS, (SEQ ID NO: 255)

TLRSGINVGTYRIY, (SEQ ID NO: 261)

RASQSVSSYLA, (SEQ ID NO: 270)

GLTSGAVSSSYYPS, or (SEQ ID NO: 279)

TGNNNNVGFAGAA; (SEQ ID NO: 287)

LC-CDR2: one of

LGSNRAS, (SEQ ID NO: 75)

KVSNRDS, (SEQ ID NO: 94)

-continued (SEQ ID NO: 111)
SGSNRAS;

(SEQ ID NO: 121)
YASTRAT, (SEQ ID NO: 139)
STSNKHS, (SEQ ID NO: 146)
LGSHRAS, (SEQ ID NO: 155)
LGSNRAP, (SEQ ID NO: 162)
GASSRAT, (SEQ ID NO: 171)
LGSFRAS, (SEQ ID NO: 187)
DNSNRPS, (SEQ ID NO: 195)
STNLRSS, (SEQ ID NO: 204)
KVSDRDS, (SEQ ID NO: 212)
KVSKRDS, (SEQ ID NO: 218)
LGSDRAS, (SEQ ID NO: 227)
AASSLQS, (SEQ ID NO: 262)
YKSDSDKQQGS, (SEQ ID NO: 248)
DASTRAS, (SEQ ID NO: 33)
STNTRSS, (SEQ ID NO: 271)
DASNRAT, (SEQ ID NO: 280)
NTDIRFS,
or (SEQ ID NO: 288)
RNNDRPS;

LC-CDR3: one of (SEQ ID NO: 76)
MQGLQTPYT, (SEQ ID NO: 85)
MLGTHWPPMYI, (SEQ ID NO: 95)
MQGTHWPLT, (SEQ ID NO: 103)
MQALQTPWT, (SEQ ID NO: 112)
MQGTHWPPT, (SEQ ID NO: 122)
QHYGSSRT, (SEQ ID NO: 130)
MAGLQTPRLT, (SEQ ID NO: 140)

-continued

LLYYGGARV, (SEQ ID NO: 147)
MQALQTPLT, (SEQ ID NO: 163)
QQYGSSPRT, (SEQ ID NO: 172)
MHALSTPPWT, (SEQ ID NO: 180)
MQGTHWPGT, (SEQ ID NO: 188)
GTWDSYLNIWV, (SEQ ID NO: 196)
ELYMGSGISV, (SEQ ID NO: 205)
MQGTHWPQT, (SEQ ID NO: 219)
MQALQTPRT, (SEQ ID NO: 228)
QQANSFPPT, (SEQ ID NO: 233)
QQYGSSSA, (SEQ ID NO: 263)
MIWHSSAWV, (SEQ ID NO: 249)
QHYGTSPPFI, (SEQ ID NO: 256)
VLYMGNGISV, (SEQ ID NO: 272)
QQRSNWPLT, (SEQ ID NO: 23)
VLYMGSGISV,
or (SEQ ID NO: 289)
SAWDSSLKVQV.

In some embodiments an isolated heavy chain variable region polypeptide is provided comprising the following CDRs:

HC-CDR1: one of (SEQ ID NO: 77)
SYGMH, (SEQ ID NO: 86)
SAAAAWN, (SEQ ID NO: 96)
SYAMH, (SEQ ID NO: 113)
SFAMN, (SEQ ID NO: 123)
SYGIS, (SEQ ID NO: 131)
SYAMS, (SEQ ID NO: 148)
SYAIS, (SEQ ID NO: 173)
TYTMH, -continued (SEQ ID NO: 30)
GYYWS, (SEQ ID NO: 197)
SYWIG, (SEQ ID NO: 234)
NYGMH, (SEQ ID NO: 241)
SYAIH, (SEQ ID NO: 24)
SSSYYWG,
or (SEQ ID NO: 281)
DYYIH;

one of (SEQ ID NO: 78)
VISYDGSNKYYADSVKG, (SEQ ID NO: 87)
RTYYRSKWYSEYAVSVKS, (SEQ ID NO: 104)
WINAGNGNTKYSQKFQG, (SEQ ID NO: 114)
TIGGSGDSTFYADPVKG, (SEQ ID NO: 124)
WISAYNGNTNYAQKLQG, (SEQ ID NO: 132)
AISGSGGSTYYADSVKG, (SEQ ID NO: 149)
GIIPIFGTANYAQKFQG, (SEQ ID NO: 164)
GINWNGGSTGYADSVKG, (SEQ ID NO: 174)
WITPGNGNTHYSQNFQG, (SEQ ID NO: 31)
EINHSGSTNYNPSLKS, (SEQ ID NO: 198)
IIYPGDSDTRYSPSFQG, (SEQ ID NO: 206)
AISSNGGSTYYADSVKG, (SEQ ID NO: 220)
VISYDESNKYYADSVKG, (SEQ ID NO: 235)
FISYDGTNKYYADSVKG, (SEQ ID NO: 25)
SIYYSGSTYYNPSLKS, (SEQ ID NO: 264)
VIWYDGSNKYYADSVKG, (SEQ ID NO: 273)
SISSSSSYIYYADSVKG,
or (SEQ ID NO: 282)
WVSAYNGDTNYAQKFQG;

-continued

HC-CDR3: one of (SEQ ID NO: 79)
DLFAVVGYYYYYGMDV, (SEQ ID NO: 88)
GSIFDV, (SEQ ID NO: 97)
SRGYYGMDV, (SEQ ID NO: 105)
GGYLVGY, (SEQ ID NO: 115)
AYGSGGHYFFAY, (SEQ ID NO: 125)
DWGSSWSDY, (SEQ ID NO: 133)
TYYDFWSGRVGAFDI, (SEQ ID NO: 141)
DRGYYGMDV, (SEQ ID NO: 150)
GRGSGYPDTWFWFDP, (SEQ ID NO: 156)
SYGSGSYRSHAFDI, (SEQ ID NO: 165)
GLVPAASMDV, (SEQ ID NO: 175)
SRVGALDY, (SEQ ID NO: 181)
SRGYSGYDN, (SEQ ID NO: 189)
GLPYYYFDY, (SEQ ID NO: 199)
LGYGVPLPEYFDL, (SEQ ID NO: 221)
EPSGSWSYLYYYYYGMDV, (SEQ ID NO: 236)
HYGDYYYYYGMDV, (SEQ ID NO: 242)
VYGYGLHYYGMDV, (SEQ ID NO: 250)
SYDSSGYYYFDY, (SEQ ID NO: 26)
YAPDSSGYLVAFDI, (SEQ ID NO: 265)
MTTEDY, (SEQ ID NO: 274)
DGSAWSRPY, (SEQ ID NO: 20)
EIASYSGSYYDY,
or (SEQ ID NO: 290)
GADWNSDY.

In some embodiments an antibody, antigen binding fragment or polypeptide of the present invention comprises any 6 of the CDR sequences described herein. In some embodiments an antibody, antigen-binding fragment or polypeptide comprises any 3 light chain ('LC') CDR sequences described herein, and/or any 3 heavy chain ('HC') CDR sequences described herein.

In some embodiments the antibody, antigen binding fragment, or polypeptide further comprises variable region light chain framework sequences between the CDRs according to the formula: LCFR1-CDR1-LCFR2-CDR2-LCFR3-CDR3-LCFR4. The framework sequences may be derived from human consensus framework sequences.

In some embodiments the antibody, antigen binding fragment, or polypeptide further comprises variable region heavy chain framework sequences between the CDRs according to the formula: HCFR1-CDR1-HCFR2-CDR2-HCFR3-CDR3-HCFR4. The framework sequences may be derived from human consensus framework sequences.

In some embodiments, the antibody, antibody binding fragment, or polypeptide, may further comprise a human constant region. For example selected from one of IgG1, IgG2, IgG3 and IgG4.

In some embodiments, the antibody, antibody binding fragment, or polypeptide, may further comprise a murine constant region. For example, selected from one of IgG1, IgG2A, IgG2B and IgG3.

In another aspect of the present invention, an antibody, antigen binding fragment, or polypeptide conjugated to a drug moiety or a detectable moiety is provided. The drug moiety may be an anti-cancer drug moiety.

In another aspect of the present invention a composition is provided. The composition may be, for example, a pharmaceutical composition or medicament. The composition may comprise an antibody, antigen binding fragment, or polypeptide as described herein. The composition may comprise an antibody, antigen binding fragment, or polypeptide as described herein and at least one pharmaceutically-acceptable carrier, excipient, adjuvant or diluent. The composition may comprise an antibody, antigen binding fragment, or polypeptide as described herein and at least one anti-cancer agent, optionally with at least one pharmaceutically-acceptable carrier, excipient, adjuvant or diluent.

In another aspect of the present invention, an in vitro complex is provided comprising an antibody, or antigen binding fragment, or polypeptide as described herein bound to HER2. The in vitro complex may be isolated.

In any aspect of the present invention an antibody, antigen binding fragment, or polypeptide as described herein may induce cell death via cell membrane disruption. In any aspect of the present invention an antibody, antigen binding fragment, or polypeptide as described herein may induce cell death by apoptosis. The apoptotic process may proceed through the caspase 3/7 pathway, and optionally involve PARP cleavage. The antibody, antigen binding fragment, or polypeptide as described herein may induce the activation of caspase 3/7 and trigger PARP cleavage. Cell death caused by cell membrane disruption or apoptosis may be induced by an antibody, antigen binding fragment, or polypeptide as described herein binding to HER2.

In another aspect of the present invention a nucleic acid, optionally isolated, encoding an antibody, antigen binding fragment, or polypeptide as described herein is provided. The nucleic acid may comprise a sequence of one or more of SEQ ID NOs 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 or a coding sequence which is degenerate as a result of the genetic code, or may have a nucleotide sequence having at least 70% identity thereto, optionally one of 75%, 80%, 85%, 86%, 87%, 88%, 89%, 90%, 91%, 92%, 93%, 94%, 95%, 96%, 97%, 98%, 99%, or 100%. The nucleic acid may comprise a sequence of one or more of SEQ ID NOs 70, 71, 80, 81, 89, 90, 98, 99, 106, 107, 116, 117, 126, 127, 134, 135, 142, 143, 151, 152, 157, 158, 166, 167, 176, 177, 182, 183, 190, 191, 200, 201, 207, 208, 213, 214, 222, 223, 229, 230, 237, 238, 243, 244, 251, 252, 257, 258, 266, 267, 275, 276, 283, 284, 291, or 292, or a coding sequence which is degenerate as a result of the genetic code, or may have a nucleotide sequence having at least 70% identity thereto, optionally one of 75%, 80%, 85%, 86%, 87%, 88%, 89%, 90%, 91%, 92%, 93%, 94%, 95%, 96%, 97%, 98%, 99%, or 100%. A coding sequence which is degenerate as a result of the genetic code refers to a coding sequence which encodes an equivalent polypeptide sequence via redundancy of the genetic code. In one aspect of the present invention there is provided a vector comprising a nucleic acid described herein. In another aspect of the present invention, there is provided a cell comprising the vector. For example, the cell may be eukaryotic, or mammalian, e.g. Chinese Hamster Ovary (CHO), human or non-human, or may be a prokaryotic cell, e.g. *E. coli*.

In one aspect of the present invention a method for making an antibody, or antigen binding fragment or polypeptide as described herein is provided, the method comprising culturing a cell as described herein under conditions suitable for the expression of an antibody, or antigen binding fragment or polypeptide from a nucleic acid or vector described herein.

In another aspect of the present invention an antibody, antigen binding fragment, polypeptide, conjugate, nucleic acid, vector, cell or composition as described herein is provided for use in therapy, or in a method of medical treatment. An antibody, antigen binding fragment, polypeptide, conjugate, nucleic acid, vector, cell or composition as described herein may be used in a method of medical treatment or prophylaxis.

In another aspect of the present invention an antibody, antigen binding fragment, polypeptide, conjugate, nucleic acid, vector, cell or composition as described herein is provided for use in the treatment of cancer, e.g. is provided for use in a method of treating or preventing cancer. In some embodiments the cancer is a HER2-positive (HER2+) cancer. In some embodiments the cancer comprises a HER2-positive tumour cell. In some embodiments the cancer comprises a HER2-positive tumour. In some embodiments the treatment comprises administering the antibody, antigen binding fragment, polypeptide or composition in combination with a therapeutic agent. In some embodiments the therapeutic agent is an anti-cancer agent. In some embodiments the therapeutic agent is an anti-HER2 antibody. In some embodiments the therapeutic agent may be trastuzumab or pertuzumab.

In another aspect of the present invention, the use of an antibody, antigen binding fragment, polypeptide or composition as described herein in the manufacture of a medicament for use in the treatment of cancer is provided. In some embodiments the cancer is a HER2-positive (HER2+) cancer. In some embodiments the cancer comprises a HER2-positive tumour cell. In some embodiments the cancer comprises a HER2-positive tumour.

In another aspect of the present invention a method of treating cancer is provided, the method comprising administering an antibody, antigen binding fragment, polypeptide or composition as described herein to a patient suffering from cancer. In some embodiments the cancer is a HER2-positive (HER2+) cancer. In some embodiments the cancer comprises a HER2-positive tumour cell. In some embodiments the cancer comprises a HER2-positive tumour. In some embodiments the method comprises administering the antibody, antigen binding fragment, polypeptide or composition in combination with a therapeutic agent. In some embodiments the therapeutic agent is an anti-cancer agent. In some embodiments the therapeutic agent is an agent which targets HER2. In some embodiments the therapeutic agent is an anti-HER2 antibody. In some embodiments the therapeutic agent may be trastuzumab or pertuzumab.

In another aspect of the present invention a method of inhibiting growth of a tumour cell is provided, comprising administering to the cell an antibody, antigen binding fragment, polypeptide, or composition as described herein. The method may be in vitro or in vivo. In some embodiments a method of inhibiting growth of a tumour cell in a subject is provided, the method comprising administering to the subject a therapeutically effective amount of an antibody, antigen binding fragment, polypeptide, or composition as described herein. Also provided is an antibody, antigen binding fragment, polypeptide, or composition as described herein for use in a method of inhibiting growth of a tumour cell in a subject. In some embodiments the method of inhibiting growth of a tumour cell comprises administering the antibody, antigen binding fragment, polypeptide or composition in combination with a therapeutic agent as described herein.

Also provided is a method of killing a tumour cell, the method comprising administering to the cell an antibody, antigen binding fragment, polypeptide, or composition as described herein. The method may be performed in vitro or in vivo. In some embodiments a method of killing a tumour cell in a subject is provided, the method comprising administering to the subject a therapeutically effective amount of an antibody, antigen binding fragment, polypeptide, or composition as described herein. In some embodiments the method of killing a tumour cell comprises administering the antibody, antigen binding fragment, polypeptide or composition in combination with a therapeutic agent as described herein. Killing of a tumour cell may, for example, be as a result of membrane disruption, cell lysis, induction of apoptosis, antibody dependent cell-mediated cytotoxicity (ADCC), complement dependent cytotoxicity (CDC), or through the action of a drug conjugated to the antibody, antigen binding fragment or polypeptide. Also provided is an antibody, antigen binding fragment, polypeptide, or composition as described herein for use in a method of killing a tumour cell, e.g. in a subject, as described herein.

In another aspect of the present invention a method is provided comprising contacting a sample containing, or suspected to contain, HER2 with an antibody, antigen binding fragment, or polypeptide as described herein and detecting the formation of a complex of antibody, antigen binding fragment, or polypeptide, and HER2.

In another aspect of the present invention a method of diagnosing a disease or condition in a subject is provided, the method comprising contacting, in vitro, a sample from the subject with an antibody, antigen binding fragment, or polypeptide as described herein and detecting the formation of a complex of antibody, antigen binding fragment, or polypeptide, and HER2.

In another aspect of the present invention a method of selecting or stratifying a subject for treatment with HER2 targeted agents is provided, the method comprising contacting, in vitro, a sample from the subject with an antibody, antigen binding fragment, or polypeptide as described herein and detecting the formation of a complex of antibody, or antigen binding fragment, and HER2.

In a further aspect of the present invention a use of an antibody, antigen binding fragment, or polypeptide as described herein for the detection of HER2 in vitro is provided. In another aspect of the present invention a use of an antibody, antigen binding fragment, or polypeptide as described herein as an in vitro diagnostic agent is provided.

In methods of the present invention the antibody, antigen binding fragment or polypeptide may be provided as a composition as described herein.

The present invention also provides a chimeric antigen receptor (CAR) comprising an antibody, antigen binding fragment or polypeptide according to the present invention.

The present invention also provides an in vitro complex, optionally isolated, comprising a CAR according to the present invention bound to HER2.

The present invention also provides a nucleic acid, optionally isolated, encoding a CAR according to the present invention.

The present invention also provides an expression vector comprising a nucleic acid according to the present invention.

The present invention also provides a cell comprising a CAR, a nucleic acid, or an expression vector according to the present invention.

The present invention also provides a composition comprising a CAR, a nucleic acid, an expression vector or a cell according to the present invention.

The present invention also provides a CAR, a nucleic acid, an expression vector, a cell or a composition according to the present invention for use in a method of medical treatment or prophylaxis. The present invention also provides a CAR, a nucleic acid, an expression vector, a cell or a composition according to the present invention for use in a method of treating or preventing cancer.

In any aspect or embodiment the antibody may be clone P1A3, P1C5, P1E4, or P1F1 as described herein. In any aspect or embodiment the antibody may be clone PFA4, PFB4, PFB5, PFC3, PFD4, PFE1, PFF5, or PFG3 as described herein. In any aspect or embodiment the antibody may be clone PFA1, PFA2, PFA5, PFB1, PFB2, PFB3, PFC2, PFC4, PFD1, PFD2, PFD3, PFE2, PFE5, PFF2, PFF3, PFF4, PFG1, PFG2, PFG4, or PFG5 as described herein.

DESCRIPTION

Antibodies and Antigen-Binding Molecules

The present invention provides antibodies and antigen-binding molecules capable of binding to HER2.

Antibodies according to the present invention preferably bind to HER2 (the antigen), preferably human or murine HER2, optionally with a $K_D$ in the range 4 to 23 nM.

Antibodies according to the present invention may be provided in isolated form. The antibodies may be provided in substantially purified form.

Antibodies according to the present invention may exhibit least one of the following properties:

a) Binds to human HER2 with a $K_D$ of 1 μM or less, preferably one of ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM ≤3 nM, ≤2 nM, ≤1 nM, ≤500 pM (e.g. as determined by SPR);
b) Binds to HER2-overexpressing or HER2-expressing cells, optionally does not bind to HER2-negative cells;
c) Binds to an epitope of HER2, optionally human HER2, which is different to the epitope of HER2 to which trastuzumab (Herceptin®) binds;

d) Induces cell death of HER2-expressing cells, optionally by disruption of cell membranes;
e) Induces cell death of HER2-expressing cells by apoptosis, optionally via caspase 3/7 pathway activation and cleaved PARP activation; Induces cell death of HER2-expressing cells within 40 minutes of application;
g) Inhibits tumour growth, optionally in vivo;
h) Shows a synergistic effect on inhibition of tumour growth, optionally in vivo, optionally when used in combination with trastuzumab or pertuzumab.

By "antibody" we include a fragment or derivative thereof, or a synthetic antibody or synthetic antibody fragment. Fragments and derivatives thereof may be referred to as "antigen-binding molecules" or "antigen-binding fragments".

An "antibody" or "antigen-binding molecule" refers to a molecule which is capable of binding to a target antigen, and encompasses monoclonal antibodies, polyclonal antibodies, monospecific and multispecific antibodies (e.g., bispecific antibodies), and antibody fragments (e.g. Fv, scFv, Fab, scFab, F(ab')2, Fab2, diabodies, triabodies, scFv-Fc, minibodies, single domain antibodies (e.g. VhH), etc.), as long as they display binding to the relevant target molecule(s). The antibody/antigen-binding molecule of the present invention comprises a moiety capable of binding to a target antigen(s). In some embodiments, the moiety capable of binding to a target antigen comprises an antibody heavy chain variable region (VH) and an antibody light chain variable region (VL) of an antibody capable of specific binding to the target antigen. In some embodiments, the moiety capable of binding to a target antigen comprises or consists of an aptamer capable of binding to the target antigen, e.g. a nucleic acid aptamer (reviewed, for example, in Zhou and Rossi Nat Rev Drug Discov. 2017 16(3):181-202). In some embodiments, the moiety capable of binding to a target antigen comprises or consists of a antigen-binding peptide/polypeptide, e.g. a peptide aptamer, thioredoxin, monobody, anticalin, Kunitz domain, avimer, knottin, fynomer, atrimer, DARPin, affibody, nanobody (i.e. a single-domain antibody (sdAb)) affilin, armadillo repeat protein (ArmRP), OBody or fibronectin—reviewed e.g. in Reverdatto et al., Curr Top Med Chem. 2015; 15(12): 1082-1101, which is hereby incorporated by reference in its entirety (see also e.g. Boersma et al., J Biol Chem (2011) 286:41273-85 and Emanuel et al., Mabs (2011) 3:38-48).

In view of today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimeric antibodies are discussed by Neuberger et al (1988, 8th International Biotechnology Symposium Part 2, 792-799).

Monoclonal antibodies (mAbs) are useful in the methods of the invention and are a homogenous population of antibodies specifically targeting a single epitope on an antigen.

Polyclonal antibodies are useful in the methods of the invention. Monospecific polyclonal antibodies are preferred. Suitable polyclonal antibodies can be prepared using methods well known in the art.

Antigen binding fragments of antibodies such as Fab and $Fab_2$ fragments may also be used and/or provided, as can genetically engineered antibodies and antibody fragments. The variable heavy (VH) and variable light (VL) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) Proc. Natl. Acad. Sd. USA 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al (1988) Science 242, 423; Huston et al (1988) Proc. Natl. Acad. Sd. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

By "ScFv molecules" we mean molecules wherein the $V_H$ and $V_L$ partner domains are covalently linked, e.g. by a flexible oligopeptide.

Fab, Fv, ScFv and dAb antibody fragments can all be expressed in and secreted from *E. coli*, thus allowing the facile production of large amounts of the said fragments. Synthetic antibodies which bind to HER2 may also be made using phage display technology as is well known in the art.

Antibodies generally comprise six complementarity-determining regions CDRs; three in the heavy chain variable ($V_H$) region: HC-CDR1, HC-CDR2 and HC-CDR3, and three in the light chain variable ($V_L$) region: LC-CDR1, LC-CDR2, and LC-CDR3. The six CDRs together define the paratope of the antibody, which is the part of the antibody which binds to the target antigen.

The VH region and VL region comprise framework regions (FRs) either side of each CDR, which provide a scaffold for the CDRs. From N-terminus to C-terminus, VH regions comprise the following structure: N term-[HC-FR1]-[HC-CDR1]-[HC-FR2]-[HC-CDR2]-[HC-FR3]-[HC-CDR3]-[HC-FR4]-C term; and VL regions comprise the following structure: N term-[LC-FR1]-[LC-CDR1]-[LC-FR2]-[LC-CDR2]-[LC-FR3]-[LC-CDR3]-[LC-FR4]-C term.

There are several different conventions for defining antibody CDRs and FRs, such as those described in Kabat et al., Sequences of Proteins of Immunological Interest, 5th Ed. Public Health Service, National Institutes of Health, Bethesda, MD (1991), Chothia et al., J. Mol. Biol. 196:901-917 (1987), VBASE2, as described in Retter et al., Nucl. Acids Res. (2005) 33 (suppl 1): D671-0674, and the international IMGT (ImMunoGeneTics) information system (LeFranc et al., Nucleic Acids Res. (2015) 43 (Database issue):D413-22), which uses the IMGT V-DOMAIN numbering rules as described in Lefranc et al., Dev. Comp. Immunol. (2003) 27:55-77.

In some embodiments, the antibody/antigen-binding molecule comprises the CDRs of an antigen-binding molecule which is capable of binding to HER2. In some embodiments, the antibody/antigen-binding molecule comprises the FRs of an antigen-binding molecule which is capable of binding to HER2. In some embodiments, the antigen-binding molecule comprises the CDRs and the FRs of an antigen-binding molecule which is capable of binding to HER2. That is, in some embodiments the antigen-binding molecule comprises the VH region and the VL region of an antigen-binding molecule which is capable of binding to HER2.

Antibodies may be produced by a process of affinity maturation in which a modified antibody is generated that has an improvement in the affinity of the antibody for antigen, compared to an unmodified parent antibody. Affinity-matured antibodies may be produced by procedures known in the art, e.g., Marks et al., *Rio/Technology* 10:779-783 (1992); Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):331 0-15 9 (1995); and Hawkins et al, *J. Mol. Biol.* 226:889-896 (1992). The antibodies, antigen binding fragments or polypeptides according to the present invention may undergo affinity maturation.

Antibodies, antigen binding fragments or polypeptides according to the present invention preferably exhibit specific binding to HER2. An antibody, antigen binding fragment or polypeptide that specifically binds to a target molecule preferably binds the target with greater affinity, and/or with greater duration than it binds to other targets.

Binding of an antibody, antigen binding fragment or polypeptide according to the present invention to a given molecule can be measured by techniques well known to the person skilled in the art, including ELISA, Surface Plasmon Resonance (SPR; see e.g. Hearty et al., Methods Mol Biol (2012) 907:411-442), Bio-Layer Interferometry (see e.g. Lad et al., (2015) J Biomol Screen 20(4): 498-507), flow cytometry or by a radioimmunoassay (RIA) enzyme-linked immunosorbent assay. Through such analysis binding to a given target can be measured and quantified. In some embodiments, the binding may be the response detected in a given assay. Binding affinity of an antibody for its target is often described in terms of its dissociation constant ($K_D$).

The extent of binding of an antibody to an unrelated target may be less than about 10% of the binding of the antibody to the target as measured, e.g., by ELISA, SPR, Bio-Layer Interferometry or by RIA.

Alternatively, the binding specificity may be reflected in terms of binding affinity where the anti-HER2 antibody of the present invention binds to HER2 with a $K_D$ that is at least 0.1 order of magnitude (i.e. $0.1\times10^n$, where n is an integer representing the order of magnitude) greater than the $K_D$ of the antibody towards another target molecule. This may optionally be one of at least 0.2, 0.3, 0.4, 0.5, 0.6, 0.7, 0.8, 0.9, 1.0, 1.5, or 2.0.

Antibodies, antigen binding fragments or polypeptides according to the present invention preferably have a dissociation constant ($K_D$) of one of ≤25 nM, ≤20 nM, ≤15 nM, ≤10 nM, ≤5 nM, ≤3 nM, ≤2 nM, ≤1.5 nM, ≤1.4 nM, ≤1.3 nM, ≤1.25 nM, ≤1.24 nM, ≤1.23 nM, ≤1.22 nM, ≤1.21 nM, ≤1.2 nM, ≤1.15 nM, ≤1.1 nM ≤1.05 nM, ≤1 nM, ≤900 pM, ≤800 pM, ≤700 pM, ≤600 pM, or ≤500 pM as determined by analysis according to SPR, Bio-Layer Interferometry or by RIA. The $K_D$ may be in the range about 0.1 to about 3 nM. The $K_D$ may be in the range about 0.1 to about 10 nM. The $K_D$ may be in the range about 0.1 to about 15 nM. The $K_D$ may be in the range about 0.1 to about 25 nM. The $K_D$ may be in the range about 1 to about 100 nM. The $K_D$ may be in the range about 50 to about 500 nM.

The antibodies, antigen-binding fragments or polypeptides according to the present invention may exhibit high binding affinity for HER2. In some embodiments the antibodies, antigen-binding fragments or polypeptides according to the present invention have a dissociation constant ($K_D$) of 4 to 25 nM. The antibodies, antigen-binding fragments or polypeptides according to the present invention may exhibit intermediate or low binding affinity for HER2. In some embodiments the antibodies, antigen-binding fragments or polypeptides according to the present invention have a dissociation constant ($K_D$) of 12 to 350 nM. In some embodiments the antibodies, antigen-binding fragments or polypeptides according to the present invention have a dissociation constant ($K_D$) of 14 to 310 nM. In some embodiments the antibodies, antigen-binding fragments or polypeptides according to the present invention have a dissociation constant ($K_D$) of 25 to 310 nM. In some embodiments the antibodies, antigen-binding fragments or polypeptides according to the present invention have a dissociation constant ($K_D$) of 150 to 310 nM.

Antibodies, antigen binding fragments, or polypeptides of the present invention preferably bind to HER2-overexpressing or HER2-expressing cells. Antibodies, antigen binding fragments, or polypeptides may preferably bind to HER2-overexpressing cells. Preferably, antibodies, antigen binding fragments, or polypeptides as described herein do not bind to HER2-negative cells, i.e. cells that do not express HER2.

Antibodies, antigen binding fragments, or polypeptides of the present invention preferably bind to a HER2 epitope different to that bound by trastuzumab (Herceptin®). Trastuzumab is reported to bind at the C-terminal portion of subdomain IV of the HER2 extracellular domain (Cho et al., (2003) Nature 421: 756-760). Epitope binding assays can be performed by methods known in the art, such as by SPR as described herein (see e.g. Hearty et al., Methods Mol Biol (2012) 907:411-442). Briefly, the antibody of interest is immobilised on the SPR microchip, a flow of recombinant HER-2 is applied to bind to the immobilised antibody, then the other antibodies of interest are flown and their binding measured. Dendrogram traces can identify whether antibodies of interest share a common epitopes with trastuzumab (similar binding profile), or bind to different epitopes (different binding profile), as described herein. In some embodiments antibodies, antigen binding fragments, or polypeptides of the present invention preferably bind to a HER2 epitope different to that bound by pertuzumab (Perjeta).

Antibodies, antigen binding fragments, or polypeptides of the present invention preferably induce cell death of HER2-expressing cells. In some embodiments the antibodies, antigen binding fragments, or polypeptides of the present invention induce cell death by disrupting the cell membrane. Cell death can be measured using methods well known in the art and described herein, such as by staining with propidium iodide. Insertion of propidium iodide into a cell indicates cell lysis.

In some embodiments the antibodies, antigen binding fragments, or polypeptides of the present invention induce cell death of HER2-expressing cells by apoptosis. Apoptosis can be measured using methods well known in the art and described herein, such as by staining with Annexin-V and propidium iodide. Cells stained with Annexin-V are apoptotic.

The caspase 3/7 pathway is involved in the apoptotic process. After activation caspase 3/7 activates cleaved PARP in the nucleus which in its turn can trigger the release of pro-apoptotic factors by mitochondria and can block the processes of DNA repair. In some embodiments the antibodies, antigen binding fragments, or polypeptides of the present invention induce cell death of HER2-expressing cells by apoptosis via caspase 3/7 pathway activation and cleaved PARP activation. Caspase 3/7 pathway activation and cleaved PARP activation can be measured using methods well known in the art.

In some embodiments the antibodies, antigen binding fragments, or polypeptides of the present invention induce cell death of HER2-expressing cells within 40 minutes of application. Induced cell death may be measured by propidium iodide uptake.

Antibodies, antigen binding fragments, or polypeptides of the present invention preferably inhibit tumour growth. In some embodiments the inhibition of tumour growth is in vivo. Tumour growth may be measured by methods well known in the art and as described herein, for example using a cell proliferation assay. In some embodiments the antibodies, antigen binding fragments, or polypeptides of the present invention show a synergistic effect on inhibition of tumour growth. In some embodiments the antibodies, antigen binding fragments, or polypeptides of the present invention show a synergistic effect on inhibition of tumour growth when used in combination with trastuzumab and/or pertuzumab. In some embodiments the antibodies, antigen binding fragments, or polypeptides of the present invention are capable of inducing death of HER2-expressing cells at a similar efficiency to that induced by trastuzumab and/or pertuzumab.

In some embodiments the antibodies, antigen binding fragments, or polypeptides of the present invention are capable of inducing death of HER2-expressing cells at an increased efficiency to that induced by trastuzumab and/or pertuzumab. In some embodiments the antibodies, antigen binding fragments, or polypeptides of the present invention are capable of inducing antibody dependent cell-mediated cytotoxicity (ADCC) or complement dependent cytotoxicity (CDC), measured for example by LDH release by Promega Cytotox 96 non-radioactive cytotoxicity assay kit.

In some embodiments the antibodies, antigen binding fragments, or polypeptides of the present invention are capable of reducing tumour size e.g. compared to the size of a tumour not treated with an antibody, antigen binding fragment, or polypeptide of the present invention.

In some embodiments the antibodies, antigen binding fragments, or polypeptides of the present invention are capable of conferring long-term protection against cancer, cancer cells, tumours and/or tumour cells after administration of the antibodies, antigen binding fragments, or polypeptides ends. The protection conferred may be longer than other HER2 therapies known in the art, e.g. trastuzumab or pertuzumab. The present invention provides antigen-binding polypeptides. In aspects of the present invention the antigen-binding polypeptides are capable of binding to HER2. The polypeptides may be provided in isolated or substantially purified form.

An "antigen-binding polypeptide" refers to a polypeptide which is capable of binding to a target molecule, and encompasses monoclonal antibodies, polyclonal antibodies, monospecific and multispecific antibodies (e.g., bispecific antibodies), and antibody fragments, as long as they display binding to the relevant target molecule(s). An antigen-binding polypeptide as used herein also refers to a non-covalent or covalent complex of more than one polypeptide (e.g. 2, 3, 4, 6, or 8 polypeptides), e.g. a bispecific antigen-binding polypeptide comprising two heavy chain polypeptides and two light chain polypeptides.

The antigen-binding polypeptides described herein preferably display specific binding to the relevant target (e.g. HER2). As used herein, "specific binding" refers to binding which is selective for the antigen, and which can be discriminated from non-specific binding to non-target antigen. An antigen-binding polypeptide that specifically binds to a target molecule preferably binds the target with greater affinity, and/or with greater duration than it binds to other, non-target molecules.

In some embodiments, the antigen-binding polypeptide binds to the same or an overlapping epitope of the target molecule as a reference antigen-binding polypeptide which is capable of binding to the target molecule (i.e. HER2). In some embodiments, the antigen-binding polypeptide displays competitive binding with a reference antigen-binding polypeptide which is capable of binding to the target molecule. Whether a given antigen-binding polypeptide displays such competitive binding can be determined by various methods known to the skilled person, including competition ELISA.

In some embodiments, the antigen-binding polypeptide comprises the complementarity-determining regions (CDRs) of an antigen-binding polypeptide which is capable of binding to the target molecule (i.e. HER2). Antibodies generally comprise six CDRs; three in the light chain variable region (VL): LC-CDR1, LC-CDR2, LC-CDR3, and three in the heavy chain variable region (VH): HC-CDR1, HC-CDR2 and HC-CDR3. The six CDRs together define the paratope of the antibody, which is the part of the antibody which binds to the target molecule. There are several different conventions for defining antibody CDRs, such as those described in Kabat et al., Sequences of Proteins of Immunological Interest, 5th Ed. Public Health Service, National Institutes of Health, Bethesda, MD (1991), Chothia et al., J. Mol. Biol. 196:901-917 (1987), and VBASE2, as described in Retter et al., Nucl. Acids Res. (2005) 33 (suppl 1): D671-0674. Unless otherwise specified, CDRs of the antigen-binding polypeptides described herein are defined according to Kabat et al., Sequences of Proteins of Immunological Interest, 5th Ed. Public Health Service, National Institutes of Health, Bethesda, MD (1991).

In the present specification where a polypeptide comprises more than one domain or region, it will be appreciated that the plural domains/regions are preferably present in the same polypeptide chain. That is, the polypeptide comprises more than one domain or region is a fusion polypeptide comprising the domains/regions.

The antigen-binding polypeptide may be designed and prepared using the sequences of monoclonal antibodies (mAbs) capable of binding to HER2. Antigen-binding regions of antibodies, such as single chain variable fragment (scFv), Fab and Fab2 fragments may also be used/provided. An 'antigen-binding region' is any fragment of an antibody which is capable of binding to the target for which the given antibody is specific.

In some embodiments, the antigen-binding polypeptide of the present invention is a HER2-binding polypeptide. In some embodiments, the antigen-binding polypeptide comprises or consists of a HER2-binding polypeptide. In some embodiments the antigen-binding polypeptide comprises a heavy chain variable (VH) region comprising HC-CDR1, HC-CDR2 and HC-CDR3 of a HER2-binding antibody clone described herein, or a variant thereof in which one or two or three amino acids in one or more of HC-CDR1, HC-CDR2, HC-CDR3 are substituted with another amino acid. In some embodiments the antigen-binding polypeptide comprises a light chain variable (VL) region comprising LC-CDR1, LC-CDR2 and LC-CDR3 of a HER2-binding antibody clone described herein, or a variant thereof in which one or two or three amino acids in one or more of LC-CDR1, LC-CDR2, LC-CDR3 are substituted with another amino acid. In some embodiments the antigen-binding polypeptide comprises a VH region comprising HC-CDR1, HC-CDR2 and HC-CDR3 and a VL region comprising LC-CDR1, LC-CDR2 and LC-CDR3 of a HER2-binding antibody clone described herein, or a variant thereof in which one or two or three amino acids in one or more of HC-CDR1, HC-CDR2, HC-CDR3, LC-CDR1, LC-CDR2 or LC-CDR3 are substituted with another amino acid.

In some embodiments the antigen-binding polypeptide comprises a VH region which comprises or consists of an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to VH region of a HER2-binding antibody clone described herein. In some embodiments the antigen-binding polypeptide comprises a VL region which comprises or consists of an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to VL region of a HER2-binding antibody clone described herein. In some embodiments the antigen-binding polypeptide comprises a VH region which comprises or consists of an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to VH region of a HER2-binding antibody clone described herein and a VL region which comprises or consists of an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to VL region of a HER2-binding antibody clone described herein.

In some embodiments, the antigen-binding polypeptide may comprise a variant of a reference VL/VH region, e.g. comprising 1, 2, 3, 4, 5, 6, 7, 8, 9 or 10 substitutions with respect to the amino acid sequence of the reference VL/VH region(s). In some embodiments the substitution(s) are not in the CDRs. In some embodiments the substitution(s) are in the framework region(s)—i.e. the amino acid sequences of the VL/VH region(s) other than the CDRs.

In some embodiments, the substitutions are conservative substitutions, for example according to the following Table. In some embodiments, amino acids in the same block in the middle column are substituted. In some embodiments, amino acids in the same line in the rightmost column are substituted:

| | | |
|---|---|---|
| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

In some embodiments the HER2-binding antigen-binding polypeptide according to the invention comprises or consists of an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of SEQ ID NOs:1 to 4. In some embodiments the HER2-binding antigen-binding polypeptide according to the invention comprises or consists of an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of SEQ ID NOs:5 to 8.

In some embodiments the HER2-binding antigen-binding polypeptide according to the invention comprises or consists of an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of SEQ ID NOs: 72, 82, 91, 100, 108, 118, 128, 136, 144, 153, 159, 168, 178, 184, 192, 202, 209, 215, 224, 231, 239, 245, 253, 259, 268, 277, 285, or 293. In some embodiments the HER2-binding antigen-binding polypeptide according to the invention comprises or consists of an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of SEQ ID NOs: 73, 83, 92, 101, 109, 119, 129, 137, 145, 154, 160, 169, 179, 135, 193, 203, 210, 216, 225, 232, 240, 246, 254, 260, 269, 278, 286, or 294.

In some embodiments the HER2-binding antigen-binding polypeptide according to the present invention lacks HC-CDR1, HC-CDR2, HC-CDR3, LC-CDR1, LC-CDR2, and LC-CDR3 of one or more of the following clones: P1A3, P1C5, P1E4, and P1F1, In some embodiments the HER2-binding antigen-binding polypeptide according to the present invention lacks the VL domain sequence and/or the VH domain sequence of one or more of said clones.

The VL and VH region of an antigen-binding region of an antibody together constitute the Fv region. In some embodiments, the antigen-binding polypeptide according to the present invention comprises, or consists of, an Fv region which binds to HER2.

In some embodiments, the polypeptide additionally comprises one or more antibody heavy chain constant regions (CH). In some embodiments, the polypeptide additionally comprises one or more antibody light chain constant regions (CL). In some embodiments, the polypeptide comprises a CH1, CH2 region and/or a CH3 region of an immunoglobulin (Ig).

The VL and light chain constant (CL) region, and the VH region and heavy chain constant 1 (CH1) region of an antigen-binding region of an antibody together constitute the Fab region. In some embodiments, the antigen-binding polypeptide of the antigen-binding polypeptide described herein comprises, or consists of, a Fab region which binds to HER2.

In some embodiments the polypeptide comprises one or more regions of an immunoglobulin heavy chain constant sequence. In some embodiments the polypeptide comprises a CH1 region as described herein. In some embodiments the polypeptide comprises a CH1-CH2 hinge region as described herein. In some embodiments the polypeptide comprises a CH2 region as described herein. In some embodiments the polypeptide comprises a CH3 region as described herein.

In some embodiments the polypeptide lacks one or more regions of an immunoglobulin heavy chain constant sequence. In some embodiments the polypeptide lacks a CH2 region. In some embodiments the polypeptide lacks a CH3 region. In some embodiments the polypeptide lacks a CH2 region and also lacks a CH3 region.

In some embodiments, the polypeptide according to the present invention comprises a structure from N- to C-terminus according to one of the following:

(i) VH
(ii) VL
(iii) VH-CH1
(iv) VL-CL
(v) VL-CH1
(vi) VH-CL
(vii) VH-CH1-CH2-CH3
(viii) VL-CL-CH2-CH3
(ix) VL-CH1-CH2-CH3
(x) VH-CL-CH2-CH3

Also provided by the present invention are antibodies and antigen-binding molecules composed of the polypeptides of the present invention. In some embodiments, the antibody/antigen-binding molecule of the present invention comprises one of the following combinations of polypeptides:

(A) VH+VL
(B) VH-CH1+VL-CL
(C) VL-CH1+VH-CL
(D) VH-CH1-CH2-CH3+VL-CL
(E) VH-CL-CH2-CH3+VL-CH1
(F) VL-CH1-CH2-CH3+VH-CL
(G) VL-CL-CH2-CH3+VH-CH1
(H) VH-CH1-CH2-CH3+VL-CL-CH2-CH3
(I) VH-CL-CH2-CH3+VL-CH1-CH2-CH3

In some embodiments the antigen-binding molecule comprises more than one of a polypeptide of the combinations shown in (A) to (I) above. By way of example, with reference to (D) above, in some embodiments the antigen-binding molecule comprises two polypeptides comprising the structure VH-CH1-CH2-CH3, and two polypeptides comprising the structure VL-CL.

In some embodiments, the antigen-binding polypeptide described herein comprises, or consists of, a whole antibody which binds to HER2. As used herein, "whole antibody" refers to an antibody having a structure which is substantially similar to the structure of an immunoglobulin (Ig). Different kinds of immunoglobulins and their structures are described e.g. in Schroeder and Cavacini J Allergy Clin Immunol. (2010) 125(202): S41-S52, which is hereby incorporated by reference in its entirety.

Immunoglobulins of type G (i.e. IgG) are ~150 kDa glycoproteins comprising two heavy chains and two light chains. From N- to C-terminus, the heavy chains comprise a VH followed by a heavy chain constant region comprising three constant domains (CH1, CH2, and CH3), and similarly the light chain comprise a VL followed by a CL. Depending on the heavy chain, immunoglobulins may be classed as IgG (e.g. IgG1, IgG2, IgG3, IgG4), IgA (e.g. IgA1, IgA2), IgD, IgE, or IgM. The light chain may be kappa (κ) or lambda (λ).

In some embodiments, the antigen-binding polypeptide described herein comprises, or consists of, an IgG (e.g. IgG1, IgG2, IgG3, IgG4), IgA (e.g. IgA1, IgA2), IgD, IgE, or IgM which binds to HER2.

The antigen binding polypeptides according to the present invention may be provided in any suitable format.

In some aspects, the antibody is clone P1A3, or a variant of P1A3. P1A3 comprises the following CDR sequences:

Light Chain:

```
LC-CDR1:
                                (SEQ ID NO: 15)
GLSSGSVSTGHYAS

LC-CDR2:
                                (SEQ ID NO: 16)
NTNTRSS

LC-CDR3:
                                (SEQ ID NO: 17)
VLYVGDGIWV
```

Heavy Chain:

```
HC-CDR1:
                                (SEQ ID NO: 18)
SYYIH

HC-CDR2:
                                (SEQ ID NO: 19)
IINPGNGDTNYAQRFQG

HC-CDR3:
                                (SEQ ID NO: 20)
EIASYSGSYYDY
```

Unless otherwise specified, CDRs of the antigen-binding polypeptides described herein are defined according to Kabat et al., Sequences of Proteins of Immunological Interest, 5th Ed. Public Health Service, National Institutes of Health, Bethesda, MD (1991)

In some aspects, the antibody is clone P1C5, or a variant of P1C5. P1C5 comprises the following CDR sequences:

Light Chain:

```
LC-CDR1:
                                (SEQ ID NO: 21)
GLSSGSVSTGYYPS

LC-CDR2:
                                (SEQ ID NO: 22)
STNSRSS

LC-CDR3:
                                (SEQ ID NO: 23)
VLYMGSGISV
```

Heavy Chain:

```
HC-CDR1:
                                (SEQ ID NO: 24)
SSSYYWG

HC-CDR2:
                                (SEQ ID NO: 25)
SIYYSGSTYYNPSLKS

HC-CDR3:
                                (SEQ ID NO: 26)
YAPDSSGYLVAFDI.
```

In some aspects, the antibody is clone P1E4, or a variant of P1E4. F1E4 comprises the following CDR sequences:
Light Chain:

```
LC-CDR1:
                         (SEQ ID NO: 27)
GLSSGSVSTSYYPS

LC-CDR2:
                         (SEQ ID NO: 28)
TTNIRSS

LC-CDR3:
                         (SEQ ID NO: 29)
MLYMGSGIWV
```

Heavy Chain:

```
HC-CDR1:
                         (SEQ ID NO: 30)
GYYWS

HC-CDR2:
                         (SEQ ID NO: 31)
EINHSGSTNYNPSLKS

HC-CDR3:
                         (SEQ ID NO: 32)
MGINSGGYLYGMDV.
```

In some aspects, the antibody is clone P1F1, or a variant of P1F1. P1F1 comprises the following CDR sequences:
Light Chain:

```
LC-CDR1:
                         (SEQ ID NO: 27)
GLSSGSVSTSYYPS

LC-CDR2:
                         (SEQ ID NO: 33)
STNTRSS

LC-CDR3:
                         (SEQ ID NO: 34)
VLYMGSGIWV
```

Heavy Chain:

```
HC-CDR1:
                         (SEQ ID NO: 35)
SSNVVWS

HC-CDR2:
                         (SEQ ID NO: 36)
EIYHSGSTNYNPSLKS

HC-CDR3:
                         (SEQ ID NO: 37)
MGANSGGYLYGMDV.
```

Antibodies according to the present invention may comprise the CDRs of P1A3, P1C5, P1E4 or P1F1 or one of SEQ ID NOs 1 and 5; 2 and 6; 3 and 7; or 4 and 8. In an antibody according to the present invention one or two or three or four of the six CDR sequences may vary. A variant may have one or two amino acid substitutions in one or two of the six CDR sequences.

The amino acid sequences of the VL and VH chains of P1A3 (SEQ ID NO:1 and 5), P1C5 (SEQ ID NO:2 and 6), P1E4 (SEQ ID NO:3 and 7) and P1F1 (SEQ ID NO:4 and 8) have been determined as shown in FIGS. 1A-1D (VL) and 2A-2D (VH). The encoding nucleotide sequences are shown in SEQ ID NOs:39 and 43 (P1A3), 40 and 44 (P1C5), 41 and 45 (P1E4), 42 and 46 (P1F1), and in FIGS. 16 and 17.

In some aspects, antibodies according to the present invention may comprise one or more of the amino acid sequences described herein. Antibodies according to the present invention may be encoded by one or more of the nucleotide sequences described herein. In some aspects the antibody is clone A1, A2, A4, A5, B1, B2, B3, B4, B5, 02, 03, 04, 01, D2, D3, D4, E1, E2, E5, F2, F3, F4, F5, G1, G2, G3, G4, or G5, as described herein, or a variant of said clones.

In some aspects and embodiments, an antibody, antigen binding fragment or polypeptide comprises at least one VL region according to one of (1) to (31) below:

(1) (P1A3) a VL region incorporating the following CDRs:
- LC-CDR1 having the amino acid sequence of SEQ ID NO:15
- LC-CDR2 having the amino acid sequence of SEQ ID NO:16
- LC-CDR3 having the amino acid sequence of SEQ ID NO:17,
- or a variant thereof in which one or two or three amino acids in one or more of LC-CDR1, LC-CDR2, or LC-CDR3 are substituted with another amino acid.

(2) (P1C5) a VL region incorporating the following CDRs:
- LC-CDR1 having the amino acid sequence of SEQ ID NO:21
- LC-CDR2 having the amino acid sequence of SEQ ID NO:22
- LC-CDR3 having the amino acid sequence of SEQ ID NO:23,
- or a variant thereof in which one or two or three amino acids in one or more of LC-CDR1, LC-CDR2, or LC-CDR3 are substituted with another amino acid.

(3) (P1E4) a VL region incorporating the following CDRs:
- LC-CDR1 having the amino acid sequence of SEQ ID NO:27
- LC-CDR2 having the amino acid sequence of SEQ ID NO:28
- LC-CDR3 having the amino acid sequence of SEQ ID NO:29,
- or a variant thereof in which one or two or three amino acids in one or more of LC-CDR1, LC-CDR2, or LC-CDR3 are substituted with another amino acid.

(4) (P1F1) a VL region incorporating the following CDRs:
- LC-CDR1 having the amino acid sequence of SEQ ID NO:27
- LC-CDR2 having the amino acid sequence of SEQ ID NO:33
- LC-CDR3 having the amino acid sequence of SEQ ID NO:34,
- or a variant thereof in which one or two or three amino acids in one or more of LC-CDR1, LC-CDR2, or LC-CDR3 are substituted with another amino acid.

(5) (PFA1) a VL region incorporating the following CDRs:
- LC-CDR1 having the amino acid sequence of SEQ ID NO:74
- LC-CDR2 having the amino acid sequence of SEQ ID NO:75
- LC-CDR3 having the amino acid sequence of SEQ ID NO:76,
- or a variant thereof in which one or two or three amino acids in one or more of LC-CDR1, LC-CDR2, or LC-CDR3 are substituted with another amino acid.

(6) (PFA2) a VL region incorporating the following CDRs:
- LC-CDR1 having the amino acid sequence of SEQ ID NO:84
- LC-CDR2 having the amino acid sequence of SEQ ID NO:75

LC-CDR3 having the amino acid sequence of SEQ ID NO:85, or a variant thereof in which one or two or three amino acids in one or more of LC-CDR1, LC-CDR2, or LC-CDR3 are substituted with another amino acid.

(7) (PFA4) a VL region incorporating the following CDRs:

LC-CDR1 having the amino acid sequence of SEQ ID NO:93

LC-CDR2 having the amino acid sequence of SEQ ID NO:94

LC-CDR3 having the amino acid sequence of SEQ ID NO:95, or a variant thereof in which one or two or three amino acids in one or more of LC-CDR1, LC-CDR2, or LC-CDR3 are substituted with another amino acid.

(8) (PFA5) a VL region incorporating the following CDRs:

LC-CDR1 having the amino acid sequence of SEQ ID NO:102

LC-CDR2 having the amino acid sequence of SEQ ID NO:75

LC-CDR3 having the amino acid sequence of SEQ ID NO:103, or a variant thereof in which one or two or three amino acids in one or more of LC-CDR1, LC-CDR2, or LC-CDR3 are substituted with another amino acid.

(9) (PFB1) a VL region incorporating the following CDRs:

LC-CDR1 having the amino acid sequence of SEQ ID NO:110

LC-CDR2 having the amino acid sequence of SEQ ID NO:111

LC-CDR3 having the amino acid sequence of SEQ ID NO:112, or a variant thereof in which one or two or three amino acids in one or more of LC-CDR1, LC-CDR2, or LC-CDR3 are substituted with another amino acid.

(10) (PFB2) a VL region incorporating the following CDRs:

LC-CDR1 having the amino acid sequence of SEQ ID NO:120

LC-CDR2 having the amino acid sequence of SEQ ID NO:121

LC-CDR3 having the amino acid sequence of SEQ ID NO:122, or a variant thereof in which one or two or three amino acids in one or more of LC-CDR1, LC-CDR2, or LC-CDR3 are substituted with another amino acid.

(11) (PFB3) a VL region incorporating the following CDRs:

LC-CDR1 having the amino acid sequence of SEQ ID NO:102

LC-CDR2 having the amino acid sequence of SEQ ID NO:75

LC-CDR3 having the amino acid sequence of SEQ ID NO:130, or a variant thereof in which one or two or three amino acids in one or more of LC-CDR1, LC-CDR2, or LC-CDR3 are substituted with another amino acid.

(12) (PFB4) a VL region incorporating the following CDRs:

LC-CDR1 having the amino acid sequence of SEQ ID NO:138

LC-CDR2 having the amino acid sequence of SEQ ID NO:139

LC-CDR3 having the amino acid sequence of SEQ ID NO:140, or a variant thereof in which one or two or three amino acids in one or more of LC-CDR1, LC-CDR2, or LC-CDR3 are substituted with another amino acid.

(13) (PFB5) a VL region incorporating the following CDRs:

LC-CDR1 having the amino acid sequence of SEQ ID NO:102

LC-CDR2 having the amino acid sequence of SEQ ID NO:146

LC-CDR3 having the amino acid sequence of SEQ ID NO:147, or a variant thereof in which one or two or three amino acids in one or more of LC-CDR1, LC-CDR2, or LC-CDR3 are substituted with another amino acid.

(14) (PFC2; PFG5) a VL region incorporating the following CDRs:

LC-CDR1 having the amino acid sequence of SEQ ID NO:102

LC-CDR2 having the amino acid sequence of SEQ ID NO:155

LC-CDR3 having the amino acid sequence of SEQ ID NO:95, or a variant thereof in which one or two or three amino acids in one or more of LC-CDR1, LC-CDR2, or LC-CDR3 are substituted with another amino acid.

(15) (PFC3) a VL region incorporating the following CDRs:

LC-CDR1 having the amino acid sequence of SEQ ID NO:161

LC-CDR2 having the amino acid sequence of SEQ ID NO:162

LC-CDR3 having the amino acid sequence of SEQ ID NO:163, or a variant thereof in which one or two or three amino acids in one or more of LC-CDR1, LC-CDR2, or LC-CDR3 are substituted with another amino acid.

(16) (PFC4) a VL region incorporating the following CDRs:

LC-CDR1 having the amino acid sequence of SEQ ID NO:170

LC-CDR2 having the amino acid sequence of SEQ ID NO:171

LC-CDR3 having the amino acid sequence of SEQ ID NO:172, or a variant thereof in which one or two or three amino acids in one or more of LC-CDR1, LC-CDR2, or LC-CDR3 are substituted with another amino acid.

(17) (PFD1) a VL region incorporating the following CDRs:

LC-CDR1 having the amino acid sequence of SEQ ID NO:93

LC-CDR2 having the amino acid sequence of SEQ ID NO:94

LC-CDR3 having the amino acid sequence of SEQ ID NO:180, or a variant thereof in which one or two or three amino acids in one or more of LC-CDR1, LC-CDR2, or LC-CDR3 are substituted with another amino acid.

(18) (PFD2) a VL region incorporating the following CDRs:

LC-CDR1 having the amino acid sequence of SEQ ID NO:186

LC-CDR2 having the amino acid sequence of SEQ ID NO:187

LC-CDR3 having the amino acid sequence of SEQ ID NO:188, or a variant thereof in which one or two or three amino acids in one or more of LC-CDR1, LC-CDR2, or LC-CDR3 are substituted with another amino acid.

(19) (PFD3) a VL region incorporating the following CDRs:

LC-CDR1 having the amino acid sequence of SEQ ID NO:194

LC-CDR2 having the amino acid sequence of SEQ ID NO:195

LC-CDR3 having the amino acid sequence of SEQ ID NO:196, or a variant thereof in which one or two or three amino acids in one or more of LC-CDR1, LC-CDR2, or LC-CDR3 are substituted with another amino acid.

(20) (PFD4) a VL region incorporating the following CDRs:
LC-CDR1 having the amino acid sequence of SEQ ID NO:93
LC-CDR2 having the amino acid sequence of SEQ ID NO:204
LC-CDR3 having the amino acid sequence of SEQ ID NO:205,
or a variant thereof in which one or two or three amino acids in one or more of LC-CDR1, LC-CDR2, or LC-CDR3 are substituted with another amino acid.

(21) (PFE1) a VL region incorporating the following CDRs:
LC-CDR1 having the amino acid sequence of SEQ ID NO:211
LC-CDR2 having the amino acid sequence of SEQ ID NO:212
LC-CDR3 having the amino acid sequence of SEQ ID NO:95,
or a variant thereof in which one or two or three amino acids in one or more of LC-CDR1, LC-CDR2, or LC-CDR3 are substituted with another amino acid.

(22) (PFE2) a VL region incorporating the following CDRs:
LC-CDR1 having the amino acid sequence of SEQ ID NO:217
LC-CDR2 having the amino acid sequence of SEQ ID NO:218
LC-CDR3 having the amino acid sequence of SEQ ID NO:219,
or a variant thereof in which one or two or three amino acids in one or more of LC-CDR1, LC-CDR2, or LC-CDR3 are substituted with another amino acid.

(23) (PFE5) a VL region incorporating the following CDRs:
LC-CDR1 having the amino acid sequence of SEQ ID NO:226
LC-CDR2 having the amino acid sequence of SEQ ID NO:227
LC-CDR3 having the amino acid sequence of SEQ ID NO:228,
or a variant thereof in which one or two or three amino acids in one or more of LC-CDR1, LC-CDR2, or LC-CDR3 are substituted with another amino acid.

(24) (PFF2) a VL region incorporating the following CDRs:
LC-CDR1 having the amino acid sequence of SEQ ID NO:161
LC-CDR2 having the amino acid sequence of SEQ ID NO:162
LC-CDR3 having the amino acid sequence of SEQ ID NO:233,
or a variant thereof in which one or two or three amino acids in one or more of LC-CDR1, LC-CDR2, or LC-CDR3 are substituted with another amino acid.

(25) (PFF3) a VL region incorporating the following CDRs:
LC-CDR1 having the amino acid sequence of SEQ ID NO:102
LC-CDR2 having the amino acid sequence of SEQ ID NO:75
LC-CDR3 having the amino acid sequence of SEQ ID NO:180,
or a variant thereof in which one or two or three amino acids in one or more of LC-CDR1, LC-CDR2, or LC-CDR3 are substituted with another amino acid.

(26) (PFF4) a VL region incorporating the following CDRs:
LC-CDR1 having the amino acid sequence of SEQ ID NO:247
LC-CDR2 having the amino acid sequence of SEQ ID NO:248
LC-CDR3 having the amino acid sequence of SEQ ID NO:249,
or a variant thereof in which one or two or three amino acids in one or more of LC-CDR1, LC-CDR2, or LC-CDR3 are substituted with another amino acid.

(27) (PFF5) a VL region incorporating the following CDRs:
LC-CDR1 having the amino acid sequence of SEQ ID NO:255
LC-CDR2 having the amino acid sequence of SEQ ID NO:33
LC-CDR3 having the amino acid sequence of SEQ ID NO:256,
or a variant thereof in which one or two or three amino acids in one or more of LC-CDR1, LC-CDR2, or LC-CDR3 are substituted with another amino acid.

(28) (PFG1) a VL region incorporating the following CDRs:
LC-CDR1 having the amino acid sequence of SEQ ID NO:261
LC-CDR2 having the amino acid sequence of SEQ ID NO:262
LC-CDR3 having the amino acid sequence of SEQ ID NO:263,
or a variant thereof in which one or two or three amino acids in one or more of LC-CDR1, LC-CDR2, or LC-CDR3 are substituted with another amino acid.

(29) (PFG2) a VL region incorporating the following CDRs:
LC-CDR1 having the amino acid sequence of SEQ ID NO:270
LC-CDR2 having the amino acid sequence of SEQ ID NO:271
LC-CDR3 having the amino acid sequence of SEQ ID NO:272,
or a variant thereof in which one or two or three amino acids in one or more of LC-CDR1, LC-CDR2, or LC-CDR3 are substituted with another amino acid.

(30) (PFG3) a VL region incorporating the following CDRs:
LC-CDR1 having the amino acid sequence of SEQ ID NO:279
LC-CDR2 having the amino acid sequence of SEQ ID NO:280
LC-CDR3 having the amino acid sequence of SEQ ID NO:23,
or a variant thereof in which one or two or three amino acids in one or more of LC-CDR1, LC-CDR2, or LC-CDR3 are substituted with another amino acid.

(31) (PFG4) a VL region incorporating the following CDRs:
LC-CDR1 having the amino acid sequence of SEQ ID NO:287
LC-CDR2 having the amino acid sequence of SEQ ID NO:288
LC-CDR3 having the amino acid sequence of SEQ ID NO:289,
or a variant thereof in which one or two or three amino acids in one or more of LC-CDR1, LC-CDR2, or LC-CDR3 are substituted with another amino acid.

In some aspects and embodiments, an antibody, antigen binding fragment or polypeptide comprises at least one VL region according to one of (32) to (63) below:

(32) (P1A3) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:1.

(33) (P1C5) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:2.

(34) (P1E4) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:3.

(35) (P1F1) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:4.

(36) (PFA1) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:72.

(37) (PFA2) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:82.

(38) (PFA4) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:91.

(39) (PFA5) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:100.

(40) (PFB1) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:108.

(41) (PFB2) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:118.

(42) (PFB3) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:128.

(43) (PFB4) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:136.

(44) (PFB5) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:144.

(45) (PFC2) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:153.

(46) (PFC3) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:159.

(47) (PFC4) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:168.

(48) (PFD1) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:178.

(49) (PFD2) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:184.

(50) (PFD3) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:192.

(51) (PFD4) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:202.

(52) (PFE1) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:209.

(53) (PFE2) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:215.

(54) (PFE5) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:224.

(55) (PFF2) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:231.

(56) (PFF3) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:239.

(57) (PFF4) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:245.

(58) (PFF5) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:253.

(59) (PFG1) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:259.

(60) (PFG2) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:268.

(61) (PFG3) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:277.

(62) (PFG4) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:285.

(63) (PFG5) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:293.

In some aspects and embodiments, an antibody, antigen binding fragment or polypeptide comprises at least one VH region according to one of (64) to (92) below:

(64) (P1A3) a VH region incorporating the following CDRs:
- HC-CDR1 having the amino acid sequence of SEQ ID NO:18
- HC-CDR2 having the amino acid sequence of SEQ ID NO:19
- HC-CDR3 having the amino acid sequence of SEQ ID NO:20,
- or a variant thereof in which one or two or three amino acids in one or more of HC-CDR1, HC-CDR2, or HC-CDR3 are substituted with another amino acid.

(65) (P1C5; PFF5) a VH region incorporating the following CDRs:
- HC-CDR1 having the amino acid sequence of SEQ ID NO:24
- HC-CDR2 having the amino acid sequence of SEQ ID NO:25
- HC-CDR3 having the amino acid sequence of SEQ ID NO:26,
- or a variant thereof in which one or two or three amino acids in one or more of HC-CDR1, HC-CDR2, or HC-CDR3 are substituted with another amino acid.

(66) (P1E4) a VH region incorporating the following CDRs:
- HC-CDR1 having the amino acid sequence of SEQ ID NO:30
- HC-CDR2 having the amino acid sequence of SEQ ID NO:31
- HC-CDR3 having the amino acid sequence of SEQ ID NO:32,
- or a variant thereof in which one or two or three amino acids in one or more of HC-CDR1, HC-CDR2, or HC-CDR3 are substituted with another amino acid.

(67) (P1F1) a VH region incorporating the following CDRs:
- HC-CDR1 having the amino acid sequence of SEQ ID NO:35
- HC-CDR2 having the amino acid sequence of SEQ ID NO:36
- HC-CDR3 having the amino acid sequence of SEQ ID NO:37,
- or a variant thereof in which one or two or three amino acids in one or more of HC-CDR1, HC-CDR2, or HC-CDR3 are substituted with another amino acid.

(68) (PFA1) a VH region incorporating the following CDRs:
- HC-CDR1 having the amino acid sequence of SEQ ID NO:77
- HC-CDR2 having the amino acid sequence of SEQ ID NO:78
- HC-CDR3 having the amino acid sequence of SEQ ID NO:79,
- or a variant thereof in which one or two or three amino acids in one or more of HC-CDR1, HC-CDR2, or HC-CDR3 are substituted with another amino acid.

(69) (PFA2) a VH region incorporating the following CDRs:
- HC-CDR1 having the amino acid sequence of SEQ ID NO:86
- HC-CDR2 having the amino acid sequence of SEQ ID NO:87
- HC-CDR3 having the amino acid sequence of SEQ ID NO:88,
- or a variant thereof in which one or two or three amino acids in one or more of HC-CDR1, HC-CDR2, or HC-CDR3 are substituted with another amino acid.

(70) (PFA4) a VH region incorporating the following CDRs:
- HC-CDR1 having the amino acid sequence of SEQ ID NO:96
- HC-CDR2 having the amino acid sequence of SEQ ID NO:78
- HC-CDR3 having the amino acid sequence of SEQ ID NO:97,
- or a variant thereof in which one or two or three amino acids in one or more of HC-CDR1, HC-CDR2, or HC-CDR3 are substituted with another amino acid.

(71) (PFA5) a VH region incorporating the following CDRs:
- HC-CDR1 having the amino acid sequence of SEQ ID NO:96
- HC-CDR2 having the amino acid sequence of SEQ ID NO:104

HC-CDR3 having the amino acid sequence of SEQ ID NO:105, or a variant thereof in which one or two or three amino acids in one or more of HC-CDR1, HC-CDR2, or HC-CDR3 are substituted with another amino acid.

(72) (PFB1) a VH region incorporating the following CDRs:

HC-CDR1 having the amino acid sequence of SEQ ID NO:113

HC-CDR2 having the amino acid sequence of SEQ ID NO:114

HC-CDR3 having the amino acid sequence of SEQ ID NO:115, or a variant thereof in which one or two or three amino acids in one or more of HC-CDR1, HC-CDR2, or HC-CDR3 are substituted with another amino acid.

(73) (PFB2) a VH region incorporating the following CDRs:

HC-CDR1 having the amino acid sequence of SEQ ID NO:123

HC-CDR2 having the amino acid sequence of SEQ ID NO:124

HC-CDR3 having the amino acid sequence of SEQ ID NO:125, or a variant thereof in which one or two or three amino acids in one or more of HC-CDR1, HC-CDR2, or HC-CDR3 are substituted with another amino acid.

(74) (PFB3) a VH region incorporating the following CDRs:

HC-CDR1 having the amino acid sequence of SEQ ID NO:131

HC-CDR2 having the amino acid sequence of SEQ ID NO:132

HC-CDR3 having the amino acid sequence of SEQ ID NO:133, or a variant thereof in which one or two or three amino acids in one or more of HC-CDR1, HC-CDR2, or HC-CDR3 are substituted with another amino acid.

(75) (PFB4) a VH region incorporating the following CDRs:

HC-CDR1 having the amino acid sequence of SEQ ID NO:77

HC-CDR2 having the amino acid sequence of SEQ ID NO:78

HC-CDR3 having the amino acid sequence of SEQ ID NO:141, or a variant thereof in which one or two or three amino acids in one or more of HC-CDR1, HC-CDR2, or HC-CDR3 are substituted with another amino acid.

(76) (PFB5) a VH region incorporating the following CDRs:

HC-CDR1 having the amino acid sequence of SEQ ID NO:148

HC-CDR2 having the amino acid sequence of SEQ ID NO:149

HC-CDR3 having the amino acid sequence of SEQ ID NO:150, or a variant thereof in which one or two or three amino acids in one or more of HC-CDR1, HC-CDR2, or HC-CDR3 are substituted with another amino acid.

(77) (PFC2; PFG5) a VH region incorporating the following CDRs:

HC-CDR1 having the amino acid sequence of SEQ ID NO:96

HC-CDR2 having the amino acid sequence of SEQ ID NO:78

HC-CDR3 having the amino acid sequence of SEQ ID NO:156, or a variant thereof in which one or two or three amino acids in one or more of HC-CDR1, HC-CDR2, or HC-CDR3 are substituted with another amino acid.

(78) (PFC3) a VH region incorporating the following CDRs:

HC-CDR1 having the amino acid sequence of SEQ ID NO:131

HC-CDR2 having the amino acid sequence of SEQ ID NO:164

HC-CDR3 having the amino acid sequence of SEQ ID NO:165, or a variant thereof in which one or two or three amino acids in one or more of HC-CDR1, HC-CDR2, or HC-CDR3 are substituted with another amino acid.

(79) (PFC4) a VH region incorporating the following CDRs:

HC-CDR1 having the amino acid sequence of SEQ ID NO:173

HC-CDR2 having the amino acid sequence of SEQ ID NO:174

HC-CDR3 having the amino acid sequence of SEQ ID NO:175, or a variant thereof in which one or two or three amino acids in one or more of HC-CDR1, HC-CDR2, or HC-CDR3 are substituted with another amino acid.

(80) (PFD1) a VH region incorporating the following CDRs:

HC-CDR1 having the amino acid sequence of SEQ ID NO:77

HC-CDR2 having the amino acid sequence of SEQ ID NO:78

HC-CDR3 having the amino acid sequence of SEQ ID NO:181, or a variant thereof in which one or two or three amino acids in one or more of HC-CDR1, HC-CDR2, or HC-CDR3 are substituted with another amino acid.

(81) (PFD2) a VH region incorporating the following CDRs:

HC-CDR1 having the amino acid sequence of SEQ ID NO:30

HC-CDR2 having the amino acid sequence of SEQ ID NO:31

HC-CDR3 having the amino acid sequence of SEQ ID NO:189, or a variant thereof in which one or two or three amino acids in one or more of HC-CDR1, HC-CDR2, or HC-CDR3 are substituted with another amino acid.

(82) (PFD3) a VH region incorporating the following CDRs:

HC-CDR1 having the amino acid sequence of SEQ ID NO:197

HC-CDR2 having the amino acid sequence of SEQ ID NO:198

HC-CDR3 having the amino acid sequence of SEQ ID NO:199, or a variant thereof in which one or two or three amino acids in one or more of HC-CDR1, HC-CDR2, or HC-CDR3 are substituted with another amino acid.

(83) (PFD4) a VH region incorporating the following CDRs:

HC-CDR1 having the amino acid sequence of SEQ ID NO:96

HC-CDR2 having the amino acid sequence of SEQ ID NO:206

HC-CDR3 having the amino acid sequence of SEQ ID NO:97, or a variant thereof in which one or two or three amino acids in one or more of HC-CDR1, HC-CDR2, or HC-CDR3 are substituted with another amino acid.

(84) (PFE1; PFE5) a VH region incorporating the following CDRs:

HC-CDR1 having the amino acid sequence of SEQ ID NO:96

HC-CDR2 having the amino acid sequence of SEQ ID NO:78

HC-CDR3 having the amino acid sequence of SEQ ID NO:97, or a variant thereof in which one or two or three amino acids in one or more of HC-CDR1, HC-CDR2, or HC-CDR3 are substituted with another amino acid.

(85) (PFE2) a VH region incorporating the following CDRs:

HC-CDR1 having the amino acid sequence of SEQ ID NO:96

HC-CDR2 having the amino acid sequence of SEQ ID NO:220

HC-CDR3 having the amino acid sequence of SEQ ID NO:221, or a variant thereof in which one or two or three amino acids in one or more of HC-CDR1, HC-CDR2, or HC-CDR3 are substituted with another amino acid.

(86) (PFF2) a VH region incorporating the following CDRs:

HC-CDR1 having the amino acid sequence of SEQ ID NO:234

HC-CDR2 having the amino acid sequence of SEQ ID NO:235

HC-CDR3 having the amino acid sequence of SEQ ID NO:236, or a variant thereof in which one or two or three amino acids in one or more of HC-CDR1, HC-CDR2, or HC-CDR3 are substituted with another amino acid.

(87) (PFF3) a VH region incorporating the following CDRs:

HC-CDR1 having the amino acid sequence of SEQ ID NO:241

HC-CDR2 having the amino acid sequence of SEQ ID NO:206

HC-CDR3 having the amino acid sequence of SEQ ID NO:242, or a variant thereof in which one or two or three amino acids in one or more of HC-CDR1, HC-CDR2, or HC-CDR3 are substituted with another amino acid.

(88) (PFF4) a VH region incorporating the following CDRs:

HC-CDR1 having the amino acid sequence of SEQ ID NO:148

HC-CDR2 having the amino acid sequence of SEQ ID NO:149

HC-CDR3 having the amino acid sequence of SEQ ID NO:250, or a variant thereof in which one or two or three amino acids in one or more of HC-CDR1, HC-CDR2, or HC-CDR3 are substituted with another amino acid.

(89) (PFG1) a VH region incorporating the following CDRs:

HC-CDR1 having the amino acid sequence of SEQ ID NO:77

HC-CDR2 having the amino acid sequence of SEQ ID NO:264

HC-CDR3 having the amino acid sequence of SEQ ID NO:265, or a variant thereof in which one or two or three amino acids in one or more of HC-CDR1, HC-CDR2, or HC-CDR3 are substituted with another amino acid.

(90) (PFG2) a VH region incorporating the following CDRs:

HC-CDR1 having the amino acid sequence of SEQ ID NO:131

HC-CDR2 having the amino acid sequence of SEQ ID NO:273

HC-CDR3 having the amino acid sequence of SEQ ID NO:274, or a variant thereof in which one or two or three amino acids in one or more of HC-CDR1, HC-CDR2, or HC-CDR3 are substituted with another amino acid.

(91) (PFG3) a VH region incorporating the following CDRs:

HC-CDR1 having the amino acid sequence of SEQ ID NO:281

HC-CDR2 having the amino acid sequence of SEQ ID NO:282

HC-CDR3 having the amino acid sequence of SEQ ID NO:20, or a variant thereof in which one or two or three amino acids in one or more of HC-CDR1, HC-CDR2, or HC-CDR3 are substituted with another amino acid.

(92) (PFG4) a VH region incorporating the following CDRs:

HC-CDR1 having the amino acid sequence of SEQ ID NO:148

HC-CDR2 having the amino acid sequence of SEQ ID NO:149

HC-CDR3 having the amino acid sequence of SEQ ID NO:290, or a variant thereof in which one or two or three amino acids in one or more of HC-CDR1, HC-CDR2, or HC-CDR3 are substituted with another amino acid.

In some aspects and embodiments, an antibody, antigen binding fragment or polypeptide comprises at least one VH region according to one of (93) to (124) below:

(93) (P1A3) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:5.

(94) (P1C5) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:6.

(95) (P1E4) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:7.

(96) (P1F1) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:8.

(97) (PFA1) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:73.

(98) (PFA2) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:83.

(99) (PFA4) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:92.

(100) (PFA5) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:101.

(101) (PFB1) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:109.

(102) (PFB2) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:119.

(103) (PFB3) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:129.

(104) (PFB4) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:137.

(105) (PFB5) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:145.

(106) (PFC2) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:154.

(107) (PFC3) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:160.

(108) (PFC4) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:169.

(109) (PFD1) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:179.

(110) (PFD2) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:185.

(111) (PFD3) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:193.

(112) (PFD4) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:203.

(113) (PFE1) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:210.

(114) (PFE2) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:216.

(115) (PFE5) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:225.

(116) (PFF2) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:232.

(117) (PFF3) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:240.

(118) (PFF4) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:246.

(119) (PFF5) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:254.

(120) (PFG1) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:260.

(121) (PFG2) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:269.

(122) (PFG3) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:278.

(123) (PFG4) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:286.

(124) (PFG5) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:294.

In some embodiments the antigen-binding molecule comprises at least one VL region according to any one of (1) to (63) above, and at least one VH region according to any one of (64) to (124) above.

The light and heavy chain CDRs may also be particularly useful in conjunction with a number of different framework regions. Accordingly, light and/or heavy chains having LC-CDR1-3 or HC-CDR1-3 may possess an alternative framework region. Suitable framework regions are well known in the art and are described for example in M. Lefranc & G. Lefranc (2001) "The Immunoglobulin FactsBook", Academic Press, incorporated herein by reference.

In this specification, antibodies may have $V_L$ and/or $V_H$ chains comprising an amino acid sequence that has a high percentage sequence identity to one or more of the $V_L$ and/or $V_H$ amino acid sequences of SEQ ID NOs 1 and 5; 2 and 6; 3 and 7; or 4 and 8, or to one of the amino acid sequences shown in FIGS. 1 and 2.

For example, antibodies according to the present invention include antibodies that bind HER2 and have a $V_L$ or $V_H$ chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the $V_L$ or $V_H$ chain amino acid sequence of one of SEQ ID NOs 1 to 8, or to one of the amino acid sequences shown in FIGS. 1 and 2.

In some embodiments, an antibody, antigen-binding molecule or polypeptide provided herein comprises the CDRs. $V_L$ and/or $V_H$ chains of PFA4, PFB4, PFB5, PFC3, PFD4, PFE1, PFF5, or PFG3. In some embodiments, an antibody, antigen-binding molecule or polypeptide provided herein comprises the CDRs, $V_L$ and/or $V_H$ chains of PFA4, PFB4, PFC3, PFD4, PFE1, PFF5, or PFG3. In some embodiments, an antibody, antigen-binding molecule or polypeptide provided herein comprises the CDRs, $V_L$ and/or $V_H$ chains of PFB4, PFC3, PFD4, PFE1, PFF5, or PFG3. In some embodiments, an antibody, antigen-binding molecule or polypeptide provided herein comprises the CDRs, $V_L$ and/or $V_H$ chains of PFB4, PFC3, PFE1, PFF5, or PFG3. In some embodiments, an antibody, antigen-binding molecule or polypeptide provided herein comprises the CDRs, $V_L$ and/or $V_H$ chains of PFB4, PFC3, PFE1, PFF5, or PFG3.

In some embodiments, an antibody, antigen-binding molecule or polypeptide provided herein comprises the CDRs, $V_L$ and/or $V_H$ chains of P1A3, P1C5, P1E4, P1F1, PFA4, PFB4, PFC3, PFD4 or PFE1.

Multivalent Antibodies

Whole antibodies, and $F(ab')_2$ fragments are "bivalent". By "bivalent" we mean that the said antibodies and $F(ab')_2$ fragments have two antigen combining sites. In contrast, Fab, Fv, ScFv and dAb fragments are monovalent, having only one antigen combining site.

The present application also provides an antibody or antigen binding fragment which is capable of binding to HER2, and which is a bispecific antibody or a bispecific antigen binding fragment. In some embodiments the bispecific antibody or bispecific antigen binding fragment may be isolated. The term "bispecific" means that the antigen-binding molecule is able to bind specifically to at least two distinct antigenic determinants.

In some embodiments the bispecific antibodies and bispecific antigen binding fragment comprise an antigen binding fragment or a polypeptide according to the present invention. In some embodiments, the bispecific antibodies and bispecific antigen binding fragments comprise an antigen binding fragment capable of binding to HER2, wherein the antigen binding fragment which is capable of binding to HER2 comprises or consists of an antigen binding fragment or a polypeptide according to the present invention.

In some embodiments the bispecific antibodies and bispecific antigen binding fragments comprise an antigen binding fragment capable of binding to HER2, and an antigen binding fragment capable of binding to another target protein. In some embodiments the bispecific antibodies/antigen binding fragments comprise an antigen binding molecule capable of binding to HER2 and an antigen binding molecule capable of binding to an antigen other than HER2. In some embodiments the antigen other than HER2 is an immune cell surface molecule. In some embodiments the antigen other than HER2 is a cancer cell antigen. In some embodiments the antigen other than HER2 is a receptor molecule, e.g. a cell surface receptor.

A cancer cell antigen is an antigen which is expressed or over-expressed by a cancer cell. A cancer cell antigen may be any peptide/polypeptide, glycoprotein, lipoprotein, glycan, glycolipid, lipid, or fragment thereof. A cancer cell antigen's expression may be associated with a cancer. A cancer cell antigen may be abnormally expressed by a cancer cell (e.g. the cancer cell antigen may be expressed with abnormal localisation), or may be expressed with an abnormal structure by a cancer cell. A cancer cell antigen may be capable of eliciting an immune response. In some embodiments, the antigen is expressed at the cell surface of the cancer cell (i.e. the cancer cell antigen is a cancer cell surface antigen). In some embodiments, the part of the antigen which is bound by the antigen-binding molecule described herein is displayed on the external surface of the cancer cell (i.e. is extracellular). The cancer cell antigen may be a cancer-associated antigen. In some embodiments the cancer cell antigen is an antigen whose expression is associated with the development, progression or severity of symptoms of a cancer. The cancer-associated antigen may be associated with the cause or pathology of the cancer, or may be expressed abnormally as a consequence of the cancer. In some embodiments, the cancer cell antigen is an antigen whose expression is upregulated (e.g. at the RNA and/or protein level) by cells of a cancer, e.g. as compared to the level of expression of by comparable non-cancerous cells (e.g. non-cancerous cells derived from the same tissue/cell type). In some embodiments, the cancer-associated antigen may be preferentially expressed by cancerous cells, and not expressed by comparable non-cancerous cells (e.g. non-cancerous cells derived from the same tissue/cell type). In some embodiments, the cancer-associated antigen may be the product of a mutated oncogene or mutated tumor suppressor gene. In some embodiments, the cancer-associated antigen may be the product of an overexpressed cellular protein, a cancer antigen produced by an oncogenic virus, an oncofetal antigen, or a cell surface glycolipid or glycoprotein.

An immune cell surface molecule may be any peptide/polypeptide, glycoprotein, lipoprotein, glycan, glycolipid, lipid, or fragment thereof expressed at or on the cell surface of an immune cell. In some embodiments, the part of the immune cell surface molecule which is bound by the antigen-binding molecule of the present invention is on the external surface of the immune cell (i.e. is extracellular). The immune cell surface molecule may be expressed at the cell surface of any immune cell. In some embodiments, the immune cell may be a cell of hematopoietic origin, e.g. a neutrophil, eosinophil, basophil, dendritic cell, lymphocyte, or monocyte. The lymphocyte may be e.g. a T cell, B cell, natural killer (NK) cell, NKT cell or innate lymphoid cell (ILC), or a precursor thereof (e.g. a thymocyte or pre-B cell). In some embodiments the immune cell surface molecule may be a costimulatory molecule (e.g. CD28, OX40, 4-1BB, ICOS or CD27) or a ligand thereof. In some embodiments the immune cell surface molecule may be a checkpoint inhibitor (e.g. PD-1, CTLA-4, LAG-3, TIM-3, TIGIT or BTLA) or a ligand thereof.

In some embodiments the bispecific antibodies/antigen binding fragments comprise an antigen binding fragment/molecule as provided herein and an antigen binding fragment/molecule capable of binding to HER2. In some embodiments the bispecific antibodies/antigen binding fragments comprise an antigen binding fragment/molecule capable of binding HER2 at a first epitope and an antigen binding fragment/molecule capable of binding to HER2 at a second epitope. For example, the bispecific antibodies/antigen binding fragments comprise an antigen binding fragment/molecule as provided herein and an antigen binding fragment/molecule derived from trastuzumab and/or pertuzumab.

The antigen binding fragment capable of binding to another target protein may be capable of binding to another protein other than HER2.

The antibodies and antigen binding polypeptides as described herein may be multispecific. Multispecific antibodies and antigen binding polypeptides may be provided in any suitable format, such as those formats described in Kontermann MAbs 2012, 4(2): 182-197, which is hereby incorporated by reference in its entirety. For example, an antigen-binding polypeptide may be a bispecific antibody conjugate (e.g. an IgG2, F(ab')2 or CovX-Body), a bispecific IgG or IgG-like molecule (e.g. an IgG, scFv4-Ig, IgG-scFv, scFv-IgG, DVD-Ig, IgG-sVD, sVD-IgG, 2 in 1-IgG, mAb2, or Tandemab common LC), an asymmetric bispecific IgG or IgG-like molecule (e.g. a kih IgG, kih IgG common LC, CrossMab, kih IgG-scFab, mAb-Fv, charge pair or SEED-body), a small bispecific antibody molecule (e.g. a Diabody (Db), dsDb, DART, scDb, tandAbs, tandem scFv (taFv), tandem dAb/VHH, triple body, triple head, Fab-scFv, or F(ab')2-scFv2), a bispecific Fc and CH3 fusion protein (e.g. a taFv-Fc, Di-diabody, scDb-CH3, scFv-Fc-scFv, HCAb-VHH, scFv-kih-Fc, or scFv-kih-CH3), or a bispecific fusion protein (e.g. a scFv2-albumin, scDb-albumin, taFv-toxin, DNL-Fab3, DNL-Fab4-IgG, DNL-Fab4-IgG-cytokine2). See in particular FIG. 2 of Kontermann MAbs 2012, 4(2): 182-19. By "multispecific" it is meant that the antigen-binding molecule displays specific binding to more than one target.

The skilled person is able to design and prepare bispecific antibodies. Methods for producing bispecific antibodies include chemically crosslinking of antibodies or antibody fragments, e.g. with reducible disulphide or non-reducible thioether bonds, for example as described in Segal and Bast, 2001. Production of Bispecific Antibodies. Current Protocols in Immunology. 14:IV:2.13:2.13.1-2.13.16, which is hereby incorporated by reference in its entirety. For example, N-succinimidyl-3-(−2-pyridyldithio)-propionate (SPDP) can be used to chemically crosslink e.g. Fab fragments via hinge region SH— groups, to create disulfide-linked bispecific F(ab)2 heterodimers. Other methods for producing bispecific antibodies include fusing antibody-producing hybridomas e.g. with polyethylene glycol, to produce a quadroma cell capable of secreting bispecific antibody, for example as described in D. M. and Bast, B. J. 2001. Production of Bispecific Antibodies. Current Protocols in Immunology. 14:IV:2.13:2.13.1-2.13.16.

Bispecific antibodies can also be produced recombinantly, by expression from e.g. a nucleic acid construct encoding polypeptides for the antigen binding molecules, for example as described in Antibody Engineering: Methods and Protocols, Second Edition (Humana Press, 2012), at Chapter 40: Production of Bispecific Antibodies: Diabodies and Tandem scFv (Hornig and Farber-Schwarz), or French, How to make bispecific antibodies, Methods Mol. Med. 2000; 40:333-339, the entire contents of both of which are hereby incorporated by reference. For example, a DNA construct encoding the light and heavy chain variable domains for the two antigen-binding fragments (i.e. the light and heavy chain variable domains for the antigen-binding fragment capable of binding HER2, and the light and heavy chain variable domains for the antigen-binding fragment capable of binding to another target protein/to another epitope on HER2), and including sequences encoding a suitable linker or dimerization domain between the antigen-binding fragments can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

Antibody Conjugates

The present invention also provides antibody conjugates, comprising an antibody, antigen binding fragment or polypeptide according to the invention conjugated to a chemical moiety.

In some embodiments, the chemical moiety may be a moiety for providing a therapeutic effect. In some embodiments, the chemical moiety may be a drug moiety (e.g. a cytotoxic or cytostatic agent). A cytotoxic agent is an agent that kills cells. A cytostatic agent is an agent that inhibits growth of cells.

The use of an antibody-drug conjugate targets delivery of the drug moiety to cancer cells expressing HER2 and may promote intracellular accumulation therein.

In some embodiments, the chemical moiety may be at least one anti-cancer agent. "At least one anti-cancer agent" refers to one, or two, or three, or four, or more agents that are effective in the treatment of malignant, or cancerous, disease such as the cancers described herein. An anti-cancer agent may also be described herein as a therapeutic agent, additional agent, or an additional therapeutic agent.

In some embodiments, the drug moiety may be a chemotherapeutic drug as described hereinbelow. In some embodiments the drug moiety may be a hormone capable of controlling tumour growth, such as ethinyloestradiol, medroxyprogesterone, norethisterone, megestrol, diethylstilboestrol, or fosfestrol. In some embodiments the drug moiety may be a hormone antagonist such as tamoxifen, toremifene, aminoglutethimide, anastrozole, letrozole, exemestane, trilostane, goserelin, buserelin, goserelin, leuprorelin, triptorelin, cyproterone acetate, flutamide, or bicalutamide.

In some embodiments the chemical moiety may be a detectable moiety. Suitable moieties and means for their detection are well known to those in the art and include the radioactive isotope or non-isotopic entities described hereinabove.

The antibody conjugate may comprise a linker which may be cleaved so as to release the drug at the target location.

Chimeric Antigen Receptors

An antibody, antigen binding fragment or polypeptide according to the present invention may be incorporated into a chimeric antigen receptor (CAR) capable of binding to HER2. Thus, the present invention also provides CARs comprising the antibodies, antigen-binding molecules or polypeptides of the present invention.

Chimeric Antigen Receptors (CARs) are recombinant receptors that provide both antigen-binding and T cell activating functions. CAR structure and engineering is reviewed, for example, in Dotti et al., Immunol Rev (2014) 257(1), hereby incorporated by reference in its entirety. CARs comprise an antigen-binding region linked to a cell membrane anchor region and a signalling region. An optional hinge region may provide separation between the antigen-binding region and cell membrane anchor region, and may act as a flexible linker.

An antibody, antigen binding fragment or polypeptide according to the present invention may be used as the antigen binding domain of a chimeric antigen receptor (CAR). In some embodiments, the CAR comprises a VL domain and a VH domain according to any embodiment of an antibody, antigen binding fragment or polypeptide described herein. Accordingly, the antigen bound by the CAR according to the present invention is HER2.

Also provided is an in vitro complex, optionally isolated, comprising the CAR bound to HER2.

CARs may be combined with costimulatory ligands, chimeric costimulatory receptors or cytokines to further enhance T cell potency, specificity and safety (Sadelain et al., The basic principles of chimeric antigen receptor (CAR) design. Cancer Discov. 2013 April; 3(4): 388-398. doi: 10.1158/2159-8290.CD-12-0548, specifically incorporated herein by reference).

The present invention provides a nucleic acid, optionally isolated, encoding a CAR as described herein. Also provided is an expression vector comprising the nucleic acid. The present invention also provides a cell comprising a CAR, nucleic acid, or an expression vector as described herein. Compositions comprising a CAR, nucleic acid, expression vector or cell as described herein are also provided. The CAR may be used to generate tumour-targeted T cells e.g. T cells targeted to tumour cells expressing or overexpressing HER2, for which the CAR is specific.

The cells may be immune cells e.g. T cells, antigen-specific T cells (e.g. virus-specific T cells), antigen-specific CD4 T cells, antigen-specific CD8 T cells, effector memory CD4 T cells, effector memory CD8 T cells, central memory CD4 T cells, central memory CD8 T cells, cytotoxic CD8+ T cells (i.e. CTLs) NK cells or antigen-specific NK cells.

Engineering of CARs into cells may be performed during culture, in vitro, for transduction and expansion, such as happens during expansion of T cells for adoptive T cell therapy. The transduction may utilize a variety of methods, but stable gene transfer is required to enable sustained CAR expression in clonally expanding and persisting T cells.

In addition to the HER2 specificity determining elements described herein, CAR molecules may be further engineered to express co-stimulatory endodomains such as those derived from CD28 and tumor necrosis factor receptor superfamily member 9 (TNFRSF9; 4-1 BB) to promote T cell proliferation and persistence upon encountering tumor cells (Nishio and Dotti., OncoImmunology 4:2, e988098; February 2015).

A CAR typically combines an antigen binding domain with an intracellular domain of the CD3-zeta chain or FcγRI protein in a single chimeric protein. The structural features of a CAR are described by Sjouke et al., (The pharmacology of second-generation chimeric antigen receptors. Nature Reviews Drug Discovery, 14, 499 509 (2015) doi:10.1038/nrd4597). A CAR typically has an extracellular antigen-binding domain linked to a transmembrane domain and endodomain. An optional hinge or spacer domain may provide separation between the binding moiety and transmembrane domain and may act as a flexible linker.

In accordance with the present invention, the antigen recognition domain of the CAR may be, or may be derived from, an antibody, antigen binding fragment or polypeptide which is capable of binding to HER2, as described herein. The antigen-binding region of the CAR of the present invention may be provided with any suitable format, e.g. scFv, scFab, etc.

In some embodiments the antigen recognition domain of the CAR may be, or may be derived from, clone P1A3, P1C5, P1E4, or P1F1 as described herein.

In some embodiments the CAR may comprise an antibody, antigen binding fragment or polypeptide described herein which exhibits intermediate or lower binding to HER2, as described herein. Intermediate and/or lower affinity antigen-binding regions may be capable of discriminating cancer cells overexpressing a target protein from normal cells expressing physiological target levels, as described in e.g. Liu et al., Cancer Res. 2015; (75) (17) 3596-3607. This approach may spare non-cancer cells whilst specifically targeting cancer cells and reduce off-target toxicity. In some embodiments the antigen recognition domain of the CAR may be, or may be derived from, clone PFA4, PFB4, PFB5, PFC3, PFD4, PFE1, PFF5, or PFG3 as described herein. In some embodiments the antigen recognition domain of the CAR may be, or may be derived from, clone PFA4, PFB4, PFC3, PFD4, PFE1, PFF5, or PFG3 as described herein.

Hinge or spacer regions may be flexible domains allowing the binding moiety to orient in different directions. Hinge or spacer regions may be derived from IgG1, IgH or the $CH_2CH_3$ region of immunoglobulin.

Transmembrane domains may be hydrophobic alpha helix that spans the cell membrane. The transmembrane domain associated with the endodomain is commonly used. The transmembrane region may be termed the cell membrane anchor region. In some embodiments, the CAR comprises a cell membrane anchor region comprising or consisting of an amino acid sequence which comprises, consists of, or is derived from, the transmembrane region amino acid sequence for one of CD3-ζ, CD4, CD8 or CD28. As used herein, a region which is 'derived from' a reference amino acid sequence comprises an amino acid sequence having at least 60%, e.g. one of at least 65%, 70%, 75%, 80%, 85%, 90%, 91%, 92%, 93%, 94%, 95%, 96%, 97%, 98%, 99% or 100% sequence identity to the reference sequence.

The endodomain is responsible for receptor clustering/dimerization after antigen binding and for initiation of signal transduction to the cell. One commonly used transmembrane domain is the CD3-zeta transmembrane and endodomain.

Intracellular domains from one or more co-stimulatory protein receptors, such as CD28 4-1BB, OX40, ICOS, may optionally be incorporated into the cytoplasmic tail of the CAR to provide additional co-stimulatory signaling, which may be beneficial in terms of anti-tumor activity.

A CAR described herein may comprise an extracellular domain having an antigen recognition domain, a transmembrane domain, and a cytoplasmic domain. A transmembrane domain that is naturally associated with one of the domains in the CAR may be used or the transmembrane domain can be selected or modified by amino acid substitution to avoid binding of such domains to the transmembrane domains of the same or different surface membrane proteins to minimize interactions with other members of the receptor complex. The cytoplasmic domain may be designed to comprise the CD28 and/or 4-1BB signaling domain by itself or be combined with any other desired cytoplasmic domain(s). The cytoplasmic domain may be designed to further comprise the signaling domain of CD3-zeta. For example, the cytoplasmic domain of the CAR can include but is not limited to CD3-zeta, 4-1 BB and CD28 signaling modules and combinations thereof.

Also provided herein are CAR T cells comprising as a CAR an antigen binding fragment capable of binding to HER2, as described herein.

CAR T cells as described herein can be generated by introducing a lentiviral vector in vitro comprising a desired CAR, for example a CAR comprising anti-HER2, CD8a hinge and transmembrane domain, and human 4-1BB and CD3zeta signaling domains, into the cells. CAR T cells as described herein can also be generated by electroporation of mRNA encoding a desired CAR. The CART cells of the invention are able to replicate in vivo resulting in long-term persistence that can lead to sustained tumor control.

In some embodiments a CAR T cell according to the present invention promotes cytolysis of cells, e.g. cancer or tumour cells.

The present invention provides a CAR, nucleic acid, expression vector, cell, or composition as described herein for use in a method of medical treatment or prophylaxis. Also described herein is the administration of a genetically modified T cell expressing a CAR, nucleic acid or expression vector as described herein for use in a method of medical treatment or prophylaxis. In some embodiments a CAR or T cell as described herein is used for the treatment of a patient having cancer or at risk of having cancer. In some embodiments the cancer to be treated is a cancer described herein. In some embodiments the cancer is a cancer of the breast. In some embodiments the cancer to be treated is a cancer of the ovary, uterus, lung, e.g. adenocarcinoma of the lung, or the gastrointestinal tract e.g. stomach, salivary duct.

Administration may be by lymphocyte infusion. Preferably, autologous lymphocyte infusion is used in the treatment, i.e. the lymphocytes are derived from the patient to which they are introduced. Autologous PBMCs (peripheral blood mononuclear cells) are collected from a patient in need of treatment and T cells are activated and expanded using methods known in the art and then infused back into the patient. The generation, activation and expansion of cells may be performed in vitro or ex vivo. In some cases the cells may be obtained from an individual who is not the patient and introduced into the patient i.e. allogenic cell therapy.

Adoptive T cell transfer is described, for example, in Chia W K et al., Molecular Therapy (2014), 22(1): 132-139, Kalos and June 2013, Immunity 39(1): 49-60 and Cobbold et al., (2005) J. Exp. Med. 202: 379-386, which are hereby incorporated by reference in their entirety. Accordingly, the skilled person is able to determine appropriate reagents and procedures for adoptive transfer of immune cells described herein.

Methods of Detection

Antibodies, antigen binding fragments, polypeptides, conjugates, CARs or cells as described herein may be detectably labelled or, at least, capable of detection. For example, the antibody may be labelled with a radioactive atom or a coloured molecule or a fluorescent molecule or a molecule which can be readily detected in any other way. Suitable detectable molecules include fluorescent proteins, luciferase, enzyme substrates, and radiolabels. The binding moiety may be directly labelled with a detectable label or it may be indirectly labelled. For example, the binding moiety may be an unlabelled antibody which can be detected by another antibody which is itself labelled. Alternatively, the second antibody may have bound to it biotin and binding of labelled streptavidin to the biotin is used to indirectly label the first antibody.

Antibodies, antigen binding fragments, polypeptides, conjugates, CARs or cells described herein may be used in methods that involve the binding of the antibody or antigen binding fragment to HER2. Such methods may involve detection of the bound complex of antibody, antigen binding fragment, polypeptide, conjugate, CAR or cell, and HER2. As such, in one embodiment a method is provided, the method comprising contacting a sample containing, or suspected to contain, HER2 with an antibody, antigen binding fragment, polypeptide, conjugate, CAR or cell as described herein and detecting the formation of a complex of antibody, antigen binding fragment, polypeptide, conjugate, CAR or cell, and HER2.

Suitable method formats are well known in the art, including immunoassays such as sandwich assays, e.g. ELISA. The method may involve labelling the antibody, antigen binding fragment, polypeptide, conjugate, CAR or cell, or HER2, or both, with a detectable label, e.g. fluorescent, luminescent or radio-label. HER2 expression may be measured by immunohistochemistry (IHC) or fluorescence in situ hybridization (FISH), for example in a tissue sample obtained by biopsy.

Methods of this kind may provide the basis of a method of diagnosis of a disease or condition requiring detection and or quantitation of HER2. Such methods may be performed in vitro on a patient sample, or following processing of a patient sample. Once the sample is collected, the patient is not required to be present for the in vitro method of diagnosis to be performed and therefore the method may be one which is not practised on the human or animal body.

The methods may involve determining the amount of HER2 present in a patient sample. The methods may further comprise comparing the determined amount against a standard or reference value as part of the process of reaching a diagnosis. Other diagnostic tests may be used in conjunction with those described here to enhance the accuracy of the diagnosis or prognosis or to confirm a result obtained by using the tests described here.

The level of HER2 present in a patient sample may be indicative that a patient may respond to treatment with an anti-HER2 antibody, antigen binding fragment, polypeptide, conjugate, CAR or cell. The presence of a high level of HER2 in a sample may be used to select a patient for treatment with an anti-HER2 antibody, antigen binding fragment, polypeptide, conjugate, CAR or cell. The antibodies, antigen binding fragments, polypeptides, conjugates, CARs or cells of the present invention may therefore be used to select a patient for treatment with anti-HER2 therapy.

Detection of HER2 in a sample may be used for the purpose of diagnosis of a cancerous condition in the patient, diagnosis of a predisposition to a cancerous condition or for providing a prognosis (prognosticating) of a cancerous condition. The diagnosis or prognosis may relate to an existing (previously diagnosed) cancerous condition, which may be benign or malignant, may relate to a suspected cancerous condition or may relate to the screening for cancerous conditions in the patient (which may be previously undiagnosed).

A sample may be taken from any tissue or bodily fluid. The sample may comprise or may be derived from: a quantity of blood; a quantity of serum derived from the individual's blood which may comprise the fluid portion of the blood obtained after removal of the fibrin clot and blood cells; a tissue sample or biopsy; or cells isolated from said individual.

Methods according to the present invention are preferably performed in vitro. The term "in vitro" is intended to encompass experiments with cells in culture whereas the term "in vivo" is intended to encompass experiments with intact multi-cellular organisms.

An antibody, antigen binding fragment, polypeptide, conjugate, CAR or cell as described herein may be used in methods for detecting, localizing or imaging a cancer (e.g. a tumour), e.g. in vivo.

An antibody, antigen binding fragment, polypeptide, conjugate, CAR or cell may be suitably labeled directly or indirectly with a detectable label (e.g. a signal-generating label), such as a radioactive isotope or non-isotopic entity, for detection. Radioisotopes include Iodine123, Iodine125, Iodine126, Iodine131, Iodine133, Bromine77, Technetium99m, Indium111, Indium113m, Gallium67, Gallium68, Ruthenium95, Ruthenium97, Ruthenium103, Ruthenium105, Mercury207, Mercury203, Rhenium99m, Rhenium101, Rhenium105, Scandium47, Tellurium121 m, Tellurium122m, Tellurium125m, Thulium165, Thulium167, Thulium168, Copper67, Fluorine18, Yttrium90, Palladium100, Bismuth217 and Antimony211. Nonisotopic entities may be selected from enzymes (e.g. peroxidase, alkaline phosphatase, glucose oxidase, beta-galactosidase, luciferase), dyes, haptens, luminescent agents such as radioluminescent, chemiluminescent (e.g. acridinium ester, luminol, isoluminol), bioluminescent, fluorescent (e.g. fluorescein, rhodamine, eosine and NDB, green fluorescent protein (GFP) chelates of rare earths such as europium (Eu), terbium (Tb) and samarium (Sm), tetramethyl rhodamine, Texas Red, 4-methyl umbelliferone, 7-amino-4-methyl coumarin, Cy3, Cy5) or phosphorescent agents, antibodies, receptors and ligands such as biotin, avidin, streptavidin or digoxigenin.

Detection techniques are well known to those of skill in the art and can be selected to correspond with the labelling agent. Suitable techniques include PCR amplification of oligonucleotide tags, mass spectrometry, detection of fluorescence or colour, e.g. upon enzymatic conversion of a substrate by a reporter protein, or detection of radioactivity.

In some embodiments, the methods comprise administering the antibody, antibody fragment, polypeptide, conjugate, CAR or cell to a subject, e.g. a patient diagnosed with or suspected of having a cancer and detecting the antibody, antigen binding fragment, polypeptide, conjugate, CAR or cell. In some embodiments, the methods comprise detecting signal from the antibody, antigen binding fragment, polypeptide, conjugate, CAR or cell. In some embodiments the method comprises conversion of the signal to an image.

The present invention also provides methods for selecting/stratifying a subject for treatment with a HER2-targeted agent using the antibody, antigen binding fragment, polypeptide, conjugate, CAR, or cell according to the invention. In some embodiments the method comprises contacting a sample from the subject with an antibody, antigen binding fragment, polypeptide, conjugate, CAR or cell. In some embodiments the sample is contacted in vitro. In some embodiments, a subject is selected for treatment in accordance with the invention, or is identified as a subject which would benefit from such treatment, based on detection of the presence of HER2, or nucleic acid encoding HER2, e.g. in a sample obtained from the individual.

Therapeutic Applications

Antibodies, antigen binding fragments, polypeptides, conjugates, nucleic acids, vectors, CARs and cells according to the present invention and compositions comprising such agents may be provided for use in methods of medical treatment. Treatment may be provided to subjects having a disease or condition in need of treatment. The disease or condition may be a cancer. The disease or condition may be a cancer in which HER2 is overexpressed.

The present invention provides an antibody, antigen binding fragment, polypeptide, conjugate, nucleic acid, vector, CAR or cell according to the present invention for use in a method of medical treatment or prophylaxis. The present invention also provides the use of an antibody, antigen binding fragment, polypeptide, conjugate, nucleic acid, vector, CAR or cell according to the present invention in the manufacture of a medicament for treating or preventing a disease or condition. The present invention also provides a method of treating or preventing a disease or condition, comprising administering to a subject a therapeutically or prophylactically effective amount of an antibody, antigen binding fragment, polypeptide, conjugate, nucleic acid, vector, CAR or cell according to the present invention.

HER2 is a member of the epidermal growth factor receptor family and functions as a preferential heterodimerization-signalling partner with other members of the EGFR family (EGFR/HER1, HER3, and HER4), playing an important role in all stages of cell development including cellular proliferation and differentiation (Karunagaran et al., (1996) EMBO J. 15: 254-264; Klapper et al., (1999) PNAS 96: 4995-5000). As a key gene for cell survival, HER2 gene amplification and protein overexpression lead to malignant transformation (Neve et al., (2001) Ann Oncol. 12 Suppl 10:S9-13).

HER2 is expressed in a number of cancers, including breast, ovarian, gastric endometrium, bladder, lung, colon, prostate, and head and neck cancers. Overexpression of HER2 is directly associated with poor clinical outcomes. HER2 overexpression occurs in approximately 15-30% of breast cancers and 10-30% of gastric cancers (Iqbal & Iqbal (2014) Molecular Biology International, vol. 2014, Article ID 852748).

In some embodiments the cancer may comprise cells overexpressing HER2. In some embodiments the cancer may comprise cells expressing HER2 for which the antibody, antigen binding fragment, or polypeptide is specific.

Antibodies, antigen binding fragments, polypeptides, conjugates, nucleic acids, vectors, compositions, CARs or cells according to the present invention may be provided for use to treat cancers which express or overexpress HER2. For example, tumour cells overexpressing HER2 may be killed directly by treatment with antibodies, antigen binding fragments, polypeptides, conjugates, CARs or cells according to the present invention, e.g. by cell lysis or apoptosis, by antibody dependent cell-mediated cytotoxicity (ADCC), complement dependent cytotoxicity (CDC), or using anti-HER2 antibody-drug conjugates.

'Treatment' may, for example, be reduction in the development or progression of a disease/condition, alleviation of the symptoms of a disease/condition or reduction in the pathology of a disease/condition. Treatment or alleviation of a disease/condition may be effective to prevent progression of the disease/condition, e.g. to prevent worsening of the condition or to slow the rate of development. In some embodiments treatment or alleviation may lead to an improvement in the disease/condition, e.g. a reduction in the symptoms of the disease/condition or reduction in some other correlate of the severity/activity of the disease/condition. Prevention/prophylaxis of a disease/condition may refer to prevention of a worsening of the condition or prevention of the development of the disease/condition, e.g. preventing an early stage disease/condition developing to a later, chronic, stage.

The treatment may be aimed at prevention of the development or progression of a cancer. As such, the antibodies, antigen binding fragments, polypeptides, conjugates, nucleic acids, vectors, compositions, CARs or cells may be used to formulate pharmaceutical compositions or medicaments and subjects may be prophylactically treated against development of a disease state. This may take place before the onset of symptoms of the disease state, and/or may be given to subjects considered to be at greater risk of development or progression of cancer.

The treatment may be aimed at reducing the number of HER2-expressing cells; inducing cell death of HER2-expressing cells; reducing tumour size; or inhibiting/preventing tumour growth.

In some embodiments a cancer, cell, tumour or subject to be treated has been determined, optionally in vitro, to be HER2-positive (HER2+). In some embodiments a method of treatment or prevention described herein comprises determining, optionally in vitro, whether HER2 is expressed by a cancer, cell, or tumour of the subject to be treated. The determination may be performed in a sample obtained from the subject.

In some embodiments a cancer, cell, tumour or subject to be treated is one that cannot receive or does not respond to other therapies directed at HER2+ cancer. In some embodiments, a subject to be treated cannot receive and/or has been determined that they cannot receive/be treated with trastuzumab and/or pertuzumab. For example, trastuzumab has been associated with cardiotoxic effects (Murray, CMAJ. 2006; 174(1): 36-37).

In some embodiments a cancer, cell, tumour or subject to be treated is one that has already been treated with another therapy directed at HER2+ cancer. In some embodiments, a subject to be treated has already been administered and/or treated with trastuzumab and/or pertuzumab.

Cancer

A cancer may be any unwanted cell proliferation (or any disease manifesting itself by unwanted cell proliferation), neoplasm or tumour or increased risk of or predisposition to the unwanted cell proliferation, neoplasm or tumour. The cancer may be benign or malignant and may be primary or secondary (metastatic). A neoplasm or tumour may be any abnormal growth or proliferation of cells and may be located in any tissue. Examples of tissues include the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

In some embodiments the cancer to be treated is a cancer of the breast. In some embodiments the cancer to be treated is a cancer of the ovary, uterus, lung, e.g. adenocarcinoma of the lung, or the gastrointestinal tract e.g. stomach, salivary duct.

Tumours to be treated may be nervous or non-nervous system tumours. Nervous system tumours may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, haematologic cancer and sarcoma.

In some embodiments the cancer is a cancer encoding or expressing HER2. In some embodiments the cancer is a cancer overexpressing HER2. As used herein, a "HER2-positive cancer" or "HER2+ cancer" is a cancer expressing or overexpressing the HER2 gene and/or protein.

As used herein, "a cancer encoding or expressing HER2" or "a cancer overexpressing HER2" includes any cell encoding or expressing HER2. In some embodiments, the cell may be a cell of a tumour. Such cells may be identified as HER2-positive cells or HER2-positive tumour cells. As used herein, "a tumour cell" includes one or more tumour cells.

A cancer or cell expressing or overexpressing HER2 may be identified by methods including immunohistochemistry (IHC), fluorescence in situ hybridisation (FISH), chromogenic in situ hybridization (CISH) and silver enhanced in situ hybridization (SISH), as well as other methods known in the art (Wolff et al., Arch Pathol Lab Med. 2007; 131(1): 18-43, hereby incorporated by reference in its entirety). Other methods include the HERmark® test, an assay using the VeraTag system to measure total HER2 as well as HER2 homodimers and heterodimers to predict efficacy of anti-HER2 therapies (Shi et al. (2009) Diagn Mol Pathol. March; 18(1):11-21, hereby incorporated by reference in its entirety).

HER2 testing results by IHC fall into three categories: positive, equivocal and negative. A positive status is given a score of 3+ and indicates a uniform intense membrane staining of ≥30% of invasive tumour cells. An equivocal status is given a score of 2+ and indicates complete membrane staining, non-uniform or weak in intensity in at least 10% of the cells or intense complete membrane staining in 530% of tumour cells. A negative status is given a score of 1+ or 0 and indicates that there is weak or incomplete membrane staining in any proportion of tumour cells, or no staining, respectively (Wolff et al., supra). In the context of the present invention, a score of 3+ or 2+ is considered to be "HER2-positive".

Fluorescent (FISH) or chromogenic (CISH) in situ hybridization for HER2 gene amplification has become an integral part of the diagnostic work up for patients with breast cancer. The principles of in situ hybridization are simple: DNA probes complementary to genomic sequences of interest are generated, labeled and then hybridized to the target tissue. FISH/CISH methods can be applied to a wide range of samples: cell lines, frozen tissue, paraffin embedded tissue and micro-tissue arrays. FISH utilizes fluorescence microscopy while CISH employs light microscopy (Gutierrez and Schiff (2011) Arch Pathol Lab Med. 135(1): 55-62). CISH has some advantages in the detection of gene amplification over FISH: 1) permanent staining, samples can be archived; 2) use of bright field microscopy; 3) easy identification of the target cells; 4) tumor heterogeneity is easily assessed, but CISH does not permit a determination of the actual gene copy number (Lambros et al., Hum Pathol. 2007 August; 38(8):1105-22). HER2 FISH positive is defined as an average of >6 HER2 gene copies/nucleus for test systems without an internal control probe or HER2/CEP 17 ratio of more than 2.2, where CEP17 is a centromeric probe for chromosome 17 on which the HER2 gene resides. The equivocal range for HER2 FISH assays is defined as HER/CEP ratios from 1.8 to 2.2 or average gene copy number between 4.0 and 6.0 for those systems without an internal control. Negative HER2 FISH amplification is defined as HER2/CEP17 ratio of less than 1.8 or an average of fewer than four copies of HER2 gene per nucleus for systems without an internal control probe (Wolff et al. supra). In the context of the present invention, a FISH status of positive or equivocal is considered to be "HER2-positive".

Formulating Pharmaceutically Useful Compositions and Medicaments

Antibodies, antigen binding fragments, polypeptides, conjugates, nucleic acids, vectors, CARs and cells according to the present invention may be formulated as pharmaceutical compositions for clinical use and may comprise a pharmaceutically acceptable carrier, diluent, excipient or adjuvant.

In accordance with the present invention methods are also provided for the production of pharmaceutically useful compositions, such methods of production may comprise one or more steps selected from: isolating an antibody, antigen binding fragment, polypeptide, conjugate, nucleic acid, vector, CAR, or cell as described herein; and/or mixing an isolated antibody, antigen binding fragment, polypeptide, conjugate, nucleic acid, vector, CAR, or cell as described herein with a pharmaceutically acceptable carrier, adjuvant, excipient or diluent.

For example, a further aspect of the present invention relates to a method of formulating or producing a medicament or pharmaceutical composition for use in the treatment of a cancer, the method comprising formulating a pharmaceutical composition or medicament by mixing an antibody, antigen binding fragment, polypeptide, conjugate, conjugate, nucleic acid, vector, CAR, or cell as described herein with a pharmaceutically acceptable carrier, adjuvant, excipient or diluent.

Antibodies, antigen binding fragments, polypeptides, conjugates, nucleic acids, vectors, CARs, cells, medicaments and pharmaceutical compositions according to aspects of the present invention may be formulated for administration by a number of routes, including but not limited to, parenteral, intravenous, intra-arterial, intramuscular, intratumoural, oral and nasal. The medicaments and compositions may be formulated for injection or formulated in solid form. Antibodies, antigen binding fragments, polypeptides, conjugates, nucleic acids, vectors, CARs, cells and therapeutic agents may be formulated in fluid or solid form. Fluid formulations may be formulated for administration by injection to a selected region of the human or animal body.

Administration of an antibody, antigen binding fragment, polypeptide, conjugate, nucleic acid, vector, composition, CAR or cell is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins, incorporated herein by reference.

Antibodies, antigen binding fragments, polypeptides, conjugates, nucleic acids, vectors, CARs, cells, medicaments and pharmaceutical compositions may be administered alone or in combination with other treatments, either simultaneously or sequentially dependent upon the condition to be treated. The other treatment may be one or more therapeutic agents.

In this specification an antibody, antigen binding fragment, polypeptide, conjugate, nucleic acid, vector, CAR, cell or composition of the present invention and a therapeutic agent may be administered simultaneously or sequentially. The therapeutic agent may be a chemotherapeutic agent.

In some embodiments, treatment with an antibody, antigen binding fragment, polypeptide, conjugate, nucleic acid, vector, composition, CAR, or cell of the present invention may be accompanied by chemotherapy.

In some embodiments, treatment with an antibody, antigen binding fragment, polypeptide, conjugate, nucleic acid, vector, composition, CAR, or cell of the present invention may be accompanied by at least one anti-cancer agent. "At least one anti-cancer agent" refers to one, or two, or three, or four, or more agents that are effective in the treatment of malignant, or cancerous, disease such as the cancers described herein.

Simultaneous administration refers to administration of the antibody, antigen binding fragment, polypeptide, conjugate, nucleic acid, vector, composition, CAR, or cell together with the therapeutic or anti-cancer agent, for example as a pharmaceutical composition containing both agents (combined preparation), or immediately after each other and optionally via the same route of administration, e.g. to the same artery, vein or other blood vessel.

Sequential administration refers to administration of one of the antibody, antigen binding fragment, polypeptide, conjugate, nucleic acid, vector, composition, CAR, or cell or therapeutic agent/anti-cancer agent followed after a given time interval by separate administration of the other agent. It is not required that the two agents are administered by the same route, although this is the case in some embodiments. The time interval may be any time interval.

A therapeutic agent or anti-cancer agent as described herein may be an anti-HER2 antibody or an agent which targets HER2. In some embodiments a therapeutic agent or anti-cancer agent as described herein is one or more of trastuzumab (Herceptin®), trastuzumab emtansine (Kadcyla®), lapatinib (Tyverb®), and/or pertuzumab (Perjeta®). In some embodiments an antibody, antigen-binding molecule or polypeptide as described herein is administered in combination, e.g. simultaneously or sequentially, with one or more of the above agents, such as trastuzumab (Herceptin®) and/or pertuzumab (Perjeta®).

A therapeutic agent or anti-cancer agent as described herein may be formulated so as to be suitable for injection or infusion to a tumour or to the blood.

Chemotherapy/Radiotherapy

Chemotherapy and radiotherapy respectively refer to treatment of a cancer with a drug or with ionising radiation (e.g. radiotherapy using X-rays or γ-rays).

The drug may be a chemical entity, e.g. small molecule pharmaceutical, antibiotic, DNA intercalator, protein inhibitor (e.g. kinase inhibitor), or a biological agent, e.g. antibody, antibody fragment, nucleic acid or peptide aptamer, nucleic acid (e.g. DNA, RNA), peptide, polypeptide, or protein. The drug may be formulated as a pharmaceutical composition or medicament. The formulation may comprise one or more drugs (e.g. one or more active agents) together with one or more pharmaceutically acceptable diluents, excipients or carriers.

A treatment may involve administration of more than one drug. A drug may be administered alone or in combination with other treatments, either simultaneously or sequentially dependent upon the condition to be treated. For example, the chemotherapy may be a co-therapy involving administration of two drugs, one or more of which may be intended to treat the cancer.

The chemotherapy may be administered by one or more routes of administration, e.g. parenteral, intravenous injection, oral, subcutaneous, intradermal or intratumoral.

The chemotherapy may be administered according to a treatment regime. The treatment regime may be a pre-determined timetable, plan, scheme or schedule of chemotherapy administration which may be prepared by a physician or medical practitioner and may be tailored to suit the patient requiring treatment.

The treatment regime may indicate one or more of: the type of chemotherapy to administer to the patient; the dose of each drug or radiation; the time interval between administrations; the length of each treatment; the number and nature of any treatment holidays, if any etc. For a co-therapy a single treatment regime may be provided which indicates how each drug is to be administered.

Chemotherapeutic drugs and biologics may be selected from: alkylating agents such as cisplatin, carboplatin, mechlorethamine, cyclophosphamide, chlorambucil, ifosfamide; purine or pyrimidine anti-metabolites such as azathiopurine or mercaptopurine; alkaloids and terpenoids, such as *vinca* alkaloids (e.g. vincristine, vinblastine, vinorelbine, vindesine), podophyllotoxin, etoposide, teniposide, taxanes such as paclitaxel (Taxol™), docetaxel; topoisomerase inhibitors such as the type I topoisomerase inhibitors camptothecins irinotecan and topotecan, or the type II topoisomerase inhibitors amsacrine, etoposide, etoposide phosphate, teniposide; antitumor antibiotics (e.g. anthracyline antibiotics) such as dactinomycin, doxorubicin (Adriamycin™), epirubicin, bleomycin, rapamycin; antibody based agents, such as anti-PD-1 antibodies, anti-PD-L1 antibodies, anti-TIM-3 antibodies, anti-CTLA-4, anti-4-1BB, anti-GITR, anti-CD27, anti-BLTA, anti-OX43, anti-VEGF, anti-TNFα, anti-IL-2, antiGpIIb/IIIa, anti-CD-52, anti-CD20, anti-RSV, anti-HER2/neu(erbB2), anti-TNF receptor, anti-EGFR antibodies, monoclonal antibodies or antibody fragments, examples include: cetuximab, panitumumab, infliximab, basiliximab, bevacizumab (Avastin®), abciximab, daclizumab, gemtuzumab, alemtuzumab, rituximab (Mabthera®), palivizumab, trastuzumab, etanercept, adalimumab, nimotuzumab; EGFR inhibitors such as erlotinib, cetuximab and gefitinib; anti-angiogenic agents such as bevacizumab (Avastin®); cancer vaccines such as Sipuleucel-T (Provenge®).

Further chemotherapeutic drugs may be selected from: 13-cis-Retinoic Acid, 2-Chlorodeoxyadenosine, 5-Azacitidine, 5-Fluorouracil, 6-Mercaptopurine, 6-Thioguanine, Abraxane, Accutane®, Actinomycin-D Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Aranesp®, Aredia®, Arimidex®, Aromasin®, Arranon®, Arsenic Trioxide, Asparaginase, ATRA Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, Calcium Leucovorin, Campath®, Camptosar®, Camptothecin-11, Capecitabine, Carac™, Carboplatin, Carmustine, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine Cytosar-U®, Cytoxan®, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Eligard™, Ellence™, Eloxatin™, Elspar®, Emcyt®, Epirubicin, Epoetin Alfa, Erbitux, Erlotinib, Erwinia L-asparaginase, Estramustine, Ethyol Etopophos®, Etoposide, Etoposide Phosphate, Eulexin®, Everolimus, Evista®, Exemestane, Faslodex®, Femara®, Filgrastim, Floxuridine, Fludara®, Fludarabine, Fluoroplex®, Fluorouracil, Fluoxymesterone, Flutamide, Folinic Acid, FUDR®, Fulvestrant, Gefitinib, Gemcitabine, Gemtuzumab ozogamicin, Gleevec™, Gliadel® Wafer, Goserelin, Granulocyte-Colony Stimulating Factor, Granulocyte Macrophage Colony Stimulating Factor, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin- C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™ Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant Purinethol®, Raloxifene, Revlimid®, Rheumatrex®, Rituxan®, Rituximab, Roferon-A® (Interferon Alfa-2a), Rubex®, Rubidomycin hydrochloride, Sandostatin® Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, Zometa®.

In some embodiments the antibody/antigen binding fragment according to the present invention is administered in combination with one or more of doxorubicin, epirubicin, paclitaxel, docetaxel, fluorouracil, cyclophosphamide, methotrexate and capecitabine.

Dosage Regimes

Multiple doses of the antibody, antigen binding fragment, polypeptide, conjugate, nucleic acid, vector, CAR or cell may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

Kits

In some aspects of the present invention a kit of parts is provided. In some embodiments the kit may have at least one container having a predetermined quantity of the antibody, antigen binding fragment, polypeptide, conjugate, nucleic acid, vector, CAR or cell according to the invention. The kit may provide the antibody, antigen binding fragment, polypeptide, conjugate, nucleic acid, vector, CAR or cell in the form of a medicament or pharmaceutical composition, and may be provided together with instructions for administration to a patient in order to treat a specified disease or condition. The antibody, antigen binding fragment or polypeptide may be formulated so as to be suitable for injection or infusion to a tumour or to the blood.

In some embodiments the kit may further comprise at least one container having a predetermined quantity of another therapeutic agent (e.g. chemotherapeutic agent or anti-cancer agent). In such embodiments, the kit may also comprise a second medicament or pharmaceutical composition such that the two medicaments or pharmaceutical compositions may be administered simultaneously or separately such that they provide a combined treatment for the specific disease or condition. The therapeutic agent or anti-cancer agent may also be formulated so as to be suitable for injection or infusion to a tumour or to the blood.

Subjects

The subject to be treated with an antibody, antigen binding fragment, polypeptide, conjugate, nucleic acid, vector, CAR or cell according to the invention may be any animal or human. The subject is preferably mammalian, more preferably human. The subject may be a non-human mammal, but is more preferably human. The subject may be male or female. The subject may be a patient. A subject may have been diagnosed with a disease or condition requiring treatment, or be suspected of having such a disease or condition.

Sequence Identity

Percentage (%) sequence identity is defined as the percentage of amino acid residues in a candidate sequence that are identical with residues in the given listed sequence (referred to by the SEQ ID NO) after aligning the sequences and introducing gaps if necessary, to achieve the maximum sequence identity, and not considering any conservative substitutions as part of the sequence identity. Sequence identity is preferably calculated over the entire length of the respective sequences.

Where the aligned sequences are of different length, sequence identity of the shorter comparison sequence may be determined over the entire length of the longer given sequence or, where the comparison sequence is longer than the given sequence, sequence identity of the comparison sequence may be determined over the entire length of the shorter given sequence.

Alignment for purposes of determining percent amino acid sequence identity can be achieved in various ways known to a person of skill in the art, for instance, using publicly available computer software such as ClustalW 1.82., ClustalW, T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4. The default parameters of ClustalO are described in Siding, J. (2005) 'Protein homology detection by HMM-HMM comparison'. Bioinformatics 21, 951-960.

Recombinant Production

The immunogens, antibodies, fragments, polypeptides, conjugates and CARs according the invention may be produced by recombinant expression. Molecular biology techniques suitable for recombinant production are well known in the art, such as those set out in Green and Sambrook, Molecular Cloning: A Laboratory Manual ($4^{th}$ Edition), Cold Spring Harbor Press, 2012, which is hereby incorporated by reference in its entirety.

In some embodiments, a nucleic acid described herein is purified or isolated, e.g. from other nucleic acid, or naturally-occurring biological material. In some embodiments the nucleic acid(s) comprise or consist of DNA and/or RNA.

Expression may be from a nucleotide sequence. The nucleotide sequence may be contained in a vector. A "vector" as used herein is an oligonucleotide molecule (DNA or RNA) used as a vehicle to transfer foreign genetic material into a cell. The vector may be an expression vector for expression of the foreign genetic material in the cell. Such vectors may include a promoter sequence operably linked to the nucleotide sequence encoding the sequence to be expressed. A vector may also include a termination codon and expression enhancers. Any suitable vectors, promoters, enhancers and termination codons known in the art may be used to express a peptide or polypeptide from a vector according to the invention. In some embodiments, the vector may be a plasmid, MAC, virus, etc. In some embodiments, the vector may be a eukaryotic expression vector, e.g. a vector comprising the elements necessary for expression of protein from the vector in a eukaryotic cell. In some embodiments, the vector may be a mammalian expression vector, e.g. comprising a cytomegalovirus (CMV) or SV40 promoter to drive protein expression.

The term "operably linked" may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. The resulting transcript may then be translated into a desired peptide or polypeptide.

For recombinant production according to the invention, any cell suitable for the expression of polypeptides may be used. The cell may be a prokaryote or eukaryote. In some embodiments the cell is a prokaryotic cell, such as a cell of archaea or bacteria. In some embodiments the bacteria may be Gram-negative bacteria such as bacteria of the family Enterobacteriaceae, for example *Escherichia coli*.

In some embodiments, the cell is a eukaryotic cell such as a yeast cell, a plant cell, insect cell or a mammalian cell, e.g. CHO, HEK, HeLa or COS cells. In some embodiments the host cell is a non-human cell, e.g. a non-human mammalian cell.

In some cases the cell is not a prokaryotic cell because some prokaryotic cells do not allow for the same folding or post-translational modifications as eukaryotic cells. In addition, very high expression levels are possible in eukaryotes and proteins can be easier to purify from eukaryotes using appropriate tags. Specific plasmids may also be utilised which enhance secretion of the protein into the media.

Production may involve culture or fermentation of a eukaryotic cell modified to express the peptide or polypeptide. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted peptide or polypeptide. Culture, fermentation and separation techniques are well known to those of skill in the art, and are described, for example, in Green and Sambrook, Molecular Cloning: A Laboratory Manual ($4^{th}$ Edition; incorporated by reference herein above).

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culture of cells that express the immunogen, antibody, fragment, polypeptide, conjugate or CAR, the peptide/polypeptide of interest is preferably isolated. Any suitable method for separating proteins from cell culture known in the art may be used. In order to isolate the peptide/polypeptide from a culture, it may be necessary to first separate the cultured cells from media containing the peptide/polypeptide of interest. If the peptide/polypeptide of interest is secreted from the cells, the cells may be separated from the culture media that contains the secreted peptide/polypeptide of interest by centrifugation. If the peptide/polypeptide of interest collects within the cell it will be necessary to disrupt the cells prior to centrifugation, for example using sonification, rapid freeze-thaw or osmotic lysis. Centrifugation will produce a pellet containing the cultured cells, or cell debris of the cultured cells, and a supernatant containing culture medium and the peptide/polypeptide of interest.

It may then be desirable to isolate the peptide/polypeptide of interest from the supernatant or culture medium, which may contain other protein and non-protein components. A common approach to separating protein components from a supernatant or culture medium is by precipitation. Proteins of different solubilities are precipitated at different concentrations of precipitating agent such as ammonium sulfate. For example, at low concentrations of precipitating agent, water soluble proteins are extracted. Thus, by adding different increasing concentrations of precipitating agent, proteins of different solubilities may be distinguished. Dialysis may be subsequently used to remove ammonium sulfate from the separated proteins.

Other methods for distinguishing different proteins are known in the art, for example ion exchange chromatography and size chromatography. These may be used as an alternative to precipitation, or may be performed subsequently to precipitation.

Once the peptide/polypeptide of interest has been isolated from culture it may be desired or necessary to concentrate the peptide or polypeptide. A number of methods for concentrating proteins are known in the art, such as ultrafiltration or lyophilisation.

Sequences

| SEQ ID NO: | Description | Sequence |
|---|---|---|
| 1 | P1A3 (lambda) (light chain VD) (FIG. 1A) | QAVVTQEPSL SVSPGGTVTL TC**GLSSGSVS TGHYASWYQQ TPGQAPRTLF YNTNTRSS**GV PDRFSGSIVG NKAALTITGA QADDESDYYC **VLYVGDGIWV** FGGGTKLTVL GQPKAAPSVT LFPPSSEELQ ANKATLVCLI SDFYPGAVTV AWKADSSPVK AGVETTTPSK QSNNKYAASS YLSLTPEQWK SHKSYSCQVT HEGSTVEKTV APTECS |

-continued

Sequences

| SEQ ID NO: | Description | Sequence |
|---|---|---|
| 2 | P1C5 (lambda) (light chain VD) (FIG. 1B) | QTVVTQEPSF SVSPGGTVTL TC**GLSSGSVS TGYYPS**WYQQ TPGQAPRTLI Y**STNSRSS**GV<br>PDRFSGSILG NKAALTITGA QADDESDYYC VLYMGSGISV FGGGTKLTVL GQPKAAPSVT<br>LFPPSSEELQ ANKATLVCLI SDFYPGAVTV AWKADSSPVK AGVETTTPSK QSNNKYAASS<br>YLSLTPEQWK SHKSYSCQVT HEGSTVEKTV APTECS |
| 3 | P1E4 (lambda) (light chain VD) (FIG. 1C) | QTVVTQEPSF SVSPGGTVTL TC**GLSSGSVS TSYYPS**WYQQ IPGQAPRTLI Y**TTNIRSS**GV<br>PDRFGGSILG NKAALTITGA QAEDESDYYC **MLYMGSGIWV** FGGGTKLTVL GQPKTAPSVT<br>LFPPSSEELQ ANKATLVCLI SDFYPGAVTV AWKADSSPVK AGVETTTPSK QSNNKYAASS<br>YLSLTPEQWK SHKSYSCQVT HEGSTVEKTV APAECS |
| 4 | P1F1 (lambda) (light chain VD) (FIG. 1D) | QTVVTQEPSF SVSPGGTVTL TC**GLSSGSVS TSYYPS**WYQQ TPGQAPRTLI Y**STNTRSS**GV<br>PDRFSGSILG NKAALTITGA QADDESDYYC **VLYMGSGIWV** FGGGTKLTVL GQPKAAPSVT<br>LFPPSSEELQ ANKATLVCLI SDFYPGAVTV AWKADSSPVK AGVETTTPSK QSNNKYAASS<br>YLSLTPEQWK SHKSYSCQVT HEGSTVEKTV APTECS |
| 5 | P1A (heavy chain VD; FIG. 2A) | EVQLVQSGTE VKKPGASVRV SCKSSGYTFT **SYYIH**WVRQA PGQGLEWMA**I INPGNGDTNY**<br>**AQRFQG**RVTM TRDTSTSTVY MELRSLRSDD TAVYFCAR**EI ASYSGSYYDY** WGQGTLVTVS S |
| 6 | P1C5 (heavy chain VD; FIG. 2B) | QVQLQESGPG LVKPSETLSL TCTVSGGSIS **SSSYYWG**WIR QPPGKGLEWI G**SIYYSGSTY**<br>**YNPSLKS**RVT ISVDTSKNQF SLKLSSVTAA DTAVYYCAR**Y APDSSGYLVA FDI**WGQGTMV<br>TVSS |
| 7 | P1E4 (heavy chain VD; FIG. 2C) | QVQLQQWGAG LLKPSETLSL TCAVYGGSFS **GYYWS**WIRQP PGKGLEWIG**E INHSGSTNYN**<br>**PSLKS**RVTIS VDTSKNQFSL KLSSVTTADT AVYYCAR**MGI NSGGYLYGMD V**WGQGTTVTV SS |
| 8 | P1F1 (heavy chain VD; FIG. 2D) | QVQLVESGPG LVKPSGTLSL TCAVSGGSIS **SSNWWS**WVRQ PPGKGLEWIG **EIYHSGSTNY**<br>**NPSLKS**RVTI SVDTSKNQFS LKLSSVTAAD TAVYYCAR**MG ANSGGYLYGM DV**WGQGTTVT VSS |
| 9 | LC-CDR1 consensus | $GLSSGSVSTX_1X_2YX_3S$ |
| 10 | LC-CDR2 consensus | $X_4TNX_5RSS$ |
| 11 | LC-CDR3 consensus | $X_6LYX_7GX_8GIX_9V$ |
| 12 | HC-CDR1 consensus | $X_{10}X_{11}X_{12}X_{13}X_{14}X_{15}X_{16}$ |
| 13 | HC-CDR2 consensus | $X_{17}X_{18}X_{19}X_{20}X_{21}X_{22}GX_{23}TX_{24}YX_{25}X_{26}X_{27}X_{28}X_{29}X_{30}$ |
| 14 | HC-CDR3 consensus | $X_{31}X_{32}X_{33}X_{34}X_{35}SX_{36}X_{37}YX_{38}X_{39}X_{40}X_{41}X_{42}X_{43}$ |
| 15 | P1A3 LC-CDR1 | GLSSGSVSTGHYAS |
| 16 | P1A3 LC-CDR2 | NTNTRSS |
| 17 | P1A3 LC-CDR3 | VLYVGDGIWV |
| 18 | P1A3 HC-CDR1 | SYYIH |
| 19 | P1A3 HC-CDR2 | IINPGNGDTNYAQRFQG |
| 20 | P1A3 HC-CDR3<br>PFG3 HC-CDR3 | EIASYSGSYYDY |
| 21 | P1C5 LC-CDR1 | GLSSGSVSTGYYPS |
| 22 | P1C5 LC-CDR2 | STNSRSS |
| 23 | P1C5 LC-CDR3<br>PFG3 LC-CDR3 | VLYMGSGISV |
| 24 | P1C5 HC-CDR1<br>PFF5 HC-CDR1 | SSSYYWG |

-continued

| Sequences | | |
|---|---|---|
| SEQ ID NO: | Description | Sequence |
| 25 | P1C5 HC-CDR2<br>PFF5 HC-CDR2 | SIYYSGSTYYNPSLKS |
| 26 | P1C5 HC-CDR3<br>PFF5 HC-CDR3 | YAPDSSGYLVAFDI |
| 27 | P1E4 LC-CDR1<br>P1F1 LC-CDR1 | GLSSGSVSTSYYPS |
| 28 | P1E4 LC-CDR2 | TTNIRSS |
| 29 | P1E4 LC-CDR3 | MLYMGSGIWV |
| 30 | P1E4 HC-CDR1<br>P1D2 HC-CDR1 | GYYWS |
| 31 | P1E4 HC-CDR2<br>P1D2 HC-CDR2 | EINHSGSTNYNPSLKS |
| 32 | P1E4 HC-CDR3 | MGINSGGYLYGMDV |
| 33 | P1F1 LC-CDR2<br>PFF5 LC-CDR2 | STNTRSS |
| 34 | P1F1 LC-CDR3 | VLYMGSGIWV |
| 35 | P1F1 HC-CDR1 | SSNWWS |
| 36 | P1F1 HC-CDR2 | EIYHSGSTNYNPSLKS |
| 37 | P1F1 HC-CDR3 | MGANSGGYLYGMDV |
| 38 | P1A3 (lambda)<br>LC Nucleotide<br>sequence | CAG GCT GTG GTG ACT CAG GAG CCA TCG TTG TCA GTG TCC CCT GGA GGG ACA<br>GTC ACA CTC ACT TGT **GGC TTG AGC TCT GGC TCA GTC TCT ACT GGT CAC TAC**<br>**GCC AGC** TGG TAC CAG CAG ACC CCA GGC CAG GCT CCA CGC ACG CTC TTC TAC<br>**AAC ACA AAC ACT CGC TCT TCT** GGG GTC CCT GAT CGC TTC TCT GGC TCC ATC<br>GTT GGG AAC AAA GCT GCC CTC ACC ATC ACG GGG GCC CAG GCA GAT GAT GAA<br>TCT GAC TAT TAC TGT **GTG CTG TAT GTG GGT GAT GGC ATT TGG GTT** TTC GGC<br>GGA GGG ACC AAG CTG ACC GTC CTA GGT CAG CCC AAG GCT GCC CCC TCG GTC<br>ACT CTG TTC CCA CCC TCC TCT GAG GAG CTT CAA GCC AAC AAG GCC ACA CTG<br>GTG TGT CTC ATA AGT GAC TTC TAC CCG GGA GCC GTG ACA GTG GCC TGG AAG<br>GCA GAT AGC AGC CCC GTC AAG GCG GGA GTG GAG ACC ACC ACA CCC TCC AAA<br>CAA AGC AAC AAC AAG TAC GCG GCC AGC AGC TAC CTG AGC CTG ACG CCT GAG<br>CAG TGG AAG TCC CAC AAA AGC TAC AGC TGC CAG GTC ACG CAT GAA GGG AGC<br>ACC GTG GAG AAG ACA GTG GCC CCT ACA GAA TGT TCA |
| 39 | P1C5 (lambda)<br>LC Nucleotide<br>sequence | CAG ACT GTG GTG ACT CAG GAG CCA TCG TTC TCA GTG TCC CCT GGA GGG ACA<br>GTC ACA CTC ACT TGT **GGC TTG AGC TCT GGC TCA GTC TCT ACT GGT TAC TAC**<br>**CCC AGC** TGG TAC CAG CAG ACC CCA GGC CAG GCT CCA CGC ACG CTC ATC TAC<br>**AGC ACA AAC AGT CGC TCT TCT** GGG GTC CCT GAT CGC TTC TCT GGC TCC ATC<br>CTT GGG AAC AAA GCT GCC CTC ACC ATC ACG GGG GCC CAG GCA GAT GAT GAA<br>TCT GAT TAT TAC TGT **GTG CTG TAT ATG GGT AGT GGC ATT TCG GTG** TTC GGC<br>GGA GGG ACC AAG CTG ACC GTC CTA GGT CAG CCC AAG GCT GCC CCC TCG GTC<br>ACT CTG TTC CCA CCC TCC TCT GAG GAG CTT CAA GCC AAC AAG GCC ACA CTG<br>GTG TGT CTC ATA AGT GAC TTC TAC CCG GGA GCC GTG ACA GTG GCC TGG AAG<br>GCA GAT AGC AGC CCC GTC AAG GCG GGA GTG GAG ACC ACC ACA CCC TCC AAA<br>CAA AGC AAC AAC AAG TAC GCG GCC AGC AGC TAC CTG AGC CTG ACG CCT GAG<br>CAG TGG AAG TCC CAC AAA AGC TAC AGC TGC CAG GTC ACG CAT GAA GGG AGC<br>ACC GTG GAG AAG ACA GTG GCC CCT ACA GAA TGT TCA |
| 40 | P1E4 (lambda)<br>LC Nucleotide<br>sequence | CAG ACT GTG GTG ACT CAG GAG CCA TCG TTC TCA GTG TCC CCT GGA GGG ACC<br>GTC ACA CTC ACT TGT **GGC CTG AGC TCT GGC TCA GTC TCT ACT AGT TAC TAC**<br>**CCC AGC** TGG TAC CAA CAG ATT CCA GGC CAG GCT CCA CGC ACG CTC ATT TAC<br>**ACC ACA AAC ATT CGC TCT TCT** GGG GTC CCT GAT CGC TTC GGT GGC TCC ATC<br>CTT GGG AAC AAA GCT GCC CTC ACC ATC ACG GGG GCC CAG GCA GAA GAT GAA<br>TCT GAT TAC TAC TGT **ATG CTC TAT ATG GGG AGT GGC ATT TGG GTG** TTC GGC<br>GGA GGG ACC AAA CTG ACC GTC CTA GGT CAG CCC AAG ACT GCC CCC TCG GTC<br>ACT CTG TTC CCA CCC TCC TCT GAG GAG CTT CAA GCC AAC AAG GCC ACA CTG<br>GTG TGT CTC ATA AGT GAC TTC TAC CCG GGA GCC GTG ACA GTG GCC TGG AAG<br>GCA GAT AGC AGC CCC GTC AAG GCG GGA GTG GAG ACC ACC ACA CCC TCC AAA<br>CAA AGC AAC AAC AAG TAC GCG GCC AGC AGC TAC CTG AGC CTG ACG CCT GAG<br>CAG TGG AAG TCC CAC AAA AGC TAC AGC TGC CAG GTC ACG CAT GAA GGG AGC<br>ACC GTG GAG AAG ACA GTG GCC CCT GCA GAA TGC TCT |

-continued

Sequences

| SEQ ID NO: | Description | Sequence |
|---|---|---|
| 41 | P1F1 (lambda) LC VD Nucleotide sequence | CAG ACT GTG GTG ACT CAG GAG CCA TCG TTC TCA GTG TCC CCT GGA GGG ACA GTC ACA CTC ACT TGT **GGC TTG AGC TCT GGC TCA GTC TCT ACT AGT TAC TAC CCC AGC** TGG TAC CAG CAG ACC CCA GGC CAG GCT CCA CGC ACG CTC ATC TAC **AGC ACA AAC ACT CGC TCT TCT** GGG GTC CCT GAT CGC TTC TCT GGC TCC ATC CTT GGG AAC AAA GCT GCC CTC ACC ATC ACG GGG GCC CAG GCA GAT GAT GAA TCT GAT TAT TAC TGT **GTG CTG TAT ATG GGT AGT GGC ATT TGG GTG** TTC GGC GGA GGG ACC AAG CTG ACC GTC CTA GGT CAG CCC AAG GCT GCC CCC TCG GTC ACT CTG TTC CCA CCC TCC TCT GAG GAG CTT CAA GCC AAC AAG GCC ACA CTG GTG TGT CTC ATA AGT GAC TTC TAC CCG GGA GCC GTG ACA GTG GCC TGG AAG GCA GAT AGC AGC CCC GTC AAG GCG GGA GTG GAG ACC ACC ACA CCC TCC AAA CAA AGC AAC AAC AAG TAC GCG GCC AGC AGC TAC CTG AGC CTG ACG CCT GAG CAG TGG AAG TCC CAC AAA AGC TAC AGC TGC CAG GTC ACG CAT GAA GGG AGC ACC GTG GAG AAG ACA GTG GCC CCT ACA GAA TGT TCA |
| 42 | P1A3 HC VD nucleotide sequence | GAG GTC CAG CTG GTG CAG TCT GGG ACT GAG GTG AAG AAG CCT GGG GCC TCA GTG AGG GTT TCC TGC AAG TCA TCT GGA TAC ACC TTC ACC **AGC TAC TAT ATA CAC** TGG GTG CGA CAG GCC CCT GGA CAA GGA CTT GAG TGG ATG GCA **ATA ATC AAC CCT GGT AAT GGT GAC ACA AAC TAC GCA CAG AGG TTC CAG GGC** AGA GTC ACC ATG ACC AGG GAC ACG TCC ACG AGC ACA GTC TAC ATG GAG CTG AGG AGC CTG AGA TCT GAC GAC ACG GCC GTC TAT TTC TGT GCG AGA **GAG ATT GCC TCC TAT AGT GGG AGC TAC TAC GAC TAC** TGG GGC CAG GGA ACC CTG GTC ACC GTC TCA AGC |
| 43 | P1C5 HC VD nucleotide sequence | CAG GTG CAG CTG CAG GAG TCG GGC CCA GGA CTG GTG AAG CCT TCG GAG ACC CTG TCC CTC ACC TGC ACT GTC TCT GGT GGC TCC ATC AGC **AGT AGT AGT TAC TAC TGG GGC** TGG ATC CGC CAG CCC CCA GGG AAG GGG CTG GAG TGG ATT GGG **AGT ATC TAT TAT AGT GGG AGC ACC TAC TAC AAC CCG TCC CTC AAG AGT** CGA GTC ACC ATA TCC GTA GAC ACG TCC AAG AAC CAG TTC TCC CTG AAG CTG AGC TCT GTG ACC GCC GCA GAC ACG GCT GTG TAT TAC TGT GCG AGA **TAC GCG CCT GAT AGT AGT GGT TAC TTG GTG GCT TTT GAT ATC** TGG GGC CAA GGG ACA ATG GTC ACC GTC TCA AGC |
| 44 | P1E4 HC VD nucleotide sequence | CAG GTG CAG CTA CAG CAG TGG GGC GCA GGA CTG TTG AAG CCT TCG GAG ACC CTG TCC CTC ACC TGC GCT GTC TAT GGT GGG TCC TTC AGT **GGT TAC TAC TGG AGC** TGG ATC CGC CAG CCC CCA GGG AAG GGG CTG GAG TGG ATT GGG **GAA ATC AAT CAT AGT GGA AGC ACC AAC TAC AAC CCG TCC CTC AAG AGT** CGA GTC ACC ATA TCA GTA GAC ACG TCC AAG AAC CAG TTC TCC CTG AAG CTG AGC TCT GTG ACC ACT GCG GAC ACG GCC GTG TAT TAC TGT GCG AGG **ATG GGA ATA AAT AGT GGT GGT TAT CTC TAC GGT ATG GAC GTC** TGG GGC CAA GGG ACC ACG GTC ACC GTC TCA AGC |
| 45 | P1F1 HC VD nucleotide sequence | CAG GTG CAG CTG GTG GAG TCT GGC CCA GGA CTG GTG AAG CCT TCG GGG ACC CTG TCC CTC ACC TGC GCT GTC TCT GGT GGC TCC ATC AGC **AGT AGT AAC TGG TGG AGT** TGG GTC CGC CAG CCC CCA GGG AAG GGG CTG GAG TGG ATT GGG **GAA ATC TAT CAT AGT GGG AGC ACC AAC TAC AAC CCG TCC CTC AAG AGT** CGA GTC ACC ATA TCA GTA GAC ACG TCC AAG AAC CAG TTC TCC CTG AAG CTG AGC TCT GTG ACC GCT GCG GAC ACG GCC GTG TAT TAC TGT GCG AGG **ATG GGA GCA AAT AGT GGT GGG TAT CTC TAC GGT ATG GAC GTC** TGG GGC CAA GGG ACC ACG GTC ACC GTC TCA AGC |
| 46 | P1A3 (lambda) LC-CDR1 Nucleotide sequence | GGC TTG AGC TCT GGC TCA GTC TCT ACT GGT CAC TAC GCC AGC |
| 47 | P1A3 (lambda) LC-CDR2 Nucleotide sequence | AAC ACA AAC ACT CGC TCT TCT |
| 48 | P1A3 (lambda) LC-CDR3 Nucleotide sequence | GTG CTG TAT GTG GGT GAT GGC ATT TGG GTT |
| 49 | P1A3 HC-CDR1 nucleotide sequence | AGC TAC TAT ATA CAC |
| 50 | P1A3 HC-CDR2 nucleotide sequence | ATA ATC AAC CCT GGT AAT GGT GAC ACA AAC TAC GCA CAG AGG TTC CAG GGC |

-continued

| Sequences | | |
|---|---|---|
| SEQ ID NO: | Description | Sequence |
| 51 | P1A3 HC-CDR3 nucleotide sequence | GAG ATT GCC TCC TAT AGT GGG AGC TAC TAC GAC TAC |
| 52 | P1C5 (lambda) LC-CDR1 Nucleotide sequence | GGC TTG AGC TCT GGC TCA GTC TCT ACT GGT TAC TAC CCC AGC |
| 53 | P1C5 (lambda) LC-CDR2 Nucleotide sequence | AGC ACA AAC AGT CGC TCT TCT |
| 54 | P1C5 (lambda) LC-CDR3 Nucleotide sequence | GTG CTG TAT ATG GGT AGT GGC ATT TCG GTG |
| 55 | P1C5 HC-CDR1 nucleotide sequence | AGT AGT AGT TAC TAC TGG GGC |
| 56 | P1C5 HC-CDR2 nucleotide sequence | AGT ATC TAT TAT AGT GGG AGC ACC TAC TAC AAC CCG TCC CTC AAG AGT |
| 57 | P1C5 HC-CDR3 nucleotide sequence | TAC GCG CCT GAT AGT AGT GGT TAC TTG GTG GCT TTT GAT ATC |
| 58 | P1E4 (lambda) LC-CDR1 Nucleotide sequence | GGC CTG AGC TCT GGC TCA GTC TCT ACT AGT TAC TAC CCC AGC |
| 59 | P1E4 (lambda) LC-CDR2 Nucleotide sequence | ACC ACA AAC ATT CGC TCT TCT |
| 60 | P1E4 (lambda) LC-CDR3 Nucleotide sequence | ATG CTC TAT ATG GGG AGT GGC ATT TGG GTG |
| 61 | P1E4 HC-CDR1 nucleotide sequence | GGT TAC TAC TGG AGC |
| 62 | P1E4 HC-CDR2 nucleotide sequence | GAA ATC AAT CAT AGT GGA AGC ACC AAC TAC AAC CCG TCC CTC AAG AGT |
| 63 | P1E4 HC-CDR3 nucleotide sequence | ATG GGA ATA AAT AGT GGT GGT TAT CTC TAC GGT ATG GAC GTC |
| 64 | P1F1 (lambda) LC-CDR1 Nucleotide sequence | GGC TTG AGC TCT GGC TCA GTC TCT ACT AGT TAC TAC CCC AGC |
| 65 | P1F1 (lambda) LC-CDR2 Nucleotide sequence | AGC ACA AAC ACT CGC TCT TCT |

-continued

Sequences

| SEQ ID NO: | Description | Sequence |
|---|---|---|
| 66 | P1F1 (lambda) LC-CDR3 Nucleotide sequence | GTG CTG TAT ATG GGT AGT GGC ATT TGG GTG |
| 67 | P1F1 HC-CDRI nucleotide sequence | AGT AGT AAC TGG TGG AGT |
| 68 | P1F1 HC-CDR2 nucleotide sequence | GAA ATC TAT CAT AGT GGG AGC ACC AAC TAC AAC CCG TCC CTC AAG AGT |
| 69 | P1F1 HC-CDR3 nucleotide sequence | ATG GGA GCA AAT AGT GGT GGG TAT CTC TAC GGT ATG GAC GTC |
| 70 | PFA1 Light chain nucleotide sequence | GAAATTGTGCTGACTCAGTCTCCATTCTCCCTGCCCGTCACCCCTGGAGAGCCGGCCTCCATCTCCTGC AGGTCTAGTCAGAGCCTCCTGCATAGTAATGGATTCAACTATTTGGATTGGTACCTGCAGAAGCCAGGG CAGTCTCCACAACTCCTGATCTATTTGGGTTCTAATCGGGCCTCCGGGGTCCCTGACAGGTTCAGTGGC AGTGGATCAGGCACAGATTTTACACTGAAAATCAGCAGAGTGGAGGCTGAGGATGTTGGGGTTTATTAC TGCATGCAAGGTCTACAGACTCCGTACACTTTTGGCCAGGGGACCAAGCTGGAGATCAAACGAACTGTG GCTGCACCATCTGTCTTCATCTTCCCGCCATCTGATGAGCAGTTGAAATCTGGAACTGCCTCTGTTGTG TGCCTGCTGAATAACTTCTATCCCAGAGAGGCCAAAGTACAGTGGAAGGTGGATAACGCCCTCCAATCG GGTAACTCCCAGGAGAGTGTCACAGAGCAGGACAGCAAGGACAGCACCTACAGCCTCAGCAGCACCCTG ACGCTGAGCAAAGCAGACTACGAGAAACACAAAGTCTACGCCTGCGAAGTCACCCATCAGGGCCTGAGC TCGCCCGTCACAAAGAGCTTCAACAGGGGAGAGTGT |
| 71 | PFA1 Heavy chain nucleotide sequence | GAGGTCCAGCTGGTACAGTCTGGGGGAGGCGTGGTCCAGCCTGGGAGGTCCCTGAGACTCTCCTGTGCA GCGTCTGGATTCACCTTCAGTAGCTATGGCATGCACTGGGTCCGCCAGGCTCCAGGCAAGGGGCTGGAG TGGGTGGCAGTTATATCATATGATGGAAGTAATAAATACTATGCAGACTCCGTGAAGGGCCGATTCACC ATCTCCAGAGACAATTCCAAGAACACCCTGTTTCTGCAAATGAACAGCCTGAGAGCCGAGGACACGGCT GTGTATTACTGTGCGAGAGATCTCTTTGCGGTGGTAGGCTACTACTACTACTACGGTATGGACGTCTGG GGCCAAGGGACCACGGTCACCGTCTCAAGCGCCTCCACCAAGGGCCCATCGGTCTTCCCCCTGGCACCC TCCTCCAAGAGCACCTCTGGGGGCACAGCGGCCCTGGGCTGCCTGGTCAAGGACTACTTCCCCGAACCG GTGACGGTGTCGTGGAACTCAGGCGCCCTGACCAGCGGCGTCCACACCTTCCCGGCTGTCCTACAGTCC TCAGGACTCTACTCCCTCAGCAGCGTAGTGACCGTGCCCTCCAGCAGCTTGGGCACCCAGACCTACATC TGCAACGTGAATCACAAGCCCAGCAACACCAAGGTGGACAAGAAAGTTGAGCCCAAATCTTGT |
| 72 | PFA1 Light chain VD | EIVLTQSPFSLPVTPGEPASISCRSSQSLLHSNGFNYLDWYLQKPGQSPQLLIYLGSNRASGVPDRFSG SGSGTDFTLKISRVEAEDVGVYYCMQGLQTPYTFGQGTKLEIKRTVAAPSVFIFPPSDEQLKSGTASVV CLLNNFYPREAKVQWKVDNALQSGNSQESVTEQDSKDSTYSLSSTLTLSKADYEKHKVYACEVTHQGLS SPVTKSFNRGEC |
| 73 | PFA1 Heavy chain VD | EVQLVQSGGGVVQPGRSLRLSCAASGFTFSSYGMHWVRQAPGKGLEWVAVISYDGSNKYYADSVKGRFT ISRDNSKNTLFLQMNSLRAEDTAVYYCARDLFAVVGYYYYYGMDVWGQGTTVTVSSASTKGPSVFPLAP SSKSTSGGTAALGCLVKDYFPEPVTVSWNSGALTSGVHTFPAVLQSSGLYSLSSVVTVPSSSLGTQTYI CNVNHKPSNTKVDKKVEPKSC |
| 74 | PFA1 LC-CDR1 | RSSQSLLHSNGFNYLD |
| 75 | PFA1 LC-CDR2 PFA2 LC-CDR2 PFA5 LC-CDR2 PFB3 LC-CDR2 PFF3 LC-CDR2 | LGSNRAS |
| 76 | PFA1 LC-CDR3 | MQGLQTPYT |
| 77 | PFA1 HC-CDR1 PFB4 HC-CDR1 PFD1 HC-CDR1 PFG1 HC-CDR1 | SYGMH |
| 78 | PFA1 HC-CDR2 PFA4 HC-CDR2 PFB4 HC-CDR2 PFC2 HC-CDR2 PFD1 HC-CDR2 PFE1 HC-CDR2 PFE5 HC-CDR2 PFG5 HC-CDR2 | VISYDGSNKYYADSVKG |

-continued

Sequences

| SEQ ID NO: | Description | Sequence |
|---|---|---|
| 79 | PFA1 HC-CDR3 | DLFAVVGYYYYYGMDV |
| 80 | PFA2 Light chain nucleotide sequence | GAAATTGTGTTGACGCAGTCTCCACTCTCCCTGCCCGTCACCCCTGGAGAGCCGGCCTCCATCTCCTGC AGGTCTAGTCAGAGTCTCCTGCACAGTGATGGGAACAAATATTTGGATTGGTACCTGCAGAAGCCAGGG CAGTCTCCACAGCTCCTGATCTATTTGGGTTCTAATCGGGCCTCCGGGGTCCCTGAGAGGTTCAGTGGC AGTGGATCAGGCACAGATTTTACACTGAAAATCAGCAGAGTGGAGGCTGAGGATGTTGGGGTTTATTAC TGCATGCTAGGTACACACTGGCCTCCGATGTACATTTTTGGCCAGGGGACCAAGCTGGAGATCAAACGA ACTGTGGCTGCACCATCTGTCTTCATCTTCCCGCCATCTGATGAGCAGTTGAAATCTGGAACTGCCTCT GTTGTGTGCCTGCTGAATAACTTCTATCCCAGAGAGGCCAAAGTACAGTGGAAGGTGGATAACGCCCTC CAATCGGGTAACTCCCAGGAGAGTGTCACAGAGCAGGACAGCAAGGACAGCACCTACAGCCTCAGCAGC ACCCTGACGCTGAGCAAAGCAGACTACGAGAAACACAAAGTCTACGCCTGCGAAGTCACCCATCAGGGC CTGAGCTCGCCCGTCACAAAGAGCTTCAACAGGGGAGAGTGT |
| 81 | PFA2 Heavy chain nucleotide sequence | CAGGTACAGCTGCAGCAGTCAGGTCCAGGACTGGTGAAGCCCTCGCAGACCCTCTCGCTCACCTGTGCC ATCTCCGGGGAAAGCGTCTCTAGCGCCGCTGCTGCTTGGAACTGGATCAGGCAGTCCCCATCGAGAGGC CTTGAGTGGCTGGGAAGGACATACTACAGGTCCAAGTGGTATAGTGAATATGCAGTATCTGTGAAAAGT CGAATAACCATCAACGGAGACACATCCAAGAACCAGGTCTCCCTGCACCTGAACGCTGTGACTCCCGAG GACACGGCTATATATTACTGTGTAAGGGGCAGTATTTTTGATGTGTGGGGCCAAGGGACAATGGTCACC GTCTCAAGCGCCTCCACCAAGGGCCCATCGGTCTTCCCCCTGGCACCCTCCTCCAAGAGCACCTCTGGG GGCACAGCGGCCCTGGGCTGCCTGGTCAAGGACTACTTCCCCGAACCGGTGACGGTGTCGTGGAACTCA GGCGCCCTGACCAGCGGCGTCCACACCTTCCCGGCTGTCCTACAGTCCTCAGGACTCTACTCCCTCAGC AGCGTAGTGACCGTGCCCTCCAGCAGCTTGGGCACCCAGACCTACATCTGCAACGTGAATCACAAGCCC AGCAACACCAAGGTGGACAAGAAAGTTGAGCCCAAATCTTGT |
| 82 | PFA2 Light chain VD | EIVLTQSPLSLPVTPGEPASISCRSSQSLLHSDGNKYLDWYLQKPGQSPQLLIYLGSNRASGVPERFSG SGSGTDFTLKISRVEAEDVGVYYCMLGTHWPPMYIFGQGTKLEIKRTVAAPSVFIFPPSDEQLKSGTAS VVCLLNNFYPREAKVQWKVDNALQSGNSQESVTEQDSKDSTYSLSSTLTLSKADYEKHKVYACEVTHQG LSSPVTKSFNRGEC |
| 83 | PFA2 Heavy chain VD | QVQLQQSGPGLVKPSQTLSLTCAISGESVSSAAAAWNWIRQSPSRGLEWLGRTYYRSKWYSEYAVSVKS RITINGDTSKNQVSLHLNAVTPEDTAIYYCVRGSIFDVWGQGTMVTVSSASTKGPSVFPLAPSSKSTSG GTAALGCLVKDYFPEPVTVSWNSGALTSGVHTFPAVLQSSGLYSLSSVVTVPSSSLGTQTYICNVNHKP SNTKVDKKVEPKSC |
| 84 | PFA2 LC-CDR1 | RSSQSLLHSDGNKYLD |
| 85 | PFA2 LC-CDR3 | MLGTHWPPMYI |
| 86 | PFA2 HC-CDR1 | SAAAAWN |
| 87 | PFA2 HC-CDR2 | RTYYRSKWYSEYAVSVKS |
| 88 | PFA2 HC-CDR3 | GSIFDV |
| 89 | PFA4 Light chain nucleotide sequence | GATGTTGTGATGACTCAGTCTCCACTCTCCCTGCCCGTCACCCTTGGACAGCCGGCCTCCATCTCCTGC AGGTCTAGTCAAAGCCTCGTATACAGTGATGGAAACACCTACTTGAATTGGTTTCAGCAGAGGCCAGGC CAATCTCCAAGGCGCCTAATTTATAAGGTTTCTAACCGGGACTCTGGGGTCCCAGACAGATTCAGCGGC AGTGGGTCAGGCACTGATTTCACACTGAAAATCAGCAGGGTGGAGGCTGAGGATGTTGGGGTTTATTAC TGCATGCAAGGTACACACTGGCCTCTCACTTTTGGCCAGGGGACCAAGCTGGAGATCAAACGAACTGTG GCTGCACCATCTGTCTTCATCTTCCCGCCATCTGATGAGCAGTTGAAATCTGGAACTGCCTCTGTTGTG TGCCTGCTGAATAACTTCTATCCCAGAGAGGCCAAAGTACAGTGGAAGGTGGATAACGCCCTCCAATCG GGTAACTCCCAGGAGAGTGTCACAGAGCAGGACAGCAAGGACAGCACCTACAGCCTCAGCAGCACCCTG ACGCTGAGCAAAGCAGACTACGAGAAACACAAAGTCTACGCCTGCGAAGTCACCCATCAGGGCCTGAGC TCGCCCGTCACAAAGAGCTTCAACAGGGGAGAGTGT |
| 90 | PFA4 Heavy chain nucleotide sequence | GAGGTCCAGCTGGTGCAGTCTGGGGGAGGCGTGGTCCAGCCTGGGAGGTCCCTGAGACTCTCCTGTGCA GCCTCTGGATTCACCTTCAGTAGCTATGCTATGCACTGGGTCCGCCAGGCTCCAGGCAAGGGGCTGGAG TGGGTGGCAGTTATATCATATGATGGAAGTAATAAATACTACGCAGACTCCGTGAAGGGCCGATTCACC ATCTCCAGAGACAATTCCAAGAACACGCTGTATCTGCAAATGAACAGCCTGAGAGCTGAGGACACGGCT GTGTATTACTGTGCGAGGAGTCGAGGCTACTACGGTATGGACGTCTGGGGCCAAGGGACCACGGTCACC GTCTCAAGCGCCTCCACCAAGGGCCCATCGGTCTTCCCCCTGGCACCCTCCTCCAAGAGCACCTCTGGG GGCACAGCGGCCCTGGGCTGCCTGGTCAAGGACTACTTCCCCGAACCGGTGACGGTGTCGTGGAACTCA GGCGCCCTGACCAGCGGCGTCCACACCTTCCCGGCTGTCCTACAGTCCTCAGGACTCTACTCCCTCAGC AGCGTAGTGACCGTGCCCTCCAGCAGCTTGGGCACCCAGACCTACATCTGCAACGTGAATCACAAGCCC AGCAACACCAAGGTGGACAAGAAAGTTGAGCCCAAATCTTGT |
| 91 | PFA4 Light chain VD | DVVMTQSPLSLPVTLGQPASISCRSSQSLVYSDGNTYLNWFQQRPGQSPRRLIYKVSNRDSGVPDRFSG SGSGTDFTLKISRVEAEDVGVYYCMQGTHWPLTFGQGTKLEIKRTVAAPSVFIFPPSDEQLKSGTASVV CLLNNFYPREAKVQWKVDNALQSGNSQESVTEQDSKDSTYSLSSTLTLSKADYEKHKVYACEVTHQGLS SPVTKSFNRGEC |

-continued

| Sequences | | |
|---|---|---|
| SEQ ID NO: | Description | Sequence |
| 92 | PFA4 Heavy chain VD | EVQLVQSGGGVVQPGRSLRLSCAASGFTFSSYAMHWVRQAPGKGLEWVAVISYDGSNKYYADSVKGRFTISRDNSKNTLYLQMNSLRAEDTAVYYCARSRGYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 93 | PFA4 LC-CDR1<br>PFD1 LC-CDR1<br>PFD4 LC-CDR1 | RSSQSLVYSDGNTYLN |
| 94 | PFA4 LC-CDR2<br>PFD1 LC-CDR2 | KVSNRDS |
| 95 | PFA4 LC-CDR3<br>PFC2 LC-CDR3<br>PFE1 LC-CDR3<br>PFG5 LC-CDR3 | MQGTHWPLT |
| 96 | PFA4 HC-CDR1<br>PFA5 HC-CDR1<br>PFC2 HC-CDR1<br>PFD4 HC-CDR1<br>PFE1 HC-CDR1<br>PFE2 HC-CDR1<br>PFE5 HC-CDR1<br>PFG5 HC-CDR1 | SYAMH |
| 97 | PFA4 HC-CDR3<br>PFD4 HC-CDR3<br>PFE1 HC-CDR3<br>PFE5 HC-CDR3 | SRGYYGMDV |
| 98 | PFA5 Light chain nucleotide sequence | GATGTTGTGATGACTCAGTCTCCACTCTCCCTGCCCGTCACCCCTGGAGAGCCGGCCTCCATCTCCTGCAGGTCTAGTCAGAGCCTCCTGCATAGTAATGGATACAACTATTTGGATTGGTACCTGCAGAAGCCAGGGCAGTCTCCACAGCTCCTGATCTATTTGGGTTCTAATCGGGCCTCCGGGGTCCCTGACAGGTTCAGTGGCAGTGGATCAGGCACAGATTTTACACTGAAAATCAGCAGAGTGGAGGCTGAGGATGTTGGGGTTTATTACTGCATGCAAGCTCTACAAACTCCGTGGACGTTCGGCCAAGGGACCAAGGTGGAAATCAAACGAACTGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAACTCTACGCCTGCGAAGTCACCCATCAGGGCCTGAGCTCGCCCGTCACAAAGAGCTTCAACAGGGGAGAGTGT |
| 99 | PFA5 Heavy chain nucleotide sequence | CAGGTGCAGCTGGTGCAATCTGGGGCTGAGGTGAAGAAGCCTGGGGCCTCAGTGAAGGTTTCCTGCAAGGCTTCTGGATACACCTTCACTAGCTATGCTATGCATTGGGTGCGCCAGGCCCCCGGACAAAGGCTTGAGTGGATGGGATGGATCAACGCTGGCAATGGTAACACAAAATATTCACAGAAGTTCCAGGGCAGAGTCACCATTACCAGGGACACATCCGCGAGCACAGCCTACATGGAGCTGAGCAGCCTGAGATCTGAAGACACGGCTGTGTATTACTGTGCGAGAGGAGGATACCTCGTAGGCTACTGGGGCCAGGGCACCCTGGTCACCGTCTCAAGCGCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTCCACACCTTCCCGGCTGTCCTACAGTCCTCAGGACTCTACTCCCTCAGCAGCGTAGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGT |
| 100 | PFA5 Light chain VD | DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKLYACEVTHQGLSSPVTKSFNRGEC |
| 101 | PFA5 Heavy chain VD | QVQLVQSGAEVKKPGASVKVSCKASGYTFTSYAMHWVRQAPGQRLEWMGWINAGNGNTKYSQKFQGRVTITRDTSASTAYMELSSLRSEDTAVYYCARGGYLVGYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 102 | PFA5 LC-CDR1<br>PFB3 LC-CDR1<br>PFB5 LC-CDR1<br>PFC2 LC-CDR1<br>PFF3 LC-CDR1<br>PFG5 LC-CDR1 | RSSQSLLHSNGYNYLD |
| 103 | PFA5 LC-CDR3 | MQALQTPWT |
| 104 | PFA5 HC-CDR2 | WINAGNGNTKYSQKFQG |

-continued

Sequences

| SEQ ID NO: | Description | Sequence |
|---|---|---|
| 105 | PFA5 HC-CDR3 | GGYLVGY |
| 106 | PFB1<br>Light chain<br>nucleotide<br>sequence | GATGTTGTGATGACTCAGTCTCCACTCTCCCTCCCCGTCACTCCTGGAGAGCCGGCCTCCATCTCCTGT<br>AGGTCTAGTCAGAGCCTCCTGCATAGTAATGGGAACACCTATTTGGATTGGTACCTGCAGAAGCCAGGG<br>CAGTCTCCACAGGTCCTGATCTATTCGGGTTCTAATCGGGCCTCTGGAGTCCCAGACAGGTTCAGCGGC<br>AGTGGGTCAGGCACTGATTTCACACTGAAAATCAGCAGGGTGGAGGCTGAGGATGTTGGGGTTTATTAC<br>TGCATGCAAGGTACACACTGGCCTCCGACGTTCGGCCAAGGGACCAAGGTGGAAATCAAACGAACTGTG<br>GCTGCACCATCTGTCTTCATCTTCCCGCCATCTGATGAGCAGTTGAAATCTGGAACTGCCTCTGTTGTG<br>TGCCTGCTGAATAACTTCTATCCCAGAGAGGCCAAAGTACAGTGGAAGGTGGATAACGCCCTCCAATCG<br>GGTAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGAGC<br>TCGCCCGTCACAAAGAGCTTCAACAGGGGAGAGTGT |
| 107 | PFB1<br>Heavy chain<br>nucleotide<br>sequence | CAGGTGCAGCTGCAGGAGTCGGGGGGAGGCTTGGTACAGCCTGGGGGGTCCCTGAGACTCTCCTGTGCA<br>GCCTCTGGATTCACCTTTAGCAGCTTTGCCATGAACTGGGTCCGCCAGGCTCCAGGGAAGGGGCTGGAG<br>TGGGTCTCAACTATTGGTGGTAGTGGTGATAGCACATTCTACGCAGACCCCGTGAAGGGCCGGTTCACC<br>GTCTCCAGAGACAATTCCAAGAACACGTTGTATCTGCAAATGAACAGCCTGAGAGCCGAGGACACGGCC<br>GTATATTACTGTGCGCAAGCCTATGGTTCGGGGGGTCATTATTTCTTTGCCTACTGGGGCCAGGGAACC<br>CTGGTCACCGTCTCAAGCGCCTCCACCAAGGGCCCATCGGTCTTCCCCCTGGCACCCTCCTCCAAGAGC<br>ACCTCTGGGGGCACAGCGGCCCTGGGCTGCCTGGTCAAGGACTACTTCCCCGAACCGGTGACGGTGTCG<br>TGGAACTCAGGCGCCCTGACCAGCGGCGTCCACACCTTCCCGGCTGTCCTACAGTCCTCAGGACTCTAC<br>TCCCTCAGCAGCGTAGTGACCGTGCCCTCCAGCAGCTTGGGCACCCAGACCTACATCTGCAACGTGAAT<br>CACAAGCCCAGCAACACCAAGGTGGACAAGAAAGTTGAGCCCAAATCTTGT |
| 108 | PFB1<br>Light chain VD | DVVMTQSPLSLPVTPGEPASISCRSSQSLLHSNGNTYLDWYLQKPGQSPQVLIYSGSNRASGVPDRFSG<br>SGSGTDFTLKISRVEAEDVGVYYCMQGTHWPPTFGQGTKVEIKRTVAAPSVFIFPPSDEQLKSGTASVV<br>CLLNNFYPREAKVQWKVDNALQSGNSQESVTEQDSKDSTYSTSSTLTLSKADYEKHKVYACEVTHQGLS<br>SPVTKSFNRGEC |
| 109 | PFB1<br>Heavy chain VD | QVQLQESGGGLVQPGGSLRLSCAASGFTFSSFAMNWVRQAPGKGLEWVSTIGGSGDSTFYADPVKGRFT<br>VSRDNSKNTLYLQMNSTRAEDTAVYYCAQAYGSGGHYFFAYWGQGTLVTVSSASTKGPSVFPLAPSSKS<br>TSGGTAALGCLVKDYFPEPVTVSWNSGALTSGVHTFPAVLQSSGLYSLSSVVTVPSSSLGTQTYICNVN<br>HKPSNTKVDKKVEPKSC |
| 110 | PFB1 LC-CDR1 | RSSQSLLHSNGNTYLD |
| 111 | PFB1 LC-CDR2 | SGSNRAS |
| 112 | PFB1 LC-CDR3 | MQGTHWPPT |
| 113 | PFB1 HC-CDR1 | SFAMN |
| 114 | PFB1 HC-CDR2 | TIGGSGDSTFYADPVKG |
| 115 | PFB1 HC-CDR3 | AYGSGGHYFFAY |
| 116 | PFB2<br>Light chain<br>nucleotide<br>sequence | GAAACGACACTCACGCAGTCTCCAGCCACCCTGTCTCTGTCTCCGGGGGAAAGAGCCACCCTCTCCTGC<br>AGGGCCAGTCAGAGTGTTAGGAACAACTTAGCCTGGTACCAGCATAAACCTGGCCAGGCTCCCAGGCTC<br>CTCATCTATTATGCATCCACCAGGGCCACTGGCATCCCAGACAGGTTCAGTGGCAGTGGGTCTGGGACA<br>GACTTCACTCTCACCATCAGCAGACTGGAGCCTGAAGATTTTGCACTGTATTACTGTCAGCACTATGGT<br>AGCTCCCGGACGTTCGGCCAAGGGACCAAGGTGGAAATCAAACGAACTGTGGCTGCACCATCTGTCTTC<br>ATCTTCCCGCCATCTGATGAGCAGTTGAAATCTGGAACTGCCTCTGTTGTGTGCCTGCTGAATAACTTC<br>TATCCCAGAGAGGCCAAAGTACAGTGGAAGGTGGATAACGCCCTCCAATCAGGTAACTCCCAGGAGAGT<br>GTCACAGAGCAGGACAGCAAGGACAGCACCTACAGCCTCAGCAGCACCCTGACGCTGAGCAAAGCAGAC<br>TACGAGAAACACAAAGTCTACGCCTGCGAAGTCACCCATCAGGGCCTGAGCTCGCCCGTCACAAAGAGC<br>TTCAACAGGGGAGAGTGT |
| 117 | PFB2<br>Heavy chain<br>nucleotide<br>sequence | GAGGTCCAGCTGGTGCAGTCTGGAGCTGAGGTGAAGAAGCCTGGGGCCTCAGTGAAGGTCTCCTGCAAG<br>GCTTCTGGTTACACCTTTACCAGCTATGGTATCAGCTGGGTGCGACAGGCCCCTGGAGAAGGGCTTGAG<br>TGGATGGGATGGATCAGCGCTTACAATGGTAACACAAACTATGCACAGAAGCTCCAGGGCAGAGTCACC<br>ATGACCACAGACACATCCACGAGCACAGCCTACATGGAGCTGAGGAGCCTGAGATCTGACGACACGGCC<br>GTGTATTACTGTGCGAGAGATTGGGGCAGCAGCTGGTCCGACTACTGGGGCCAGGGCACCCTGGTCACC<br>GTCTCAAGCGCCTCCACCAAGGGCCCATCGGTCTTCCCCCTGGCACCCTCCTCCAAGAGCACCTCTGGG<br>GGCACAGCGGCCCTGGGCTGCCTGGTCAAGGACTACTTCCCCGAACCGGTGACGGTGTCGTGGAACTCA<br>GGCGCCCTGACCAGCGGCGTCCACACCTTCCCGGCTGTCCTACAGTCCTCAGGACTCTACTCCCTCAGC<br>AGCGTAGTGACCGTGCCCTCCAGCAGCTTGGGCACCCAGACCTACATCTGCAACGTGAATCACAAGCCC<br>AGCAACACCAAGGTGGACAAGAAAGTTGAGCCCAAATCTTGT |
| 118 | PFB2<br>Light chain VD | ETTLTQSPATLSLSPGERATLSCRASQSVRNNLAWYQHKPGQAPRLLIYYASTRATGIPDRFSGSGSGT<br>DFTLTISRLEPEDFALYYCQHYGSSRTFGQGTKVEIKRTVAAPSVFIFPPSDEQLKSGTASVVCLLNNF<br>YPREAKVQWKVDNALQSGNSQESVTEQDSKDSTYSLSSTLTLSKADYEKHKVYACEVTHQGLSSPVTKS<br>FNRGEC |

-continued

| Sequences | | |
|---|---|---|
| SEQ ID NO: | Description | Sequence |
| 119 | PFB2 Heavy chain VD | EVQLVQSGAEVKKPGASVKVSCKASGYTFTSYGISWVRQAPGEGLEWMGWISAYNGNTNYAQKLQGRVT MTTDTSTSTAYMELRSTRSDDTAVYYCARDWGSSWSDYWGQGTLVTVSSASTKGPSVFPLAPSSKSTSG GTAALGCLVKDYFPEPVTVSWNSGALTSGVHTFPAVLQSSGLYSLSSVVTVPSSSLGTQTYICNVNHKP SNTKVDKKVEPKSC |
| 120 | PFB2 LC-CDR1 | RASQSVRNNLA |
| 121 | PFB2 LC-CDR2 | YASTRAT |
| 122 | PFB2 LC-CDR3 | QHYGSSRT |
| 123 | PFB2 HC-CDR1 | SYGIS |
| 124 | PFB2 HC-CDR2 | WISAYNGNTNYAQKLQG |
| 125 | PFB2 HC-CDR3 | DWGSSWSDY |
| 126 | PFB3 Light chain nucleotide sequence | GATGTTGTGATGACTCAGTCTCCACTCTCCCTGCCCGTCACCCCTGGAGAGCCGGCCTCCATCTCCTGC AGGTCTAGTCAGAGCCTCCTGCATAGTAATGGATACAACTATTTGGATTGGTACCTGCAGAAGCCAGGG CAGTCTCCACAGCTCCTGATCTATTTGGGCTCTAATCGGGCCTCCGGGGTCCCTGACAGGTTCAGTGGT AGTGGATCAGGCACAGATTTTACACTGAAAATCACCAGAGTGGAGGCTGAGGATGTTGGGGTTTATTAC TGCATGGCAGGTCTACAAACTCCTCGGCTCACCTTCGGCCCTGGGACCAAAGTGGATATCAGACGAACT GTGGCTGCACCATCTGTCTTCATCTTCCCGCCATCTGATGAGCAGTTGAAATCTGGAACTGCCTCTGTT GTGTGCCTGCTGAATAACTTCTATCCCAGAGAGGCCAAAGTACAGTGGAAGGTGGATAACGCCCTCCAA TCGGGTAACTCCCAGGAGAGTGTCACAGAGCAGGACAGCAAGGACAGCACCTACAGCCTCAGCAGCACC CTGACGCTGAGCAAAGCAGACTACGAGAAACACAAAGTCTACGCCTGCGAAGTCACCCATCAGGGCCTG AGCTCGCCCGTCACAAAGAGCTTCAACAGGGGAGAGTGT |
| 127 | PFB3 Heavy chain nucleotide sequence | CAGGTGCAGCTGCAGGAGTCGGGGGGAGGCTTGGTACAGCCTGGGGGGTCCCTGAGACTCTCCTGTGCA GCCTCTGGATTCACCTTTAGCAGCTATGCCATGAGCTGGGTCCGCCAGGCTCCAGGGAAGGGGCTGGAG TGGGTCTCAGCTATTAGTGGTAGTGGTGGTAGCACATACTACGCAGACTCCGTGAAGGGCCGATTCACC ATCTCCAGAGACAATTCCAAGAACACAGTATATCTGCAAATGAACAGCCTGAGAGCTGAGGACACGGCT GTTTATTACTGTGCGAGGACGTATTACGATTTTTGGAGTGGCAGGGTTGGGGCTTTTGATATCTGGGGC CAAGGGACCACGGTCACCGTCTCAAGCGCCTCCACCAAGGGCCCATCGGTCTTCCCCCTGGCACCCTCC TCCAAGAGCACCTCTGGGGGCACAGCGGCCCTGGGCTGCCTGGTCAAGGACTACTTCCCCGAACCGGTG ACGGTGTCGTGGAACTCAGGCGCCCTGACCAGCGGCGTCCACACCTTCCCGGCTGTCCTACAGTCCTCA GGACTCTACTCCCTCAGCAGCGTAGTGACCGTGCCCTCCAGCAGCTTGGGCACCCAGACCTACATCTGC AACGTGAATCACAAGCCCAGCAACACCAAGGTGGACAAGAAAGTTGAGCCCAAATCTTGT |
| 128 | PFB3 Light chain VD | DVVMTQSPLSLPVTPGEPASISCRSSQSLLHSNGYNYLDWYLQKPGQSPQLLIYLGSNRASGVPDRFSG SGSGTDFTLKITRVEAEDVGVYYCMAGLQTPRLTFGPGTKVDIRRTVAAPSVFIFPPSDEQLKSGTASV VCLLNNFYPREAKVQWKVDNALQSGNSQESVTEQDSKDSTYSLSSTLTLSKADYEKHKVYACEVTHQGL SSPVTKSFNRGEC |
| 129 | PFB3 Heavy chain VD | QVQLQESGGGLVQPGGSLRLSCAASGFTFSSYAMSWVRQAPGKGLEWVSAISGSGGSTYYADSVKGRFT ISRDNSKNTVYLQMNSLRAEDTAVYYCARTYYDFWSGRVGAFDIWGQGTTVTVSSASTKGPSVFPLAPS SKSTSGGTAALGCLVKDYFPEPVTVSWNSGALTSGVHTFPAVLQSSGLYSLSSVVTVPSSSLGTQTYIC NVNHKPSNTKVDKKVEPKSC |
| 130 | PFB3 LC-CDR3 | MAGLQTPRLT |
| 131 | PFB3 HC-CDR1 PFC3 HC-CDR1 PFG2 HC-CDR1 | SYAMS |
| 132 | PFB3 HC-CDR2 | AISGSGGSTYYADSVKG |
| 133 | PFB3 HC-CDR3 | TYYDFWSGRVGAFDI |
| 134 | PFB4 Light chain nucleotide sequence | CAGGCTGTGGTGATCCAGGAGCCCTCACTGACTGTGTCCCCAGGAGGGACAGTCACTCTCACCTGTGGC TCCACCACTGGAGCTGTCACCAGTGGCCATTATCCCTCCTGGTTCCAGCAGAAGCCTGGCCAAGCACCC AGGGCACTGATTTATAGTACAAGCAACAAACACTCCTGGACCCCTGCCCGGTTCTCAGGCTCCCTCCTT GGGGGCAAAGCTGCCCTGACACTGTCAGGTGTGCAGCCTGAGGACGAGGCTGAGTATTACTGCCTGCTC TACTATGGTGGTGCTCGAGTGTTCGGCGGAGGGACCAAGCTGACCGTCCTAGGTCAGCCCAAGGCTGCC CCCTCGGTCACTCTGTTCCCACCCTCCTCTGAGGAGCTTCAAGCCAACAAGGCCACACTGGTGTGTCTC ATAAGTGACTTCTACCCGGGAGCCGTGACAGTGGCCTGGAAGGCAGATAGCAGCCCCGTCAAGGCGGGA GTGGAGACCACCACACCCTCCAAACAAAGCAACAACAAGTACGCGGCCAGCAGCTACCTGAGCCTGACG CCTGAGCAGTGGAAGTCCCACAGAAGCTACAGCTGCCAGGTCACGCATGAAGGGAGCACCGTGGAGAAG ACAGTGGCCCCTGCAGAATGCTCT |
| 135 | PFB4 Heavy chain nucleotide sequence | GAGGTCCAGCTGGTACAGTCTGGGGGAGGCGTGGTCCAGCCTGGGAGGTCCCTGAGACTCTCCTGTGCA GCCTCTGGATTCACCTTCAGTAGCTATGGCATGCACTGGGTCCGCCAGGCTCCAGGCAAGGGGCTGGAG TGGGTGGCAGTTATATCATATGATGGAAGTAATAAATACTATGCAGACTCCGTGAAGGGCCGATTCACC ATCTCCAGAGACGATTCCAAGAACACGCTGTATCTGCAAATGAACAGCCTGAGAGCTGAGGACACGGCT |

-continued

| Sequences | | |
|---|---|---|
| SEQ ID NO: | Description | Sequence |
| | | GTGTATTACTGTGCGAAAGATCGCGGTTACTACGGTATGGACGTCTGGGGCCAAGGGACCACGGTCACC GTCTCAAGCGCCTCCACCAAGGGCCCATCGGTCTTCCCCCTGGCACCCTCCTCCAAGAGCACCTCTGGG GGCACAGCGGCCCTGGGCTGCCTGGTCAAGGACTACTTCCCCGAACCGGTGACGGTGTCGTGGAACTCA GGCGCCCTGACCAGCGGCGTCCACACCTTCCCGGCTGTCCTACAGTCCTCAGGACTCTACTCCCTCAGC AGCGTAGTGACCGTGCCCTCCAGCAGCTTGGGCACCCAGACCTACATCTGCAACGTGAATCACAAGCCC AGCAACACCAAGGTGGACAAGAAAGTTGAGCCCAAATCTTGT |
| 136 | PFB4 Light chain VD | QAVVIQEPSLTVSPGGTVTLTCGSTTGAVTSGHYPSWFQQKPGQAPRALIYSTSNKHSWTPARFSGSLL GGKAALTLSGVQPEDEAEYYCLLYYGGARVFGGGTKLTVLGQPKAAPSVTLFPPSSEELQANKATLVCL ISDFYPGAVTVAWKADSSPVKAGVETTTPSKQSNNKYAASSYLSLTPEQWKSHRSYSCQVTHEGSTVEK TVAPAECS |
| 137 | PFB4 Heavy chain VD | EVQLVQSGGGVVQPGRSLRLSCAASGFTFSSYGMHWVRQAPGKGLEWVAVISYDGSNKYYADSVKGRFT ISRDDSKNTLYLQMNSLRAEDTAVYYCAKDRGYYGMDVWGQGTTVTVSSASTKGPSVFPLAPSSKSTSG GTAALGCLVKDYFPEPVTVSWNSGALTSGVHTFPAVLQSSGLYSLSSVVTVPSSSLGTQTYICNVNHKP SNTKVDKKVEPKSC |
| 138 | PFB4 LC-CDR1 | GSTTGAVTSGHYPS |
| 139 | PFB4 LC-CDR2 | STSNKHS |
| 140 | PFB4 LC-CDR3 | LLYYGGARV |
| 141 | PFB4 HC-CDR3 | DRGYYGMDV |
| 142 | PFB5 Light chain nucleotide sequence | GAAATTGTGCTGACTCAGTCTCCACTCTCCCTGCCCGTCACCCCTGGAGAGCCGGCCTCCATCTCCTGC AGGTCTAGTCAGAGCCTCCTGCATAGTAATGGATACAACTATTTGGACTGGTACCTGCAGAAGCCAGGG CAGTCTCCACAGCTCCTGATCTATTTGGGTTCTCATCGGGCCTCCGGGGTCCCTGACAGGTTCAGTGGC AGTGGATCAGGCACAGATTTTACACTGAAAATCAGCAGAGTGGAGGCTGAGGATGTTGGGGTTTATTAC TGCATGCAAGCTCTACAAACTCCTCTCACTTTCGGCGGAGGGACCAAGGTGGAGATCAAACGAACTGTG GCTGCACCATCTGTCTTCATCTTCCCGCCATCTGATGAGCAGTTGAAATCTGGAACTGCCTCTGTTGTG TGCCTGCTGAATAACTTCTATCCCAGAGAGGCCAAAGTACAGTGGAAGGTGGATAACGCCCTCCAATCG GGTAACTCCCAGGAGAGTGTCACAGAGCAGGACAGCAAGGACAGCACCTACAGCCTCAGCAGCACCCTG ACGCTGAGCAAAGCAGACTACGAGAAACACAAAGTCTACGCCTGCGAAGTCACCCATCAGGGCCTGAGC TCGCCCGTCACAAAGAGCTTCAACAGGGGAGAGTGT |
| 143 | PFB5 Heavy chain nucleotide sequence | GAGGTCCAGCTGGTGCAGTCTGGGGCTGAGGTGAAGAAGCCTGGGTCCTCGGTGAAGGTCTCCTGCAAG GCTTCTGGAGGCACCTTCAGCAGCTATGCTATCAGCTGGGTGCGACAGGCCCCTGGACAAGGGCTTGAG TGGATGGGAGGGATCATCCCTATCTTTGGTACAGCAAACTACGCACAGAAGTTCCAGGGCAGAGTCACG ATTACCGCGGACGAATCCACGAGCACAGCCTACATGGAGCTGAGCAGCCTGAGATCTGAGGACACGGCC GTGTATTACTGTGCGAGAGGCCGAGGGAGCGGCTATCCCGATACGTGGTTCTGGTTCGACCCCTGGGGC CAGGGCACCCTGGTCACCGTCTCAAGCGCCTCCACCAAGGGCCCATCGGTCTTCCCCCTGGCACCCTCC TCCAAGAGCACCTCTGGGGGCACAGCGGCCCTGGGCTGCCTGGTCAAGGACTACTTCCCCGAACCGGTG ACGGTGTCGTGGAACTCAGGCGCCCTGACCAGCGGCGTCCACACCTTCCCGGCTGTCCTACAGTCCTCA GGACTCTACTCCCTCAGCAGCGTAGTGACCGTGCCCTCCAGCAGCTTGGGCACCCAGACCTACATCTGC AACGTGAATCACAAGCCCAGCAACACCAAGGTGGACAAGAAAGTTGAGCCCAAATCTTGT |
| 144 | PFB5 Light chain VD | EIVLTQSPLSLPVTPGEPASISCRSSQSLLHSNGYNYLDWYLQKPGQSPQLLIYLGSHRASGVPDRFSG SGSGTDFTLKISRVEAEDVGVYYCMQALQTPLTFGGGTKVEIKRTVAAPSVFIFPPSDEQLKSGTASVV CLLNNFYPREAKVQWKVDNALQSGNSQESVTEQDSKDSTYSLSSTLTLSKADYEKHKVYACEVTHQGLS SPVTKSFNRGEC |
| 145 | PFB5 Heavy chain VD | EVQLVQSGAEVKKPGSSVKVSCKASGGTFSSYAISWVRQAPGQGLEWMGGIIPIFGTANYAQKFQGRVT ITADESTSTAYMELSSLRSEDTAVYYCARGRGSGYPDTWFWFDPWGQGTLVTVSSASTKGPSVFPLAPS SKSTSGGTAALGCLVKDYFPEPVTVSWNSGALTSGVHTFPAVLQSSGLYSLSSVVTVPSSSLGTQTYIC NVNHKPSNTKVDKKVEPKSC |
| 146 | PFB5 LC-CDR2 | LGSHRAS |
| 147 | PFB5 LC-CDR3 | MQALQTPLT |
| 148 | PFB5 HC-CDR1 PFF4 HC-CDR1 PFG4 HC-CDR1 | SYAIS |
| 149 | PFB5 HC-CDR2 PFF4 HC-CDR2 PFG4 HC-CDR2 | GIIPIFGTANYAQKFQG |
| 150 | PFB5 HC-CDR3 | GRGSGYPDTWFWFDP |

-continued

| SEQ ID NO: | Description | Sequence |
|---|---|---|
| 151 | PFC2 Light chain nucleotide sequence | GATGTTGTGATGACTCAGTCTCCACTCTCCCTGCCCGTCACCCCTGGAGAGCCGGCCTCCATCTCCTGC AGGTCTAGTCAGAGCCTCCTGCATAGTAATGGATACAACTATTTGGATTGGTACCTGCAGAAGCCAGGG CAGTCTCCACAGCTCCTGATCTACTTGGGTTCTAATCGGGCCCCCGGGGTCCCTGACAGGTTCAGTGGC AGTGGATCAGGCACAGATTTTACACTGAAAATCAGCAGAGTGGAGGCTGAGGATGTTGGGGTTTATTAC TGCATGCAAGGTACACACTGGCCTCTCACTTTCGGCGGAGGGACCAAGGTGGAGATCAAACGAACTGTG GCTGCACCATTTGTCTTCATCTTCCCGCCATCTGATGAGCAGTTGAAATCTGGAACTGCCTCTGTTGTG TGCCTGCTGAATAACTTCTATCCCAGAGAGGCCAAAGTACAGTGGAAGGTGGATAACGCCCTCCAATCG GGTAACTCCCAGGAGAGTGTCACAGAGCAGGACAGCAAGGACAGCACCTACAGCCTCAGCAGCACCCTG ACGCTGAGCAAAGCAGACTACGAGAAACACAAAGTCTACGCCTGCGAAGTCACCCATCAGGGCCTGAGC TCGCCCGTCACAAAGAGCTTCAACAGGGGAGAGTGT |
| 152 | PFC2 Heavy chain nucleotide sequence | GAAGTGCAGCTGGTGCAGTCTGGGGGAGGCGTGGTCCAGCCTGGGAGGTCCCTGAGACTCTCCTGTGCA GCCTCTGGATTCACCTTCAGTAGCTATGCTATGCACTGGGTCCGCCAGGCTCCAGGCAAGGGGCTGGAG TGGGTGGCAGTTATATCATATGATGGAAGCAATAAATACTACGCAGACTCCGTGAAGGGCCGATTCACC ATCTCCAGAGACAATTCCAAGAACACGCTGTATCTGCAAATGAACAGCCTGAGAGCTGAGGACACGGCT GTGTATTACTGTGCGAGATCGTATGGTTCGGGGAGTTATAGGTCCCATGCTTTTGATATCTGGGGCCAA GGGACAATGGTCACCGTCTCAAGCGCCTCCACCAAGGGCCCATCGGTCTTCCCCCTGGCACCCTCCTCC AAGAGCACCTCTGGGGGCACAGCGGCCCTGGGCTGCCTGGTCAAGGACTACTTCCCCGAACCGGTGACG GTGTCGTGGAACTCAGGCGCCCTGACCAGCGGCGTCCACACCTTCCCGGCTGTCCTACAGTCCTCAGGA CTCTACTCCCTCAGCAGCGTAGTGACCGTGCCCTCCAGCAGCTTGGGCACCCAGACCTACATCTGCAAC GTGAATCACAAGCCCAGCAACACCAAGGTGGACAAGAAAGTTGAGCCCAAATCTTGT |
| 153 | PFC2 Light chain VD | DVVMTQSPLSLPVTPGEPASISCRSSQSLLHSNGYNYLDWYLQKPGQSPQLLIYLGSNRAPGVPDRFSG SGSGTDFTLKISRVEAEDVGVYYCMQGTHWPLTFGGGTKVEIKRTVAAPFVFIFPPSDEQLKSGTASVV CLLNNFYPREAKVQWKVDNALQSGNSQESVTEQDSKDSTYSLSSTLTLSKADYEKHKVYACEVTHQGLS SPVTKSFNRGEC |
| 154 | PFC2 Heavy chain VD | EVQLVQSGGGVVQPGRSLRLSCAASGFTFSSYAMHWVRQAPGKGLEWVAVISYDGSNKYYADSVKGRFT ISRDNSKNTLYLQMNSLRAEDTAVYYCARSYGSGSYRSHAFDIWGQGTMVTVSSASTKGPSVFPLAPSS KSTSGGTAALGCLVKDYFPEPVTVSWNSGALTSGVHTFPAVLQSSGLYSLSSVVTVPSSSLGTQTYICN VNHKPSNTKVDKKVEPKSC |
| 155 | PFC2 LC-CDR2 PFG5 LC-CDR2 | LGSNRAP |
| 156 | PFC2 HC-CDR3 PFG5 HC-CDR3 | SYGSGSYRSHAFDI |
| 157 | PFC3 Light chain nucleotide sequence | GAAACGACACTCACGCAGTCTCCAGGCACCCTGTCTTTGTCTCCAGGGGAAAGAGCCACCCTCTCCTGC AGGGCCAGTCAGAGTGTTAGCAGCAGCTACTTAGCCTGGTACCAGCAGAAACCTGGCCAGGCTCCCAGG CTCCTCATCTATGGTGCATCCAGCAGGGCCACTGGCATCCCAGACAGGTTCAGTGGCAGTGGGTCTGGG ACAGACTTCACTCTCACCATCAGCAGACTGGAGCCTGAAGATTTTGCAGTGTATTACTGTCAGCAGTAT GGTAGCTCACCTCGGACGTTCGGCCAAGGGACCAAGGTGGAAATCAAACGAACTGTGGCTGCACCATCT GTCTTCATCTTCCCGCCATCTGATGAGCAGTTGAAATCTGGAACTGCCTCTGTTGTGTGCCTGCTGAAT AACTTCTATCCCAGAGAGGCCAAAGTACAGTGGAAGGTGGATAACGCCCTCCAATCGGGTAACTCCCAG GAGAGTGTCACAGAGCAGGACAGCAAGGACAGCACCTACAGCCTCAGCAGCACCCTGACGCTGAGCAAA GCAGACTACGAGAAACACAAAGTCTACGCCTGCGAAGTCACCCATCAGGGCCTGAGCTCGCCCGTCACA AAGAGCTTCAACAGGGGAGAGTGT |
| 158 | PFC3 Heavy chain nucleotide sequence | CAGGTGCAGCTGGTGCAGTCTGGGGGAGGCTTGGTACAGCCTGGGGGGTCCCTGAGACTCTCCTGTGCA GCCTCTGGATTCACCTTTAGCAGCTATGCCATGAGCTGGGTCCGCCAGGCTCCAGGGAAGGGGCTGGAG TGGGTCTCTGGTATTAATTGGAATGGTGGTAGCACAGGTTATGCAGACTCTGTGAAGGGCCGATTCACC ATCTCCAGAGACAATTCCAAGAACACGCTGTATCTGCAAATGAATAGCCTGAGAGCCGAGGACACGGCC GTATATTACTGTGCGAAAGGGCTAGTACCCGCTGCGAGTATGGACGTCTGGGGCCAAGGGACCACGGTC ACCGTCTCAAGCGCCTCCACCAAGGGCCCATCGGTCTTCCCCCTGGCACCCTCCTCCAAGAGCACCTCT GGGGGCACAGCGGCCCTGGGCTGCCTGGTCAAGGACTACTTCCCCGAACCGGTGACGGTGTCGTGGAAC TCAGGCGCCCTGACCAGCGGCGTCCACACCTTCCCGGCTGTCCTACAGTCCTCAGGACTCTACTCCCTC AGCAGCGTAGTGACCGTGCCCTCCAGCAGCTTGGGCACCCAGACCTACATCTGCAACGTGAATCACAAG CCCAGCAACACCAAGGTGGACAAGAAAGTTGAGCCCAAATCTTGT |
| 159 | PFC3 Light chain VD | ETTLTQSPGTLSLSPGERATLSCRASQSVSSSYLAWYQQKPGQAPRLLIYGASSRATGIPDRFSGSGSG TDFTLTISRLEPEDFAVYYCQQYGSSPRTFGQGTKVEIKRTVAAPSVFIFPPSDEQLKSGTASVVCLLN NFYPREAKVQWKVDNALQSGNSQESVTEQDSKDSTYSLSSTLTLSKADYEKHKVYACEVTHQGLSSPVT KSFNRGEC |
| 160 | PFC3 Heavy chain VD | QVQLVQSGGGLVQPGGSLRLSCAASGFTFSSYAMSWVRQAPGKGLEWVSGINWNGGSTGYADSVKGRFT ISRDNSKNTLYLQMNSLRAEDTAVYYCAKGLVPAASMDVWGQGTTVTVSSASTKGPSVFPLAPSSKSTS GGTAALGCLVKDYFPEPVTVSWNSGALTSGVHTFPAVLQSSGLYSLSSVVTVPSSSLGTQTYICNVNHK PSNTKVDKKVEPKSC |
| 161 | PFC3 LC-CDR1 PFF2 LC-CDR1 | RASQSVSSSYLA |

-continued

Sequences

| SEQ ID NO: | Description | Sequence |
|---|---|---|
| 162 | PFC3 LC-CDR2<br>PFF2 LC-CDR2 | GASSRAT |
| 163 | PFC3 LC-CDR3 | QQYGSSPRT |
| 164 | PFC3 HC-CDR2 | GINWNGGSTGYADSVKG |
| 165 | PFC3 HC-CDR3 | GLVPAASMDV |
| 166 | PFC4<br>Light chain<br>nucleotide<br>sequence | GATGTTGTGATGACTCAGTCTCCACTCTCCCTGCCCGTCACCCCTGGACAGCCGGCCTCCATCTCCTGC<br>AGGTCTAGTCAGAGCCTCCAACATAGCAACGGATACCAGTACTTGGACTGGTACGTGCAGAAGCCAGGG<br>CAGTCTCCACAACTCCTGATCTATTTGGGTTCTTTTCGGGCCTCCGGGGTCCCCGCCAGGTTCAGTGGC<br>AGCGGATCAGGCACAGATTTTACACTGAGAATCAACAAAGTGGAGCCTGAGGACGTTGGGGTTTACTAC<br>TGCATGCACGCTCTAAGTACTCCTCCGTGGACGTTCGGCCAGGGGACCAGGGTGGAACTCAAACGAACT<br>GTGGCTGCACCATCTGTCTTCATCTTCCCGCCATCTGATGAGCAGTTGAAATCTGGAACTGCCTCTGTT<br>GTGTGCCTGCTGAATAACTTCTATCCCAGAGAGGCCAAAGTACAGTGGAAGGTGGATAACGCCCTCCAA<br>TCGGGTAACTCCCAGGAGAGTGTCACAGAGCAGGACAGCAAGGACAGCACCTACAGCCTCAGCAGCACC<br>CTGACGCTGAGCAAAGCAGACTACGAGAAACACAAAGTCTACGCCTGCGAAGTCACCCATCAGGGCCTG<br>AGCTCGCCCGTCACAAAGAGCTTCAACAGGGGAGAGTGT |
| 167 | PFC4<br>Heavy chain<br>nucleotide<br>sequence | GAGGTCCAGCTGGTGCAGTCTGGAGCTGAGGTGAGGAAGCCTGGGGCCTCAGTGAAGGTCTCCTGCAAG<br>GCTTCTGGATACACCTTCACTACCTATACTATGCATTGGGTGCGCCAGGCCCCCGGACAGAGTCTTGAG<br>TGGATGGCATGGATCACCCCTGGCAATGGTAATACACATTATTCACAGAACTTCCAGGGCAGAGTCACC<br>ATTACCAGGGACACATCCACGAGCACAGCCTACATGGAGCTGAGGAGCCTGAGATCTGACGACACGGCC<br>GTGTATTACTGTGCGAGGTCTAGGGTGGGAGCCCTTGACTACTGGGGCCAGGGAACCCTGGTCACCGTC<br>TCAAGCGCCTCCACCAAGGGCCCATCGGTCTTCCCCCTGGCACCCTCCTCCAAGAGCACCTCTGGGGGC<br>ACAGCGGCCCTGGGCTGCCTGGTCAAGGACTACTTCCCCGAACCGGTGACGGTGTCGTGGAACTCAGGC<br>GCCCTGACCAGCGGCGTCCACACCTTCCCGGCTGTCCTACAGTCCTCAGGACTCTACTCCCTCAGCAGC<br>GTAGTGACCGTGCCCTCCAGCAGCTTGGGCACCCAGACCTACATCTGCAACGTGAATCACAAGCCCAGC<br>AACACCAAGGTGGACAAGAAAGTTGAGCCCAAATCTTGT |
| 168 | PFC4<br>Light chain VD | DVVMTQSPLSLPVTPGQPASISCRSSQSLQHSNGYQYLDWYVQKPGQSPQLLIYLGSFRASGVPARFSG<br>SGSGTDFTLRINKVEPEDVGVYYCMHALSTPPWTFGQGTRVELKRTVAAPSVFIFPPSDEQLKSGTASV<br>VCLLNNFYPREAKVQWKVDNALQSGNSQESVTEQDSKDSTYSLSSTLTLSKADYEKHKVYACEVTHQGL<br>SSPVTKSFNRGEC |
| 169 | PFC4<br>Heavy chain VD | EVQLVQSGAEVRKPGASVKVSCKASGYTFTTYTMHWVRQAPGQSLEWMAWITPGNGNTHYSQNFQGRVT<br>ITRDTSTSTAYMELRSLRSDDTAVYYCARSRVGALDYWGQGTLVTVSSASTKGPSVFPLAPSSKSTSGG<br>TAALGCLVKDYFPEPVTVSWNSGALTSGVHTFPAVLQSSGLYSLSSVVTVPSSSLGTQTYICNVNHKPS<br>NTKVDKKVEPKSC |
| 170 | PFC4 LC-CDR1 | RSSQSLQHSNGYQYLD |
| 171 | PFC4 LC-CDR2 | LGSFRAS |
| 172 | PFC4 LC-CDR3 | MHALSTPPWT |
| 173 | PFC4 HC-CDR1 | TYTMH |
| 174 | PFC4 HC-CDR2 | WITPGNGNTHYSQNFQG |
| 175 | PFC4 HC-CDR3 | SRVGALDY |
| 176 | PFD1<br>Light chain<br>nucleotide<br>sequence | GATGTTGTGATGACTCAGTCTCCACTCTCCCTGCCCGTCACCCTTGGACAGCCGGCCTCCATCTCCTGC<br>AGGTCTAGTCAAAGCCTCGTATACAGTGATGGAAACACCTACTTGAATTGGTTTCAGCAGAGGCCAGGC<br>CAATCTCCAAGGCGCCTGTTTTATAAGGTTTCTAACCGGGACTCTGGGGTCCCAGACAGATTCAGCGGC<br>AGTGGGTCAGGCACTGATTTCACACTGAAAATCAGCAGGGTGGAGGCTGAGGATGTTGGGGTTTATTAC<br>TGCATGCAAGGTACACACTGGCCGGGCACTTTTGGCCAGGGGACCAAGCTGGAGATCAAACGAACTGTG<br>GCTGCACCATCTGTCTTCATCTTCCCGCCATCTGATGAGCAGTTGAAATCTGGAACTGCCTCTGTTGTG<br>TGCCTGCTGAATAACTTCTATCCCAGAGAGGCCAAAGTACAGTGGAAGGTGGATAACGCCCTCCAATCG<br>GGTAACTCCCAGGAGAGTGTCACAGAGCAGGACGGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGAGC<br>TCGCCCGTCACAAAGAGCTTCAACAGGGGAGAGTGT |
| 177 | PFD1<br>Heavy chain<br>nucleotide<br>sequence | GAGGTGCAGCTGGTGCAGTCTGGGGGAGGCGTGGTCCAGCCTGGGAGGTCCCTGAGACTCTCCTGTGCA<br>GCCTCTGGATTCACCTTCAGTAGCTATGGCATGCACTGGGTCCGCCAGGCTCCAGGCAAGGGGCTGGAG<br>TGGGTGGCAGTTATATCATATGATGGAAGTAATAAATACTATGCAGACTCCGTGAAGGGCCGATTCACC<br>ATCTCCAGAGACAATGCCAAGAACTCACTGTATCTGCAAATGAACAGCCTGAGAGCCGAGGACACGGCT<br>GTATATTACTGTGCGAGATCACGTGGATATAGTGGCTACGACAACTGGGGCCAGGGCACCCTGGTCACC<br>GTCTCAAGCGCCTCCACCAAGGGCCCATCGGTCTTCCCCCTGGCACCCTCCTCCAAGAGCACCTCTGGG<br>GGCACAGCGGCCCTGGGCTGCCTGGTCAAGGACTACTTCCCCGAACCGGTGACGGTGTCGTGGAACTCA<br>GGCGCCCTGACCAGCGGCGTCCACACCTTCCCGGCTGTCCTACAGTCCTCAGGACTCTACTCCCTCAGC<br>AGCGTAGTGACCGTGCCCTCCAGCAGCTTGGGCACCCAGACCTACATCTGCAACGTGAATCACAAGCCC<br>AGCAACACCAAGGTGGACAAGAAAGTTGAGCCCAAATCTTGT |

-continued

Sequences

| SEQ ID NO: | Description | Sequence |
|---|---|---|
| 178 | PFD1<br>Light chain VD | DVVMTQSPLSLPVTLGQPASISCRSSQSLVYSDGNTYLNWFQQRPGQSPRRLFYKVSNRDSGVPDRFSG<br>SGSGTDFTLKISRVEAEDVGVYYCMQGTHWPGTFGQGTKLEIKRTVAAPSVFIFPPSDEQLKSGTASVV<br>CLLNNFYPREAKVQWKVDNALQSGNSQESVTEQDGKESTYSLSSTLTLSKADYEKHKVYACEVTHQGLS<br>SPVTKSFNRGEC |
| 179 | PFD1<br>Heavy chain VD | EVQLVQSGGGVVQPGRSLRLSCAASGFTFSSYGMHWVRQAPGKGLEWVAVISYDGSNKYYADSVKGRFT<br>ISRDNAKNSLYLQMNSLRAEDTAVYYCARSRGYSGYDNWGQGTLVTVSSASTKGPSVFPLAPSSKSTSG<br>GTAALGCLVKDYFPEPVTVSWNSGALTSGVHTFPAVLQSSGLYSLSSVVTVPSSSLGTQTYICNVNHKP<br>SNTKVDKKVEPKSC |
| 180 | PFD1 LC-CDR3<br>PFF3 LC-CDR3 | MQGTHWPGT |
| 181 | PFD1 HC-CDR3 | SRGYSGYDN |
| 182 | PFD2<br>Light chain<br>nucleotide<br>sequence | CAGTCTGTCGTGACGCAGCCGCCCTCAGTGTCTGGGGCCCCCGGGCAGAGGGTCACCATCTCCTGCACT<br>GGGAGAAGCGCCAATATCGGGGGTTTTGATGTACAGTGGTACCGACAACTTCCAGGAACAGCCCCCCAA<br>CTCCTCATATATGACAACAGCAATCGGCCCTCAGGGGTCCCTGACCGATTCTCTGGCTCCAAGTCTGGC<br>ACCTCAGCCACCCTGGCCATCAGCGGACTTCAGACTGGCGACGAGGCCGATTATTACTGCGGAACATGG<br>GATTCCTACCTCAATATTTGGGTGTTCGGCGGAGGGACCAAGCTGACCGTCCTTAGTCAGCCCAAGGCT<br>GCCCCCTCGGTCACTCTGTTCCCGCCCTCCTCTGAGGAGCTTCAAGCCAACAAGGCCACACTGGTGTGT<br>CTCATAAGTGACTTCTACCCGGGAGCCGTGACAGTGGCCTGGAAGGCAGATAGCAGCCCCGTCAAGGCG<br>GGAGTGGAGACCACCACACCCTCCAAACAAAGCAACAACAAGTACGCGGCCAGCAGCTACCTGAGCCTG<br>ACGCCTGAGCAGTGGAAGTCCCACAAAAGCTACAGCTGCCAGGTCACGCATGAAGGGAGCACCGTGGAG<br>AAGACAGTGGCCCCTACAGAATGTTCA |
| 183 | PFD2<br>Heavy chain<br>nucleotide<br>sequence | CAGGTGCAGCTACAGCAGTGGGGCGCAGGACTGTTGAAGCCTTCGGAGACCCTGTCCCTCACCTGCGCT<br>GTCTATGGTGGGTCCTTCAGTGGTTACTACTGGAGCTGGATCCGCCAGCCCCCAGGGAAGGGGCTGGAG<br>TGGATTGGGGAAATCAATCATAGTGGAAGCACCAACTACAACCCGTCCCTCAAGAGTCGAGTCACCATA<br>TCAGTAGACACGTCCAAGAACCAGTTCTCCCTGAAGCTGAGCTCTGTGACCGCCGCGGACACGGCTGTG<br>TATTACTGTGCGAGAGGCCTTCCGTATTACTACTTTGACTACTGGGGCCAGGGCACCCTGGTCACCGTC<br>TCAAGCGCCTCCACCAAGGGCCCATCGGTCTTCCCCCTGGCACCCTCCTCCAAGAGCACCTCTGGGGGC<br>ACAGCGGCCCTGGGCTGCCTGGTCAAGGACTACTTCCCCGAACCGGTGACGGTGTCGTGGAACTCAGGC<br>GCCCTGACCAGCGGCGTCCACACCTTCCCGGCTGTCCTACAGTCCTCAGGACTCTACTCCCTCAGCAGC<br>GTAGTGACCGTGCCCTCCAGCAGCTTGGGCACCCAGACCTACATCTGCAACGTGAATCACAAGCCCAGC<br>AACACCAAGGTGGACAAGAAAGTTGAGCCCAAATCTTGT |
| 184 | PFD2<br>Light chain VD | QSVVTQPPSVSGAPGQRVTISCTGRSANIGGFDVQWYRQLPGTAPQLLIYDNSNRPSGVPDRFSGSKSG<br>TSATLAISGLQTGDFADYYCGTWDSYLNIWVFGGGTKLTVLSQPKAAPSVTLFPPSSEELQANKATLVC<br>LISDFYPGAVTVAWKADSSPVKAGVETTTPSKQSNNKYAASSYLSLTPEQWKSHKSYSCQVTHEGSTVE<br>KTVAPTECS |
| 185 | PFD2<br>Heavy chain VD | QVQLQQWGAGLLKPSETLSLTCAVYGGSFSGYYWSWIRQPPGKGLEWIGEINHSGSTNYNPSLKSRVTI<br>SVDTSKNQFSLKLSSVTAADTAVYYCARGLPYYYFDYWGQGTLVTVSSASTKGPSVFPLAPSSKSTSGG<br>TAALGCLVKDYFPEPVTVSWNSGALTSGVHTFPAVLQSSGLYSTSSVVTVPSSSLGTQTYICNVNHKPS<br>NTKVDKKVEPKSC |
| 186 | PFD2 LC-CDR1 | TGRSANIGGFDVQ |
| 187 | PFD2 LC-CDR2 | DNSNRPS |
| 188 | PFD2 LC-CDR3 | GTWDSYLNIWV |
| 189 | PFD2 HC-CDR3 | GLPYYYFDY |
| 190 | PFD3<br>Light chain<br>nucleotide<br>sequence | CAGGCTGTGGTGATCCAGGAGCCATCGTTCTCAGTGTCCCCTGGAGGGACAGTCACACTCACTTGTGCC<br>TTGACCTCTGGCTCAGTCTCTACTAGTTACTACCCCAGCTGGTACCAGCAGACCCCAGGCCAGCCTCCA<br>CGCACGCTCATTTACAGCACAAACCTTCGCTCTTCTGGGGTCCCTGATCGCTTCTCTGGCTCCATCCTT<br>GGGAACAAAGCTGCCCTCACCATCACGGGGGCCCAGGCGGATGATGAATCTGATTATTACTGTGAGTTG<br>TATATGGGTAGTGGCATTTCGGTGTTCGGCGGAGGGACCAAGGTGACCGTCCTAGGTCAGCCCAAGGCT<br>GCCCCCTCGGTCACTCTGTTCCCACCCTCCTCTGAGGAGCTTCAAGCCAACAAGGCCACACTGGTGTGT<br>CTCATAAGTGACTTCTACCCGGGAGCCGTGACAGTGGCCTGGAAGGCAGATAGCAGCCCCGTCAAGGCG<br>GGAGTGGAGACCACCACACCCTCCAAACAAAGCAACAACAAGTACGCGGCCAGCAGCTACCTGAGCCTG<br>ACGCCTGAGCAGTGGAAGTCCCACAAAAGCTACAGCTGCCAGGTCACGCATGAAGGGAGCACCGTGGAG<br>AAGACAGTGGCCCCTACAGAATGTTCA |
| 191 | PFD3<br>Heavy chain<br>nucleotide<br>sequence | GAGGTCCAGCTGGTGCAGTCTGGAGCAGAGGTGAAAAAGCCCGGGGAGTCTCTGAAGATCTCCTGTAAG<br>GGTTCTGGATACAGCTTTACCAGCTACTGGATCGGCTGGGTGCGCCAGATGCCCGGGAAAGGCCTGGAG<br>TGGATGGGGATCATCTATCCTGGTGACTCTGATACCAGATACAGCCCGTCCTTCCAAGGCCAGGTCACC<br>ATCTCAGCCGACAAGTCCATCAGCACCGCCTACCTGCAGTGGAGCAGCCTGAAGGCCTCGGACACCGCC<br>ATGTATTACTGTGCGAGACTGGGCTACGGTGTCCCCCTGCCTGAGTACTTCGATCTCTGGGGCCGTGGA<br>ACCCTGGTCACCGTCTCAAGCGCCTCCACCAAGGGCCCATCGGTCTTCCCCCTGGCACCCTCCTCCAAG<br>AGCACCTCTGGGGGCACAGCGGCCCTGGGCTGCCTGGTCAAGGACTACTTCCCCGAACCGGTGACGGTG |

-continued

| SEQ ID NO: | Description | Sequence |
| --- | --- | --- |
| | | TCGTGGAACTCAGGCGCCCTGACCAGCGGCGTCCACACCTTCCCGGCTGTCCTACAGTCCTCAGGACTCTACTCCCTCAGCAGCGTAGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGT |
| 192 | PFD3 Light chain VD | QAVVIQEPSFSVSPGGTVTLTCALTSGSVSTSYYPSWYQQTPGQPPRTLIYSTNLRSSGVPDRFSGSILGNKAALTITGAQADDESDYYCELYMGSGISVFGGGTKVTVLGQPKAAPSVTLFPPSSEELQANKATLVCLISDFYPGAVTVAWKADSSPVKAGVETTTPSKQSNNKYAASSYLSLTPEQWKSHKSYSCQVTHEGSTVEKTVAPTECS |
| 193 | PFD3 Heavy chain VD | EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARLGYGVPLPEYFDLWGRGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 194 | PFD3 LC-CDR1 | ALTSGSVSTSYYPS |
| 195 | PFD3 LC-CDR2 | STNLRSS |
| 196 | PFD3 LC-CDR3 | ELYMGSGISV |
| 197 | PFD3 HC-CDR1 | SYWIG |
| 198 | PFD3 HC-CDR2 | IIYPGDSDTRYSPSFQG |
| 199 | PFD3 HC-CDR3 | LGYGVPLPEYFDL |
| 200 | PFD4 Light chain nucleotide sequence | GATGTTGTGATGACTCAGTCTCCACTCTCCCTGCCCGTCACCCTTGGACAGCCGGCCTCCATCTCCTGCAGGTCTACTCAAAGCCTCGTATACAGTGATGGAAACACCTACTTGAATTGGTTTCAGCAGAGGCCAGGCCAATCTCCAAGGCGCCTAATTTATAAGGTTTCTGACCGGGACTCTGGGGTCCCAGACAGATTCAGCGGCAGTGGGTCAGGCACTGATTTCACACTGAAAATCAGCAGGGTGGAGGCTGAGGATGTTGGGGTTTATTACTGCATGCAAGGCACACACTGGCCTCAGACTTTTGGCCAGGGGACCAAGCTGGAGATCAAACGAACTGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTTACAAAGAGCTTCAACAGGGGAGAGTGT |
| 201 | PFD4 Heavy chain nucleotide sequence | CAGGTGCAGCTGGTGCAGTCTGGGGGAGGCTTGGTCCAGCCTGGGGGGTCCCTGAGACTCTCCTGTTCAGCCTCTGGATTCACCTTCAGTAGCTATGCTATGCACTGGGTCCGCCAGGCTCCAGGGAAGGGACTGGAATATGTTTCAGCTATTAGTAGTAATGGGGGTAGCACATACTACGCAGACTCCGTGAAGGGCAGATTCACCATCTCCAGAGACAATTCCAAGAACACGCTGTATCTTCAAATGAGCAGTCTGAGAGCTGAGGACACGGCTGTGTATTACTGTGCGAGAAGTAGGGGCTACTACGGTATGGACGTCTGGGGCCAAGGGACCACGGTCACCGTCTCAAGCGCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTCCACACCTTCCCGGCTGTCCTACAGTCCTCAGGACTCTACTCCCTCAGCAGCGTAGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGT |
| 202 | PFD4 Light chain VD | DVVMTQSPLSLPVTLGQPASISCRSSQSLVYSDGNTYLNWFQQRPGQSPRRLIYKVSDRDSGVPDRFSGSGSGTDFTLKISRVEAEDVGVYYCMQGTHWPQTFGQGTKLEIKRTVAAPSVFIFPPSDEQLKSGTASVVCLLNNFYPREAKVQWKVDNALQSGNSQESVTEQDSKDSTYSTSSTLTLSKADYEKHKVYACEVTHQGLSSPVTKSFNRGEC |
| 203 | PFD4 Heavy chain VD | QVQLVQSGGGLVQPGGSLRLSCSASGFTFSSYAMHWVRQAPGKGLEYVSAISSNGGSTYYADSVKGRFTISRDNSKNTLYLQMSSLRAEDTAVYYCARSRGYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 204 | PFD4 LC-CDR2 | KVSDRDS |
| 205 | PFD4 LC-CDR3 | MQGTHWPQT |
| 206 | PFD4 HC-CDR2<br>PFF3 HC-CDR2 | AISSNGGSTYYADSVKG |

-continued

| Sequences | | |
|---|---|---|
| SEQ ID NO: | Description | Sequence |
| 207 | PFE1 Light chain nucleotide sequence | GATGTTGTGATGACTCAGTCTCCACTCTCCCTGCCCGTCACCCTTGGACAGCCGGCCTCCATCTCCTGCACGTCTAGTCAAAGCCTCGTATACAGTGATGGAAACACCTACTTGAATTGGTTTCAGCAGAGGCCAGGCCAATCTCCAAGGCGCCTAATTTATAAGGTTTCTAAGCGGGACTCTGGGGTCCCAGACAGATTCAGCGGCAGTGGGTCAGGCACTGATTTCACACTGAAAATAAGCAGGGTGGAGGCTGAGGATGTTGCGATTTATTACTGCATGCAAGGTACACACTGGCCTCTCACTTTCGGCGGAGGGACCAAGGTGGAGATCAAACGAACTGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAACTCTACGCCTGCGAAGTCACCCATCAGGGCCTGAGCTCGCCCGTCACAAAGAGCTTCAACAGGGGAGAGTGT |
| 208 | PFE1 Heavy chain nucleotide sequence | GAGGTCCAGCTGGTGCAGTCTGGGGGAGGCGTGGTCCAGCCTGGGAGGTCCCTGAGACTCTCCTGTGCAGCCTCTGGATTCACCTTCAGTAGCTATGCTATGCACTGGGTCCGCCAGGCTCCAGGCAAGGGGCTGGAGTGGGTGGCAGTTATATCATATGATGGAAGTAATAAATACTACGCAGACTCCGTGAAGGGCCGATTCACCATCTCCAGAGACAATTCCAAGAACACGCTGTATCTGCAAATGAACAGCCTGAGAGCTGAGGACACGGCTGTGTATTACTGTGCGAGGAGTCGAGGCTACTACGGTATGGACGTCTGGGGCCAAGGGACCACGGTCACCGTCTCAAGCGCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTCCACACCTTCCCGGCTGTCCTACAGTCCTCAGGACTCTACTCCCTCAGCAGCGTAGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGT |
| 209 | PFE1 Light chain VD | DVVMTQSPLSLPVTLGQPASISCTSSQSLVYSDGNTYLNWFQQRPGQSPRRLIYKVSKRDSGVPDRFSGSGSGTDFTLKISRVEAEDVAIYYCMQGTHWPLTFGGGTKVEIKRTVAAPSVFIFPPSDEQLKSGTASVVCLLNNFYPREAKVQWKVDNALQSGNSQESVTEQDSKDSTYSTSSTLTLSKADYEKHKLYACEVTHQGLSSPVTKSFNRGEC |
| 210 | PFE1 Heavy chain VD | EVQLVQSGGGVVQPGRSLRLSCAASGFTFSSYAMHWVRQAPGKGLEWVAVISYDGSNKYYADSVKGRFTISRDNSKNTLYLQMNSLRAEDTAVYYCARSRGYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 211 | PFE1 LC-CDR1 | TSSQSLVYSDGNTYLN |
| 212 | PFE1 LC-CDR2 | KVSKRDS |
| 213 | PFE2 Light chain nucleotide sequence | GTGAAAAAATTATTATTCGCAATTCCTTTAGTTGTTCCTTTCTATTCTCACAGTGCACTTGATGTTGTGATGACTCAGTCTCCACTCTCCCTGCCCGTCACCCCTGGAGAGCCGGCCTCCATCTCCTGCAGGTCTAGTCAGAGCCTCCTGCGCAGTGATGGATACAACTTTGTGGATTGGTACCTGCAGAAGGCAGGGCAGTCTCCACAGCTCCTGATCCATTTGGGTTCTGATCGGGCCTCCGGGGTCCCTGACAGGTTCAGTGGCAGTGGATCAGGCACAGATTTTACACTGAGAATCAGCAGAGTGGAGGCTGAGGATGTTGGAGTTTATTACTGCATGCAAGCTCTACAAACTCCTCGGACGTTCGGCCAAGGGACCAAGGTGGAAATCAAACGAACTGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGT |
| 214 | PFE2 Heavy chain nucleotide sequence | GAGGTCCAGCTGGTGCAGTCTGGGGGAGGCGTGGTCCAGCCTGGGAGGTCCCTGAGACTCTCCTGTGCAGCCTCTGGATTCACCTTCAGTAGCTATGCTATGCACTGGGTCCGCCAGGCTCCAGGCAAGGGGCTGGAGTGGGTGGCAGTTATATCATATGATGAAAGCAATAAATACTACGCAGACTCCGTGAAGGGCCGATTCACCATCTCCAGAGACAATTCCAAGAACACGCTGTATCTGCAAATGAACAGCCTGAGAGCTGAGGACACGGCTGTGTATTACTGTGCGAGGGAGCCAAGCGGCAGCTGGTCGTACCTCTACTACTACTACTACGGTATGGACGTCTGGGGCCAAGGGACCACGGTCACCGTCTCAAGCGCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTCCACACCTTCCCGGCTGTCCTACAGTCCTCAGGACTCTACTCCCTCAGCAGCGTAGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGT |
| 215 | PFE2 Light chain VD | DVVMTQSPLSLPVTPGEPASISCRSSQSLLRSDGYNFVDWYLQKAGQSPQLLIHLGSDRASGVPDRFSGSGSGTDFTLRISRVEAEDVGVYYCMQALQTPRTFGQGTKVEIKRTVAAPSVFIFPPSDEQLKSGTASVVCLLNNFYPREAKVQWKVDNALQSGNSQESVTEQDSKDSTYSTSSTLTLSKADYEKHKVYACEVTHQGLSSPVTKSFNRGEC |
| 216 | PFE2 Heavy chain VD | EVQLVQSGGGVVQPGRSLRLSCAASGFTFSSYAMHWVRQAPGKGLEWVAVISYDESNKYYADSVKGRFTISRDNSKNTLYLQMNSLRAEDTAVYYCAREPSGSWSYLYYYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 217 | PFE2 LC-CDR1 | RSSQSLLRSDGYNFVD |
| 218 | PFE2 LC-CDR2 | LGSDRAS |
| 219 | PFE2 LC-CDR3 | MQALQTPRT |

-continued

Sequences

| SEQ ID NO: | Description | Sequence |
|---|---|---|
| 220 | PFE2 HC-CDR2 | VISYDESNKYYADSVKG |
| 221 | PFE2 HC-CDR3 | EPSGSWSYLYYYYYGMDV |
| 222 | PFE5 Light chain nucleotide sequence | GACATCCAGATGACCCAGTCTCCATCCTCCCTGTCTGCATCTGTAGGAGACAGAGTCACCATCACTTGT CGGGCGAGTCAGGGTATTAGCAGCTGGTTAGCCTGGTATCAGCAGAAACCAGGGAAAGCCCCTAAGCTC CTGATCTATGCTGCATCCAGTTTGCAAAGTGGGGTCCCATCAAGGTTCAGCGGCAGTGGATCTGGGACA GATTTCACTCTCACCATCAGCAGCCTGCAGCCTGAAGATTTTGCAACTTACTATTGTCAACAGGCTAAC AGTTTCCCTCCCACTTTCGGCCCTGGGACCAAAGTGGATATCAAACGAACTGTGGCTGCACCATCTGTC TTCATCTTCCCGCCATCTGATGAGCAGTTGAAATCTGGAACTGCCTCTGTTGTGTGCCTGCTGAATAAC TTCTATCCCAGAGAGGCCAAAGTACAGTGGAAGGTGGATAACGCCCTCCAATCGGGTAACTCCCAGGAG AGTGTCACAGAGCAGGACAGCAAGGACAGCACCTACAGCCTCAGCAGCACCCTGACGCTGAGCAAAGCA GACTACGAGAAACACAAAGTCTACGCCTGCGAAGTCACCCATCAGGGCCTGAGCTCGCCCGTCACAAAG AGCTTCAACAGGGGAGAGTGT |
| 223 | PFE5 Heavy chain nucleotide sequence | GAGGTCCAGCTGGTGCAGTCTGGGGGAGGCGTGGTCCAGCCTGGGAGGTCCCTGAGACTCTCCTGTGCA GCCTCTGGATTCACCTTCAGTAGCTATGCTATGCACTGGGTCCGCCAGGCTCCAGGCAAGGGGCTGGAG TGGGTGGCAGTTATATCATATGATGGAAGTAATAAATACTACGCAGACTCCGTGAAGGGCCGATTCACC ATCTCCAGAGACAATTCCAAGAACACGCTGTATCTGCAAATGAACAGCCTGAGAGCTGAGGACACGGCT GTGTATTACTGTGCGAGGAGTCGAGGCTACTACGGTATGGACGTCTGGGGCCAAGGGACCACGGTCACC GTCTCAAGCGCCTCCACCAAGGGCCCATCGGTCTTCCCCCTGGCACCCTCCTCCAAGAGCACCTCTGGG GGCACAGCGGCCCTGGGCTGCCTGGTCAAGGACTACTTCCCCGAACCGGTGACGGTGTCGTGGAACTCA GGCGCCCTGACCAGCGGCGTCCACACCTTCCCGGCTGTCCTACAGTCCTCAGGACTCTACTCCCTCAGC AGCGTAGTGACCGTGCCCTCCAGCAGCTTGGGCACCCAGACCTACATCTGCAACGTGAATCACAAGCCC AGCAACACCAAGGTGGACAAGAAAGTTGAGCCCAAATCTTGT |
| 224 | PFE5 Light chain VD | DIQMTQSPSSLSASVGDRVTITCRASQGISSWLAWYQQKPGKAPKLLIYAASSLQSGVPSRFSGSGSGT DFTLTISSLQPEDFATYYCQQANSFPPTFGPGTKVDIKRTVAAPSVFIFPPSDEQLKSGTASVVCLLNN FYPREAKVQWKVDNALQSGNSQESVTEQDSKDSTYSLSSTLTLSKADYEKHKVYACEVTHQGLSSPVTK SFNRGEC |
| 225 | PFE5 Heavy chain VD | EVQLVQSGGGVVQPGRSLRLSCAASGFTFSSYAMHWVRQAPGKGLEWVAVISYDGSNKYYADSVKGRFT ISRDNSKNTLYLQMNSTRAEDTAVYYCARSRGYYGMDVWGQGTTVTVSSASTKGPSVFPLAPSSKSTSG GTAALGCLVKDYFPEPVTVSWNSGALTSGVHTFPAVLQSSGLYSLSSVVTVPSSSLGTQTYICNVNHKP SNTKVDKKVEPKSC |
| 226 | PFE5 LC-CDR1 | RASQGISSWLA |
| 227 | PFE5 LC-CDR2 | AASSLQS |
| 228 | PFE5 LC-CDR3 | QQANSFPPT |
| 229 | PFF2 Light chain nucleotide sequence | GAAATTGTGTTGACGCAGTCTCCAGGCACCCTGTCTTTGTCTCCAGGGGAAAGAGCCACCCTCTCCTGC AGGGCCAGTCAGAGTGTTAGCAGCAGCTACTTAGCCTGGTACCAGCAGAAACCTGGCCAGGCTCCCAGG CTCCTCATCTATGGTGCATCCAGCAGGGCCACTGGCATCCCAGACAGGTTCAGTGGCAGTGGGTCTGGG ACAGACTTCACTCTCACCATCAGCAGACTGGAGCCTGAAGATTTTGCAGTGTATTACTGTCAGCAGTAT GGTAGCTCCTCCGCTTTCGGCCCTGGGACCAAAGTGGATATCAAACGAACTGTGGCTGCACCATCTGTC TTCATCTTCCCGCCATCTGATGAGCAGTTGAAATCTGGAACTGCCTCTGTTGTGTGCCTGCTGAATAAC TTCTATCCCAGAGAGGCCAAAGTACAGTGGAAGGTGGATAACGCCCTCCAATCGGGTAACTCCCAGGAG AGTGTCACAGAGCAGGACAGCAAGGACAGCACCTACAGCCTCAGCAGCACCCTGACGCTGAGCAAAGCA GACTACGAGAAACACAAAGTCTACGCCTGCGAAGTCACCCATCAGGGCCTGAGCTCGCCCGTCACAAAG AGCTTCAACAGGGGAGAGTGT |
| 230 | PFF2 Heavy chain nucleotide sequence | CAGATGCAGCTGGTGCAGTCTGGGGGAGGCGTGGTCCAGCCTGGGAGGTCACTGAGACTCTCCTGTGCA GCCTCTGGATTCAGTTTCAAAAATTATGGCATGCACTGGGTCCGCCAGGCTCCAGGCAAGGGGCTGGAG TGGGTGGCATTTATCTCATATGATGGAACTAATAAATACTATGCAGACTCCGTGAAGGGCCGATTCACC ATCTCCAGAGACAATTCCAAGAACACGCTGTATCTGCAAATGAACAGCCTGAGAGCCGAGGACACGGCC GTATATTACTGTGCGAAGCACTACGGTGACTACTACTACTACTACGGTATGGACGTCTGGGGCCAAGGG ACCACGGTCACCGTCTCAAGCGCCTCCACCAAGGGCCCATCGGTCTTCCCCCTGGCACCCTCCTCCAAG AGCACCTCTGGGGGCACAGCGGCCCTGGGCTGCCTGGTCAAGGACTACTTCCCCGAACCGGTGACGGTG TCGTGGAACTCAGGCGCCCTGACCAGCGGCGTCCACACCTTCCCGGCTGTCCTACAGTCCTCAGGACTC TACTCCCTCAGCAGCGTAGTGACCGTGCCCTCCAGCAGCTTGGGCACCCAGACCTACATCTGCAACGTG AATCACAAGCCCAGCAACACCAAGGTGGACAAGAAAGTTGAGCCCAAATCTTGT |
| 231 | PFF2 Light chain VD | EIVLTQSPGTLSLSPGERATLSCRASQSVSSSYLAWYQQKPGQAPRLLIYGASSRATGIPDRFSGSGSG TDFTLTISRLEPEDFAVYYCQQYGSSSAFGPGTKVDIKRTVAAPSVFIFPPSDEQLKSGTASVVCLLNN FYPREAKVQWKVDNALQSGNSQESVTEQDSKDSTYSLSSTLTLSKADYEKHKVYACEVTHQGLSSPVTK SFNRGEC |
| 232 | PFF2 Heavy chain VD | QMQLVQSGGGVVQPGRSLRLSCAASGFSFKNYGMHWVRQAPGKGLEWVAFISYDGTNKYYADSVKGRFT ISRDNSKNTLYLQMNSLRAEDTAVYYCAKHYGDYYYYYGMDVWGQGTTVTVSSASTKGPSVFPLAPSSK STSGGTAALGCLVKDYFPEPVTVSWNSGALTSGVHTFPAVLQSSGLYSLSSVVTVPSSSLGTQTYICNV NHKPSNTKVDKKVEPKSC |

-continued

| SEQ ID NO: | Description | Sequence |
|---|---|---|
| 233 | PFF2 LC-CDR3 | QQYGSSSA |
| 234 | PFF2 HC-CDR1 | NYGMH |
| 235 | PFF2 HC-CDR2 | FISYDGTNKYYADSVKG |
| 236 | PFF2 HC-CDR3 | HYGDYYYYYGMDV |
| 237 | PFF3 Light chain nucleotide sequence | GATGTTGTGATGACTCAGTCTCCACTCTCCCTGCCCGTCACCCCTGGAGAGCCGGCCTCCATCTCCTGC AGGTCTAGTCAGAGCCTCCTGCATAGTAATGGATACAACTATTTGGATTGGTACCTGCAGAAGCCAGGG CAGTCTCCACAGCTCCTGATCTACTTGGGTTCTAATCGGGCCTCCGGGGTCCCTGACAGGCTCAGTGGC AGTGGATCAGGCACAGATTTTACACTGAAAATCAGCAGAGTGGAGGCTGAGGATGTTGGGGTTTATTAC TGCATGCAAGGTACACACTGGCCAGGGACGTTCGGCCAAGGGACCAAGGTGGAAATCAAACGAACTGTG GCTGCACCATCTGTCTTCATCTTCCCGCCATCTGATGAGCAGTTGAAATCTGGAACTGCCTCTGTTGTG TGCCTGCTGAATAACTTCTATCCCAGAGAGGCCAAAGTACAGTGGAAGGTGGATAACGCCCTCCAATCG GGTAACTCCCAGGAGAGTGTCACAGAGCAGGACAGCAAGGACAGCACCTACAGCCTCAGCAGCACCCTG ACGCTGAGCAAAGCAGACTACGAGAAACACAAAGTCTACGCCTGCGAAGTCACCCATCAGGGCCTGAGC TCGCCCGTCACAAAGAGCTTCAACAGGGGAGAGTGT |
| 238 | PFF3 Heavy chain nucleotide sequence | CAGGTCCAGCTGGTACAGTCTGGGGGAGGCTTGGTCCAGCCTGGGGGGTCCCTGAGACTCTCCTGTTCA GCCTCTGGATTCACCTTCAGTAGCTATGCTATCCACTGGGTCCGCCAGGCTCCAGGGAAGGGACTGGAA TATGTTTCAGCTATTAGTAGTAATGGGGGTAGCACATACTACGCAGACTCCGTGAAGGGCAGATTCACC ATCTCCAGAGACAATTCCAAGAACACGCTGTATCTTCAAATGAACAGCCTGAGAGCCGAGGACACGGCT GTGTATTACTGTGCGAGAGTCTATGGATATGGTCTCCACTACTACGGTATGGACGTCTGGGGCCAAGGG ACCACGGTCACCGTCTCAAGCGCCTCCACCAAGGGCCCATCGGTCTTCCCCCTGGCACCCTCCTCCAAG AGCACCTCTGGGGGCACAGCGGCCCTGGGCTGCCTGGTCAAGGACTACTTCCCCGAACCGGTGACGGTG TCGTGGAACTCAGGCGCCCTGACCAGCGGCGTCCACACCTTCCCGGCTGTCCTACAGTCCTCAGGACTC TACTCCCTCAGCAGCGTAGTGACCGTGCCCTCCAGCAGCTTGGGCACCCAGACCTACATCTGCAACGTG AATCACAAGCCCAGCAACACCAAGGTGGACAAGAAAGTTGAGCCCAAATCTTGT |
| 239 | PFF3 Light chain VD | DVVMTQSPLSLPVTPGEPASISCRSSQSLLHSNGYNYLDWYLQKPGQSPQLLIYLGSNRASGVPDRLSG SGSGTDFTLKISRVEAEDVGVYYCMQGTHWPGTFGQGTKVEIKRTVAAPSVFIFPPSDEQLKSGTASVV CLLNNFYPREAKVQWKVDNALQSGNSQESVTEQDSKDSTYSTSSTLTLSKADYEKHKVYACEVTHQGLS SPVTKSFNRGEC |
| 240 | PFF3 Heavy chain VD | QVQLVQSGGGLVQPGGSLRLSCSASGFTFSSYAIHWVRQAPGKGLEYVSAISSNGGSTYYADSVKGRFT ISRDNSKNTLYLQMNSLRAEDTAVYYCARVYGYGLHYYGMDVWGQGTTVTVSSASTKGPSVFPLAPSSK STSGGTAALGCLVKDYFPEPVTVSWNSGALTSGVHTFPAVLQSSGLYSTSSVVTVPSSSLGTQTYICNV NHKPSNTKVDKKVEPKSC |
| 241 | PFF3 HC-CDR1 | SYAIH |
| 242 | PFF3 HC-CDR3 | VYGYGLHYYGMDV |
| 243 | PFF4 Light chain nucleotide sequence | GAAACGACACTCACGCAGTCTCCAGGCACGCTGTCTTTGTCTCCAGGGGAAAGAGCCACCCTCTCCTGC AGGGCCAGTCGGAGTGTTGGCAAGTACTTAGCCTGGTACCAGCAGAAACCTGGCCAGGCTCCCACCTTA GTCATTTATGATGCATCAACCAGGGCCTCCGGCATTCCAGACAGGTTCAGTGCCAGTGGCTCTGGGACT GACTTCACTCTCACCATCAGCAGTCTGGAGCCTGAAGATTTTGCAGTGTATTTCTGTCAGCACTATGGT ACCTCACCTCCGTTCATTTTTGGCCAAGGGACACGACTGGAGATTAAACGAACTGTGGCTGCACCATCT GTCTTCATCTTCCCGCCATCTGATGAGCAGTTGAAATCTGGAACTGCCTCTGTTGTGTGCCTGCTGAAT AACTTCTATCCCAGAGAGGCCAAAGTACAGTGGAAGGTGGATAACGCCCTCCAATCGGGTAACTCCCAG GAGAGTGTCACAGAGCAGGACAGCAAGGACAGCACCTACAGCCTCAGCAGCACCCTGACGCTGAGCAAA GCAGACTACGAGAAACACAAAGTCTACGCCTGCGAAGTCACCCATCAGGGCCTGAGCTCGCCCGTCACA AAGAGCTTCAACAGGGGAGAGTGT |
| 244 | PFF4 Heavy chain nucleotide sequence | GAAGTGCAGCTGGTGCAGTCTGGGGCTGAGGTGAAGAAGCCTGGGTCCTCGGTGAAGGTCTCCTGCAAG GCTTCTGGAGGCACCTTCAGCAGCTATGCTATCAGCTGGGTGCGACAGGCCCCTGGACAAGGGCTTGAG TGGATGGGAGGGATCATCCCTATCTTTGGTACGGCAAACTACGCACAGAAGTTCCAGGGCAGAGTCACG ATTACCGCGGACGAATCCACGAGCACAGCCTACATGGAGCTGAGCAGCCTGAGATCTGAGGACACGGCC GTGTATTACTGTGCGAGATCCTATGATAGTAGTGGTTATTACTACTTTGACTACTGGGGCCAGGGAACC CTGGTCACCGTCTCAAGCGCCTCCACCAAGGGCCCATCGGTCTTCCCCCTGGCACCCTCCTCCAAGAGC ACCTCTGGGGGCACAGCGGCCCTGGGCTGCCTGGTCAAGGACTACTTCCCCGAACCGGTGACGGTGTCG TGGAACTCAGGCGCCCTGACCAGCGGCGTCCACACCTTCCCGGCTGTCCTACAGTCCTCAGGACTCTAC TCCCTCAGCAGCGTAGTGACCGTGCCCTCCAGCAGCTTGGGCACCCAGACCTACATCTGCAACGTGAAT CACAAGCCCAGCAACACCAAGGTGGACAAGAAAGTTGAGCCCAAATCTTGT |
| 245 | PFF4 Light chain VD | ETTLTQSPGTLSTSPGERATLSCRASRSVGKYLAWYQQKPGQAPTLVIYDASTRASGIPDRFSASGSGT DFTLTISSLEPEDFAVYFCQHYGTSPPFIFGQGTRLEIKRTVAAPSVFIFPPSDEQLKSGTASVVCLLN NFYPREAKVQWKVDNALQSGNSQESVTEQDSKDSTYSTSSTLTLSKADYEKHKVYACEVTHQGLSSPVT KSFNRGEC |
| 246 | PFF4 Heavy chain VD | EVQLVQSGAEVKKPGSSVKVSCKASGGTFSSYAISWVRQAPGQGLEWMGGIIPIFGTANYAQKFQGRVT ITADESTSTAYMELSSLRSEDTAVYYCARSYDSSGYYYFDYWGQGTLVTVSSASTKGPSVFPLAPSSKS |

-continued

Sequences

| SEQ ID NO: | Description | Sequence |
|---|---|---|
| | | TSGGTAALGCLVKDYFPEPVTVSWNSGALTSGVHTFPAVLQSSGLYSLSSVVTVPSSSLGTQTYICNVNHKPSNTKVDKKVEPKSC |
| 247 | PFF4 LC-CDR1 | RASRSVGKYLA |
| 248 | PFF4 LC-CDR2 | DASTRAS |
| 249 | PFF4 LC-CDR3 | QHYGTSPPFI |
| 250 | PFF4 HC-CDR3 | SYDSSGYYYFDY |
| 251 | PFF5 Light chain nucleotide sequence | CAGGCTGTGGTGATCCAGGAGCCATCGTTCTCAGTGTCCCCTGGAGGGACAGTCACACTCACTTGTGGCTTGAGCTCTGGCTCAGTCTCTACTACTTACTACCCCAGCTGGTACCAGCAGACCCCAGGCCAGGCTCCACGCACGCTCATCTACAGCACAAACACTCGCTCTTCTGGGGTCCCTGATCGCTTCTCTGGCTCCATCCTTGGGAACAAAGCTGCCCTCACCATCACGGGGGCCCAGGCAGATGATGAATCTGATTATTACTGTGTGCTGTATATGGGTAATGGCATTTCGGTGTTCGGCGGAGGGACCAAGCTGACCGTCCTAGGTCAGCCCAAGGCTGCCCCCTCGGTCACTCTGTTCCCGCCCTCCTCTGAGGAGCTTCAAGCCAACAAGGCCACACTGGTGTGTCTCATAAGTGACTTCTACCCGGGAGCCGTGACAGTGGCCTGGAAGGCAGATAGCAGCCCCGTCAAGGCGGGAGTGGAGACCACCACACCCTCCAAACAAAGCAACAACAAGTACGCGGCCAGCAGCTACCTGAGCCTGACGCCTGAGCAGTGGAAGTCCCACAAAAGCTACAGCTGCCAGGTCACGCATGAAGGGAGCACCGTGGAGAAGACAGTGGCCCCTGCAGAATGCTCT |
| 252 | PFF5 Heavy chain nucleotide sequence | CAGGTGCAGCTGCAGGAGTCGGGCCCAGGACTGGTGAAGCCTTCGGAGACCCTGTCCCTCACCTGCACTGTCTCTGGTGGCTCCATCAGCAGTAGTAGTTACTACTGGGGCTGGATCCGCCAGCCCCCAGGGAAGGGGCTGGAGTGGATTGGGAGTATCTATTATAGTGGGAGCACCTACTACAACCCGTCCCTCAAGAGTCGAGTCACCATATCCGTAGACACGTCCAAGAACCAGTTCTCCCTGAGGCTGAGCTCTGTGAGCGCCGCAGACACGGCCGTGTATTACTGTGCGAGATACGCGCCTGATAGTAGTGGTTACCTGGTGGCTTTTGATATCTGGGGCCAAGGGACAATGGTCACCGTCTCAAGCGCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTCCACACCTTCCCGGCTGTCCTACAGTCCTCAGGACTCTACTCCCTCAGCAGCGTAGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGT |
| 253 | PFF5 Light chain VD | QAVVIQEPSFSVSPGGTVTLTCGLSSGSVSTTYYPSWYQQTPGQAPRTLIYSTNTRSSGVPDRFSGSILGNKAALTITGAQADDESDYYCVLYMGNGISVFGGGTKLTVLGQPKAAPSVTLFPPSSEELQANKATLVCLISDFYPGAVTVAWKADSSPVKAGVETTTPSKQSNNKYAASSYLSLTPEQWKSHKSYSCQVTHEGSTVEKTVAPAECS |
| 254 | PFF5 Heavy chain VD | QVQLQESGPGLVKPSETTSLTCTVSGGSISSSSYYWGWIRQPPGKGLEWIGSIYYSGSTYYNPSLKSRVTISVDTSKNQFSLRLSSVSAADTAVYYCARYAPDSSGYLVAFDIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 255 | PFF5 LC-CDR1 | GLSSGSVSTTYYPS |
| 256 | PFF5 LC-CDR3 | VLYMGNGISV |
| 257 | PFG1 Light chain nucleotide sequence | CAGGCTGTGCTGACTCAGCCGTCTTCCCTCTCTGCATCTCCTGGAGCATCAGCCAGTCTCACCTGCACCTTGCGCAGTGGCATCAATGTTGGTACCTACAGGATATACTGGTACCAGCAGAAGCCAGGGAGTCCTCCCCAGTATCTCCTGAGGTACAAATCAGACTCAGATAAGCAGCAGGGCTCTGGAGTCCCCAGCCGCTTCTCTGGATCCAAAGATGCTTCGGCCAATGCAGGGATTTTACTCATCTCTGGGCTCCAGTCTGAGGATGAGGCTGACTATTACTGTATGATTTGGCACAGCAGCGCTTGGGTGTTCGGCGGAGGGACCAAGCTGACCGTCCTAGGTCAGCCCAAGGCTGCCCCCTCGGTCACTCTGTTCCCACCCTCCTCTGAGGAGCTTCAAGCCAACAAGGCCACACTGGTGTGTCTCATAAGTGACTTCTACCCGGGAGCCGTGACAGTGGCCTGGAAGGCAGATAGCAGCCCCGTCAAGGCGGGAGTGGAGACCACCACACCCTCCAAACAAAGCAACAACAAGTACGCGGCCAGCAGCTACCTGAGCCTGACGCCTGAGCAGTGGAAGTCCCACAAAAGCTACAGCTGCCAGGTCACGCATGAAGGGAGCACCGTGGAGAAGACAGTGGCCCCTGCAGAATGCTCT |
| 258 | PFG1 Heavy chain nucleotide sequence | GAGGTCCAGCTGGTACAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGGCTGGAGTGGGTGGCAGTTATATGGTATGATGGAAGTAATAAATACTATGCAGACTCCGTGAAGGGCCGATTCACCATCTCCAGAGACAATTCCAAGAACACGCTGTATCTGCAAATGAACAGCCTGAGAGCTGAGGACACGGCTGTATATTACTGTGCCACAATGACTACTGAGGACTACTGGGGCCAGGGCACCCTGGTCACCGTCTCAAGCGCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTCCACACCTTCCCGGCTGTCCTACAGTCCTCAGGACTCTACTCCCTCAGCAGCGTAGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGT |
| 259 | PFG1 Light chain VD | QAVLTQPSSLSASPGASASLTCTLRSGINVGTYRIYWYQQKPGSPPQYLLRYKSDSDKQQGSGVPSRFSGSKDASANAGILLISGLQSEDEADYYCMIWHSSAWVFGGGTKLTVLGQPKAAPSVTLFPPSSEELQANKATLVCLISDFYPGAVTVAWKADSSPVKAGVETTTPSKQSNNKYAASSYLSLTPEQWKSHKSYSCQVTHEGSTVEKTVAPAECS |

-continued

| SEQ ID NO: | Description | Sequence |
|---|---|---|
| 260 | PFG1 Heavy chain VD | EVQLVQSGGGVVQPGRSLRLSCAASGFTFSSYGMHWVRQAPGKGLEWVAVIWYDGSNKYYADSVKGRFT ISRDNSKNTLYLQMNSTRAEDTAVYYCATMTTEDYWGQGTLVTVSSASTKGPSVFPLAPSSKSTSGGTA ALGCLVKDYFPEPVTVSWNSGALTSGVHTFPAVLQSSGLYSLSSVVTVPSSSLGTQTYICNVNHKPSNT KVDKKVEPKSC |
| 261 | PFG1 LC-CDR1 | TLRSGINVGTYRIY |
| 262 | PFG1 LC-CDR2 | YKSDSDKQQGS |
| 263 | PFG1 LC-CDR3 | MIWHSSAWV |
| 264 | PFG1 HC-CDR2 | VIWYDGSNKYYADSVKG |
| 265 | PFG1 HC-CDR3 | MTTEBY |
| 266 | PFG2 Light chain nucleotide sequence | GAAATTGTGTTGACGCAGTCTCCAGCCACCCTGTCTTTGTCTCCAGGGGAAAGAGCCACCCTCTCCTGC AGGGCCAGTCAGAGTGTTAGCAGCTACTTAGCCTGGTACCAACAGAAACCTGGCCAGGCTCCCAGGCTC CTCATCTATGATGCGTCCAACAGGGCCACTGGCATCCCAGCCAGGTTCAGTGGCAGTGGGTCTGGGACA GACTTCACTCTCACCATCAGCAGCCTAGAGCCTGAAGATTTTGCAGTTTATTACTGTCAGCAGCGTAGC AACTGGCCGCTCACTTTCGGCGGAGGGACCAAGGTGGAGATCAAACGAACTGTGGCTGCACCATCTGTC TTCATCTTCCCGCCATCTGATGAGCAGTTGAAATCTGGAACTGCCTCTGTTGTGTGCCTGCTGAATAAC TTCTATCCCAGAGAGGCCAAAGTACAGTGGAAGGTGGATAACGCCCTCCAATCGGGTAACTCCCAGGAG AGTGTCACAGAGCAGGACAGCAAGGACAGCACCTACAGCCTCAGCAGCACCCTGACGCTGAGCAAAGCA GACTACGAGAAACACAAAGTCTACGCCTGCGAAGTCACCCATCAGGGCCTGAGCTCGCCCGTCACAAAG AGCTTCAACAGGGGAGAGTGT |
| 267 | PFG2 Heavy chain nucleotide sequence | GAAGTGCAGCTGGTGCAGTCTGGGGGAGGCTTGGTACAGCCTGGGGGGTCCCTGAGACTCTCCTGTGCA GCCTCTGGATTCACCTTTAGCAGCTATGCCATGAGCTGGGTCCGCCAGGCTCCAGGGAAGGGGCTGGAG TGGGTCTCATCCATTAGTAGTAGTAGTAGTTACATATACTACGCAGACTCGGTGAAGGGCCGATTCACC ATCTCCAGAGACAACGCCAAGAATTCACTGTATCTGCAAATGAACAGCCTGAGGGCCGAGGACACGGCT GTCTATTACTGTGCGAGAGATGGCAGTGCCTGGTCACGACCCTACTGGGGCCAGGGAACCCTGGTCACC GTCTCAAGCGCCTCCACCAAGGGCCCATCGGTCTTCCCCCTGGCACCCTCCTCCAAGAGCACCTCTGGG GGCACAGCGGCCCTGGGCTGCCTGGTCAAGGACTACTTCCCCGAACCGGTGACGGTGTCGTGGAACTCA GGCGCCCTGACCAGCGGCGTCCACACCTTCCCGGCTGTCCTACAGTCCTCAGGACTCTACTCCCTCAGC AGCGTAGTGACCGTGCCCTCCAGCAGCTTGGGCACCCAGACCTACATCTGCAACGTGAATCACAAGCCC AGCAACACCAAGGTGGACAAGAAAGTTGAGCCCAAATCTTGT |
| 268 | PFG2 Light chain VD | EIVLTQSPATLSLSPGERATLSCRASQSVSSYLAWYQQKPGQAPRLLIYDASNRATGIPARFSGSGSGT DFTLTISSLEPEDFAVYYCQQRSNWPLTFGGGTKVEIKRTVAAPSVFIFPPSDEQLKSGTASVVCLLNN FYPREAKVQWKVDNALQSGNSQESVTEQDSKDSTYSTSSTLTLSKADYEKHKVYACEVTHQGLSSPVTK SFNRGEC |
| 269 | PFG2 Heavy chain VD | EVQLVQSGGGLVQPGGSLRLSCAASGFTFSSYAMSWVRQAPGKGLEWVSSISSSSSYIYYADSVKGRFT ISRDNAKNSLYLQMNSLRAEDTAVYYCARDGSAWSRPYWGQGTLVTVSSASTKGPSVFPLAPSSKSTSG GTAALGCLVKDYFPEPVTVSWNSGALTSGVHTFPAVLQSSGLYSLSSVVTVPSSSLGTQTYICNVNHKP SNTKVDKKVEPKSC |
| 270 | PFG2 LC-CDR1 | RASQSVSSYLA |
| 271 | PFG2 LC-CDR2 | DASNRAT |
| 272 | PFG2 LC-CDR3 | QQRSNWPLT |
| 273 | PFG2 HC-CDR2 | SISSSSSYIYYADSVKG |
| 274 | PFG2 HC-CDR3 | DGSAWSRPY |
| 275 | PFG3 Light chain nucleotide sequence | CAGGCTGTGGTGCTCCAGGAGCCATCGTTCTCAGTGTCCCCTGGAGGGACAGTCACACTCACTTGTGGC TTGACCTCTGGCGCAGTCTCCAGTTCTTACTACCCCAGCTGGTACCAGCAGACCCCAGGCCAGGCTCCT CGCACTCTCATTTATAACACAGACATTCGCTTTTCTGGGGTCCCTGATCGCTTCTCTGGCTCCATCCTT GGGAACAAAGCTGCCCTCACCATCACGGGGGCCCAGGCAGATGATGAATCTGATTATTACTGTGTACTA TATATGGGTAGTGGCATTTCGGTGTTCGGCGGAGGGACCAAACTGACCGTCCTAGGTCAGCCCAAGGCT GCCCCCTCGGTCACTCTGTTCCCACCCTCCTCTGAGGAGCTTCAAGCCAACAAGGCCACACTGGTGTGT CTCATAAGTGACTTCTACCCGGGAGCCGTGACAGTGGCCTGGAAGGCAGATAGCAGCCCCGTCAAGGCG GGAGTGGAGACCACCACACCCTCCAAACAAAGCAACAACAAGTACGCGGCCAGCAGCTACCTGAGCCTG ACGCCTGAGCAGTGGAAGTCCCACAAAAGCTACAGCTGCCAGGTCACGCATGAAGGGAGCACCGTGGAG AAAACAGTGGCCCCTGCAGAATGCTCT |
| 276 | PFG3 Heavy chain nucleotide sequence | GAAGTGCAGCTGGTGCAGTCTGGGGCTGAGGTGAAGAAGCCTGGGACCTCAGTGACAGTCTCCTGCAGG GCTTCTGGATTCACCTTCAGCGACTACTATATACACTGGGTGCGACAGGCCCCTGGACAAGGGCTTGAG TGGATGGGATGGGTCAGCGCTTACAATGGTGACACAAACTATGCGCAGAAGTTCCAGGGCAGAGTCACC GTGACCACAGACACATCCACGAGCACAGCCTACATGGAGCTGAGGAGCCTGAGATCTGACGACACGGCC GTGTATTTCTGTGCGAGAGAGATTGCCTCCTATAGTGGGAGCTACTACGACTACTGGGGCCAGGGCACC CTGGTCACCGTCTCAAGCGCCTCCACCAAGGGCCCATCGGTCTTCCCCCTGGCACCCTCCTCCAAGAGC |

-continued

Sequences

| SEQ ID NO: | Description | Sequence |
|---|---|---|
| | | ACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTCCACACCTTCCCGGCTGTCCTACAGTCCTCAGGACTCTACTCCCTCAGCAGCGTAGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGT |
| 277 | PFG3 Light chain VD | QAVVLQEPSFSVSPGGTVTLTCGLTSGAVSSSYYPSWYQQTPGQAPRTLIYNTDIRFSGVPDRFSGSILGNKAALTITGAQADDESDYYCVLYMGSGISVFGGGTKLTVLGQPKAAPSVTLFPPSSEELQANKATLVCLISDFYPGAVTVAWKADSSPVKAGVETTTPSKQSNNKYAASSYLSLTPEQWKSHKSYSCQVTHEGSTVEKTVAPAECS |
| 278 | PFG3 Heavy chain VD | EVQLVQSGAEVKKPGTSVTVSCRASGFTFSDYYIHWVRQAPGQGLEWMGWVSAYNGDTNYAQKFQGRVTVTTDTSTSTAYMELRSLRSDDTAVYFCAREIASYSGSYYDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 279 | PFG3 LC-CDR1 | GLTSGAVSSSYYPS |
| 280 | PFG3 LC-CDR2 | NTDIRFS |
| 281 | PFG3 HC-CDR1 | DYYIH |
| 282 | PFG3 HC-CDR2 | WVSAYNGDTNYAQKFQG |
| 283 | PFG4 Light chain nucleotide sequence | CAGTCTGTGCTGACTCAGCCACCCTCGGTGTCCAAGGCCTTGAGACAGACCGCCACCCTCACCTGCACGGGGAACAACAACAATGTTGGCTTCGCAGGAGCAGCTTGGTTTCTGCAGCACCAGGGCCACCCTCCCAAGCTCCTGGCCTACAGGAATAACGACCGGCCCTCAGGGATCTCAGAGAGATTTTCTGCTTCCAGGTCAGGCAATACTGCCTCCCTGACCATTACTGGACTCCAGCCTGAGGACGAGGCTGATTATTACTGCTCAGCATGGGACAGCAGTCTCAAAGTTCAGGTGTTCGGCGGAGGGACCAAGCTGACCGTCCTAGGTCAGCCCAAGGCTGCCCCCTCGGTCACTCTGTTCCCACCCTCCTCTGAGGAGCTTCAAGCCAACAAGGCCACACTGGTGTGTCTCATAAGTGACTTCTACCCGGGAGCCGTGACAGTGGCCTGGAAGGCAGATAGCAGCCCCGTCAAGGCGGGAGTGGAGACCACCACACCCTCCAAACAAAGCAACAACAAGTACGCGGCCAGCAGCTACCTGAGCCTGACGCCTGAGCAGTGGAAGTCCCACAAAAGCTACAGCTGCCAGGTCACGCATGAAGGGAGCACCGTGGAGAAGACAGTGGCCCCTACAGAATGTTCA |
| 284 | PFG4 Heavy chain nucleotide sequence | CAGGTACAGCTGCAGCAGTCAGGGGCTGAGGTGAAGAAGCCTGGGTCCTCGGTGAAGGTCTCCTGCAAGGCTTCTGGAGGCACCTTCAGCAGCTATGCTATCAGCTGGGTGCGACAGGCCCCTGGACAAGGGCTTGAGTGGATGGGAGGGATCATCCCTATCTTTGGTACAGCAAACTACGCACAGAAGTTCCAGGGCAGAGTCACGATTACCGCGGACAAATCCACGAGCACAGCCTACATGGAGCTGAGCAGCCTGAGATCTGAGGACACGGCCGTGTATTACTGTGCGAGAGGTGCCGACTGGAACAGTGACTACTGGGGCCAGGGAACCCTGGTCACCGTCTCAAGCGCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTCCACACCTTCCCGGCTGTCCTACAGTCCTCAGGACTCTACTCCCTCAGCAGCGTAGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGT |
| 285 | PFG4 Light chain VD | QSVLTQPPSVSKALRQTATLTCTGNNNNVGFAGAAWFLQHQGHPPKLLAYRNNDRPSGISERFSASRSGNTASLTITGLQPEDEADYYCSAMESSLKVQVFGGGTKLTVLGQPKAAPSVTLFPPSSEELQANKATLVCLISDFYPGAVTVAWKADSSPVKAGVETTTPSKQSNNKYAASSYLSLTPEQWKSHKSYSCQVTHEGSTVEKTVAPTECS |
| 286 | PFG4 Heavy chain VD | QVQLQQSGAEVKKPGSSVKVSCKASGGTFSSYAISWVRQAPGQGLEWMGGIIPIFGTANYAQKFQGRVTITADKSTSTAYMELSSLRSEDTAVYYCARGADWNSDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 287 | PFG4 LC-CDR1 | TGNNNNVGFAGAA |
| 288 | PFG4 LC-CDR2 | RNNDRPS |
| 289 | PFG4 LC-CDR3 | SAWDSSLKVQV |
| 290 | PFG4 HC-CDR3 | GADWNSDY |
| 291 | PFG5 Light chain nucleotide sequence | GATGTTGTGATGACTCAGTCTCCACTCTCCCTGCCCGTCACCCCTGGAGAGCCGGCCTCCATCTCCTGCAGGTCTAGTCAGAGCCTCCTGCATAGTAATGGATACAACTATTTGGATTGGTACCTGCAGAAGCCAGGGCAGTCTCCACAGCTCCTGATCTACTTGGGTTCTAATCGGGCCCCCGGGGTCCCTGACAGGTTCAGTGGCAGTGGATCAGGCACAGATTTTACACTGAAAATCAGCAGAGTGGAGGCTGAGGATGTTGGGGTTTATTACTGCATGCAAGGTACACACTGGCCTCTCACTTTCGGCGGAGGGACCAAGGTGGAGATCAAACGAACTGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGT |

-continued

Sequences

| SEQ ID NO: | Description | Sequence |
|---|---|---|
| 292 | PFG5 Heavy chain nucleotide sequence | GAAGTGCAGCTGGTGCAGTCTGGGGGAGGCGTGGTCCAGCCTGGGAGGTCCCTGAGACTCTCCTGTGCA GCCTCTGGATTCACCTTCAGTAGCTATGCTATGCACTGGGTCCGCCAGGCTCCAGGCAAGGGGCTGGAG TGGGTGGCAGTTATATCATATGATGGAAGCAATAAATACTACGCAGACTCCGTGAAGGGCCGATTCACC ATCTCCAGAGACAATTCCAAGAACACGCTGTATCTGCAAATGAACAGCCTGAGAGCTGAGGACACGGCT GTGTATTACTGTGCGAGATCGTATGGTTCGGGGAGTTATAGGTCCCATGCTTTTGATATCTGGGGCCAA GGGACAATGGTCACCGTCTCAAGCGCCTCCACCAAGGGCCCATCGGTCTTCCCCCTGGCACCCTCCTCC AAGAGCACCTCTGGGGGCACAGCGGCCCTGGGCTGCCTGGTCAAGGACTACTTCCCCGAACCGGTGACG GTGTCGTGGAACTCAGGCGCCCTGACCAGCGGCGTCCACACCTTCCCGGCTGTCCTACAGTCCTCAGGA CTCTACTCCCTCAGCAGCGTAGTGACCGTGCCCTCCAGCAGCTTGGGCACCCAGACCTACATCTGCAAC GTGAATCACAAGCCCAGCAACACCAAGGTGGACAAGAAAGTTGAGCCCAAATCTTGT |
| 293 | PFG5 Light chain VD | DVVMTQSPLSLPVTPGEPASISCRSSQSLLHSNGYNYLDWYLQKPGQSPQLLIYLGSNRAPGVPDRFSG SGSGTDFTLKISRVEAEDVGVYYCMQGTHWPLTFGGGTKVEIKRTVAAPSVFIFPPSDEQLKSGTASVV CLLNNFYPREAKVQWKVDNALQSGNSQESVTEQDSKDSTYSLSSTLTLSKADYEKHKVYACEVTHQGLS SPVTKSFNRGEC |
| 294 | PFG5 Heavy chain VD | EVQLVQSGGGVVQPGRSLRLSCAASGFTFSSYAMHWVRQAPGKGLEWVAVISYDGSNKYYADSVKGRFT ISRDNSKNTLYLQMNSLRAEDTAVYYCARSYGSGSYRSHAFDIWGQGTMVTVSSASTKGPSVFPLAPSS KSTSGGTAALGCLVKDYFPEPVTVSWNSGALTSGVHTFPAVLQSSGLYSLSSVVTVPSSSLGTQTYICN VNHKPSNTKVDKKVEPKSC |

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

BRIEF DESCRIPTION OF THE FIGURES

Embodiments and experiments illustrating the principles of the invention will now be discussed with reference to the accompanying figures in which:

FIG. 1. Light chain variable domain amino acid sequences for anti-HER2 antibody clones (A) P1A3, (B) P1C5, (C) P1E4, and (D) P1F1. CDRs are underlined.

FIG. 2. Heavy chain variable domain amino acid sequences for anti-HER2 antibody clones (A) P1A3, (B) P1C5, (C) P1E4, and (D) P1F1. CDRs are underlined.

FIGS. 18A and 18B. Graphs showing characteristics of anti-HER2 CART cells comprising clones A4, B4, B5, D4, E1, F5 and G3. (18A) Percentage cytolysis of BT474 human breast cancer cells by CAR T cells. (18B) Cytokine (IFNγ and IL-2) production by CAR T cells.

EXAMPLES

Example 1: Discovery

Figure 3:
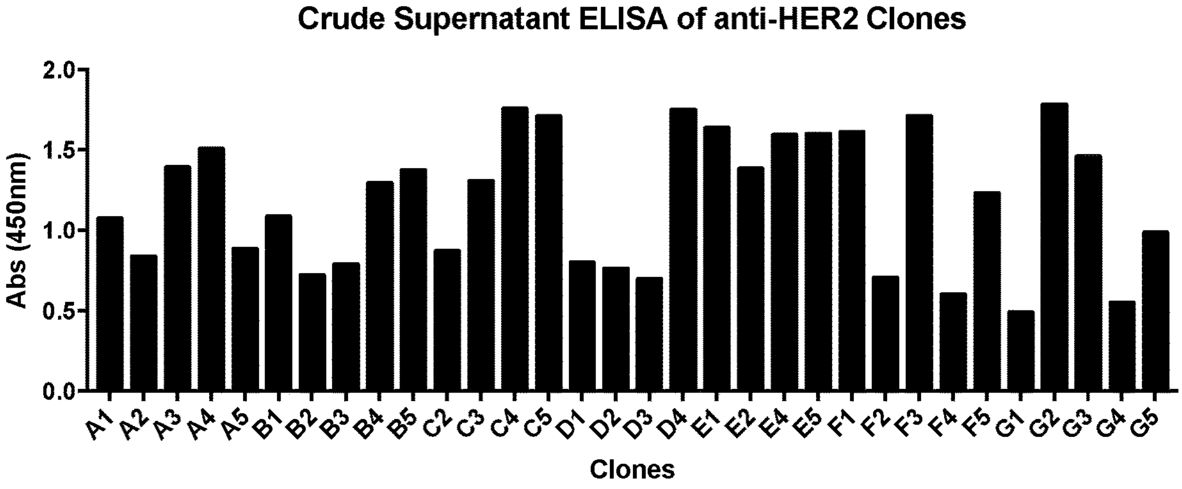
FIG. 3. Binding to immobilized HER2 protein by bacteria-produced crude Fabs selected from antibody phage display library.

Anti-human HER-2 binding antibodies were isolated from a human Fabs library by phage display, in 3 rounds of biopanning. Binding of isolated Fabs from the human Fabs library and immobilised HER-2 protein was measured by ELISA (FIG. 3). The dissociation rate ($K_d$) from HER-2 of each clone was measured by Surface Plasmon Resonance (SPR). The results are shown in Table 1.

TABLE 1

Dissociation rate ($k_d$) measured on immobilized HER2 protein by SPR

| Clone | $k_d$ (1/s) |
|---|---|
| A1 | $4.15 \times 10^{-3}$ |
| A2 | $2.18 \times 10^{-3}$ |
| A3 | $4.16 \times 10^{-3}$ |
| A4 | $1.96 \times 10^{-2}$ |
| A5 | $3.26 \times 10^{-3}$ |
| B1 | $5.65 \times 10^{-3}$ |
| B2 | $1.77 \times 10^{-4}$ |
| B3 | $1.02 \times 10^{-2}$ |
| B4 | $3.22 \times 10^{-2}$ |
| B5 | $1.70 \times 10^{-2}$ |
| C3 | $5.28 \times 10^{-2}$ |
| C5 | $4.48 \times 10^{-3}$ |
| D1 | $7.14 \times 10^{-2}$ |
| D2 | $4.86 \times 10^{-3}$ |
| D3 | $2.72 \times 10^{-2}$ |
| D4 | $3.42 \times 10^{-2}$ |
| E1 | $1.30 \times 10^{-2}$ |
| E2 | $1.87 \times 10^{-2}$ |
| E4 | $1.81 \times 10^{-3}$ |
| E5 | $1.52 \times 10^{-3}$ |
| F1 | $5.02 \times 10^{-3}$ |
| F2 | $4.70 \times 10^{-3}$ |
| F3 | $3.24 \times 10^{-3}$ |
| F5 | $1.41 \times 10^{-2}$ |
| G1 | $3.24 \times 10^{-4}$ |
| G2 | $4.99 \times 10^{-4}$ |
| G3 | $1.58 \times 10^{-2}$ |
| G4 | $6.30 \times 10^{-4}$ |

Four clones were selected initially for further characterisation: P1A3, P1C5, P1E4 and P1F1. Clones A4, B4, B5, C3, D4, E1, F5 and G3 were also selected for characterisation and investigation into utility in CARs.

Example 2: Specific Binding to HER-2

Binding onto HER-2

Interaction between the four antibody clones (P1A3, P1C5, P1E4 and P1F1) and HER-2 was tested by SPR using soluble HER-2 bound onto microchip and flowing the antibodies. In order to assess the specificity of the binding, molecules closely related to HER-2 were also used as bound antigens, namely EGFR and HER-3. The humanised anti-HER-2 antibody trastuzumab was used as a positive control.

Figure 4:
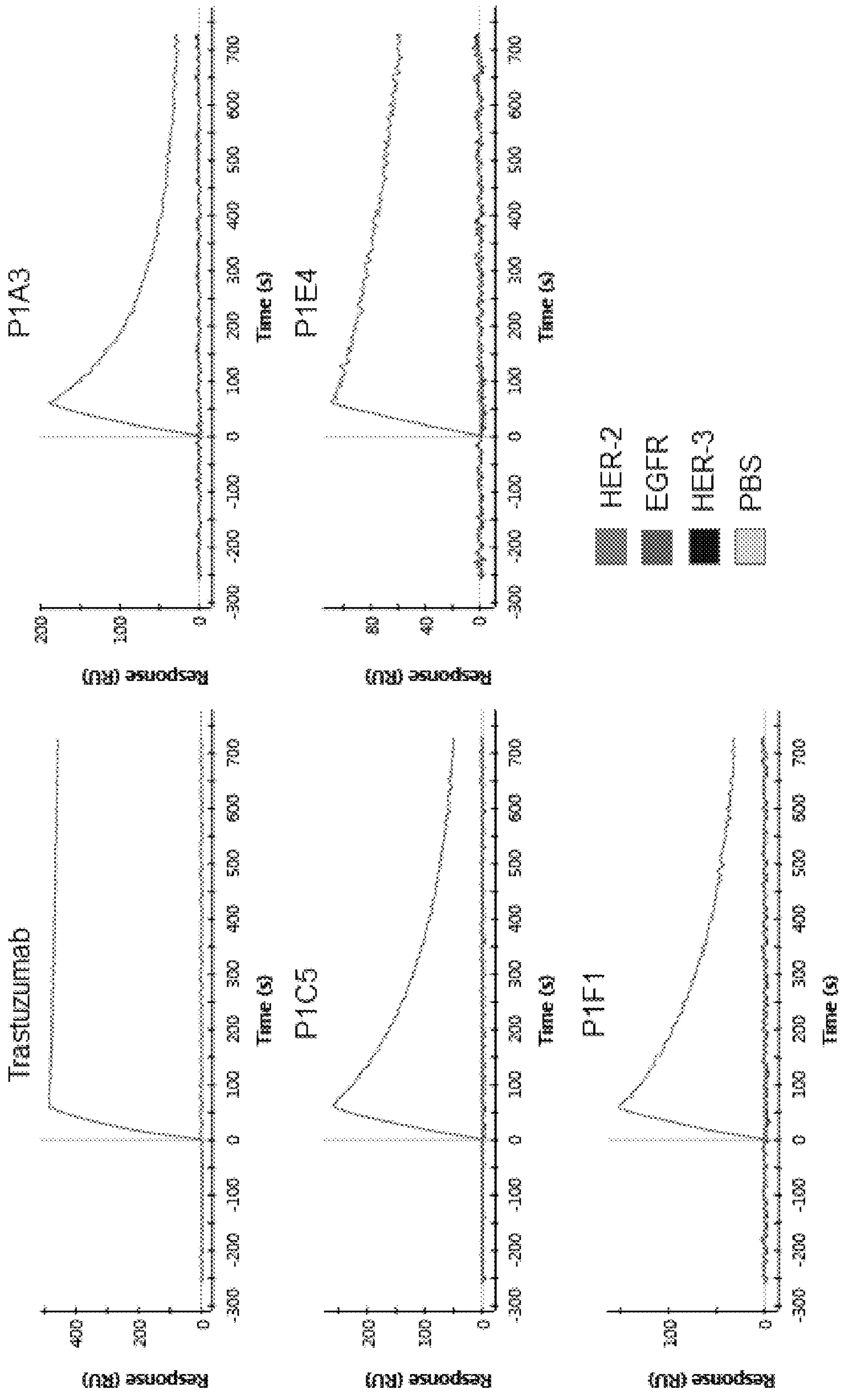
FIG. 4. Binding of P1A3, P1C5, P1E4 and P1F1 to HER-2, EGFR, and HER-3 immobilised on microchip in SPR assay. Trastuzumab was used as a HER-2 positive binder control.

The four antibodies showed specific binding to human HER-2 and no kinds of interaction with HER-3 or EGFR (FIG. 4).

Binding onto HER-2 Expressing Cells

To further characterise the binding of the antibodies to HER-2, antibodies were incubated with cells constitutively overexpressing HER-2, BT-474 and SK-BR-3, cells expressing, but not over-expressing HER-2, BT-20 and MCF-7, or with a triple negative cancer cell line, MDA-MB-468, not expressing the antigen. Both BT-474 and SK-BR-3 cell lines are classified 3+ for HER-2 expression, i.e. overexpressing. BT-20 cell line is classified as basal HER-2 cell line with an expression score of 0/1+; MCF-7 presents the same score and is classified as a luminal tumour cell line. MDA-MB-468 has a HER-2 expression score of 0 (Subik K et al. 2010, Breast Cancer (Auckl), 4:35-41).

After incubation, a secondary antibody was added to detect binding to the cells via flow cytometry. In all assays, trastuzumab was used as a positive control.

Figure 5:
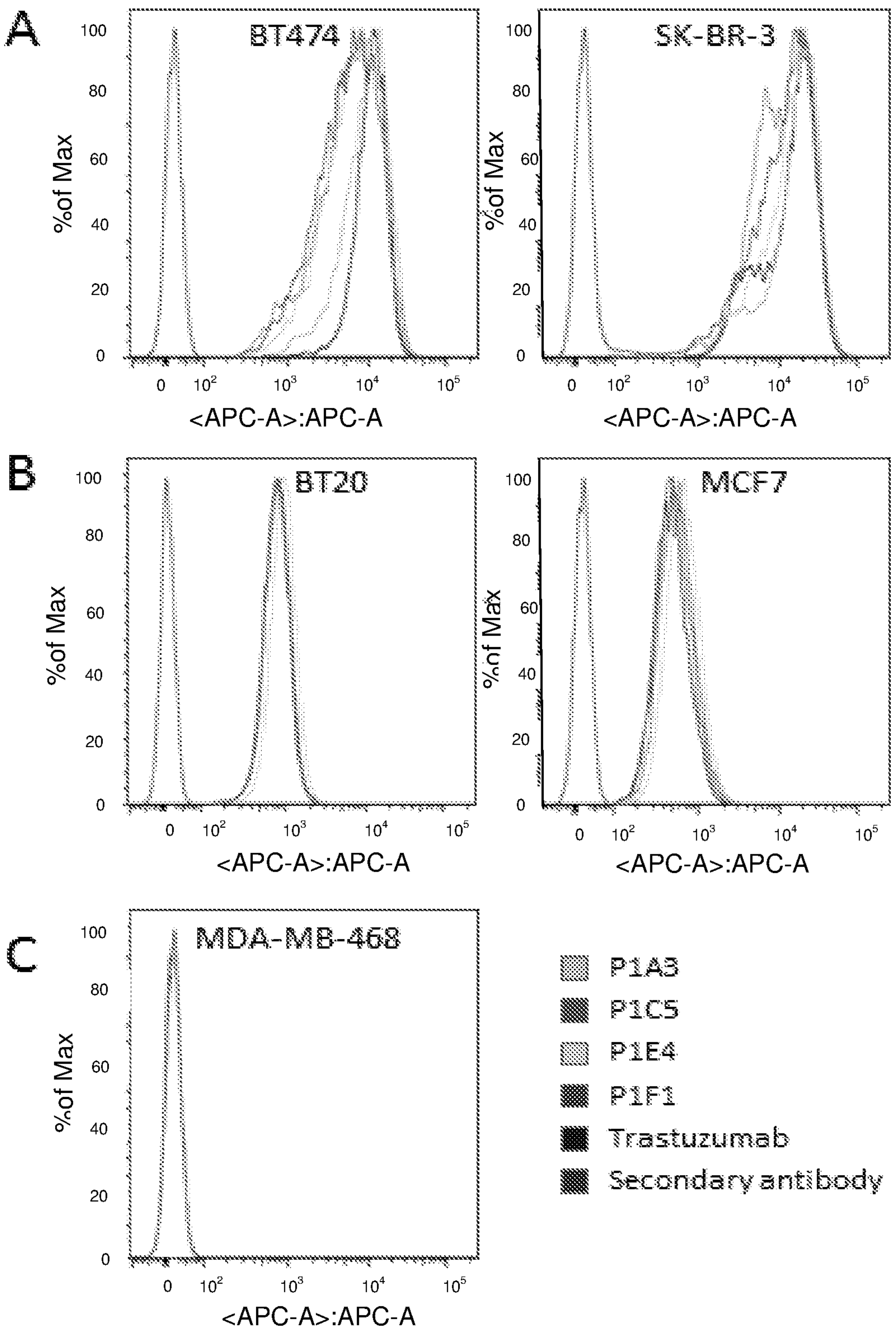
FIG. 5. Binding of P1A3, P1C5, P1E4 and P1F1 to HER-2 overexpressing cells (A), low-expressing cells (B) or non-expressing cells (C). Trastuzumab was used as a positive binder control and the secondary antibody alone as a negative control.

The four anti-HER-2 antibodies bound to HER-2 over-expressing (FIG. 5A) and expressing (FIG. 5B) cells in a similar way as trastuzumab, while no binding was observed on HER-2-negative cells (FIG. 5C).

Figure 6:
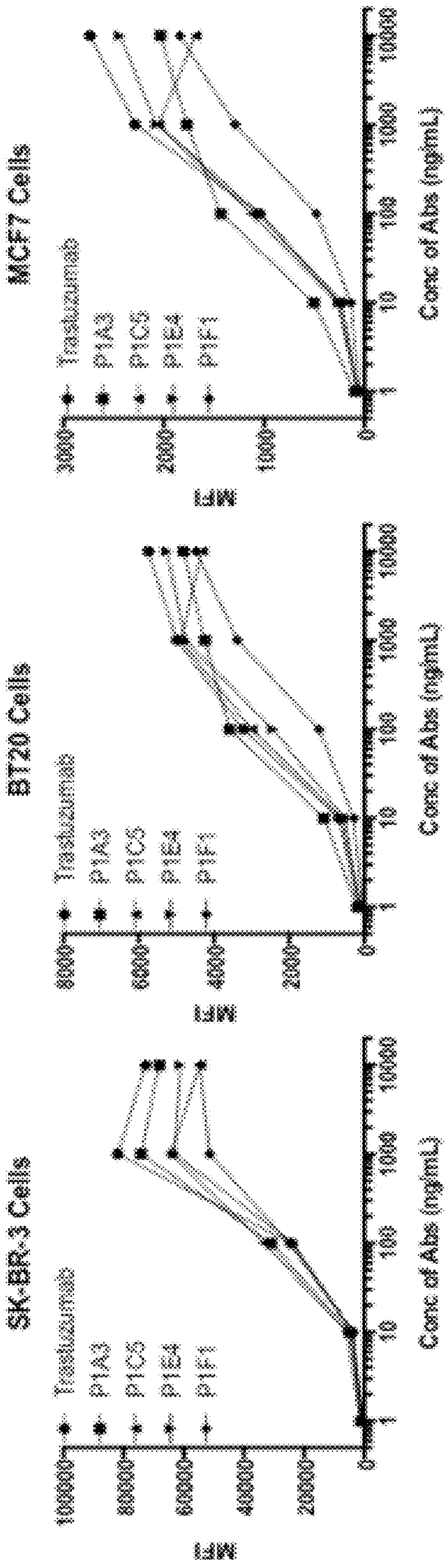
FIG. 6. Dose effect binding of P1A3, P1C5, P1E4 and P1F1 to HER-2 overexpressing cells SK-BR-3 or lower expressing BT-20 and MCF-7 cell. Shown are mean fluorescence intensities (MFIs) after incubation of the cells in the presence of various concentrations of antibodies, binding was revealed with the use of a fluoro-labelled secondary antibody, Trastuzumab was used as a positive binding control.

Antibodies were then incubated with HER-2 expressing cells at various concentrations to study the dose effect binding profile. In such an assay, E4 showed the closest binding profile to trastuzumab (FIG. 6).

Example 3: Binding to a Different Epitope than Trastuzumab

To assess whether the four anti-HER-2 antibodies P1A3, P1C5, P1E4 and P1F1 were binding the same epitope as trastuzumab, binding assays were conducted by SPR. Briefly, the antibody of interest was immobilised on the SPR microchip, a flow of recombinant HER-2 was then applied to bind to the immobilised antibody. Later on, all other antibodies were flown and their binding measured.

Figure 7:
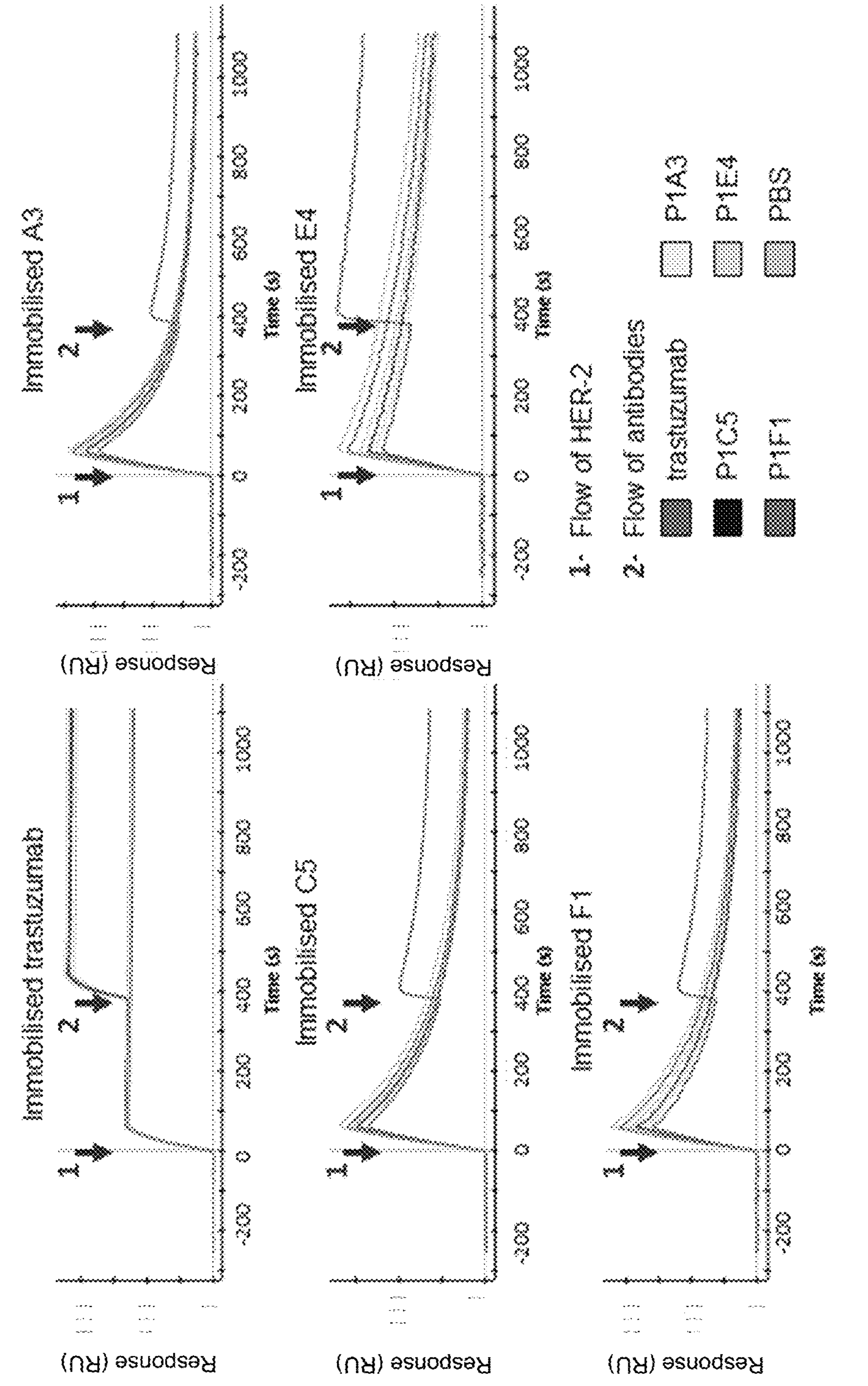
FIG. 7. Binding of trastuzumab, P1A3, P1C5, P1E4 and P1F1 to HER-2 bound to immobilised antibody. P1A3, P1C5, P1E4 and P1F1 bind to HER-2 bound onto trastuzumab (1st panel). Trastuzumab binds to HER-2 bound to any of SIgN's antibody (all other panels).

All four antibodies showed similar dendrograms suggesting that they share a common epitopes or bind to very close epitopes. However, trastuzumab showed a different binding profile, demonstrating that the four antibodies do not share trastuzumab's epitope (FIG. 7).

The binding epitopes of clones A4, B4, B5, C3, D4, E1, F5 and G3 are assessed by SPR as above. The binding profiles are compared to that of trastuzumab and clones A4, B4, B5, C3, D4, E1, F5 and G3 are found to bind a different epitope to trastuzumab.

Example 4: Affinity for Human HER-2

Affinity was measured by SPR. E4 showed the highest affinity for HER-2 amongst the four clones (Table 2).

TABLE 2 affinity of antibodies P1A3, P1C5, P1E4 and P1F1 for HER-2.

| Antibody | Affinity ($K_D$ in nM) |
|---|---|
| Trastuzumab | 0.17 |
| P1A3 | 21.4 |
| P1C5 | 12.7 |
| P1E4 | 5.3 |
| P1F1 | 11.6 |

The binding characteristics of clones A4, B4, B5, C3, D4, E1, F5 and G3 were also determined by SPR. Rate constants of association, dissociation ($k_a$, $k_d$) and the equilibrium dissociation constants ($K_D$) were determined for anti-HER2 Fab molecules. Human HER2 protein (50 μg/mL) was immobilised on the SPR sensor chip and was exposed to five different concentrations of each Fab in 2- or 3-fold dilutions over the flow cells. 1:1 Langmuir model was used to derive the constants.

The results are shown in Table 3.

TABLE 3 affinity of the A4, B4, B5, C3, C4, E1, F5 and G3 Fab for HER-2. anti-HER2 clones

| | $k_a$ [$M^{-1}s^{-1}$] | $k_d$ [$s^{-1}$] | $K_D$ [nM] |
|---|---|---|---|
| A4 | 2.03E+06 | 0.042 | 20.5 |
| B4 | 4.41E+06 | 0.078 | 17.6 |
| B5 | 1.76E+05 | 0.020 | 112 |
| C3 | 4.11E+06 | 0.063 | 15.3 |
| C4 | 1.99E+06 | 0.028 | 14.3 |

TABLE 3-continued affinity of the A4, B4, B5, C3, C4, E1, F5 and G3 Fab for HER-2. anti-HER2 clones

| | $k_a$ [$M^{-1}s^{-1}$] | $k_d$ [$s^{-1}$] | $K_D$ [nM] |
|---|---|---|---|
| E1 | 1.59E+06 | 0.026 | 16.5 |
| F5 | 4.45E+04 | 0.014 | 305 |
| G3 | 1.08E+05 | 0.019 | 183 |

Example 5: Mechanism of Action

Disruption of Membranes

Figure 8:
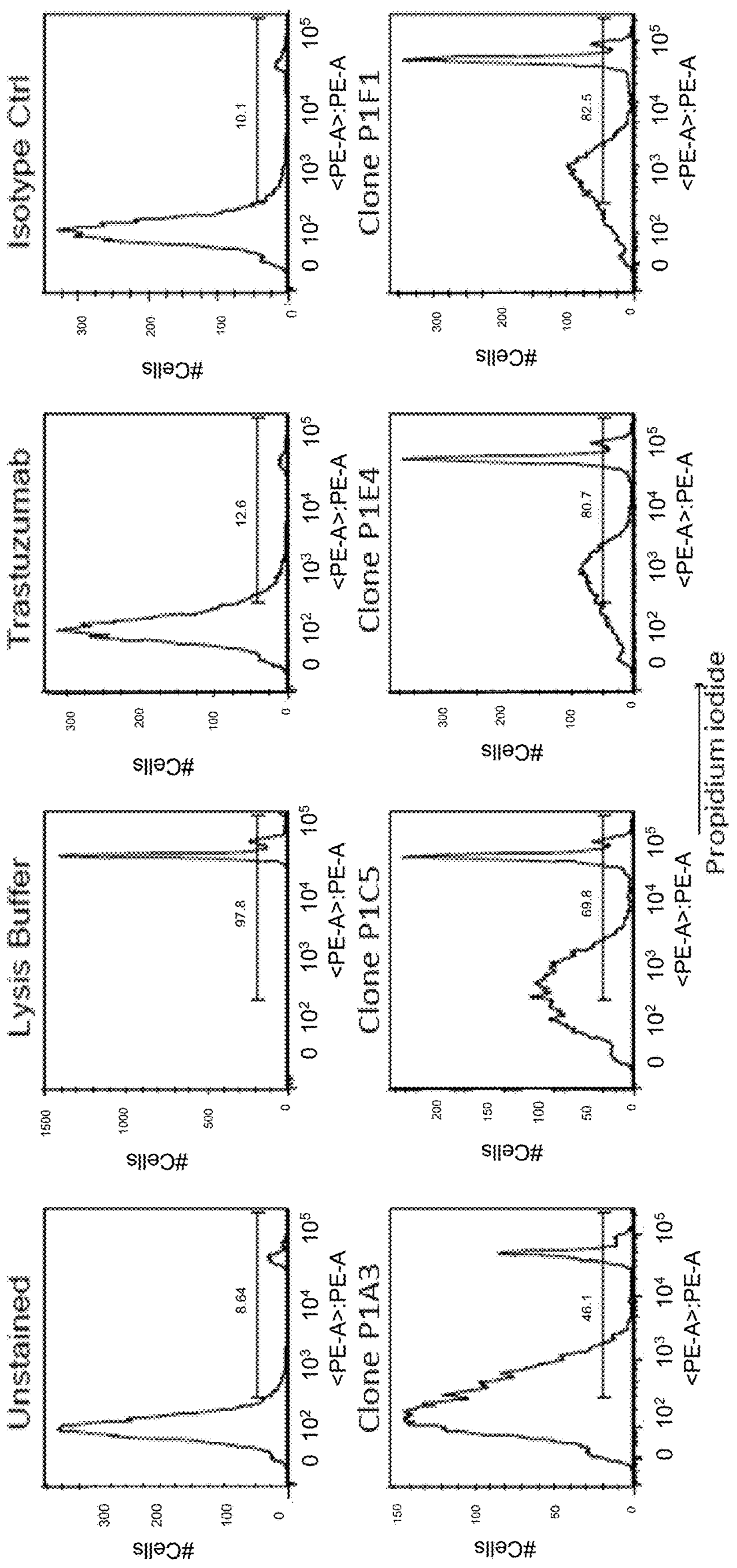
FIG. 8. Staining with propidium iodide on BT-474 cells after incubation in the presence of lysis buffer (lysis positive control), trastuzumab, an isotype control or, P1A3, P1C5, P1E4 or P1F1. Staining with propidium iodide is the proof of cell lysis.

HER2 overexpressing BT-474 cells were incubated in the presence of P1A3, P1C5, P1E4 or P1F1 and propidium iodide. Unlike trastuzumab, the 4 antibodies induced disruption of membrane, allowing propidium iodide insertion, and proving the induction of cell death (FIG. 8).

Induction of Apoptosis

HER2 overexpressing cell lines BT-474 and SK-BR-3 were incubated in the presence of P1E4 or trastuzumab and stained with Annexin-V and propidium iodide to measure apoptosis and death.

Figure 9:
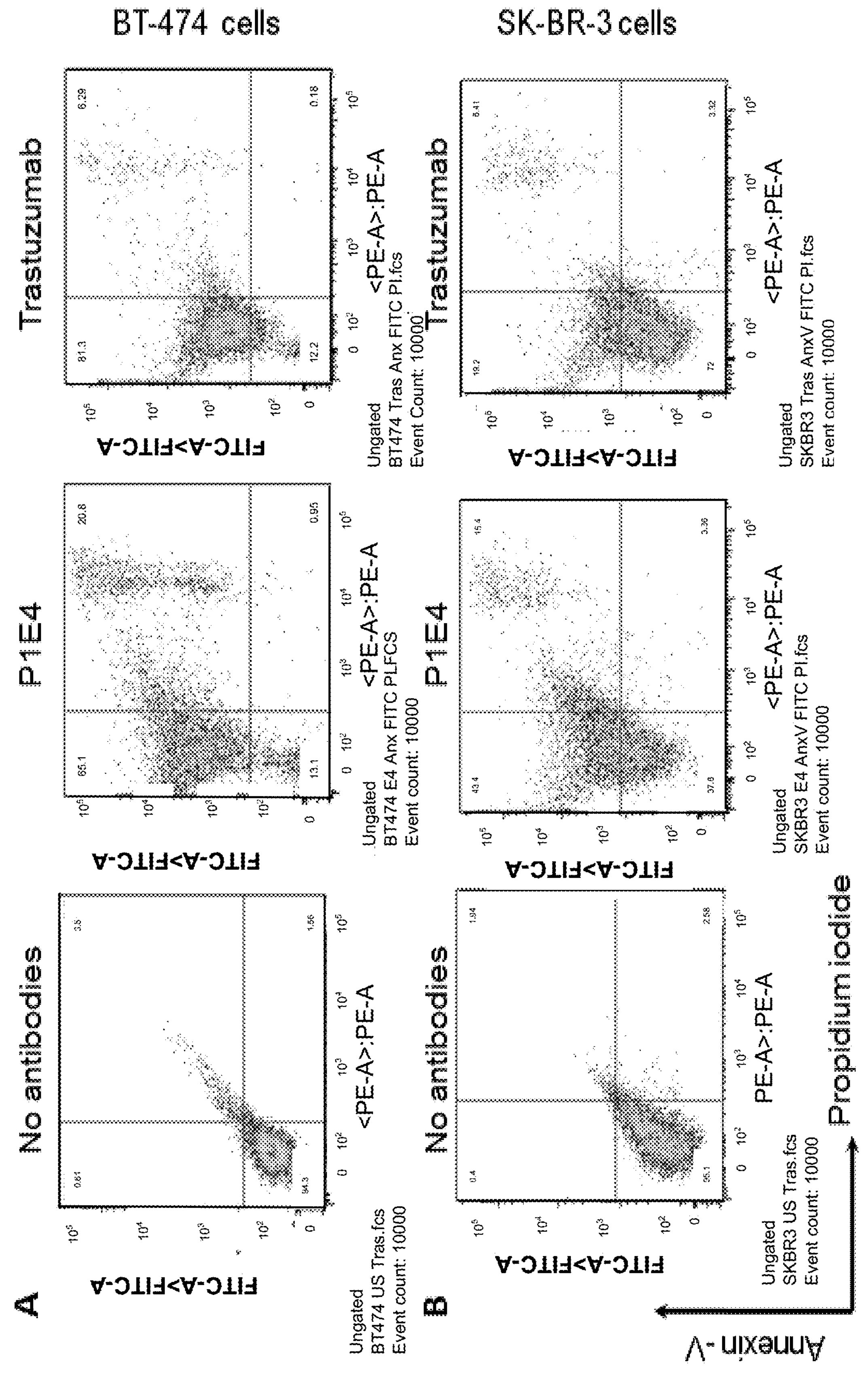
FIG. 9. P1E4-induced apoptosis. Staining with propidium iodide and Annexin-V of BT-474 cells (A) and SK-BR-3 cells (B) after incubation in the presence of P1E4 or trastuzumab.

Cells incubated with P1E4 and showing propidium iodide staining, i.e. dying/dead cells, also showed staining with Annexin-V, showing that P1E4 induces cell death by apoptosis (FIG. 9).

To further confirm the induction of apoptosis, BT-474 cells were incubated in the presence of P1E4, trastuzumab or pertuzumab (another anti-HER-2 antibody) for subsequent measurement of propidium intake, caspase 3/7 pathway activation and cleaved PARP activation. Caspase 3/7 pathway is involved in the apoptotic process. After activation caspase 3/7 activates cleaved PARP in the nucleus which in its turn can trigger the release of pro-apoptotic factors by mitochondria and can block the processes of DNA repair.

Figure 10:
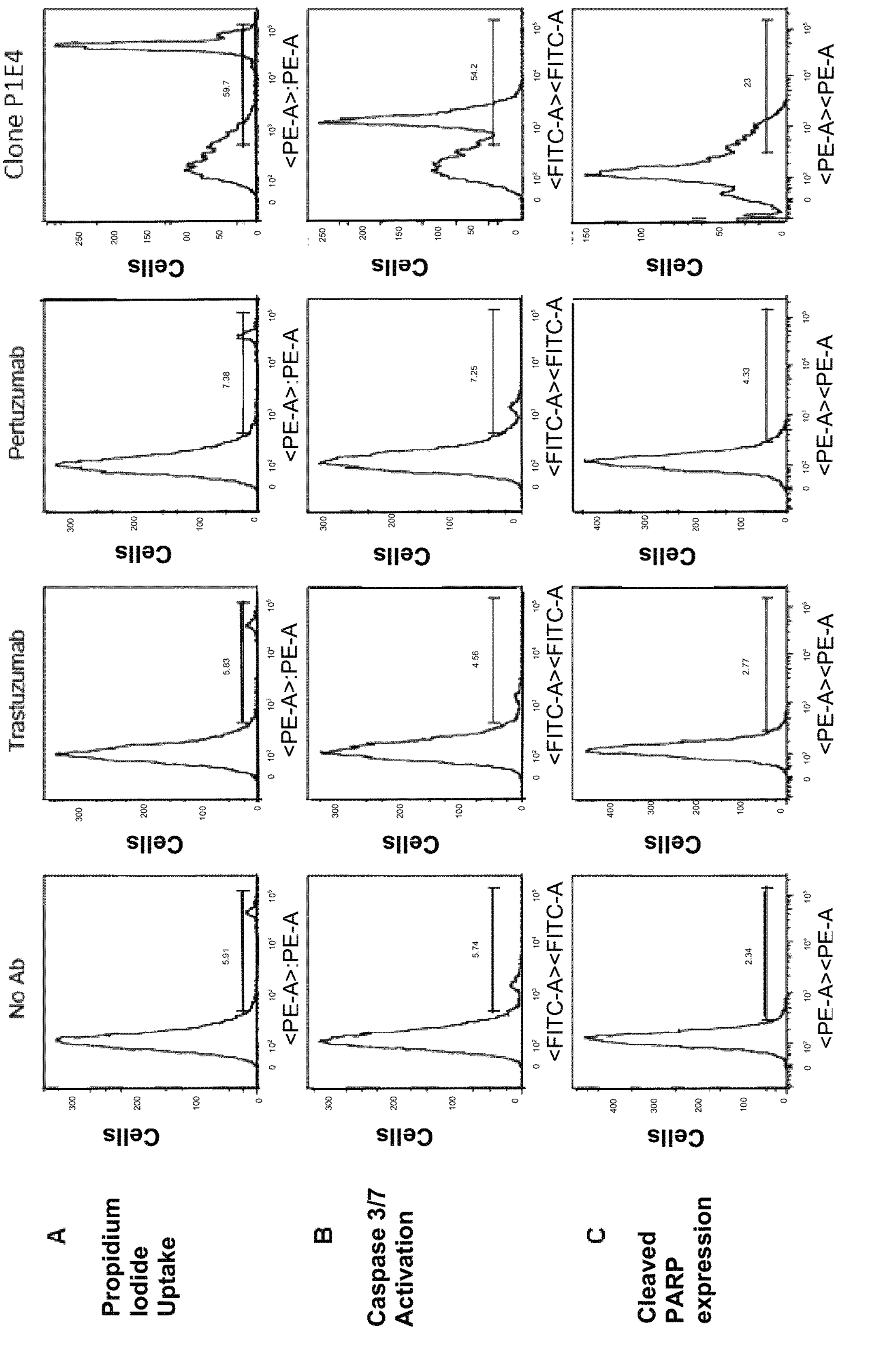
FIG. 10. Triggering of apoptosis via caspase 3/7 and cleaved PARP by P1E4. (A) Uptake of propidium iodide after incubation of BT-474 cells in the presence of trastuzumab, pertuzumab or P1E4. (B) Activation of caspase 3/7 after incubation of BT-474 cells in the presence of trastuzumab, pertuzumab or P1E4. (C) Levels of cleaved PARP in BT-474 cells after incubation with trastuzumab, pertuzumab or P1E4.

As previously shown, incubation in the presence of P1E4 resulted in uptake of propidium iodide (FIG. 10A). P1E4 induced the activation of caspase 3/7 (FIG. 10B) and triggered cleaved PARP (FIG. 10C). Neither trastuzumab nor pertuzumab showed this pathway triggering in the assay, suggesting a different mechanism of action.

The kinetic of P1E4-induced cell death was analysed. Briefly, BT-474 and SK-BR-3 cells were incubated at 37° C. with 10 μg/mL of E4 or trastuzumab. Cells were harvested at 10, 20, 30, 40, 50 and 60 minutes after addition of antibodies and induced cell death was analysed by propidium iodide uptake.

Figure 11:
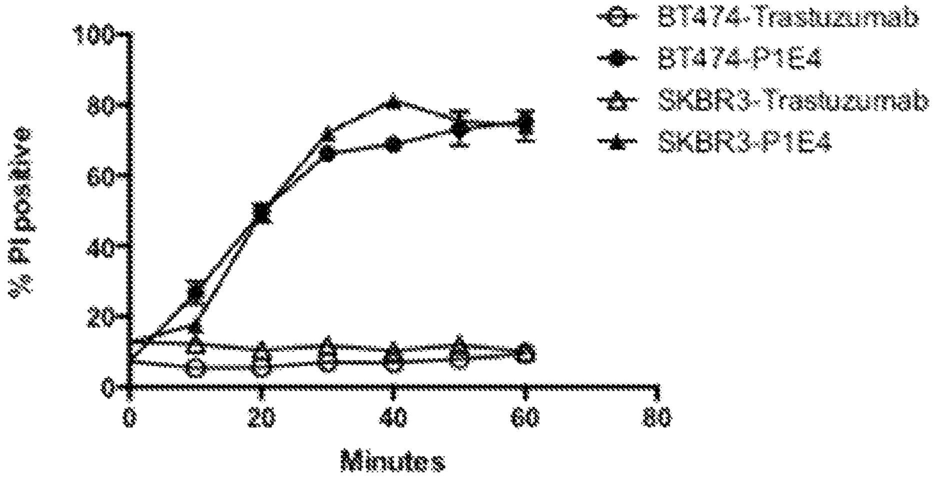
FIG. 11. Kinetic of cell lysis after incubation of BT-474 cells in the presence of P1E4 or trastuzumab. Shown is the mean proportion of propidium iodide positive cells ±SD.

As soon as 10-20 minutes after addition of P1E4, cells started to die, while cells incubated with trastuzumab did not show any signs of lysis (FIG. 11).

Clones A3, C5, F1, A4, B4, B5, C3, D4, E1, F5 and G3 are assessed for their mechanism of action and are found to induce cell death, e.g. by apoptosis.

Example 6: Efficacy

In Vitro Anti-Tumour Activity

To assess the activity of antibodies on tumour growth, BT-474 cells were incubated in the presence of various concentrations of P1E4 for 72 hours. Trastuzumab and pertuzumab were used as positive controls able to restrain tumour growth. Some cells were left growing without antibodies to serve as a growth reference. MDA-MB-468 cell line, a cell line not expressing HER-2, was used as a negative control. After 72 hours, cell numbers were measured using Promega's Celltiter 96 Aqueous One Solution cell proliferation assay (MTS).

Figure 12:
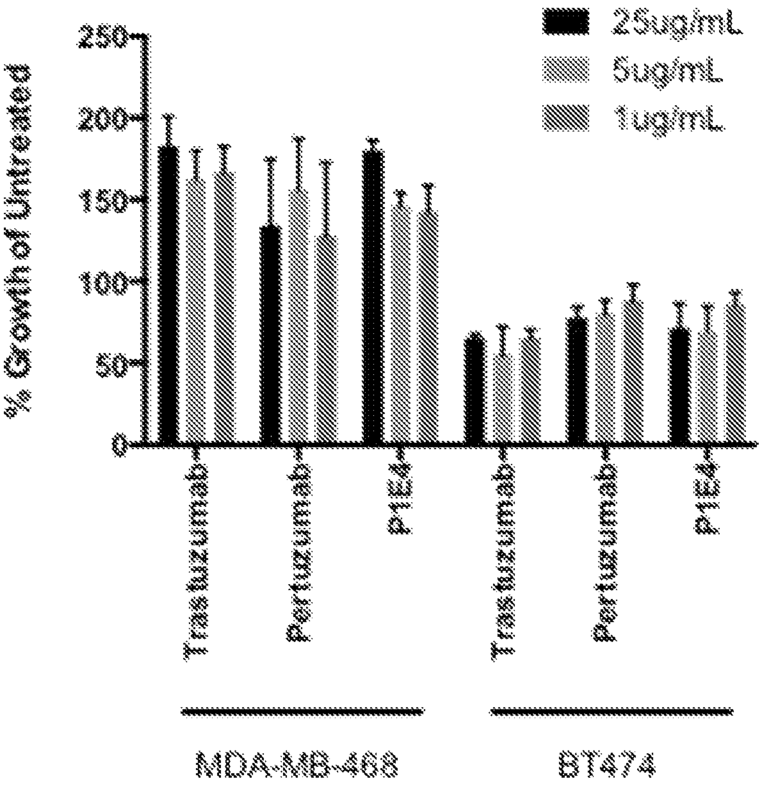
FIG. 12. Cytostatic effect of P1E4, trastuzumab and pertuzumab on B-474 tumour cell growth after incubation with 1 μg/mL, 5 μg/mL or 25 μg/mL of antibody. MDA-MB-468 cells growth was used as a negative control. Shown is the mean cellular growth ±SD compared to the growth of BT-474 cells in the absence of any treatment.

P1E4 showed a cytostatic effect on B-474 tumour growth that was comparable to that of trastuzumab or pertuzumab (FIG. 12).

Figure 13:
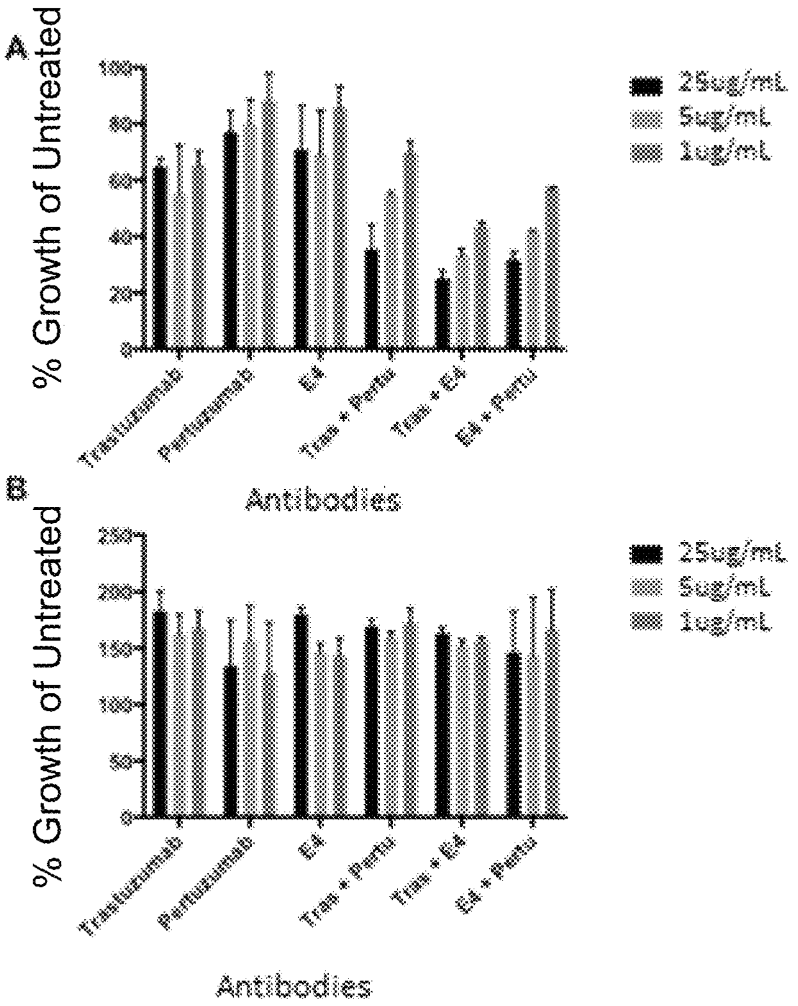
FIG. 13. Cytostatic effect of the combination P1E4, trastuzumab and pertuzumab compared to single antibodies on BT-474 tumour cell growth after incubation with 1 μg/mL, 5 μg/mL or 25 μg/mL of antibodies (A). MDA-MB-468 (HER-2 negative cells) cells growth was used as a negative control (B). Shown is the mean cellular growth ±SD compared to the growth of BT-474 cells in the absence of any treatment.

A similar assay was conducted to assess the potential synergistic effect of P1E4 and trastuzumab. The combination of P1E4 and trastuzumab showed a higher cytostatic effect than either antibody alone suggesting a synergistic effect (FIG. 13).

The antibody-dependent cellular cytotoxicity of P1A3, P1C5, P1E4 or P1F1 was also measured and compared to that of trastuzumab. BT-474 cells were plated with antibodies at various concentrations and PBMCs at the effector to target (E:T) ratio of 10:1. After 16 hours of incubation at 37° C., supernatants were harvested and assessed for LDH release by Promega Cytotox 96 non-radioactive cytotoxicity assay kit.

Figure 14:
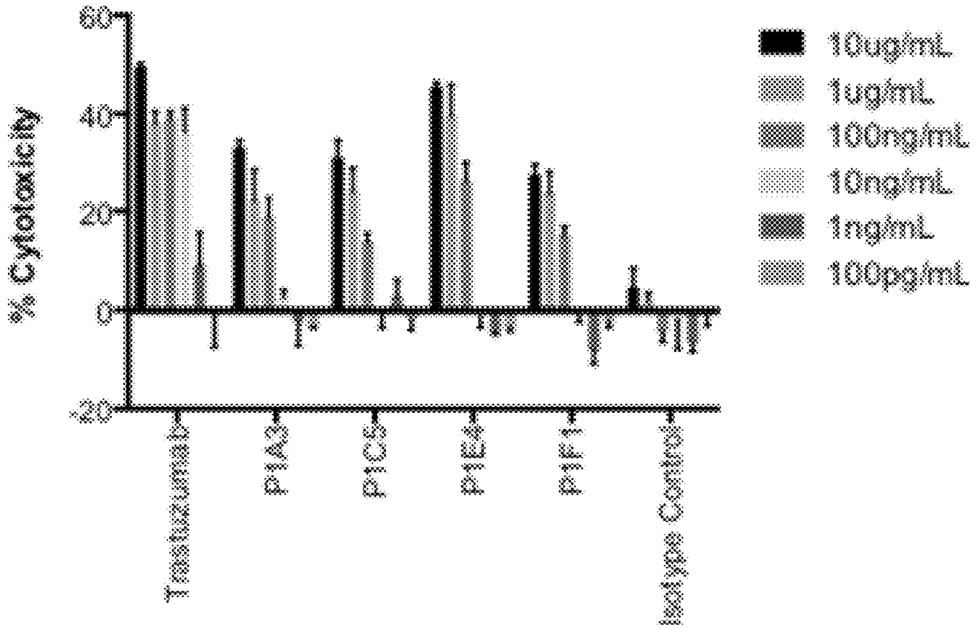
FIG. 14. ADCC induced by P1A3, P1C5, P1E4 and P1F1 in BT-474 cells compared to trastuzumab. Cells were incubated at an effector to target ratio 10:1 in the presence of various concentrations of antibodies. Shown is the mean cell death ±SD.

All four antibodies were able to induce ADCC, with P1E4 showing the strongest ADCC effect. At high concentrations, P1E4 was able to trigger cell toxicity in a similar proportion as trastuzumab, it was however less effective at low doses (FIG. 14).

Clones A4, B4, B5, C3, D4, E1, F5 and G3 are assessed for their effect on tumour growth and are found to have a cytotoxic effect.

In Vivo Anti-Tumour Efficacy

P1E4 was tested for its ability to control tumour growth in vivo. Briefly, BT-474 cells were injected in Nude mice. When tumours reached ~125 $mm^3$, i.e. when palpable, antibodies were injected intravenously every 4 days between days 1 and 17 at 10 mg/kg for trastuzumab and at 3.3, 10, 20 or 30 mg/kg for P1E4. One control group only received vehicle 10 mL/kg/injection. Tumour growth was then monitored every 3 to 4 days until day 31.

Figure 15:
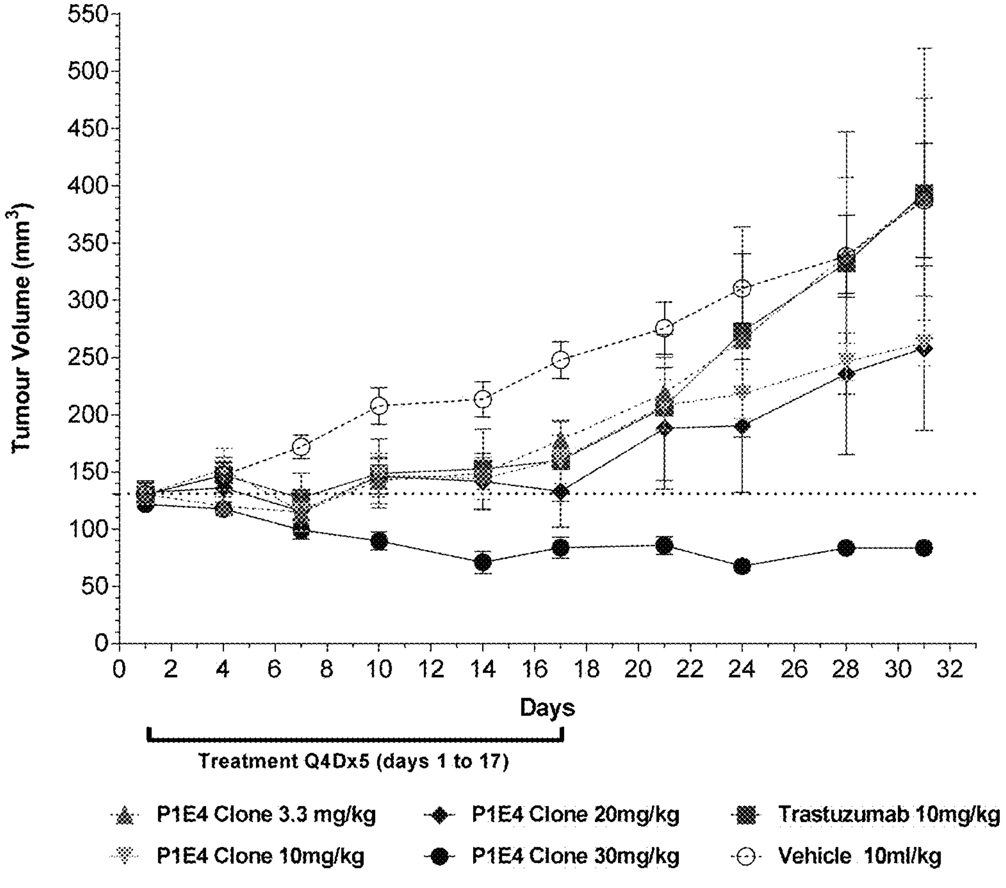
FIG. 15. Tumour control and regression by P1E4 and trastuzumab in Nude mice injected with BT-474 cells and treated with various doses of antibodies. Shown are mean tumour volumes in 5 mice per group ±SEM. The black line represents the tumour size at the beginning of antibody treatment.

While doses up to 20 mg/kg seemed to control tumour growth the during administration period, they did not confer a long-term protection and tumours started to grow at the end of the treatment. At the highest dose, P1E4 not only allowed a sensible regression of tumour size but also conferred a long-term protection with regressed tumours not growing back after administration ended (FIG. 15).

Combination treatments with P1E4, trastuzumab or pertuzumab were tested for synergistic effects on tumour growth control in vivo. Similarly as described above, nude mice harbouring BT-474 xenografts were treated with combinations of either 2 antibodies at 10 mg/kg of trastuzumab, pertuzumab or P1E4 every 4 days between days 1 and 17; tumour growth was monitored up to day 39.

Figure 16:
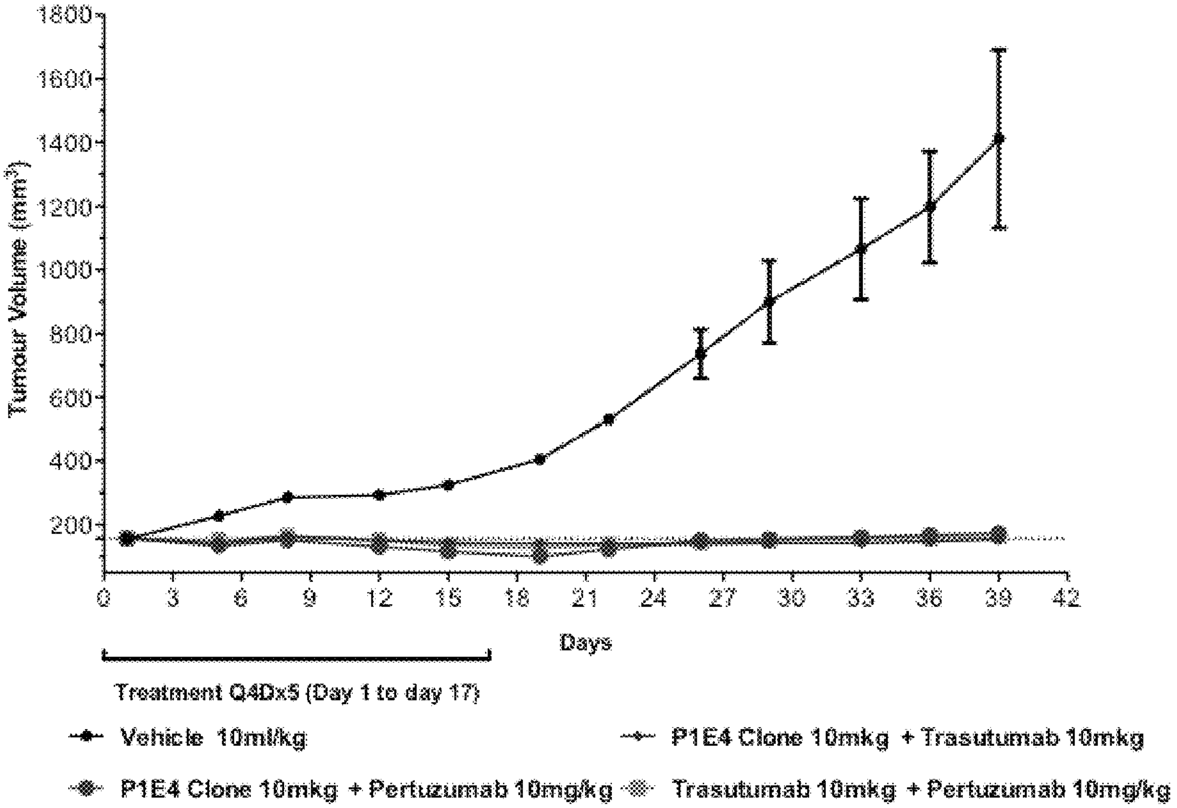
FIG. 16. Long-term effective tumour control using combinations of anti-HER2 antibodies. Nude mice injected with HER-2+ BT-474 cells were treated with combinations of P1E4, trastuzumab or pertuzumab antibodies at 10 mg/kg of antibodies. Shown are mean tumour volumes in 5 mice per group ±SEM. The black dotted line represents the tumour size at the beginning of antibody treatment.

P1E4 in combination with either trastuzumab or pertuzumab is as effective as the combination of trastuzumab and pertuzumab in controlling tumour growth (FIG. 16). Furthermore, combining P1E4 at 10 mg/kg with either trastuzumab or pertuzumab (at 10 mg/kg too) was found to be as effective in conferring a long-term protection (FIG. 16) as 30 mg/kg of P1E4 alone (FIG. 15) and much more effective than trastuzumab alone (FIG. 15).

Figure 17:
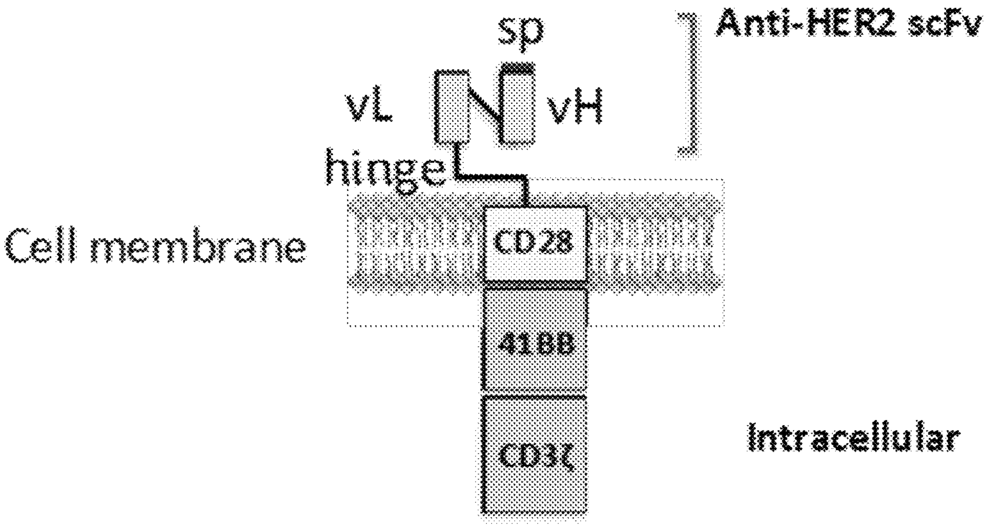
FIG. 17. Schematic representation of the construction of anti-HER2 CAR showing signal peptide (sp), anti-HER2 scFv, IgH hinge, CD28 transmembrane domain, and 4-1 BB and CD3ζ domain signalling tail.

Example 7: Generation and Activity of Chimeric Antigen Receptor (CAR) T Cells FIG. 17 shows a schematic representation of the construction of anti-HER2 CAR. The CAR consists of a signal peptide, anti-HER2 scFv, IgH hinge, the transmembrane domain of CD28 followed by a second generation CAR signalling tail composed of the 4-1 BB and CD3ζ signalling domains.

Anti-HER2 CARs comprising clones A4, B4, B5, C3, D4, E1, F5 and G3 were constructed and assessed for anti-tumour activity.

Lentiviral-Based Construction

T cells from healthy donors were activated by TransAct™ (CD3/CD28 agonists) and maintained at a density of 1 to $2\times10^6$ cells/mL in TexMACS™ medium supplemented with 50 ng/mL IL2 for 48 hours. Upon stimulation, cells were transduced with lentivirus encoding anti-HER2 CARs comprising one of the clones A4, B4, B5, D4, E1, F5 and G3.

72 hr post-transduction, anti-tumour activity (% cytolysis) were analysed in real-time manner by an electrical impedance-based tumour cell culture system (xCELLigence). BT474 cells (human breast cancer cells) were seeded at a density of 10,000 cells per well in electrode-coated 96-well plates (e-plates) in triplicates. 24 hours later, CAR T cells (the Effector cells) were added at a ratio of 3 effector cells for each target cell (BT474).

Cytokines (IFN-γ and IL-2) secreted to the medium following 48-hour co-cultures were measured by ELISA. Data in triplicates are presented as mean±SEM The results are shown in FIGS. 18A and 18B. CART cells comprising each one of the seven anti-HER2 CARs demonstrated cytolysis of tumour cells, i.e. anti-tumour activity, (18A) and increased IFN-γ and IL-2 secretion, i.e. T cell activation (18B).

Electroporation Construction

Figure 19:
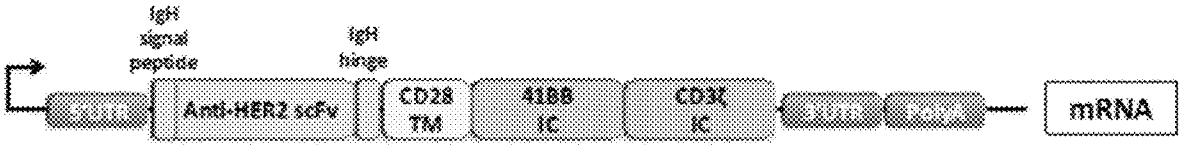
FIG. 19. Schematic representation of an anti-HER2 CAR mRNA.

FIG. 19 shows a schematic representation of an anti-HER2 CAR mRNA.

Figure 20A:
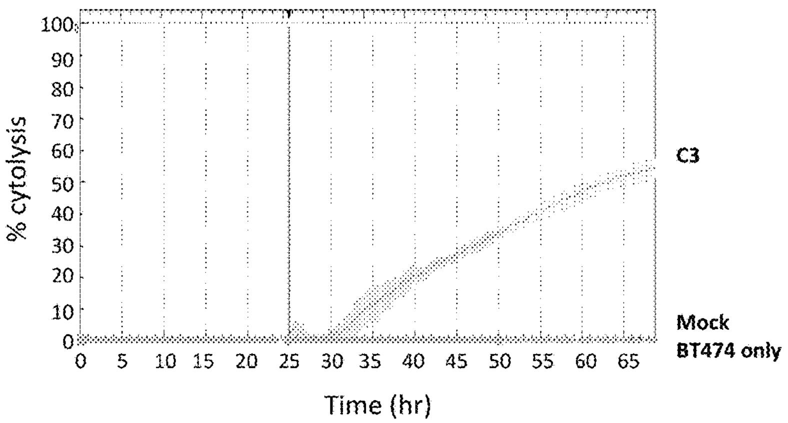
FIGS. 20A and 20B. Graphs showing characteristics of anti-HER2 CAR T cells comprising clone C3. (20A) Percentage cytolysis of BT474 human breast cancer cells by CAR T cells. (20B) Cytokine (IFNγ and IL-2) production by CAR T cells.
Figure 20B:
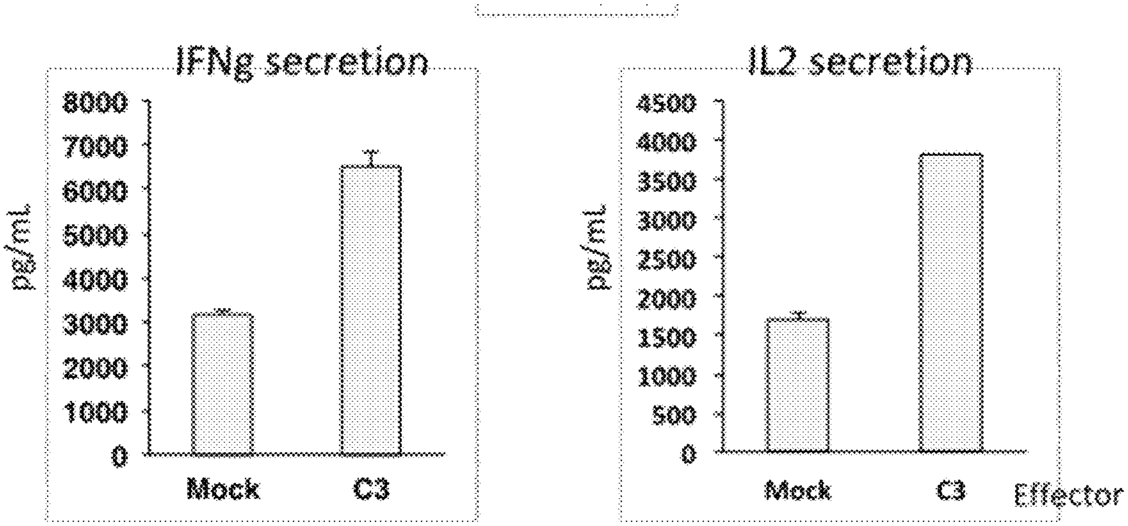

CAR T cells were generated by mRNA electroporation. T cells from healthy donors were isolated, activated and cultured for 48 hours, as described above. Activated T cells were electroporated with CAR mRNA (2 ug per $1\times10^6$ T cells) comprising clone C3 and were assessed for their cytolytic activity (%) 20 hours post-electroporation by the xCELLigence system. Cytokines (IFN-γ and IL-2) secreted to the medium following 48-hour co-cultures were measured by ELISA. Data in triplicates are presented as mean±SEM The results are shown in FIGS. 20A and 20B. CAR T cells comprising anti-HER2 CAR (C3) demonstrated cytolysis of tumour cells, i.e. anti-tumour activity, (20A) and increased IFN-γ and IL-2 secretion, i.e. T cell activation (20B).

Selectivity for Tumour Cells

Anti-HER2 CAR T cells according to the present invention are assessed for their ability to discriminate between cells overexpressing HER2 and cells with lower or physiological levels of HER2. CAR T cells having lower or intermediate affinity for HER2 may be capable of discriminating between cells expressing HER2 at high and low levels (e.g. as described in Liu et al Cancer Res. 2015; (75) (17) 3596-3607).

Anti-HER2 CAR T cells of the present invention are stimulated with HER2-overexpressing tumour cell lines, e.g. SK-BR3 (breast cancer), SK-OV3 (ovarian cancer) and/or BT-474 (breast cancer), or tumour cell lines that express HER2 at a low or undetectable level, e.g. MCF7 (breast cancer), 293T (embryonic kidney), A549 (lung cancer), 624Mel (melanoma), PC3 (prostate cancer), MDA231 (breast cancer) and/or MDA468 (breast cancer). CAR T cell activation is assessed after 24 or 48 hours by upregulation of CD137 (4-1BB), secretion of IFNγ and IL2, and/or induction of surface CD107a expression. T cells expressing a CAR comprising the antigen-binding domains of trastuzumab (a high-affinity CAR) and T cells expressing a non-HER2- specific CAR are used as controls. CD137 and CD107a expression is measured by flow cytometry (e.g. CD3+ gated), cytokine secretion in culture supernatants is measured by ELISA.

CAR-T cells comprising the antigen-binding molecules of the present invention are found to be strongly reactive to tumour cells with high HER2 expression, but are found to have low or no reactivity to tumour cell lines with low or no expression of HER2. The anti-HER2 CAR T cells are also found to secrete higher levels of cytokines when exposed to cells expressing high levels of HER2, indicating a higher degree of T cell activation compared to that seen with cells expressing low levels of, or no, HER2.

To assess if the anti-HER2 CAR T cells can discriminate between tumour cells and non-tumour cells, the T cells are contacted with tumour cells overexpressing HER2 (e.g. BT-474) and cells expressing HER2 at a physiological level e.g. primary organ cell lines. T cells expressing a non-HER2-specific CAR and cell lines that express HER2 at a high or low level are used as controls. CAR T cells are stimulated with the HER2-expressing cells for 4 hours. CAR T cell recognition and activation is evaluated by monitoring CD107a upregulation and analysed by flow cytometry by gating on CD3+ cells.

CAR-T cells comprising the antigen-binding molecules of the present invention are found to be selective for HER2-overexpressing cells. The cells are found to show strong reactivity to HER2-overexpressing cells whilst demonstrating no or weak activation when contacted with the organ cell lines.

The invention claimed is:

1. An antibody or antigen binding fragment thereof which is capable of binding to HER2, optionally isolated, wherein the antibody or antigen binding fragment thereof comprises:

a light chain variable region incorporating the following CDRs:

```
                                 (SEQ ID NO: 255)
LC-CDR1: GLSSGSVSTTYYPS

                                  (SEQ ID NO: 33)
LC-CDR2: STNTRSS

                                 (SEQ ID NO: 256)
LC-CDR3: VLYMGNGISV;
```

a heavy chain variable region incorporating the following CDRs:

```
                                  (SEQ ID NO: 24)
HC-CDR1: SSSYYWG

                                  (SEQ ID NO: 25)
HC-CDR2: SIYYSGSTYYNPSLKS

                                  (SEQ ID NO: 26)
HC-CDR3: YAPDSSGYLVAFDI.
```

2. The antibody, or antigen binding fragment thereof, according to claim 1 conjugated to a drug moiety or a detectable moiety.

3. The antibody, or antigen binding fragment thereof according to claim 2 wherein the drug moiety comprises an anti-cancer drug moiety.

4. A nucleic acid, optionally isolated, encoding an antibody, or antigen binding fragment thereof which is capable of binding to HER2, wherein the antibody or antigen binding fragment thereof comprises:

a light chain variable region incorporating the following CDRs:

```
LC-CDR1:
                              (SEQ ID NO: 255)
GLSSGSVSTTYYPS

LC-CDR2:
                               (SEQ ID NO: 33)
STNTRSS

LC-CDR3:
                              (SEQ ID NO: 256)
VLYIVIGNGISV;
```

and a heavy chain variable region incorporating the following CDRs:

```
                                  (SEQ ID NO: 24)
HC-CDR1: SSSYYWG

                                  (SEQ ID NO: 25)
HC-CDR2: SIYYSGSTYYNPSLKS

                                  (SEQ ID NO: 26)
HC-CDR3: YAPDSSGYLVAFDI.
```

5. A method of treating cancer, the method comprising administering an antibody, or antigen binding fragment thereof, to a patient suffering from cancer, wherein the antibody or antigen binding fragment thereof is capable of binding to HER2, and comprises:

a light chain variable region incorporating the following CDRs:

```
LC-CDR1:
                              (SEQ ID NO: 255)
GLSSGSVSTTYYPS

LC-CDR2:
                               (SEQ ID NO: 33)
STNTRSS

LC-CDR3:
                              (SEQ ID NO: 256)
VLYMGNGISV;
```

and a heavy chain variable region incorporating the following CDRs:

```
HC-CDR1:
                               (SEQ ID NO: 24)
SSSYYWG

HC-CDR2:
                               (SEQ ID NO: 25)
SIYYSGSTYYNPSLKS

HC-CDR3:
                               (SEQ ID NO: 26)
YAPDSSGYLVAFDI.
```

6. The method according to claim 5, wherein the cancer is a HER2-positive cancer.

7. The method according to claim 5, wherein the cancer comprises a HER2-positive tumour cell.

8. The antibody or antigen binding fragment thereof according to claim 1, wherein the antibody or antigen binding fragment thereof comprises:

a light chain variable region having at least 85% sequence identity to the light chain variable region sequence of SEQ ID NO:253; and a heavy chain variable region having at least 85% sequence identity to the heavy chain variable region sequence of SEQ ID NO:254.

9. The antibody or antigen binding fragment thereof according to claim 1, wherein the antibody or antigen binding fragment thereof binds specifically to human, rhesus macaque or murine HER2.

10. The nucleic acid according to claim 4, wherein the antibody or antigen binding fragment thereof comprises:

a light chain variable region having at least 85% sequence identity to the light chain variable region sequence of SEQ ID NO:253; and a heavy chain variable region having at least 85% sequence identity to the heavy chain variable region sequence of SEQ ID NO:254.

11. The nucleic acid according to claim 4, wherein the antibody or antigen binding fragment thereof binds specifically to human, rhesus macaque or murine HER2.

12. The nucleic acid according to claim 4, wherein the antibody or antigen binding fragment thereof is conjugated to a drug moiety or a detectable moiety.

13. The nucleic acid according to claim 12, wherein the drug moiety comprises an anti-cancer drug moiety.

14. The method according to claim 5, wherein the antibody or antigen binding fragment thereof comprises:

a light chain variable region having at least 85% sequence identity to the light chain variable region sequence of SEQ ID NO:253; and a heavy chain variable region having at least 85% sequence identity to the heavy chain variable region sequence of SEQ ID NO:254.

15. The method according to claim 5, wherein the antibody or antigen binding fragment thereof binds specifically to human, rhesus macaque or murine HER2.

16. The method according to claim 5, wherein the antibody or antigen binding thereof fragment is conjugated to a drug moiety or a detectable moiety.

17. The method according to claim 16, wherein the drug moiety comprises an anti-cancer drug moiety.

* * * * *

UNITED STATES PATENT AND TRADEMARK OFFICE

CERTIFICATE OF CORRECTION

PATENT NO. : 11,945,877 B2
APPLICATION NO. : 16/969119
DATED : April 2, 2024
INVENTOR(S) : Cheng-I Wang et al.

It is certified that error appears in the above-identified patent and that said Letters Patent is hereby corrected as shown below:

In the Claims

Claim 4 Column 327, Line 49, replace “VLYIVIGNGISV” with “VLYMGNGISV”.

Signed and Sealed this
Eighteenth Day of June, 2024

Katherine Kelly Vidal

Katherine Kelly Vidal
*Director of the United States Patent and Trademark Office*

SEQUENCE LISTING

```
<160> NUMBER OF SEQ ID NOS: 294

<210> SEQ ID NO 1
<211> LENGTH: 216
<212> TYPE: PRT
<213> ORGANISM: Artificial Sequence
<220> FEATURE:
<223> OTHER INFORMATION: P1A3 (lambda) (light chain VD) (Fig 1A)

<400> SEQUENCE: 1

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Ser Thr Gly
            20                  25                  30

His Tyr Ala Ser Trp Tyr Gln Gln Thr Pro Gly Gln Ala Pro Arg Thr
        35                  40                  45

Leu Phe Tyr Asn Thr Asn Thr Arg Ser Ser Gly Val Pro Asp Arg Phe
    50                  55                  60

Ser Gly Ser Ile Val Gly Asn Lys Ala Ala Leu Thr Ile Thr Gly Ala
65                  70                  75                  80

Gln Ala Asp Asp Glu Ser Asp Tyr Tyr Cys Val Leu Tyr Val Gly Asp
                85                  90                  95

Gly Ile Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 2
<211> LENGTH: 216
<212> TYPE: PRT
<213> ORGANISM: Artificial Sequence
```

<220> FEATURE:
<223> OTHER INFORMATION: P1C5 (lambda) (light chain VD) (Fig 1B)

<400> SEQUENCE: 2

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Gly
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Ser Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile Ser Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 3
<211> LENGTH: 216
<212> TYPE: PRT
<213> ORGANISM: Artificial Sequence
<220> FEATURE:
<223> OTHER INFORMATION: P1E4 (lambda) (light chain VD) (Fig 1C)

<400> SEQUENCE: 3

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Ile Pro Gly Gln Ala Pro Arg Thr
        35                  40                  45

Leu Ile Tyr Thr Thr Asn Ile Arg Ser Ser Gly Val Pro Asp Arg Phe
    50                  55                  60

Gly Gly Ser Ile Leu Gly Asn Lys Ala Ala Leu Thr Ile Thr Gly Ala
65                  70                  75                  80

Gln Ala Glu Asp Glu Ser Asp Tyr Tyr Cys Met Leu Tyr Met Gly Ser
                85                  90                  95

Gly Ile Trp Val Phe Gly Gly Gly Thr Lys Leu Thr Val Leu Gly Gln
            100                 105                 110

Pro Lys Thr Ala Pro Ser Val Thr Leu Phe Pro Pro Ser Ser Glu Glu

-continued

```
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Ala Glu Cys Ser
    210                 215


<210> SEQ ID NO 4
<211> LENGTH: 216
<212> TYPE: PRT
<213> ORGANISM: Artificial Sequence
<220> FEATURE:
<223> OTHER INFORMATION: P1F1 (lambda) (light chain VD) (Fig 1D)

<400> SEQUENCE: 4

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 5
<211> LENGTH: 121
<212> TYPE: PRT
<213> ORGANISM: Artificial Sequence
<220> FEATURE:
<223> OTHER INFORMATION: P1A3 (heavy chain VD) (Fig 2A)
```

<400> SEQUENCE: 5

Glu Val Gln Leu Val Gln Ser Gly Thr Glu Val Lys Lys Pro Gly Ala
1 5 10 15

Ser Val Arg Val Ser Cys Lys Ser Ser Gly Tyr Thr Phe Thr Ser Tyr
20 25 30

Tyr Ile His Trp Val Arg Gln Ala Pro Gly Gln Gly Leu Glu Trp Met
35 40 45

Ala Ile Ile Asn Pro Gly Asn Gly Asp Thr Asn Tyr Ala Gln Arg Phe
50 55 60

Gln Gly Arg Val Thr Met Thr Arg Asp Thr Ser Thr Ser Thr Val Tyr
65 70 75 80

Met Glu Leu Arg Ser Leu Arg Ser Asp Asp Thr Ala Val Tyr Phe Cys
85 90 95

Ala Arg Glu Ile Ala Ser Tyr Ser Gly Ser Tyr Tyr Asp Tyr Trp Gly
100 105 110

Gln Gly Thr Leu Val Thr Val Ser Ser
115 120

<210> SEQ ID NO 6
<211> LENGTH: 124
<212> TYPE: PRT
<213> ORGANISM: Artificial Sequence
<220> FEATURE:
<223> OTHER INFORMATION: P1C5 (heavy chain VD) (Fig 2B)

<400> SEQUENCE: 6

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Ser
20 25 30

Ser Tyr Tyr Trp Gly Trp Ile Arg Gln Pro Pro Gly Lys Gly Leu Glu
35 40 45

Trp Ile Gly Ser Ile Tyr Tyr Ser Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Tyr Ala Pro Asp Ser Ser Gly Tyr Leu Val Ala Phe Asp
100 105 110

Ile Trp Gly Gln Gly Thr Met Val Thr Val Ser Ser
115 120

<210> SEQ ID NO 7
<211> LENGTH: 122
<212> TYPE: PRT
<213> ORGANISM: Artificial Sequence
<220> FEATURE:
<223> OTHER INFORMATION: P1E4 (heavy chain VD) (Fig 2C)

<400> SEQUENCE: 7

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

```
Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Thr Ala Asp Thr Ala Val Tyr Tyr Cys Ala
                85                  90                  95

Arg Met Gly Ile Asn Ser Gly Gly Tyr Leu Tyr Gly Met Asp Val Trp
            100                 105                 110

Gly Gln Gly Thr Thr Val Thr Val Ser Ser
        115                 120


<210> SEQ ID NO 8
<211> LENGTH: 123
<212> TYPE: PRT
<213> ORGANISM: Artificial Sequence
<220> FEATURE:
<223> OTHER INFORMATION: P1F1 (heavy chain VD) (Fig 2D)

<400> SEQUENCE: 8

Gln Val Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Met Gly Ala Asn Ser Gly Gly Tyr Leu Tyr Gly Met Asp Val
            100                 105                 110

Trp Gly Gln Gly Thr Thr Val Thr Val Ser Ser
        115                 120


<210> SEQ ID NO 9
<211> LENGTH: 14
<212> TYPE: PRT
<213> ORGANISM: Artificial Sequence
<220> FEATURE:
<223> OTHER INFORMATION: LC-CDR1 consensus
<220> FEATURE:
<221> NAME/KEY: MISC_FEATURE
<222> LOCATION: (10)..(10)
<223> OTHER INFORMATION: X = G or S
<220> FEATURE:
<221> NAME/KEY: MISC_FEATURE
<222> LOCATION: (11)..(11)
<223> OTHER INFORMATION: X = H or Y
<220> FEATURE:
<221> NAME/KEY: MISC_FEATURE
<222> LOCATION: (13)..(13)
<223> OTHER INFORMATION: X = A or P

<400> SEQUENCE: 9

Gly Leu Ser Ser Gly Ser Val Ser Thr Xaa Xaa Tyr Xaa Ser
1               5                   10


<210> SEQ ID NO 10
<211> LENGTH: 7
<212> TYPE: PRT
```

<213> ORGANISM: Artificial Sequence
<220> FEATURE:
<223> OTHER INFORMATION: LC-CDR2 consensus
<220> FEATURE:
<221> NAME/KEY: MISC_FEATURE
<222> LOCATION: (1)..(1)
<223> OTHER INFORMATION: X = N, S or T
<220> FEATURE:
<221> NAME/KEY: MISC_FEATURE
<222> LOCATION: (4)..(4)
<223> OTHER INFORMATION: X = T, S or I

<400> SEQUENCE: 10

Xaa Thr Asn Xaa Arg Ser Ser
1               5

<210> SEQ ID NO 11
<211> LENGTH: 10
<212> TYPE: PRT
<213> ORGANISM: Artificial Sequence
<220> FEATURE:
<223> OTHER INFORMATION: LC-CDR3 consensus
<220> FEATURE:
<221> NAME/KEY: MISC_FEATURE
<222> LOCATION: (1)..(1)
<223> OTHER INFORMATION: X = V or M
<220> FEATURE:
<221> NAME/KEY: MISC_FEATURE
<222> LOCATION: (4)..(4)
<223> OTHER INFORMATION: X = V or M
<220> FEATURE:
<221> NAME/KEY: MISC_FEATURE
<222> LOCATION: (6)..(6)
<223> OTHER INFORMATION: X = D or S
<220> FEATURE:
<221> NAME/KEY: MISC_FEATURE
<222> LOCATION: (9)..(9)
<223> OTHER INFORMATION: X = W or S

<400> SEQUENCE: 11

Xaa Leu Tyr Xaa Gly Xaa Gly Ile Xaa Val
1               5                   10

<210> SEQ ID NO 12
<211> LENGTH: 7
<212> TYPE: PRT
<213> ORGANISM: Artificial Sequence
<220> FEATURE:
<223> OTHER INFORMATION: HC-CDR1 consensus
<220> FEATURE:
<221> NAME/KEY: MISC_FEATURE
<222> LOCATION: (1)..(1)
<223> OTHER INFORMATION: X = S or absent
<220> FEATURE:
<221> NAME/KEY: MISC_FEATURE
<222> LOCATION: (2)..(2)
<223> OTHER INFORMATION: X = S or absent
<220> FEATURE:
<221> NAME/KEY: MISC_FEATURE
<222> LOCATION: (3)..(3)
<223> OTHER INFORMATION: X = S or G
<220> FEATURE:
<221> NAME/KEY: MISC_FEATURE
<222> LOCATION: (4)..(4)
<223> OTHER INFORMATION: X = Y or N
<220> FEATURE:
<221> NAME/KEY: MISC_FEATURE
<222> LOCATION: (5)..(5)
<223> OTHER INFORMATION: X = Y or W
<220> FEATURE:
<221> NAME/KEY: MISC_FEATURE
<222> LOCATION: (6)..(6)
<223> OTHER INFORMATION: X = I or W
<220> FEATURE:
<221> NAME/KEY: MISC_FEATURE
<222> LOCATION: (7)..(7)
<223> OTHER INFORMATION: X = H, G or S

<400> SEQUENCE: 12

Xaa Xaa Xaa Xaa Xaa Xaa Xaa
1               5

<210> SEQ ID NO 13
<211> LENGTH: 17
<212> TYPE: PRT
<213> ORGANISM: Artificial Sequence
<220> FEATURE:
<223> OTHER INFORMATION: HC-CDR2 consensus
<220> FEATURE:
<221> NAME/KEY: MISC_FEATURE
<222> LOCATION: (1)..(1)
<223> OTHER INFORMATION: X = I or absent
<220> FEATURE:
<221> NAME/KEY: MISC_FEATURE
<222> LOCATION: (2)..(2)
<223> OTHER INFORMATION: X = I, S or E
<220> FEATURE:
<221> NAME/KEY: MISC_FEATURE
<222> LOCATION: (3)..(3)
<223> OTHER INFORMATION: X = N or I
<220> FEATURE:
<221> NAME/KEY: MISC_FEATURE
<222> LOCATION: (4)..(4)
<223> OTHER INFORMATION: X = P, Y or N
<220> FEATURE:
<221> NAME/KEY: MISC_FEATURE
<222> LOCATION: (5)..(5)
<223> OTHER INFORMATION: X = G, Y or H
<220> FEATURE:
<221> NAME/KEY: MISC_FEATURE
<222> LOCATION: (6)..(6)
<223> OTHER INFORMATION: X = N or S
<220> FEATURE:
<221> NAME/KEY: MISC_FEATURE
<222> LOCATION: (8)..(8)
<223> OTHER INFORMATION: X = D or S
<220> FEATURE:
<221> NAME/KEY: MISC_FEATURE
<222> LOCATION: (10)..(10)
<223> OTHER INFORMATION: X = N or Y
<220> FEATURE:
<221> NAME/KEY: MISC_FEATURE
<222> LOCATION: (12)..(12)
<223> OTHER INFORMATION: X = A or N
<220> FEATURE:
<221> NAME/KEY: MISC_FEATURE
<222> LOCATION: (13)..(13)
<223> OTHER INFORMATION: X = Q or P
<220> FEATURE:
<221> NAME/KEY: MISC_FEATURE
<222> LOCATION: (14)..(14)
<223> OTHER INFORMATION: X = R or S
<220> FEATURE:
<221> NAME/KEY: MISC_FEATURE
<222> LOCATION: (15)..(15)
<223> OTHER INFORMATION: X = F or L
<220> FEATURE:
<221> NAME/KEY: MISC_FEATURE
<222> LOCATION: (16)..(16)
<223> OTHER INFORMATION: X = Q or K
<220> FEATURE:
<221> NAME/KEY: MISC_FEATURE
<222> LOCATION: (17)..(17)
<223> OTHER INFORMATION: X = G or S

<400> SEQUENCE: 13

Xaa Xaa Xaa Xaa Xaa Xaa Gly Xaa Thr Xaa Tyr Xaa Xaa Xaa Xaa Xaa
1               5                   10                  15

Xaa

<210> SEQ ID NO 14
<211> LENGTH: 15
<212> TYPE: PRT
<213> ORGANISM: Artificial Sequence
<220> FEATURE:
<223> OTHER INFORMATION: HC-CDR3 consensus
<220> FEATURE:
<221> NAME/KEY: MISC_FEATURE
<222> LOCATION: (1)..(1)
<223> OTHER INFORMATION: X = E or absent
<220> FEATURE:
<221> NAME/KEY: MISC_FEATURE
<222> LOCATION: (2)..(2)
<223> OTHER INFORMATION: X = I, Y or M
<220> FEATURE:
<221> NAME/KEY: MISC_FEATURE
<222> LOCATION: (3)..(3)
<223> OTHER INFORMATION: X = A or G
<220> FEATURE:
<221> NAME/KEY: MISC_FEATURE
<222> LOCATION: (4)..(4)
<223> OTHER INFORMATION: X = S, P, I or A
<220> FEATURE:
<221> NAME/KEY: MISC_FEATURE
<222> LOCATION: (5)..(5)
<223> OTHER INFORMATION: X = Y, D or N
<220> FEATURE:
<221> NAME/KEY: MISC_FEATURE
<222> LOCATION: (7)..(7)
<223> OTHER INFORMATION: X = G or S
<220> FEATURE:
<221> NAME/KEY: MISC_FEATURE
<222> LOCATION: (8)..(8)
<223> OTHER INFORMATION: X = G or S
<220> FEATURE:
<221> NAME/KEY: MISC_FEATURE
<222> LOCATION: (10)..(10)
<223> OTHER INFORMATION: X = L or absent
<220> FEATURE:
<221> NAME/KEY: MISC_FEATURE
<222> LOCATION: (11)..(11)
<223> OTHER INFORMATION: X = V or Y
<220> FEATURE:
<221> NAME/KEY: MISC_FEATURE
<222> LOCATION: (12)..(12)
<223> OTHER INFORMATION: X = A, D or G
<220> FEATURE:
<221> NAME/KEY: MISC_FEATURE
<222> LOCATION: (13)..(13)
<223> OTHER INFORMATION: X = F, M or Y
<220> FEATURE:
<221> NAME/KEY: MISC_FEATURE
<222> LOCATION: (14)..(14)
<223> OTHER INFORMATION: X = D or absent
<220> FEATURE:
<221> NAME/KEY: MISC_FEATURE
<222> LOCATION: (15)..(15)
<223> OTHER INFORMATION: X = I, V or absent

<400> SEQUENCE: 14

```
Xaa Xaa Xaa Xaa Xaa Ser Xaa Xaa Tyr Xaa Xaa Xaa Xaa Xaa Xaa
1               5                   10                  15
```

<210> SEQ ID NO 15
<211> LENGTH: 14
<212> TYPE: PRT
<213> ORGANISM: Artificial Sequence
<220> FEATURE:
<223> OTHER INFORMATION: P1A3 LC-CDR1

<400> SEQUENCE: 15

```
Gly Leu Ser Ser Gly Ser Val Ser Thr Gly His Tyr Ala Ser
1               5                   10
```

-continued

<210> SEQ ID NO 16
<211> LENGTH: 7
<212> TYPE: PRT
<213> ORGANISM: Artificial Sequence
<220> FEATURE:
<223> OTHER INFORMATION: P1A3 LC-CDR2

<400> SEQUENCE: 16

Asn Thr Asn Thr Arg Ser Ser
1               5

<210> SEQ ID NO 17
<211> LENGTH: 10
<212> TYPE: PRT
<213> ORGANISM: Artificial Sequence
<220> FEATURE:
<223> OTHER INFORMATION: P1A3 LC-CDR3

<400> SEQUENCE: 17

Val Leu Tyr Val Gly Asp Gly Ile Trp Val
1               5                   10

<210> SEQ ID NO 18
<211> LENGTH: 5
<212> TYPE: PRT
<213> ORGANISM: Artificial Sequence
<220> FEATURE:
<223> OTHER INFORMATION: P1A3 HC-CDR1

<400> SEQUENCE: 18

Ser Tyr Tyr Ile His
1               5

<210> SEQ ID NO 19
<211> LENGTH: 17
<212> TYPE: PRT
<213> ORGANISM: Artificial Sequence
<220> FEATURE:
<223> OTHER INFORMATION: P1A3 HC-CDR2

<400> SEQUENCE: 19

Ile Ile Asn Pro Gly Asn Gly Asp Thr Asn Tyr Ala Gln Arg Phe Gln
1               5                   10                  15

Gly

<210> SEQ ID NO 20
<211> LENGTH: 12
<212> TYPE: PRT
<213> ORGANISM: Artificial Sequence
<220> FEATURE:
<223> OTHER INFORMATION: P1A3 HC-CDR3 PFG3 HC-CDR3

<400> SEQUENCE: 20

Glu Ile Ala Ser Tyr Ser Gly Ser Tyr Tyr Asp Tyr
1               5                   10

<210> SEQ ID NO 21
<211> LENGTH: 14
<212> TYPE: PRT
<213> ORGANISM: Artificial Sequence
<220> FEATURE:
<223> OTHER INFORMATION: P1C5 LC-CDR1

<400> SEQUENCE: 21

Gly Leu Ser Ser Gly Ser Val Ser Thr Gly Tyr Tyr Pro Ser
1               5                   10

-continued

<210> SEQ ID NO 22
<211> LENGTH: 7
<212> TYPE: PRT
<213> ORGANISM: Artificial Sequence
<220> FEATURE:
<223> OTHER INFORMATION: P1C5 LC-CDR2

<400> SEQUENCE: 22

Ser Thr Asn Ser Arg Ser Ser
1 5

<210> SEQ ID NO 23
<211> LENGTH: 10
<212> TYPE: PRT
<213> ORGANISM: Artificial Sequence
<220> FEATURE:
<223> OTHER INFORMATION: P1C5 LC-CDR3 PFG3 LC-CDR3

<400> SEQUENCE: 23

Val Leu Tyr Met Gly Ser Gly Ile Ser Val
1 5 10

<210> SEQ ID NO 24
<211> LENGTH: 7
<212> TYPE: PRT
<213> ORGANISM: Artificial Sequence
<220> FEATURE:
<223> OTHER INFORMATION: P1C5 HC-CDR1 PFF5 HC-CDR1

<400> SEQUENCE: 24

Ser Ser Ser Tyr Tyr Trp Gly
1 5

<210> SEQ ID NO 25
<211> LENGTH: 16
<212> TYPE: PRT
<213> ORGANISM: Artificial Sequence
<220> FEATURE:
<223> OTHER INFORMATION: P1C5 HC-CDR2 PFF5 HC-CDR2

<400> SEQUENCE: 25

Ser Ile Tyr Tyr Ser Gly Ser Thr Tyr Tyr Asn Pro Ser Leu Lys Ser
1 5 10 15

<210> SEQ ID NO 26
<211> LENGTH: 14
<212> TYPE: PRT
<213> ORGANISM: Artificial Sequence
<220> FEATURE:
<223> OTHER INFORMATION: P1C5 HC-CDR3 PFF5 HC-CDR3

<400> SEQUENCE: 26

Tyr Ala Pro Asp Ser Ser Gly Tyr Leu Val Ala Phe Asp Ile
1 5 10

<210> SEQ ID NO 27
<211> LENGTH: 14
<212> TYPE: PRT
<213> ORGANISM: Artificial Sequence
<220> FEATURE:
<223> OTHER INFORMATION: P1E4 LC-CDR1 P1F1 LC-CDR1

<400> SEQUENCE: 27

Gly Leu Ser Ser Gly Ser Val Ser Thr Ser Tyr Tyr Pro Ser
1 5 10

<210> SEQ ID NO 28
<211> LENGTH: 7
<212> TYPE: PRT
<213> ORGANISM: Artificial Sequence
<220> FEATURE:
<223> OTHER INFORMATION: P1E4 LC-CDR2

<400> SEQUENCE: 28

Thr Thr Asn Ile Arg Ser Ser
1               5

<210> SEQ ID NO 29
<211> LENGTH: 10
<212> TYPE: PRT
<213> ORGANISM: Artificial Sequence
<220> FEATURE:
<223> OTHER INFORMATION: P1E4 LC-CDR3

<400> SEQUENCE: 29

Met Leu Tyr Met Gly Ser Gly Ile Trp Val
1               5                   10

<210> SEQ ID NO 30
<211> LENGTH: 5
<212> TYPE: PRT
<213> ORGANISM: Artificial Sequence
<220> FEATURE:
<223> OTHER INFORMATION: P1E4 HC-CDR1 P1D2 HC-CDR1

<400> SEQUENCE: 30

Gly Tyr Tyr Trp Ser
1               5

<210> SEQ ID NO 31
<211> LENGTH: 16
<212> TYPE: PRT
<213> ORGANISM: Artificial Sequence
<220> FEATURE:
<223> OTHER INFORMATION: P1E4 HC-CDR2  P1D2 HC-CDR2

<400> SEQUENCE: 31

Glu Ile Asn His Ser Gly Ser Thr Asn Tyr Asn Pro Ser Leu Lys Ser
1               5                   10                  15

<210> SEQ ID NO 32
<211> LENGTH: 14
<212> TYPE: PRT
<213> ORGANISM: Artificial Sequence
<220> FEATURE:
<223> OTHER INFORMATION: P1E4 HC-CDR3

<400> SEQUENCE: 32

Met Gly Ile Asn Ser Gly Gly Tyr Leu Tyr Gly Met Asp Val
1               5                   10

<210> SEQ ID NO 33
<211> LENGTH: 7
<212> TYPE: PRT
<213> ORGANISM: Artificial Sequence
<220> FEATURE:
<223> OTHER INFORMATION: P1F1 LC-CDR2 PFF5 LC-CDR2

<400> SEQUENCE: 33

Ser Thr Asn Thr Arg Ser Ser
1               5

<210> SEQ ID NO 34

<211> LENGTH: 10
<212> TYPE: PRT
<213> ORGANISM: Artificial Sequence
<220> FEATURE:
<223> OTHER INFORMATION: P1F1 LC-CDR3

<400> SEQUENCE: 34

Val Leu Tyr Met Gly Ser Gly Ile Trp Val
1 5 10

<210> SEQ ID NO 35
<211> LENGTH: 6
<212> TYPE: PRT
<213> ORGANISM: Artificial Sequence
<220> FEATURE:
<223> OTHER INFORMATION: P1F1 HC-CDR1

<400> SEQUENCE: 35

Ser Ser Asn Trp Trp Ser
1 5

<210> SEQ ID NO 36
<211> LENGTH: 16
<212> TYPE: PRT
<213> ORGANISM: Artificial Sequence
<220> FEATURE:
<223> OTHER INFORMATION: P1F1 HC-CDR2

<400> SEQUENCE: 36

Glu Ile Tyr His Ser Gly Ser Thr Asn Tyr Asn Pro Ser Leu Lys Ser
1 5 10 15

<210> SEQ ID NO 37
<211> LENGTH: 14
<212> TYPE: PRT
<213> ORGANISM: Artificial Sequence
<220> FEATURE:
<223> OTHER INFORMATION: P1F1 HC-CDR3

<400> SEQUENCE: 37

Met Gly Ala Asn Ser Gly Gly Tyr Leu Tyr Gly Met Asp Val
1 5 10

<210> SEQ ID NO 38
<211> LENGTH: 648
<212> TYPE: DNA
<213> ORGANISM: Artificial Sequence
<220> FEATURE:
<223> OTHER INFORMATION: P1A3 (lambda) LC Nucleotide sequence

<400> SEQUENCE: 38
caggctgtgg tgactcagga gccatcgttg tcagtgtccc ctggagggac agtcacactc 60
acttgtggct tgagctctgg ctcagtctct actggtcact acgccagctg gtaccagcag 120
accccaggcc aggctccacg cacgctcttc tacaacacaa acactcgctc ttctggggtc 180
cctgatcgct tctctggctc catcgttggg aacaaagctg ccctcaccat cacgggggcc 240
caggcagatg atgaatctga ctattactgt gtgctgtatg tgggtgatgg catttgggtt 300
ttcggcggag ggaccaagct gaccgtccta ggtcagccca aggctgcccc ctcggtcact 360
ctgttcccac cctcctctga ggagcttcaa gccaacaagg ccacactggt gtgtctcata 420
agtgacttct acccgggagc cgtgacagtg gcctggaagg cagatagcag ccccgtcaag 480
gcgggagtgg agaccaccac accctccaaa caaagcaaca acaagtacgc ggccagcagc 540
tacctgagcc tgacgcctga gcagtggaag tcccacaaaa gctacagctg ccaggtcacg 600
catgaaggga gcaccgtgga gaagacagtg gcccctacag aatgttca 648

<210> SEQ ID NO 39
<211> LENGTH: 648
<212> TYPE: DNA
<213> ORGANISM: Artificial Sequence
<220> FEATURE:
<223> OTHER INFORMATION: P1C5 (lambda) LC Nucleotide sequence

<400> SEQUENCE: 39
cagactgtgg tgactcagga gccatcgttc tcagtgtccc ctggagggac agtcacactc 60
acttgtggct tgagctctgg ctcagtctct actggttact accccagctg gtaccagcag 120
accccaggcc aggctccacg cacgctcatc tacagcacaa acagtcgctc ttctggggtc 180
cctgatcgct tctctggctc catccttggg aacaaagctg ccctcaccat cacgggggcc 240
caggcagatg atgaatctga ttattactgt gtgctgtata tgggtagtgg catttcggtg 300
ttcggcggag ggaccaagct gaccgtccta ggtcagccca aggctgcccc ctcggtcact 360
ctgttcccac cctcctctga ggagcttcaa gccaacaagg ccacactggt gtgtctcata 420
agtgacttct acccgggagc cgtgacagtg gcctggaagg cagatagcag ccccgtcaag 480
gcgggagtgg agaccaccac accctccaaa caaagcaaca acaagtacgc ggccagcagc 540
tacctgagcc tgacgcctga gcagtggaag tcccacaaaa gctacagctg ccaggtcacg 600
catgaaggga gcaccgtgga gaagacagtg gcccctacag aatgttca 648

<210> SEQ ID NO 40
<211> LENGTH: 648
<212> TYPE: DNA
<213> ORGANISM: Artificial Sequence
<220> FEATURE:
<223> OTHER INFORMATION: P1E4 (lambda) LC Nucleotide sequence

<400> SEQUENCE: 40
cagactgtgg tgactcagga gccatcgttc tcagtgtccc ctggagggac cgtcacactc 60
acttgtggcc tgagctctgg ctcagtctct actagttact accccagctg gtaccaacag 120
attccaggcc aggctccacg cacgctcatt tacaccacaa acattcgctc ttctggggtc 180
cctgatcgct tcggtggctc catccttggg aacaaagctg ccctcaccat cacgggggcc 240
caggcagaag atgaatctga ttactactgt atgctctata tggggagtgg catttgggtg 300
ttcggcggag ggaccaaact gaccgtccta ggtcagccca agactgcccc ctcggtcact 360
ctgttcccac cctcctctga ggagcttcaa gccaacaagg ccacactggt gtgtctcata 420
agtgacttct acccgggagc cgtgacagtg gcctggaagg cagatagcag ccccgtcaag 480
gcgggagtgg agaccaccac accctccaaa caaagcaaca acaagtacgc ggccagcagc 540
tacctgagcc tgacgcctga gcagtggaag tcccacaaaa gctacagctg ccaggtcacg 600
catgaaggga gcaccgtgga gaagacagtg gcccctgcag aatgctct 648

<210> SEQ ID NO 41
<211> LENGTH: 648
<212> TYPE: DNA
<213> ORGANISM: Artificial Sequence
<220> FEATURE:
<223> OTHER INFORMATION: P1F1 (lambda) LC VD Nucleotide sequence

<400> SEQUENCE: 41
cagactgtgg tgactcagga gccatcgttc tcagtgtccc ctggagggac agtcacactc 60

-continued

```
acttgtggct tgagctctgg ctcagtctct actagttact accccagctg gtaccagcag    120

accccaggcc aggctccacg cacgctcatc tacagcacaa acactcgctc ttctggggtc    180

cctgatcgct tctctggctc catccttggg aacaaagctg ccctcaccat cacgggggcc    240

caggcagatg atgaatctga ttattactgt gtgctgtata tgggtagtgg catttgggtg    300

ttcggcggag ggaccaagct gaccgtccta ggtcagccca aggctgcccc ctcggtcact    360

ctgttcccac cctcctctga ggagcttcaa gccaacaagg ccacactggt gtgtctcata    420

agtgacttct acccgggagc cgtgacagtg gcctggaagg cagatagcag ccccgtcaag    480

gcgggagtgg agaccaccac accctccaaa caaagcaaca acaagtacgc ggccagcagc    540

tacctgagcc tgacgcctga gcagtggaag tcccacaaaa gctacagctg ccaggtcacg    600

catgaaggga gcaccgtgga gaagacagtg gcccctacag aatgttca                648
```

<210> SEQ ID NO 42
<211> LENGTH: 363
<212> TYPE: DNA
<213> ORGANISM: Artificial Sequence
<220> FEATURE:
<223> OTHER INFORMATION: P1A3 HC VD nucleotide sequence

<400> SEQUENCE: 42

```
gaggtccagc tggtgcagtc tgggactgag gtgaagaagc ctggggcctc agtgagggtt     60

tcctgcaagt catctggata caccttcacc agctactata tacactgggt gcgacaggcc    120

cctggacaag gacttgagtg gatggcaata atcaaccctg gtaatggtga cacaaactac    180

gcacagaggt tccagggcag agtcaccatg accagggaca cgtccacgag cacagtctac    240

atggagctga ggagcctgag atctgacgac acggccgtct atttctgtgc gagagagatt    300

gcctcctata gtgggagcta ctacgactac tggggccagg gaaccctggt caccgtctca    360

agc                                                                  363
```

<210> SEQ ID NO 43
<211> LENGTH: 372
<212> TYPE: DNA
<213> ORGANISM: Artificial Sequence
<220> FEATURE:
<223> OTHER INFORMATION: P1C5 HC VD nucleotide sequence

<400> SEQUENCE: 43

```
caggtgcagc tgcaggagtc gggcccagga ctggtgaagc cttcggagac cctgtccctc     60

acctgcactg tctctggtgg ctccatcagc agtagtagtt actactgggg ctggatccgc    120

cagcccccag ggaaggggct ggagtggatt gggagtatct attatagtgg gagcacctac    180

tacaacccgt ccctcaagag tcgagtcacc atatccgtag acacgtccaa gaaccagttc    240

tccctgaagc tgagctctgt gaccgccgca gacacggctg tgtattactg tgcgagatac    300

gcgcctgata gtagtggtta cttggtggct tttgatatct ggggccaagg gacaatggtc    360

accgtctcaa gc                                                        372
```

<210> SEQ ID NO 44
<211> LENGTH: 366
<212> TYPE: DNA
<213> ORGANISM: Artificial Sequence
<220> FEATURE:
<223> OTHER INFORMATION: P1E4 HC VD nucleotide sequence

<400> SEQUENCE: 44

```
caggtgcagc tacagcagtg ggcgcagga ctgttgaagc cttcggagac cctgtccctc     60
```

acctgcgctg tctatggtgg gtccttcagt ggttactact ggagctggat ccgccagccc 120
ccagggaagg ggctggagtg gattggggaa atcaatcata gtggaagcac caactacaac 180
ccgtccctca agagtcgagt caccatatca gtagacacgt ccaagaacca gttctccctg 240
aagctgagct ctgtgaccac tgcggacacg gccgtgtatt actgtgcgag gatgggaata 300
aatagtggtg gttatctcta cggtatggac gtctggggcc aagggaccac ggtcaccgtc 360
tcaagc 366

<210> SEQ ID NO 45
<211> LENGTH: 369
<212> TYPE: DNA
<213> ORGANISM: Artificial Sequence
<220> FEATURE:
<223> OTHER INFORMATION: P1F1 HC VD nucleotide sequence

<400> SEQUENCE: 45
caggtgcagc tggtggagtc tggcccagga ctggtgaagc cttcggggac cctgtccctc 60
acctgcgctg tctctggtgg ctccatcagc agtagtaact ggtggagttg ggtccgccag 120
cccccaggga aggggctgga gtggattggg gaaatctatc atagtgggag caccaactac 180
aacccgtccc tcaagagtcg agtcaccata tcagtagaca cgtccaagaa ccagttctcc 240
ctgaagctga gctctgtgac cgctgcggac acggccgtgt attactgtgc gaggatggga 300
gcaaatagtg gtgggtatct ctacggtatg gacgtctggg gccaagggac cacggtcacc 360
gtctcaagc 369

<210> SEQ ID NO 46
<211> LENGTH: 42
<212> TYPE: DNA
<213> ORGANISM: Artificial Sequence
<220> FEATURE:
<223> OTHER INFORMATION: P1A3 (lambda) LC-CDR1 Nucleotide sequence

<400> SEQUENCE: 46
ggcttgagct ctggctcagt ctctactggt cactacgcca gc 42

<210> SEQ ID NO 47
<211> LENGTH: 21
<212> TYPE: DNA
<213> ORGANISM: Artificial Sequence
<220> FEATURE:
<223> OTHER INFORMATION: P1A3 (lambda) LC-CDR2 Nucleotide sequence

<400> SEQUENCE: 47
aacacaaaca ctcgctcttc t 21

<210> SEQ ID NO 48
<211> LENGTH: 30
<212> TYPE: DNA
<213> ORGANISM: Artificial Sequence
<220> FEATURE:
<223> OTHER INFORMATION: P1A3 (lambda) LC-CDR3 Nucleotide sequence

<400> SEQUENCE: 48
gtgctgtatg tgggtgatgg catttgggtt 30

<210> SEQ ID NO 49
<211> LENGTH: 15
<212> TYPE: DNA
<213> ORGANISM: Artificial Sequence
<220> FEATURE:

<223> OTHER INFORMATION: P1A3 HC-CDR1 nucleotide sequence

<400> SEQUENCE: 49
agctactata tacac 15

<210> SEQ ID NO 50
<211> LENGTH: 51
<212> TYPE: DNA
<213> ORGANISM: Artificial Sequence
<220> FEATURE:
<223> OTHER INFORMATION: P1A3 HC-CDR2 nucleotide sequence

<400> SEQUENCE: 50
ataatcaacc ctggtaatgg tgacacaaac tacgcacaga ggttccaggg c 51

<210> SEQ ID NO 51
<211> LENGTH: 36
<212> TYPE: DNA
<213> ORGANISM: Artificial Sequence
<220> FEATURE:
<223> OTHER INFORMATION: P1A3 HC-CDR3 nucleotide sequence

<400> SEQUENCE: 51
gagattgcct cctatagtgg gagctactac gactac 36

<210> SEQ ID NO 52
<211> LENGTH: 42
<212> TYPE: DNA
<213> ORGANISM: Artificial Sequence
<220> FEATURE:
<223> OTHER INFORMATION: P1C5 (lambda) LC-CDR1 Nucleotide sequence

<400> SEQUENCE: 52
ggcttgagct ctggctcagt ctctactggt tactacccca gc 42

<210> SEQ ID NO 53
<211> LENGTH: 21
<212> TYPE: DNA
<213> ORGANISM: Artificial Sequence
<220> FEATURE:
<223> OTHER INFORMATION: P1C5 (lambda) LC-CDR2 Nucleotide sequence

<400> SEQUENCE: 53
agcacaaaca gtcgctcttc t 21

<210> SEQ ID NO 54
<211> LENGTH: 30
<212> TYPE: DNA
<213> ORGANISM: Artificial Sequence
<220> FEATURE:
<223> OTHER INFORMATION: P1C5 (lambda) LC-CDR3 Nucleotide sequence

<400> SEQUENCE: 54
gtgctgtata tgggtagtgg catttcggtg 30

<210> SEQ ID NO 55
<211> LENGTH: 21
<212> TYPE: DNA
<213> ORGANISM: Artificial Sequence
<220> FEATURE:
<223> OTHER INFORMATION: P1C5 HC-CDR1 nucleotide sequence

<400> SEQUENCE: 55
agtagtagtt actactgggg c 21

<210> SEQ ID NO 56
<211> LENGTH: 48
<212> TYPE: DNA
<213> ORGANISM: Artificial Sequence
<220> FEATURE:
<223> OTHER INFORMATION: P1C5 HC-CDR2 nucleotide sequence

<400> SEQUENCE: 56
agtatctatt atagtgggag cacctactac aacccgtccc tcaagagt 48

<210> SEQ ID NO 57
<211> LENGTH: 42
<212> TYPE: DNA
<213> ORGANISM: Artificial Sequence
<220> FEATURE:
<223> OTHER INFORMATION: P1C5 HC-CDR3 nucleotide sequence

<400> SEQUENCE: 57
tacgcgcctg atagtagtgg ttacttggtg gcttttgata tc 42

<210> SEQ ID NO 58
<211> LENGTH: 42
<212> TYPE: DNA
<213> ORGANISM: Artificial Sequence
<220> FEATURE:
<223> OTHER INFORMATION: P1E4 (lambda) LC-CDR1 Nucleotide sequence

<400> SEQUENCE: 58
ggcctgagct ctggctcagt ctctactagt tactacccca gc 42

<210> SEQ ID NO 59
<211> LENGTH: 21
<212> TYPE: DNA
<213> ORGANISM: Artificial Sequence
<220> FEATURE:
<223> OTHER INFORMATION: P1E4 (lambda) LC-CDR2 Nucleotide sequence

<400> SEQUENCE: 59
accacaaaca ttcgctcttc t 21

<210> SEQ ID NO 60
<211> LENGTH: 30
<212> TYPE: DNA
<213> ORGANISM: Artificial Sequence
<220> FEATURE:
<223> OTHER INFORMATION: P1E4 (lambda) LC-CDR3 Nucleotide sequence

<400> SEQUENCE: 60
atgctctata tggggagtgg catttgggtg 30

<210> SEQ ID NO 61
<211> LENGTH: 15
<212> TYPE: DNA
<213> ORGANISM: Artificial Sequence
<220> FEATURE:
<223> OTHER INFORMATION: P1E4 HC-CDR1 nucleotide sequence

<400> SEQUENCE: 61
ggttactact ggagc 15

<210> SEQ ID NO 62
<211> LENGTH: 48
<212> TYPE: DNA
<213> ORGANISM: Artificial Sequence
<220> FEATURE:
<223> OTHER INFORMATION: P1E4 HC-CDR2 nucleotide sequence

<400> SEQUENCE: 62
gaaatcaatc atagtggaag caccaactac aacccgtccc tcaagagt 48

<210> SEQ ID NO 63
<211> LENGTH: 42
<212> TYPE: DNA
<213> ORGANISM: Artificial Sequence
<220> FEATURE:
<223> OTHER INFORMATION: P1E4 HC-CDR3 nucleotide sequence

<400> SEQUENCE: 63
atgggaataa atagtggtgg ttatctctac ggtatggacg tc 42

<210> SEQ ID NO 64
<211> LENGTH: 42
<212> TYPE: DNA
<213> ORGANISM: Artificial Sequence
<220> FEATURE:
<223> OTHER INFORMATION: P1F1 (lambda) LC-CDR1 Nucleotide sequence

<400> SEQUENCE: 64
ggcttgagct ctggctcagt ctctactagt tactacccca gc 42

<210> SEQ ID NO 65
<211> LENGTH: 21
<212> TYPE: DNA
<213> ORGANISM: Artificial Sequence
<220> FEATURE:
<223> OTHER INFORMATION: P1F1 (lambda) LC-CDR2 Nucleotide sequence

<400> SEQUENCE: 65
agcacaaaca ctcgctcttc t 21

<210> SEQ ID NO 66
<211> LENGTH: 30
<212> TYPE: DNA
<213> ORGANISM: Artificial Sequence
<220> FEATURE:
<223> OTHER INFORMATION: P1F1 (lambda) LC-CDR3 Nucleotide sequence

<400> SEQUENCE: 66
gtgctgtata tgggtagtgg catttgggtg 30

<210> SEQ ID NO 67
<211> LENGTH: 18
<212> TYPE: DNA
<213> ORGANISM: Artificial Sequence
<220> FEATURE:
<223> OTHER INFORMATION: P1F1 HC-CDR1 nucleotide sequence

<400> SEQUENCE: 67
agtagtaact ggtggagt 18

<210> SEQ ID NO 68
<211> LENGTH: 48
<212> TYPE: DNA
<213> ORGANISM: Artificial Sequence
<220> FEATURE:
<223> OTHER INFORMATION: P1F1 HC-CDR2 nucleotide sequence

<400> SEQUENCE: 68
gaaatctatc atagtgggag caccaactac aacccgtccc tcaagagt 48

<210> SEQ ID NO 69
<211> LENGTH: 42

<212> TYPE: DNA
<213> ORGANISM: Artificial Sequence
<220> FEATURE:
<223> OTHER INFORMATION: P1F1 HC-CDR3 nucleotide sequence

<400> SEQUENCE: 69
atgggagcaa atagtggtgg gtatctctac ggtatggacg tc 42

<210> SEQ ID NO 70
<211> LENGTH: 657
<212> TYPE: DNA
<213> ORGANISM: Artificial Sequence
<220> FEATURE:
<223> OTHER INFORMATION: PFA1 Light chain nucleotide sequence

<400> SEQUENCE: 70
gaaattgtgc tgactcagtc tccattctcc ctgcccgtca cccctggaga gccggcctcc 60
atctcctgca ggtctagtca gagcctcctg catagtaatg gattcaacta tttggattgg 120
tacctgcaga agccagggca gtctccacaa ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaaggtct acagactccg 300
tacacttttg gccaggggac caagctggag atcaaacgaa ctgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtc acaaagagct tcaacagggg agagtgt 657

<210> SEQ ID NO 71
<211> LENGTH: 684
<212> TYPE: DNA
<213> ORGANISM: Artificial Sequence
<220> FEATURE:
<223> OTHER INFORMATION: PFA1 Heavy chain nucleotide sequence

<400> SEQUENCE: 71
gaggtccagc tggtacagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatcatatg atggaagtaa taaatactat 180
gcagactccg tgaagggccg attcaccatc tccagagaca attccaagaa caccctgttt 240
ctgcaaatga acagcctgag agccgaggac acggctgtgt attactgtgc gagagatctc 300
tttgcggtgg taggctacta ctactactac ggtatggacg tctggggcca agggaccacg 360
gtcaccgtct caagcgcctc caccaagggc ccatcggtct tccccctggc accctcctcc 420
aagagcacct ctgggggcac agcggccctg ggctgcctgg tcaaggacta cttccccgaa 480
ccggtgacgg tgtcgtggaa ctcaggcgcc ctgaccagcg gcgtccacac cttcccggct 540
gtcctacagt cctcaggact ctactccctc agcagcgtag tgaccgtgcc ctccagcagc 600
ttgggcaccc agacctacat ctgcaacgtg aatcacaagc ccagcaacac caaggtggac 660
aagaaagttg agcccaaatc ttgt 684

<210> SEQ ID NO 72
<211> LENGTH: 219
<212> TYPE: PRT

<213> ORGANISM: Artificial Sequence
<220> FEATURE:
<223> OTHER INFORMATION: PFA1 Light chain VD

<400> SEQUENCE: 72

```
Glu Ile Val Leu Thr Gln Ser Pro Phe Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Phe Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gln Thr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 73
<211> LENGTH: 228
<212> TYPE: PRT
<213> ORGANISM: Artificial Sequence
<220> FEATURE:
<223> OTHER INFORMATION: PFA1 Heavy chain VD

<400> SEQUENCE: 73

```
Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Leu Phe Ala Val Val Gly Tyr Tyr Tyr Tyr Tyr Gly Met
            100                 105                 110
```

-continued

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys
225

<210> SEQ ID NO 74
<211> LENGTH: 16
<212> TYPE: PRT
<213> ORGANISM: Artificial Sequence
<220> FEATURE:
<223> OTHER INFORMATION: PFA1 LC-CDR1

<400> SEQUENCE: 74

Arg Ser Ser Gln Ser Leu Leu His Ser Asn Gly Phe Asn Tyr Leu Asp
1               5                   10                  15

<210> SEQ ID NO 75
<211> LENGTH: 7
<212> TYPE: PRT
<213> ORGANISM: Artificial Sequence
<220> FEATURE:
<223> OTHER INFORMATION: PFA1 LC-CDR2 PFA2 LC-CDR2 PFA5 LC-CDR2 PFB3 LC-CDR2 PFF3 LC-CDR2

<400> SEQUENCE: 75

Leu Gly Ser Asn Arg Ala Ser
1               5

<210> SEQ ID NO 76
<211> LENGTH: 9
<212> TYPE: PRT
<213> ORGANISM: Artificial Sequence
<220> FEATURE:
<223> OTHER INFORMATION: PFA1 LC-CDR3

<400> SEQUENCE: 76

Met Gln Gly Leu Gln Thr Pro Tyr Thr
1               5

<210> SEQ ID NO 77
<211> LENGTH: 5
<212> TYPE: PRT
<213> ORGANISM: Artificial Sequence
<220> FEATURE:
<223> OTHER INFORMATION: PFA1 HC-CDR1 PFB4 HC-CDR1 PFD1 HC-CDR1 PFG1 HC-CDR1

<400> SEQUENCE: 77

Ser Tyr Gly Met His
1               5

-continued

<210> SEQ ID NO 78
<211> LENGTH: 17
<212> TYPE: PRT
<213> ORGANISM: Artificial Sequence
<220> FEATURE:
<223> OTHER INFORMATION: PFA1 HC-CDR2 PFA4 HC-CDR2 PFB4 HC-CDR2 PFC2
HC-CDR2 PFD1 HC-CDR2 PFE1 HC-CDR2 PFE5 HC-CDR2 PFG5 HC-CDR2

<400> SEQUENCE: 78

Val Ile Ser Tyr Asp Gly Ser Asn Lys Tyr Tyr Ala Asp Ser Val Lys
1 5 10 15

Gly

<210> SEQ ID NO 79
<211> LENGTH: 16
<212> TYPE: PRT
<213> ORGANISM: Artificial Sequence
<220> FEATURE:
<223> OTHER INFORMATION: PFA1 HC-CDR3

<400> SEQUENCE: 79

Asp Leu Phe Ala Val Val Gly Tyr Tyr Tyr Tyr Tyr Gly Met Asp Val
1 5 10 15

<210> SEQ ID NO 80
<211> LENGTH: 663
<212> TYPE: DNA
<213> ORGANISM: Artificial Sequence
<220> FEATURE:
<223> OTHER INFORMATION: PFA2 Light chain nucleotide sequence

<400> SEQUENCE: 80
gaaattgtgt tgacgcagtc tccactctcc ctgcccgtca cccctggaga gccggcctcc 60
atctcctgca ggtctagtca gagtctcctg cacagtgatg ggaacaaata tttggattgg 120
tacctgcaga agccagggca gtctccacag ctcctgatct atttgggttc taatcgggcc 180
tccggggtcc ctgagaggtt cagtggcagt ggatcaggca cagattttac actgaaaatc 240
agcagagtgg aggctgagga tgttggggtt tattactgca tgctaggtac acactggcct 300
ccgatgtaca tttttggcca ggggaccaag ctggagatca aacgaactgt ggctgcacca 360
tctgtcttca tcttcccgcc atctgatgag cagttgaaat ctggaactgc ctctgttgtg 420
tgcctgctga ataacttcta tcccagagag gccaaagtac agtggaaggt ggataacgcc 480
ctccaatcgg gtaactccca ggagagtgtc acagagcagg acagcaagga cagcacctac 540
agcctcagca gcaccctgac gctgagcaaa gcagactacg agaaacacaa agtctacgcc 600
tgcgaagtca cccatcaggg cctgagctcg cccgtcacaa agagcttcaa caggggagag 660
tgt 663

<210> SEQ ID NO 81
<211> LENGTH: 663
<212> TYPE: DNA
<213> ORGANISM: Artificial Sequence
<220> FEATURE:
<223> OTHER INFORMATION: PFA2 Heavy chain nucleotide sequence

<400> SEQUENCE: 81
caggtacagc tgcagcagtc aggtccagga ctggtgaagc cctcgcagac cctctcgctc 60
acctgtgcca tctccgggga aagcgtctct agcgccgctg ctgcttggaa ctggatcagg 120
cagtccccat cgagaggcct tgagtggctg ggaaggacat actacaggtc caagtggtat 180
agtgaatatg cagtatctgt gaaaagtcga ataaccatca acggagacac atccaagaac 240

```
caggtctccc tgcacctgaa cgctgtgact cccgaggaca cggctatata ttactgtgta    300

aggggcagta tttttgatgt gtggggccaa gggacaatgg tcaccgtctc aagcgcctcc    360

accaagggcc catcggtctt ccccctggca ccctcctcca agagcacctc tgggggcaca    420

gcggccctgg gctgcctggt caaggactac ttccccgaac cggtgacggt gtcgtggaac    480

tcaggcgccc tgaccagcgg cgtccacacc ttcccggctg tcctacagtc ctcaggactc    540

tactccctca gcagcgtagt gaccgtgccc tccagcagct tgggcaccca gacctacatc    600

tgcaacgtga atcacaagcc cagcaacacc aaggtggaca agaaagttga gcccaaatct    660

tgt                                                                  663


<210> SEQ ID NO 82
<211> LENGTH: 221
<212> TYPE: PRT
<213> ORGANISM: Artificial Sequence
<220> FEATURE:
<223> OTHER INFORMATION: PFA2 Light chain VD

<400> SEQUENCE: 82

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Asn Lys Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Glu Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Leu Gly
                85                  90                  95

Thr His Trp Pro Pro Met Tyr Ile Phe Gly Gln Gly Thr Lys Leu Glu
            100                 105                 110

Ile Lys Arg Thr Val Ala Ala Pro Ser Val Phe Ile Phe Pro Pro Ser
        115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val Thr Lys Ser Phe Asn Arg Gly Glu Cys
    210                 215                 220


<210> SEQ ID NO 83
<211> LENGTH: 221
<212> TYPE: PRT
<213> ORGANISM: Artificial Sequence
<220> FEATURE:
<223> OTHER INFORMATION: PFA2 Heavy chain VD

<400> SEQUENCE: 83
```

-continued

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Glu Ser Val Ser Ser Ala
            20                  25                  30

Ala Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Ser Glu Tyr Ala
    50                  55                  60

Val Ser Val Lys Ser Arg Ile Thr Ile Asn Gly Asp Thr Ser Lys Asn
65                  70                  75                  80

Gln Val Ser Leu His Leu Asn Ala Val Thr Pro Glu Asp Thr Ala Ile
                85                  90                  95

Tyr Tyr Cys Val Arg Gly Ser Ile Phe Asp Val Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220
```

<210> SEQ ID NO 84
<211> LENGTH: 16
<212> TYPE: PRT
<213> ORGANISM: Artificial Sequence
<220> FEATURE:
<223> OTHER INFORMATION: PFA2 LC-CDR1

<400> SEQUENCE: 84

```
Arg Ser Ser Gln Ser Leu Leu His Ser Asp Gly Asn Lys Tyr Leu Asp
1               5                   10                  15
```

<210> SEQ ID NO 85
<211> LENGTH: 11
<212> TYPE: PRT
<213> ORGANISM: Artificial Sequence
<220> FEATURE:
<223> OTHER INFORMATION: PFA2 LC-CDR3

<400> SEQUENCE: 85

```
Met Leu Gly Thr His Trp Pro Pro Met Tyr Ile
1               5                   10
```

<210> SEQ ID NO 86
<211> LENGTH: 7
<212> TYPE: PRT
<213> ORGANISM: Artificial Sequence
<220> FEATURE:
<223> OTHER INFORMATION: PFA2 HC-CDR1

<400> SEQUENCE: 86

```
Ser Ala Ala Ala Ala Trp Asn
```

1 5

<210> SEQ ID NO 87
<211> LENGTH: 18
<212> TYPE: PRT
<213> ORGANISM: Artificial Sequence
<220> FEATURE:
<223> OTHER INFORMATION: PFA2 HC-CDR2

<400> SEQUENCE: 87

Arg Thr Tyr Tyr Arg Ser Lys Trp Tyr Ser Glu Tyr Ala Val Ser Val
1 5 10 15

Lys Ser

<210> SEQ ID NO 88
<211> LENGTH: 6
<212> TYPE: PRT
<213> ORGANISM: Artificial Sequence
<220> FEATURE:
<223> OTHER INFORMATION: PFA2 HC-CDR3

<400> SEQUENCE: 88

Gly Ser Ile Phe Asp Val
1 5

<210> SEQ ID NO 89
<211> LENGTH: 657
<212> TYPE: DNA
<213> ORGANISM: Artificial Sequence
<220> FEATURE:
<223> OTHER INFORMATION: PFA4 Light chain nucleotide sequence

<400> SEQUENCE: 89
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggcca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggcct 300
ctcacttttg gccaggggac caagctggag atcaaacgaa ctgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtc acaaagagct tcaacagggg agagtgt 657

<210> SEQ ID NO 90
<211> LENGTH: 663
<212> TYPE: DNA
<213> ORGANISM: Artificial Sequence
<220> FEATURE:
<223> OTHER INFORMATION: PFA4 Heavy chain nucleotide sequence

<400> SEQUENCE: 90
gaggtccagc tggtgcagtc tgggggaggc gtggtccagc ctgggaggtc cctgagactc 60
tcctgtgcag cctctggatt caccttcagt agctatgcta tgcactgggt ccgccaggct 120
ccaggcaagg ggctggagtg ggtggcagtt atatcatatg atggaagtaa taaatactac 180
gcagactccg tgaagggccg attcaccatc tccagagaca attccaagaa cacgctgtat 240

-continued

```
ctgcaaatga acagcctgag agctgaggac acggctgtgt attactgtgc gaggagtcga    300

ggctactacg gtatggacgt ctggggccaa gggaccacgg tcaccgtctc aagcgcctcc    360

accaagggcc catcggtctt cccctggca ccctcctcca agagcacctc tgggggcaca    420

gcggccctgg gctgcctggt caaggactac ttccccgaac cggtgacggt gtcgtggaac    480

tcaggcgccc tgaccagcgg cgtccacacc ttcccggctg tcctacagtc ctcaggactc    540

tactccctca gcagcgtagt gaccgtgccc tccagcagct tgggcaccca gacctacatc    600

tgcaacgtga atcacaagcc cagcaacacc aaggtggaca agaaagttga gcccaaatct    660

tgt                                                                  663


<210> SEQ ID NO 91
<211> LENGTH: 219
<212> TYPE: PRT
<213> ORGANISM: Artificial Sequence
<220> FEATURE:
<223> OTHER INFORMATION: PFA4 Light chain VD

<400> SEQUENCE: 91

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 92
<211> LENGTH: 221
<212> TYPE: PRT
<213> ORGANISM: Artificial Sequence
<220> FEATURE:
<223> OTHER INFORMATION: PFA4 Heavy chain VD

<400> SEQUENCE: 92
```

Glu Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Arg Gly Tyr Tyr Gly Met Asp Val Trp Gly Gln Gly Thr
100 105 110

Thr Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys
210 215 220

<210> SEQ ID NO 93
<211> LENGTH: 16
<212> TYPE: PRT
<213> ORGANISM: Artificial Sequence
<220> FEATURE:
<223> OTHER INFORMATION: PFA4 LC-CDR1 PFD1 LC-CDR1 PFD4 LC-CDR1

<400> SEQUENCE: 93

Arg Ser Ser Gln Ser Leu Val Tyr Ser Asp Gly Asn Thr Tyr Leu Asn
1 5 10 15

<210> SEQ ID NO 94
<211> LENGTH: 7
<212> TYPE: PRT
<213> ORGANISM: Artificial Sequence
<220> FEATURE:
<223> OTHER INFORMATION: PFA4 LC-CDR2 PFD1 LC-CDR2

<400> SEQUENCE: 94

Lys Val Ser Asn Arg Asp Ser
1 5

<210> SEQ ID NO 95
<211> LENGTH: 9
<212> TYPE: PRT
<213> ORGANISM: Artificial Sequence
<220> FEATURE:
<223> OTHER INFORMATION: PFA4 LC-CDR3 PFC2 LC-CDR3 PFE1 LC-CDR3 PFG5
LC-CDR3

<400> SEQUENCE: 95

Met Gln Gly Thr His Trp Pro Leu Thr
1 5

<210> SEQ ID NO 96
<211> LENGTH: 5
<212> TYPE: PRT
<213> ORGANISM: Artificial Sequence
<220> FEATURE:
<223> OTHER INFORMATION: PFA4 HC-CDR1 PFA5 HC-CDR1PFC2 HC-CDR1 PFD4 HC-CDR1 PFE1 HC-CDR1 PFE2 HC-CDR1 PFE5 HC-CDR1 PFG5 HC-CDR1

<400> SEQUENCE: 96

Ser Tyr Ala Met His
1 5

<210> SEQ ID NO 97
<211> LENGTH: 9
<212> TYPE: PRT
<213> ORGANISM: Artificial Sequence
<220> FEATURE:
<223> OTHER INFORMATION: PFA4 HC-CDR3 PFD4 HC-CDR3 PFE1 HC-CDR3 PFE5 HC-CDR3

<400> SEQUENCE: 97

Ser Arg Gly Tyr Tyr Gly Met Asp Val
1 5

<210> SEQ ID NO 98
<211> LENGTH: 657
<212> TYPE: DNA
<213> ORGANISM: Artificial Sequence
<220> FEATURE:
<223> OTHER INFORMATION: PFA5 Light chain nucleotide sequence

<400> SEQUENCE: 98
gatgttgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactccg 300
tggacgttcg gccaagggac caaggtggaa atcaaacgaa ctgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaactcta cgcctgcgaa 600
gtcacccatc agggcctgag ctcgcccgtc acaaagagct tcaacagggg agagtgt 657

<210> SEQ ID NO 99
<211> LENGTH: 657
<212> TYPE: DNA
<213> ORGANISM: Artificial Sequence
<220> FEATURE:
<223> OTHER INFORMATION: PFA5 Heavy chain nucleotide sequence

<400> SEQUENCE: 99
caggtgcagc tggtgcaatc tggggctgag gtgaagaagc ctggggcctc agtgaaggtt 60
tcctgcaagg cttctggata caccttcact agctatgcta tgcattgggt gcgccaggcc 120
cccggacaaa ggcttgagtg gatgggatgg atcaacgctg gcaatggtaa cacaaaatat 180

```
tcacagaagt tccagggcag agtcaccatt accagggaca catccgcgag cacagcctac    240

atggagctga gcagcctgag atctgaagac acggctgtgt attactgtgc gagaggagga    300

tacctcgtag gctactgggg ccagggcacc ctggtcaccg tctcaagcgc ctccaccaag    360

ggcccatcgg tcttcccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtcca caccttcccg gctgtcctac agtcctcagg actctactcc    540

ctcagcagcg tagtgaccgt gccctccagc agcttgggca cccagaccta catctgcaac    600

gtgaatcaca agcccagcaa caccaaggtg gacaagaaag ttgagcccaa atcttgt       657
```

<210> SEQ ID NO 100
<211> LENGTH: 219
<212> TYPE: PRT
<213> ORGANISM: Artificial Sequence
<220> FEATURE:
<223> OTHER INFORMATION: PFA5 Light chain VD

<400> SEQUENCE: 100

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 101
<211> LENGTH: 219
<212> TYPE: PRT
<213> ORGANISM: Artificial Sequence
<220> FEATURE:
<223> OTHER INFORMATION: PFA5 Heavy chain VD

<400> SEQUENCE: 101

```
Gln Val Gln Leu Val Gln Ser Gly Ala Glu Val Lys Lys Pro Gly Ala
```

```
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Leu Val Gly Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys
    210                 215


<210> SEQ ID NO 102
<211> LENGTH: 16
<212> TYPE: PRT
<213> ORGANISM: Artificial Sequence
<220> FEATURE:
<223> OTHER INFORMATION: PFA5 LC-CDR1 PFB3 LC-CDR1 PFB5 LC-CDR1 PFC2
      LC-CDR1 PFF3 LC-CDR1 PFG5 LC-CDR1

<400> SEQUENCE: 102

Arg Ser Ser Gln Ser Leu Leu His Ser Asn Gly Tyr Asn Tyr Leu Asp
1               5                   10                  15


<210> SEQ ID NO 103
<211> LENGTH: 9
<212> TYPE: PRT
<213> ORGANISM: Artificial Sequence
<220> FEATURE:
<223> OTHER INFORMATION: PFA5 LC-CDR3

<400> SEQUENCE: 103

Met Gln Ala Leu Gln Thr Pro Trp Thr
1               5


<210> SEQ ID NO 104
<211> LENGTH: 17
<212> TYPE: PRT
<213> ORGANISM: Artificial Sequence
<220> FEATURE:
<223> OTHER INFORMATION: PFA5 HC-CDR2

<400> SEQUENCE: 104

Trp Ile Asn Ala Gly Asn Gly Asn Thr Lys Tyr Ser Gln Lys Phe Gln
```

1 5 10 15

Gly

<210> SEQ ID NO 105
<211> LENGTH: 7
<212> TYPE: PRT
<213> ORGANISM: Artificial Sequence
<220> FEATURE:
<223> OTHER INFORMATION: PFA5 HC-CDR3

<400> SEQUENCE: 105

Gly Gly Tyr Leu Val Gly Tyr
1 5

<210> SEQ ID NO 106
<211> LENGTH: 657
<212> TYPE: DNA
<213> ORGANISM: Artificial Sequence
<220> FEATURE:
<223> OTHER INFORMATION: PFB1 Light chain nucleotide sequence

<400> SEQUENCE: 106
gatgttgtga tgactcagtc tccactctcc ctccccgtca ctcctggaga gccggcctcc 60
atctcctgta ggtctagtca gagcctcctg catagtaatg ggaacaccta tttggattgg 120
tacctgcaga agccagggca gtctccacag gtcctgatct attcgggttc taatcgggcc 180
tctggagtcc cagacaggtt cagcggcagt gggtcaggca ctgatttcac actgaaaatc 240
agcagggtgg aggctgagga tgttggggtt tattactgca tgcaaggtac acactggcct 300
ccgacgttcg gccaagggac caaggtggaa atcaaacgaa ctgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtc acaaagagct tcaacagggg agagtgt 657

<210> SEQ ID NO 107
<211> LENGTH: 672
<212> TYPE: DNA
<213> ORGANISM: Artificial Sequence
<220> FEATURE:
<223> OTHER INFORMATION: PFB1 Heavy chain nucleotide sequence

<400> SEQUENCE: 107
caggtgcagc tgcaggagtc gggggaggc ttggtacagc ctgggggtc cctgagactc 60 tcctgtgcag cctctggatt cacctttagc agctttgcca tgaactgggt ccgccaggct 120
ccagggaagg ggctggagtg ggtctcaact attggtggta gtggtgatag cacattctac 180
gcagaccccg tgaagggccg gttcaccgtc tccagagaca attccaagaa cacgttgtat 240
ctgcaaatga acagcctgag agccgaggac acggccgtat attactgtgc gcaagcctat 300
ggttcggggg gtcattattt ctttgcctac tggggccagg gaaccctggt caccgtctca 360
agcgcctcca ccaagggccc atcggtcttc cccctggcac cctcctccaa gagcacctct 420
gggggcacag cggccctggg ctgcctggtc aaggactact tccccgaacc ggtgacggtg 480
tcgtggaact caggcgccct gaccagcggc gtccacacct tcccggctgt cctacagtcc 540
tcaggactct actccctcag cagcgtagtg accgtgccct ccagcagctt gggcacccag 600

```
acctacatct gcaacgtgaa tcacaagccc agcaacacca aggtggacaa gaaagttgag    660

cccaaatctt gt                                                        672


<210> SEQ ID NO 108
<211> LENGTH: 219
<212> TYPE: PRT
<213> ORGANISM: Artificial Sequence
<220> FEATURE:
<223> OTHER INFORMATION: PFB1Light chain VD

<400> SEQUENCE: 108

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Thr Tyr Leu Asp Trp Tyr Leu Gln Lys Pro Gly Gln Ser
        35                  40                  45

Pro Gln Val Leu Ile Tyr Ser Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 109
<211> LENGTH: 224
<212> TYPE: PRT
<213> ORGANISM: Artificial Sequence
<220> FEATURE:
<223> OTHER INFORMATION: PFB1 Heavy chain VD

<400> SEQUENCE: 109

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Asn Trp Val Arg Gln Ala Pro Gly Lys Gly Leu Glu Trp Val
        35                  40                  45

Ser Thr Ile Gly Gly Ser Gly Asp Ser Thr Phe Tyr Ala Asp Pro Val
    50                  55                  60

Lys Gly Arg Phe Thr Val Ser Arg Asp Asn Ser Lys Asn Thr Leu Tyr
```

-continued

```
65                  70                  75                  80

Leu Gln Met Asn Ser Leu Arg Ala Glu Asp Thr Ala Val Tyr Tyr Cys
                85                  90                  95

Ala Gln Ala Tyr Gly Ser Gly Gly His Tyr Phe Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220


<210> SEQ ID NO 110
<211> LENGTH: 16
<212> TYPE: PRT
<213> ORGANISM: Artificial Sequence
<220> FEATURE:
<223> OTHER INFORMATION: PFB1 LC-CDR1

<400> SEQUENCE: 110

Arg Ser Ser Gln Ser Leu Leu His Ser Asn Gly Asn Thr Tyr Leu Asp
1               5                   10                  15


<210> SEQ ID NO 111
<211> LENGTH: 7
<212> TYPE: PRT
<213> ORGANISM: Artificial Sequence
<220> FEATURE:
<223> OTHER INFORMATION: PFB1 LC-CDR2

<400> SEQUENCE: 111

Ser Gly Ser Asn Arg Ala Ser
1               5


<210> SEQ ID NO 112
<211> LENGTH: 9
<212> TYPE: PRT
<213> ORGANISM: Artificial Sequence
<220> FEATURE:
<223> OTHER INFORMATION: PFB1 LC-CDR3

<400> SEQUENCE: 112

Met Gln Gly Thr His Trp Pro Pro Thr
1               5


<210> SEQ ID NO 113
<211> LENGTH: 5
<212> TYPE: PRT
<213> ORGANISM: Artificial Sequence
<220> FEATURE:
<223> OTHER INFORMATION: PFB1 HC-CDR1

<400> SEQUENCE: 113

Ser Phe Ala Met Asn
```

-continued 1 5

<210> SEQ ID NO 114
<211> LENGTH: 17
<212> TYPE: PRT
<213> ORGANISM: Artificial Sequence
<220> FEATURE:
<223> OTHER INFORMATION: PFB1 HC-CDR2

<400> SEQUENCE: 114

Thr Ile Gly Gly Ser Gly Asp Ser Thr Phe Tyr Ala Asp Pro Val Lys
1 5 10 15

Gly

<210> SEQ ID NO 115
<211> LENGTH: 12
<212> TYPE: PRT
<213> ORGANISM: Artificial Sequence
<220> FEATURE:
<223> OTHER INFORMATION: PFB1 HC-CDR3

<400> SEQUENCE: 115

Ala Tyr Gly Ser Gly Gly His Tyr Phe Phe Ala Tyr
1 5 10

<210> SEQ ID NO 116
<211> LENGTH: 639
<212> TYPE: DNA
<213> ORGANISM: Artificial Sequence
<220> FEATURE:
<223> OTHER INFORMATION: PFB2 Light chain nucleotide sequence

<400> SEQUENCE: 116
gaaacgacac tcacgcagtc tccagccacc ctgtctctgt ctccggggga aagagccacc 60
ctctcctgca gggccagtca gagtgttagg aacaacttag cctggtacca gcataaacct 120
ggccaggctc ccaggctcct catctattat gcatccacca gggccactgg catcccagac 180
aggttcagtg gcagtgggtc tgggacagac ttcactctca ccatcagcag actggagcct 240
gaagattttg cactgtatta ctgtcagcac tatggtagct cccggacgtt cggccaaggg 300
accaaggtgg aaatcaaacg aactgtggct gcaccatctg tcttcatctt cccgccatct 360
gatgagcagt tgaaatctgg aactgcctct gttgtgtgcc tgctgaataa cttctatccc 420
agagaggcca aagtacagtg gaaggtggat aacgccctcc aatcaggtaa ctcccaggag 480
agtgtcacag agcaggacag caaggacagc acctacagcc tcagcagcac cctgacgctg 540
agcaaagcag actacgagaa acacaaagtc tacgcctgcg aagtcaccca tcagggcctg 600
agctcgcccg tcacaaagag cttcaacagg ggagagtgt 639

<210> SEQ ID NO 117
<211> LENGTH: 663
<212> TYPE: DNA
<213> ORGANISM: Artificial Sequence
<220> FEATURE:
<223> OTHER INFORMATION: PFB2 Heavy chain nucleotide sequence

<400> SEQUENCE: 117
gaggtccagc tggtgcagtc tggagctgag gtgaagaagc ctggggcctc agtgaaggtc 60
tcctgcaagg cttctggtta cacctttacc agctatggta tcagctgggt gcgacaggcc 120
cctggagaag ggcttgagtg gatgggatgg atcagcgctt acaatggtaa cacaaactat 180
gcacagaagc tccagggcag agtcaccatg accacagaca catccacgag cacagcctac 240

```
atggagctga ggagcctgag atctgacgac acggccgtgt attactgtgc gagagattgg    300

ggcagcagct ggtccgacta ctggggccag ggcaccctgg tcaccgtctc aagcgcctcc    360

accaagggcc catcggtctt ccccctggca ccctcctcca agagcacctc tgggggcaca    420

gcggccctgg gctgcctggt caaggactac ttccccgaac cggtgacggt gtcgtggaac    480

tcaggcgccc tgaccagcgg cgtccacacc ttcccggctg tcctacagtc ctcaggactc    540

tactccctca gcagcgtagt gaccgtgccc tccagcagct tgggcaccca gacctacatc    600

tgcaacgtga atcacaagcc cagcaacacc aaggtggaca agaaagttga gcccaaatct    660

tgt                                                                  663


<210> SEQ ID NO 118
<211> LENGTH: 213
<212> TYPE: PRT
<213> ORGANISM: Artificial Sequence
<220> FEATURE:
<223> OTHER INFORMATION: PFB2 Light chain VD

<400> SEQUENCE: 118

Glu Thr Thr Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Asn Asn
            20                  25                  30

Leu Ala Trp Tyr Gln His Lys Pro Gly Gln Ala Pro Arg Leu Leu Ile
        35                  40                  45

Tyr Tyr Ala Ser Thr Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Leu Tyr Tyr Cys Gln His Tyr Gly Ser Ser Arg Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 119
<211> LENGTH: 221
<212> TYPE: PRT
<213> ORGANISM: Artificial Sequence
<220> FEATURE:
<223> OTHER INFORMATION: PFB2 Heavy chain VD

<400> SEQUENCE: 119
```

-continued

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Glu Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Trp Gly Ser Ser Trp Ser Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220


<210> SEQ ID NO 120
<211> LENGTH: 11
<212> TYPE: PRT
<213> ORGANISM: Artificial Sequence
<220> FEATURE:
<223> OTHER INFORMATION: PFB2 LC-CDR1

<400> SEQUENCE: 120

Arg Ala Ser Gln Ser Val Arg Asn Asn Leu Ala
1               5                   10


<210> SEQ ID NO 121
<211> LENGTH: 7
<212> TYPE: PRT
<213> ORGANISM: Artificial Sequence
<220> FEATURE:
<223> OTHER INFORMATION: PFB2 LC-CDR2

<400> SEQUENCE: 121

Tyr Ala Ser Thr Arg Ala Thr
1               5


<210> SEQ ID NO 122
<211> LENGTH: 8
<212> TYPE: PRT
<213> ORGANISM: Artificial Sequence
<220> FEATURE:
<223> OTHER INFORMATION: PFB2 LC-CDR3

<400> SEQUENCE: 122

Gln His Tyr Gly Ser Ser Arg Thr
```

1 5

<210> SEQ ID NO 123
<211> LENGTH: 5
<212> TYPE: PRT
<213> ORGANISM: Artificial Sequence
<220> FEATURE:
<223> OTHER INFORMATION: PFB2 HC-CDR1

<400> SEQUENCE: 123

Ser Tyr Gly Ile Ser
1 5

<210> SEQ ID NO 124
<211> LENGTH: 17
<212> TYPE: PRT
<213> ORGANISM: Artificial Sequence
<220> FEATURE:
<223> OTHER INFORMATION: PFB2 HC-CDR2

<400> SEQUENCE: 124

Trp Ile Ser Ala Tyr Asn Gly Asn Thr Asn Tyr Ala Gln Lys Leu Gln
1 5 10 15

Gly

<210> SEQ ID NO 125
<211> LENGTH: 9
<212> TYPE: PRT
<213> ORGANISM: Artificial Sequence
<220> FEATURE:
<223> OTHER INFORMATION: PFB2 HC-CDR3

<400> SEQUENCE: 125

Asp Trp Gly Ser Ser Trp Ser Asp Tyr
1 5

<210> SEQ ID NO 126
<211> LENGTH: 660
<212> TYPE: DNA
<213> ORGANISM: Artificial Sequence
<220> FEATURE:
<223> OTHER INFORMATION: PFB3 Light chain nucleotide sequence

<400> SEQUENCE: 126
gatgttgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatct atttgggctc taatcgggcc 180
tccggggtcc ctgacaggtt cagtggtagt ggatcaggca cagattttac actgaaaatc 240
accagagtgg aggctgagga tgttggggtt tattactgca tggcaggtct acaaactcct 300
cggctcacct tcggccctgg gaccaaagtg gatatcagac gaactgtggc tgcaccatct 360
gtcttcatct tcccgccatc tgatgagcag ttgaaatctg gaactgcctc tgttgtgtgc 420
ctgctgaata acttctatcc cagagaggcc aaagtacagt ggaaggtgga taacgccctc 480
caatcgggta actcccagga gagtgtcaca gagcaggaca gcaaggacag cacctacagc 540
ctcagcagca ccctgacgct gagcaaagca gactacgaga aacacaaagt ctacgcctgc 600
gaagtcaccc atcagggcct gagctcgccc gtcacaaaga gcttcaacag gggagagtgt 660

<210> SEQ ID NO 127
<211> LENGTH: 681
<212> TYPE: DNA

<213> ORGANISM: Artificial Sequence
<220> FEATURE:
<223> OTHER INFORMATION: PFB3 Heavy chain nucleotide sequence

<400> SEQUENCE: 127
caggtgcagc tgcaggagtc gggggaggc ttggtacagc ctgggggtc cctgagactc 60 tcctgtgcag cctctggatt cacctttagc agctatgcca tgagctgggt ccgccaggct 120
ccagggaagg ggctggagtg ggtctcagct attagtggta gtggtggtag cacatactac 180
gcagactccg tgaagggccg attcaccatc tccagagaca attccaagaa cacagtatat 240
ctgcaaatga acagcctgag agctgaggac acggctgttt attactgtgc gaggacgtat 300
tacgattttt ggagtggcag ggttggggct tttgatatct ggggccaagg gaccacggtc 360
accgtctcaa gcgcctccac caagggccca tcggtcttcc ccctggcacc ctcctccaag 420
agcacctctg ggggcacagc ggccctgggc tgcctggtca aggactactt ccccgaaccg 480
gtgacggtgt cgtggaactc aggcgccctg accagcggcg tccacacctt cccggctgtc 540
ctacagtcct caggactcta ctccctcagc agcgtagtga ccgtgccctc cagcagcttg 600
ggcacccaga cctacatctg caacgtgaat cacaagccca gcaacaccaa ggtggacaag 660
aaagttgagc ccaaatcttg t 681

<210> SEQ ID NO 128
<211> LENGTH: 220
<212> TYPE: PRT
<213> ORGANISM: Artificial Sequence
<220> FEATURE:
<223> OTHER INFORMATION: PFB3 Light chain VD

<400> SEQUENCE: 128

Asp Val Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Thr Arg Val Glu Ala Glu Asp Val Gly Val Tyr Tyr Cys Met Ala Gly
85 90 95

Leu Gln Thr Pro Arg Leu Thr Phe Gly Pro Gly Thr Lys Val Asp Ile
100 105 110

Arg Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
    210                 215                 220

<210> SEQ ID NO 129
<211> LENGTH: 227
<212> TYPE: PRT
<213> ORGANISM: Artificial Sequence
<220> FEATURE:
<223> OTHER INFORMATION: PFB3 Heavy chain VD

<400> SEQUENCE: 129

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Thr Tyr Tyr Asp Phe Trp Ser Gly Arg Val Gly Ala Phe Asp
            100                 105                 110

Ile Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225

<210> SEQ ID NO 130
<211> LENGTH: 10
<212> TYPE: PRT
<213> ORGANISM: Artificial Sequence
<220> FEATURE:
<223> OTHER INFORMATION: PFB3 LC-CDR3

<400> SEQUENCE: 130

Met Ala Gly Leu Gln Thr Pro Arg Leu Thr
1               5                   10

<210> SEQ ID NO 131
<211> LENGTH: 5
<212> TYPE: PRT
<213> ORGANISM: Artificial Sequence
<220> FEATURE:
<223> OTHER INFORMATION: PFB3 HC-CDR1 PFC3 HC-CDR1 PFG2 HC-CDR1

<400> SEQUENCE: 131

Ser Tyr Ala Met Ser
1 5

<210> SEQ ID NO 132
<211> LENGTH: 17
<212> TYPE: PRT
<213> ORGANISM: Artificial Sequence
<220> FEATURE:
<223> OTHER INFORMATION: PFB3 HC-CDR2

<400> SEQUENCE: 132

Ala Ile Ser Gly Ser Gly Gly Ser Thr Tyr Tyr Ala Asp Ser Val Lys
1 5 10 15

Gly

<210> SEQ ID NO 133
<211> LENGTH: 15
<212> TYPE: PRT
<213> ORGANISM: Artificial Sequence
<220> FEATURE:
<223> OTHER INFORMATION: PFB3 HC-CDR3

<400> SEQUENCE: 133

Thr Tyr Tyr Asp Phe Trp Ser Gly Arg Val Gly Ala Phe Asp Ile
1 5 10 15

<210> SEQ ID NO 134
<211> LENGTH: 645
<212> TYPE: DNA
<213> ORGANISM: Artificial Sequence
<220> FEATURE:
<223> OTHER INFORMATION: PFB4 Light chain nucleotide sequence

<400> SEQUENCE: 134
caggctgtgg tgatccagga gccctcactg actgtgtccc caggagggac agtcactctc 60
acctgtggct ccaccactgg agctgtcacc agtggccatt atccctcctg gttccagcag 120
aagcctggcc aagcacccag gcactgatt tatagtacaa gcaacaaaca ctcctggacc 180
cctgcccggt tctcaggctc cctccttggg ggcaaagctg ccctgacact gtcaggtgtg 240
cagcctgagg acgaggctga gtattactgc ctgctctact atggtggtgc tcgagtgttc 300
ggcggaggga ccaagctgac cgtcctaggt cagcccaagg ctgccccctc ggtcactctg 360
ttcccaccct cctctgagga gcttcaagcc aacaaggcca cactggtgtg tctcataagt 420
gacttctacc cgggagccgt gacagtggcc tggaaggcag atagcagccc cgtcaaggcg 480
ggagtggaga ccaccacacc ctccaaacaa agcaacaaca agtacgcggc cagcagctac 540
ctgagcctga cgcctgagca gtggaagtcc cacagaagct acagctgcca ggtcacgcat 600
gaagggagca ccgtggagaa gacagtggcc cctgcagaat gctct 645

<210> SEQ ID NO 135
<211> LENGTH: 663
<212> TYPE: DNA
<213> ORGANISM: Artificial Sequence
<220> FEATURE:
<223> OTHER INFORMATION: PFB4 Heavy chain nucleotide sequence

<400> SEQUENCE: 135
gaggtccagc tggtacagtc tgggggaggc gtggtccagc ctgggaggtc cctgagactc 60
tcctgtgcag cctctggatt caccttcagt agctatggca tgcactgggt ccgccaggct 120

-continued

```
ccaggcaagg ggctggagtg ggtggcagtt atatcatatg atggaagtaa taaatactat    180

gcagactccg tgaagggccg attcaccatc tccagagacg attccaagaa cacgctgtat    240

ctgcaaatga acagcctgag agctgaggac acggctgtgt attactgtgc gaaagatcgc    300

ggttactacg gtatggacgt ctggggccaa gggaccacgg tcaccgtctc aagcgcctcc    360

accaagggcc catcggtctt ccccctggca ccctcctcca agagcacctc tgggggcaca    420

gcggccctgg gctgcctggt caaggactac ttccccgaac cggtgacggt gtcgtggaac    480

tcaggcgccc tgaccagcgg cgtccacacc ttcccggctg tcctacagtc ctcaggactc    540

tactccctca gcagcgtagt gaccgtgccc tccagcagct tgggcaccca gacctacatc    600

tgcaacgtga atcacaagcc cagcaacacc aaggtggaca agaaagttga gcccaaatct    660

tgt                                                                  663
```

<210> SEQ ID NO 136
<211> LENGTH: 215
<212> TYPE: PRT
<213> ORGANISM: Artificial Sequence
<220> FEATURE:
<223> OTHER INFORMATION: PFB4 Light chain VD

<400> SEQUENCE: 136

```
Gln Ala Val Val Ile Gln Glu Pro Ser Leu Thr Val Ser Pro Gly Gly
1               5                   10                  15

Thr Val Thr Leu Thr Cys Gly Ser Thr Thr Gly Ala Val Thr Ser Gly
            20                  25                  30

His Tyr Pro Ser Trp Phe Gln Gln Lys Pro Gly Gln Ala Pro Arg Ala
        35                  40                  45

Leu Ile Tyr Ser Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Leu Leu Tyr Tyr Gly Gly
                85                  90                  95

Ala Arg Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Ala Glu Cys Ser
    210                 215
```

<210> SEQ ID NO 137
<211> LENGTH: 221
<212> TYPE: PRT
<213> ORGANISM: Artificial Sequence
<220> FEATURE:
<223> OTHER INFORMATION: PFB4 Heavy chain VD -continued

<400> SEQUENCE: 137

Glu Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asp Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Arg Gly Tyr Tyr Gly Met Asp Val Trp Gly Gln Gly Thr
100 105 110

Thr Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys
210 215 220

<210> SEQ ID NO 138
<211> LENGTH: 14
<212> TYPE: PRT
<213> ORGANISM: Artificial Sequence
<220> FEATURE:
<223> OTHER INFORMATION: PFB4 LC-CDR1

<400> SEQUENCE: 138

Gly Ser Thr Thr Gly Ala Val Thr Ser Gly His Tyr Pro Ser
1 5 10

<210> SEQ ID NO 139
<211> LENGTH: 7
<212> TYPE: PRT
<213> ORGANISM: Artificial Sequence
<220> FEATURE:
<223> OTHER INFORMATION: PFB4 LC-CDR2

<400> SEQUENCE: 139

Ser Thr Ser Asn Lys His Ser
1 5

<210> SEQ ID NO 140
<211> LENGTH: 9
<212> TYPE: PRT
<213> ORGANISM: Artificial Sequence
<220> FEATURE:
<223> OTHER INFORMATION: PFB4 LC-CDR3

<400> SEQUENCE: 140

Leu Leu Tyr Tyr Gly Gly Ala Arg Val
1 5

<210> SEQ ID NO 141
<211> LENGTH: 9
<212> TYPE: PRT
<213> ORGANISM: Artificial Sequence
<220> FEATURE:
<223> OTHER INFORMATION: PFB4 HC-CDR3

<400> SEQUENCE: 141

Asp Arg Gly Tyr Tyr Gly Met Asp Val
1 5

<210> SEQ ID NO 142
<211> LENGTH: 657
<212> TYPE: DNA
<213> ORGANISM: Artificial Sequence
<220> FEATURE:
<223> OTHER INFORMATION: PFB5 Light chain nucleotide sequence

<400> SEQUENCE: 142
gaaattgtgc tgactcagtc tccactctcc ctgcccgtca cccctggaga gccggcctcc 60
atctcctgca ggtctagtca gagcctcctg catagtaatg gatacaacta tttggactgg 120
tacctgcaga agccagggca gtctccacag ctcctgatct atttgggttc tcatcgggcc 180
tccggggtcc ctgacaggtt cagtggcagt ggatcaggca cagattttac actgaaaatc 240
agcagagtgg aggctgagga tgttggggtt tattactgca tgcaagctct acaaactcct 300
ctcactttcg gcggagggac caaggtggag atcaaacgaa ctgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtc acaaagagct tcaacagggg agagtgt 657

<210> SEQ ID NO 143
<211> LENGTH: 681
<212> TYPE: DNA
<213> ORGANISM: Artificial Sequence
<220> FEATURE:
<223> OTHER INFORMATION: PFB5 Heavy chain nucleotide sequence

<400> SEQUENCE: 143
gaggtccagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggacg aatccacgag cacagcctac 240
atggagctga gcagcctgag atctgaggac acggccgtgt attactgtgc gagaggccga 300
gggagcggct atcccgatac gtggttctgg ttcgacccct ggggccaggg caccctggtc 360
accgtctcaa gcgcctccac caagggccca tcggtcttcc ccctggcacc ctcctccaag 420
agcacctctg ggggcacagc ggccctgggc tgcctggtca aggactactt ccccgaaccg 480
gtgacggtgt cgtggaactc aggcgccctg accagcggcg tccacacctt cccggctgtc 540
ctacagtcct caggactcta ctccctcagc agcgtagtga ccgtgccctc cagcagcttg 600
ggcacccaga cctacatctg caacgtgaat cacaagccca gcaacaccaa ggtggacaag 660
aaagttgagc ccaaatcttg t 681

<210> SEQ ID NO 144
<211> LENGTH: 219
<212> TYPE: PRT
<213> ORGANISM: Artificial Sequence
<220> FEATURE:
<223> OTHER INFORMATION: PFB5 Light chain VD

<400> SEQUENCE: 144

Glu Ile Val Leu Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser His Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Leu Thr Phe Gly Gly Gly Thr Lys Val Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 145
<211> LENGTH: 227
<212> TYPE: PRT
<213> ORGANISM: Artificial Sequence
<220> FEATURE:
<223> OTHER INFORMATION: PFB5 Heavy chain VD

<400> SEQUENCE: 145

Glu Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

-continued

```
Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gly Ser Gly Tyr Pro Asp Thr Trp Phe Trp Phe Asp
            100                 105                 110

Pro Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225


<210> SEQ ID NO 146
<211> LENGTH: 7
<212> TYPE: PRT
<213> ORGANISM: Artificial Sequence
<220> FEATURE:
<223> OTHER INFORMATION: PFB5 LC-CDR2

<400> SEQUENCE: 146

Leu Gly Ser His Arg Ala Ser
1               5


<210> SEQ ID NO 147
<211> LENGTH: 9
<212> TYPE: PRT
<213> ORGANISM: Artificial Sequence
<220> FEATURE:
<223> OTHER INFORMATION: PFB5 LC-CDR3

<400> SEQUENCE: 147

Met Gln Ala Leu Gln Thr Pro Leu Thr
1               5


<210> SEQ ID NO 148
<211> LENGTH: 5
<212> TYPE: PRT
<213> ORGANISM: Artificial Sequence
<220> FEATURE:
<223> OTHER INFORMATION: PFB5 HC-CDR1 PFF4 HC-CDR1 PFG4 HC-CDR1

<400> SEQUENCE: 148

Ser Tyr Ala Ile Ser
1               5


<210> SEQ ID NO 149
<211> LENGTH: 17
<212> TYPE: PRT
<213> ORGANISM: Artificial Sequence
<220> FEATURE:
<223> OTHER INFORMATION: PFB5 HC-CDR2 PFF4 HC-CDR2 PFG4 HC-CDR2
```

<400> SEQUENCE: 149

Gly Ile Ile Pro Ile Phe Gly Thr Ala Asn Tyr Ala Gln Lys Phe Gln
1 5 10 15

Gly

<210> SEQ ID NO 150
<211> LENGTH: 15
<212> TYPE: PRT
<213> ORGANISM: Artificial Sequence
<220> FEATURE:
<223> OTHER INFORMATION: PFB5 HC-CDR3

<400> SEQUENCE: 150

Gly Arg Gly Ser Gly Tyr Pro Asp Thr Trp Phe Trp Phe Asp Pro
1 5 10 15

<210> SEQ ID NO 151
<211> LENGTH: 657
<212> TYPE: DNA
<213> ORGANISM: Artificial Sequence
<220> FEATURE:
<223> OTHER INFORMATION: PFC2 Light chain nucleotide sequence

<400> SEQUENCE: 151
gatgttgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatct acttgggttc taatcgggcc 180
cccggggtcc ctgacaggtt cagtggcagt ggatcaggca cagattttac actgaaaatc 240
agcagagtgg aggctgagga tgttggggtt tattactgca tgcaaggtac acactggcct 300
ctcactttcg gcggagggac caaggtggag atcaaacgaa ctgtggctgc accatttgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtc acaaagagct tcaacagggg agagtgt 657

<210> SEQ ID NO 152
<211> LENGTH: 678
<212> TYPE: DNA
<213> ORGANISM: Artificial Sequence
<220> FEATURE:
<223> OTHER INFORMATION: PFC2 Heavy chain nucleotide sequence

<400> SEQUENCE: 152
gaagtgcagc tggtgcagtc tggggggaggc gtggtccagc ctgggaggtc cctgagactc 60
tcctgtgcag cctctggatt caccttcagt agctatgcta tgcactgggt ccgccaggct 120
ccaggcaagg ggctggagtg ggtggcagtt atatcatatg atggaagcaa taaatactac 180
gcagactccg tgaagggccg attcaccatc tccagagaca attccaagaa cacgctgtat 240
ctgcaaatga acagcctgag agctgaggac acggctgtgt attactgtgc gagatcgtat 300
ggttcgggga gttataggtc ccatgctttt gatatctggg gccaagggac aatggtcacc 360
gtctcaagcg cctccaccaa gggcccatcg gtcttccccc tggcaccctc ctccaagagc 420
acctctgggg gcacagcggc cctgggctgc ctggtcaagg actacttccc cgaaccggtg 480

-continued acggtgtcgt ggaactcagg cgccctgacc agcggcgtcc acaccttccc ggctgtccta 540
cagtcctcag gactctactc cctcagcagc gtagtgaccg tgccctccag cagcttgggc 600
acccagacct acatctgcaa cgtgaatcac aagcccagca acaccaaggt ggacaagaaa 660
gttgagccca aatcttgt 678

<210> SEQ ID NO 153
<211> LENGTH: 219
<212> TYPE: PRT
<213> ORGANISM: Artificial Sequence
<220> FEATURE:
<223> OTHER INFORMATION: PFC2 Light chain VD

<400> SEQUENCE: 153

Asp Val Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Pro Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Leu Thr Phe Gly Gly Gly Thr Lys Val Glu Ile Lys
100 105 110

Arg Thr Val Ala Ala Pro Phe Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 154
<211> LENGTH: 226
<212> TYPE: PRT
<213> ORGANISM: Artificial Sequence
<220> FEATURE:
<223> OTHER INFORMATION: PFC2 Heavy chain VD

<400> SEQUENCE: 154

Glu Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Met His Trp Val Arg Gln Ala Pro Gly Lys Gly Leu Glu Trp Val
35 40 45

-continued

```
Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Gly Ser Gly Ser Tyr Arg Ser His Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225


<210> SEQ ID NO 155
<211> LENGTH: 7
<212> TYPE: PRT
<213> ORGANISM: Artificial Sequence
<220> FEATURE:
<223> OTHER INFORMATION: PFC2 LC-CDR2 PFG5 LC-CDR2

<400> SEQUENCE: 155

Leu Gly Ser Asn Arg Ala Pro
1               5


<210> SEQ ID NO 156
<211> LENGTH: 14
<212> TYPE: PRT
<213> ORGANISM: Artificial Sequence
<220> FEATURE:
<223> OTHER INFORMATION: PFC2 HC-CDR3 PFG5 HC-CDR3

<400> SEQUENCE: 156

Ser Tyr Gly Ser Gly Ser Tyr Arg Ser His Ala Phe Asp Ile
1               5                   10


<210> SEQ ID NO 157
<211> LENGTH: 645
<212> TYPE: DNA
<213> ORGANISM: Artificial Sequence
<220> FEATURE:
<223> OTHER INFORMATION: PFC3 Light chain nucleotide sequence

<400> SEQUENCE: 157

gaaacgacac tcacgcagtc tccaggcacc ctgtctttgt ctccagggga aagagccacc      60

ctctcctgca gggccagtca gagtgttagc agcagctact tagcctggta ccagcagaaa     120

cctggccagg ctcccaggct cctcatctat ggtgcatcca gcagggccac tggcatccca     180

gacaggttca gtggcagtgg gtctgggaca gacttcactc tcaccatcag cagactggag     240
```

cctgaagatt ttgcagtgta ttactgtcag cagtatggta gctcacctcg gacgttcggc 300
caagggacca aggtggaaat caaacgaact gtggctgcac catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480
caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgt 645

<210> SEQ ID NO 158
<211> LENGTH: 666
<212> TYPE: DNA
<213> ORGANISM: Artificial Sequence
<220> FEATURE:
<223> OTHER INFORMATION: PFC3 Heavy chain nucleotide sequence

<400> SEQUENCE: 158
caggtgcagc tggtgcagtc tgggggaggc ttggtacagc ctggggggtc cctgagactc 60
tcctgtgcag cctctggatt cacctttagc agctatgcca tgagctgggt ccgccaggct 120
ccagggaagg ggctggagtg ggtctctggt attaattgga atggtggtag cacaggttat 180
gcagactctg tgaagggccg attcaccatc tccagagaca attccaagaa cacgctgtat 240
ctgcaaatga atagcctgag agccgaggac acggccgtat attactgtgc gaaagggcta 300
gtacccgctg cgagtatgga cgtctggggc caagggacca cggtcaccgt ctcaagcgcc 360
tccaccaagg gcccatcggt cttccccctg gcaccctcct ccaagagcac ctctgggggc 420
acagcggccc tgggctgcct ggtcaaggac tacttccccg aaccggtgac ggtgtcgtgg 480
aactcaggcg ccctgaccag cggcgtccac accttcccgg ctgtcctaca gtcctcagga 540
ctctactccc tcagcagcgt agtgaccgtg ccctccagca gcttgggcac ccagacctac 600
atctgcaacg tgaatcacaa gcccagcaac accaaggtgg acaagaaagt tgagcccaaa 660
tcttgt 666

<210> SEQ ID NO 159
<211> LENGTH: 215
<212> TYPE: PRT
<213> ORGANISM: Artificial Sequence
<220> FEATURE:
<223> OTHER INFORMATION: PFC3 Light chain VD

<400> SEQUENCE: 159

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 160
<211> LENGTH: 222
<212> TYPE: PRT
<213> ORGANISM: Artificial Sequence
<220> FEATURE:
<223> OTHER INFORMATION: PFC3 Heavy chain VD

<400> SEQUENCE: 160

Gln Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Gly Ile Asn Trp Asn Gly Gly Ser Thr Gly Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Leu Val Pro Ala Ala Ser Met Asp Val Trp Gly Gln Gly
100 105 110

Thr Thr Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys
210 215 220

<210> SEQ ID NO 161
<211> LENGTH: 12
<212> TYPE: PRT
<213> ORGANISM: Artificial Sequence -continued

<220> FEATURE:
<223> OTHER INFORMATION: PFC3 LC-CDR1 PFF2 LC-CDR1

<400> SEQUENCE: 161

Arg Ala Ser Gln Ser Val Ser Ser Ser Tyr Leu Ala
1               5                   10

<210> SEQ ID NO 162
<211> LENGTH: 7
<212> TYPE: PRT
<213> ORGANISM: Artificial Sequence
<220> FEATURE:
<223> OTHER INFORMATION: PFC3 LC-CDR2 PFF2 LC-CDR2

<400> SEQUENCE: 162

Gly Ala Ser Ser Arg Ala Thr
1               5

<210> SEQ ID NO 163
<211> LENGTH: 9
<212> TYPE: PRT
<213> ORGANISM: Artificial Sequence
<220> FEATURE:
<223> OTHER INFORMATION: PFC3 LC-CDR3

<400> SEQUENCE: 163

Gln Gln Tyr Gly Ser Ser Pro Arg Thr
1               5

<210> SEQ ID NO 164
<211> LENGTH: 17
<212> TYPE: PRT
<213> ORGANISM: Artificial Sequence
<220> FEATURE:
<223> OTHER INFORMATION: PFC3 HC-CDR2

<400> SEQUENCE: 164

Gly Ile Asn Trp Asn Gly Gly Ser Thr Gly Tyr Ala Asp Ser Val Lys
1               5                   10                  15

Gly

<210> SEQ ID NO 165
<211> LENGTH: 10
<212> TYPE: PRT
<213> ORGANISM: Artificial Sequence
<220> FEATURE:
<223> OTHER INFORMATION: PFC3 HC-CDR3

<400> SEQUENCE: 165

Gly Leu Val Pro Ala Ala Ser Met Asp Val
1               5                   10

<210> SEQ ID NO 166
<211> LENGTH: 660
<212> TYPE: DNA
<213> ORGANISM: Artificial Sequence
<220> FEATURE:
<223> OTHER INFORMATION: PFC4 Light chain nucleotide sequence

<400> SEQUENCE: 166
gatgttgtga tgactcagtc tccactctcc ctgcccgtca cccctggaca gccggcctcc      60
atctcctgca ggtctagtca gagcctccaa catagcaacg gataccagta cttggactgg     120
tacgtgcaga agccagggca gtctccacaa ctcctgatct atttgggttc ttttcgggcc     180
tccggggtcc ccgccaggtt cagtggcagc ggatcaggca cagattttac actgagaatc     240

```
aacaaagtgg agcctgagga cgttggggtt tactactgca tgcacgctct aagtactcct    300

ccgtggacgt tcggccaggg gaccagggtg gaactcaaac gaactgtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660
```

```
<210> SEQ ID NO 167
<211> LENGTH: 660
<212> TYPE: DNA
<213> ORGANISM: Artificial Sequence
<220> FEATURE:
<223> OTHER INFORMATION: PFC4 Heavy chain nucleotide sequence

<400> SEQUENCE: 167

gaggtccagc tggtgcagtc tggagctgag gtgaggaagc ctggggcctc agtgaaggtc     60

tcctgcaagg cttctggata caccttcact acctatacta tgcattgggt gcgccaggcc    120

cccggacaga gtcttgagtg gatggcatgg atcacccctg gcaatggtaa tacacattat    180

tcacagaact tccagggcag agtcaccatt accagggaca catccacgag cacagcctac    240

atggagctga ggagcctgag atctgacgac acggccgtgt attactgtgc gaggtctagg    300

gtgggagccc ttgactactg gggccaggga accctggtca ccgtctcaag cgcctccacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt ccacaccttc ccggctgtcc tacagtcctc aggactctac    540

tccctcagca gcgtagtgac cgtgccctcc agcagcttgg gcacccagac ctacatctgc    600

aacgtgaatc acaagcccag caacaccaag gtggacaaga aagttgagcc caaatcttgt    660
```

```
<210> SEQ ID NO 168
<211> LENGTH: 220
<212> TYPE: PRT
<213> ORGANISM: Artificial Sequence
<220> FEATURE:
<223> OTHER INFORMATION: PFC4 Light chain VD

<400> SEQUENCE: 168

Asp Val Val Met Thr Gln Ser Pro Leu Ser Leu Pro Val Thr Pro Gly
1               5                   10                  15

Gln Pro Ala Ser Ile Ser Cys Arg Ser Ser Gln Ser Leu Gln His Ser
            20                  25                  30

Asn Gly Tyr Gln Tyr Leu Asp Trp Tyr Val Gln Lys Pro Gly Gln Ser
        35                  40                  45

Pro Gln Leu Leu Ile Tyr Leu Gly Ser Phe Arg Ala Ser Gly Val Pro
    50                  55                  60

Ala Arg Phe Ser Gly Ser Gly Ser Gly Thr Asp Phe Thr Leu Arg Ile
65                  70                  75                  80

Asn Lys Val Glu Pro Glu Asp Val Gly Val Tyr Tyr Cys Met His Ala
                85                  90                  95

Leu Ser Thr Pro Pro Trp Thr Phe Gly Gln Gly Thr Arg Val Glu Leu
            100                 105                 110

Lys Arg Thr Val Ala Ala Pro Ser Val Phe Ile Phe Pro Pro Ser Asp
```

-continued

```
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 169
<211> LENGTH: 220
<212> TYPE: PRT
<213> ORGANISM: Artificial Sequence
<220> FEATURE:
<223> OTHER INFORMATION: PFC4 Heavy chain VD

<400> SEQUENCE: 169

Glu Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Thr Tyr
            20                  25                  30

Thr Met His Trp Val Arg Gln Ala Pro Gly Gln Ser Leu Glu Trp Met
        35                  40                  45

Ala Trp Ile Thr Pro Gly Asn Gly Asn Thr His Tyr Ser Gln Asn Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Arg Val Gly Ala Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
    210                 215                 220


<210> SEQ ID NO 170
<211> LENGTH: 16
<212> TYPE: PRT
<213> ORGANISM: Artificial Sequence
<220> FEATURE:
<223> OTHER INFORMATION: PFC4 LC-CDR1
```

<400> SEQUENCE: 170

Arg Ser Ser Gln Ser Leu Gln His Ser Asn Gly Tyr Gln Tyr Leu Asp
1 5 10 15

<210> SEQ ID NO 171
<211> LENGTH: 7
<212> TYPE: PRT
<213> ORGANISM: Artificial Sequence
<220> FEATURE:
<223> OTHER INFORMATION: PFC4 LC-CDR2

<400> SEQUENCE: 171

Leu Gly Ser Phe Arg Ala Ser
1 5

<210> SEQ ID NO 172
<211> LENGTH: 10
<212> TYPE: PRT
<213> ORGANISM: Artificial Sequence
<220> FEATURE:
<223> OTHER INFORMATION: PFC4 LC-CDR3

<400> SEQUENCE: 172

Met His Ala Leu Ser Thr Pro Pro Trp Thr
1 5 10

<210> SEQ ID NO 173
<211> LENGTH: 5
<212> TYPE: PRT
<213> ORGANISM: Artificial Sequence
<220> FEATURE:
<223> OTHER INFORMATION: PFC4 HC-CDR1

<400> SEQUENCE: 173

Thr Tyr Thr Met His
1 5

<210> SEQ ID NO 174
<211> LENGTH: 17
<212> TYPE: PRT
<213> ORGANISM: Artificial Sequence
<220> FEATURE:
<223> OTHER INFORMATION: PFC4 HC-CDR2

<400> SEQUENCE: 174

Trp Ile Thr Pro Gly Asn Gly Asn Thr His Tyr Ser Gln Asn Phe Gln
1 5 10 15

Gly

<210> SEQ ID NO 175
<211> LENGTH: 8
<212> TYPE: PRT
<213> ORGANISM: Artificial Sequence
<220> FEATURE:
<223> OTHER INFORMATION: PFC4 HC-CDR3

<400> SEQUENCE: 175

Ser Arg Val Gly Ala Leu Asp Tyr
1 5

<210> SEQ ID NO 176
<211> LENGTH: 657
<212> TYPE: DNA
<213> ORGANISM: Artificial Sequence
<220> FEATURE:

<223> OTHER INFORMATION: PFD1 Light chain nucleotide sequence

<400> SEQUENCE: 176

```
gatgttgtga tgactcagtc tccactctcc ctgcccgtca cccttggaca gccggcctcc     60

atctcctgca ggtctagtca aagcctcgta tacagtgatg gaaacaccta cttgaattgg    120

tttcagcaga ggccaggcca atctccaagg cgcctgtttt ataaggtttc taaccgggac    180

tctggggtcc cagacagatt cagcggcagt gggtcaggca ctgatttcac actgaaaatc    240

agcagggtgg aggctgagga tgttggggtt tattactgca tgcaaggtac acactggccg    300

ggcacttttg gccaggggac caagctggag atcaaacgaa ctgtggctgc accatctgtc    360

ttcatcttcc cgccatctga tgagcagttg aaatctggaa ctgcctctgt tgtgtgcctg    420

ctgaataact tctatcccag agaggccaaa gtacagtgga aggtggataa cgccctccaa    480

tcgggtaact cccaggagag tgtcacagag caggacggca aggacagcac ctacagcctc    540

agcagcaccc tgacgctgag caaagcagac tacgagaaac acaaagtcta cgcctgcgaa    600

gtcacccatc agggcctgag ctcgcccgtc acaaagagct tcaacagggg agagtgt       657
```

<210> SEQ ID NO 177
<211> LENGTH: 663
<212> TYPE: DNA
<213> ORGANISM: Artificial Sequence
<220> FEATURE:
<223> OTHER INFORMATION: PFD1 Heavy chain nucleotide sequence

<400> SEQUENCE: 177

```
gaggtgcagc tggtgcagtc tgggggaggc gtggtccagc ctgggaggtc cctgagactc     60

tcctgtgcag cctctggatt caccttcagt agctatggca tgcactgggt ccgccaggct    120

ccaggcaagg ggctggagtg ggtggcagtt atatcatatg atggaagtaa taaatactat    180

gcagactccg tgaagggccg attcaccatc tccagagaca atgccaagaa ctcactgtat    240

ctgcaaatga acagcctgag agccgaggac acggctgtat attactgtgc gagatcacgt    300

ggatatagtg gctacgacaa ctggggccag ggcaccctgg tcaccgtctc aagcgcctcc    360

accaagggcc catcggtctt ccccctggca ccctcctcca agagcacctc tgggggcaca    420

gcggccctgg gctgcctggt caaggactac ttccccgaac cggtgacggt gtcgtggaac    480

tcaggcgccc tgaccagcgg cgtccacacc ttcccggctg tcctacagtc ctcaggactc    540

tactccctca gcagcgtagt gaccgtgccc tccagcagct tgggcaccca gacctacatc    600

tgcaacgtga atcacaagcc cagcaacacc aaggtggaca agaaagttga gcccaaatct    660

tgt                                                                  663
```

<210> SEQ ID NO 178
<211> LENGTH: 219
<212> TYPE: PRT
<213> ORGANISM: Artificial Sequence
<220> FEATURE:
<223> OTHER INFORMATION: PFD1 Light chain VD

<400> SEQUENCE: 178

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45
```

Pro Arg Arg Leu Phe Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Gly Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Gly Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 179
<211> LENGTH: 221
<212> TYPE: PRT
<213> ORGANISM: Artificial Sequence
<220> FEATURE:
<223> OTHER INFORMATION: PFD1 Heavy chain VD

<400> SEQUENCE: 179

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Arg Gly Tyr Ser Gly Tyr Asp Asn Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

```
Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220


<210> SEQ ID NO 180
<211> LENGTH: 9
<212> TYPE: PRT
<213> ORGANISM: Artificial Sequence
<220> FEATURE:
<223> OTHER INFORMATION: PFD1 LC-CDR3 PFF3 LC-CDR3

<400> SEQUENCE: 180

Met Gln Gly Thr His Trp Pro Gly Thr
1               5


<210> SEQ ID NO 181
<211> LENGTH: 9
<212> TYPE: PRT
<213> ORGANISM: Artificial Sequence
<220> FEATURE:
<223> OTHER INFORMATION: PFD1 HC-CDR3

<400> SEQUENCE: 181

Ser Arg Gly Tyr Ser Gly Tyr Asp Asn
1               5


<210> SEQ ID NO 182
<211> LENGTH: 648
<212> TYPE: DNA
<213> ORGANISM: Artificial Sequence
<220> FEATURE:
<223> OTHER INFORMATION: PFD2 Light chain nucleotide sequence

<400> SEQUENCE: 182

cagtctgtcg tgacgcagcc gccctcagtg tctggggccc ccgggcagag ggtcaccatc      60

tcctgcactg ggagaagcgc caatatcggg ggttttgatg tacagtggta ccgacaactt     120

ccaggaacag ccccccaact cctcatatat gacaacagca atcggccctc aggggtccct     180

gaccgattct ctggctccaa gtctggcacc tcagccaccc tggccatcag cggacttcag     240

actggcgacg aggccgatta ttactgcgga acatgggatt cctacctcaa tatttgggtg     300

ttcggcggag ggaccaagct gaccgtcctt agtcagccca aggctgcccc ctcggtcact     360

ctgttcccgc cctcctctga ggagcttcaa gccaacaagg ccacactggt gtgtctcata     420

agtgacttct acccgggagc cgtgacagtg gcctggaagg cagatagcag ccccgtcaag     480

gcgggagtgg agaccaccac accctccaaa caaagcaaca acaagtacgc ggccagcagc     540

tacctgagcc tgacgcctga gcagtggaag tcccacaaaa gctacagctg ccaggtcacg     600

catgaaggga gcaccgtgga gaagacagtg gcccctacag aatgttca                  648


<210> SEQ ID NO 183
<211> LENGTH: 660
<212> TYPE: DNA
<213> ORGANISM: Artificial Sequence
<220> FEATURE:
<223> OTHER INFORMATION: PFD2 Heavy chain nucleotide sequence

<400> SEQUENCE: 183

caggtgcagc tacagcagtg gggcgcagga ctgttgaagc cttcggagac cctgtccctc      60

acctgcgctg tctatggtgg gtccttcagt ggttactact ggagctggat ccgccagccc     120

ccagggaagg ggctggagtg gattggggaa atcaatcata gtggaagcac caactacaac     180
```

ccgtccctca agagtcgagt caccatatca gtagacacgt ccaagaacca gttctccctg 240
aagctgagct ctgtgaccgc cgcggacacg gctgtgtatt actgtgcgag aggccttccg 300
tattactact ttgactactg gggccagggc accctggtca ccgtctcaag cgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt ccacaccttc ccggctgtcc tacagtcctc aggactctac 540
tccctcagca gcgtagtgac cgtgccctcc agcagcttgg gcacccagac ctacatctgc 600
aacgtgaatc acaagcccag caacaccaag gtggacaaga aagttgagcc caaatcttgt 660

<210> SEQ ID NO 184
<211> LENGTH: 216
<212> TYPE: PRT
<213> ORGANISM: Artificial Sequence
<220> FEATURE:
<223> OTHER INFORMATION: PFD2 Light chain VD

<400> SEQUENCE: 184

Gln Ser Val Val Thr Gln Pro Pro Ser Val Ser Gly Ala Pro Gly Gln
1               5                   10                  15

Arg Val Thr Ile Ser Cys Thr Gly Arg Ser Ala Asn Ile Gly Gly Phe
            20                  25                  30

Asp Val Gln Trp Tyr Arg Gln Leu Pro Gly Thr Ala Pro Gln Leu Leu
        35                  40                  45

Ile Tyr Asp Asn Ser Asn Arg Pro Ser Gly Val Pro Asp Arg Phe Ser
    50                  55                  60

Gly Ser Lys Ser Gly Thr Ser Ala Thr Leu Ala Ile Ser Gly Leu Gln
65                  70                  75                  80

Thr Gly Asp Glu Ala Asp Tyr Tyr Cys Gly Thr Trp Asp Ser Tyr Leu
                85                  90                  95

Asn Ile Trp Val Phe Gly Gly Gly Thr Lys Leu Thr Val Leu Ser Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 185
<211> LENGTH: 220
<212> TYPE: PRT
<213> ORGANISM: Artificial Sequence
<220> FEATURE:
<223> OTHER INFORMATION: PFD2 Heavy chain VD

<400> SEQUENCE: 185

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Leu Pro Tyr Tyr Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
    210                 215                 220
```

<210> SEQ ID NO 186
<211> LENGTH: 13
<212> TYPE: PRT
<213> ORGANISM: Artificial Sequence
<220> FEATURE:
<223> OTHER INFORMATION: PFD2 LC-CDR1

<400> SEQUENCE: 186

```
Thr Gly Arg Ser Ala Asn Ile Gly Gly Phe Asp Val Gln
1               5                   10
```

<210> SEQ ID NO 187
<211> LENGTH: 7
<212> TYPE: PRT
<213> ORGANISM: Artificial Sequence
<220> FEATURE:
<223> OTHER INFORMATION: PFD2 LC-CDR2

<400> SEQUENCE: 187

```
Asp Asn Ser Asn Arg Pro Ser
1               5
```

<210> SEQ ID NO 188
<211> LENGTH: 11
<212> TYPE: PRT
<213> ORGANISM: Artificial Sequence
<220> FEATURE:
<223> OTHER INFORMATION: PFD2 LC-CDR3

<400> SEQUENCE: 188

```
Gly Thr Trp Asp Ser Tyr Leu Asn Ile Trp Val
```

1 5 10

<210> SEQ ID NO 189
<211> LENGTH: 9
<212> TYPE: PRT
<213> ORGANISM: Artificial Sequence
<220> FEATURE:
<223> OTHER INFORMATION: PFD2 HC-CDR3

<400> SEQUENCE: 189

Gly Leu Pro Tyr Tyr Tyr Phe Asp Tyr
1 5

<210> SEQ ID NO 190
<211> LENGTH: 648
<212> TYPE: DNA
<213> ORGANISM: Artificial Sequence
<220> FEATURE:
<223> OTHER INFORMATION: PFD3 Light chain nucleotide sequence

<400> SEQUENCE: 190
caggctgtgg tgatccagga gccatcgttc tcagtgtccc ctggagggac agtcacactc 60
acttgtgcct tgacctctgg ctcagtctct actagttact accccagctg gtaccagcag 120
accccaggcc agcctccacg cacgctcatt tacagcacaa accttcgctc ttctggggtc 180
cctgatcgct tctctggctc catccttggg aacaaagctg ccctcaccat cacgggggcc 240
caggcggatg atgaatctga ttattactgt gagttgtata tgggtagtgg catttcggtg 300
ttcggcggag ggaccaaggt gaccgtccta ggtcagccca aggctgcccc ctcggtcact 360
ctgttcccac cctcctctga ggagcttcaa gccaacaagg ccacactggt gtgtctcata 420
agtgacttct acccgggagc cgtgacagtg gcctggaagg cagatagcag ccccgtcaag 480
gcgggagtgg agaccaccac accctccaaa caaagcaaca acaagtacgc ggccagcagc 540
tacctgagcc tgacgcctga gcagtggaag tcccacaaaa gctacagctg ccaggtcacg 600
catgaaggga gcaccgtgga gaagacagtg gcccctacag aatgttca 648

<210> SEQ ID NO 191
<211> LENGTH: 675
<212> TYPE: DNA
<213> ORGANISM: Artificial Sequence
<220> FEATURE:
<223> OTHER INFORMATION: PFD3 Heavy chain nucleotide sequence

<400> SEQUENCE: 191
gaggtccagc tggtgcagtc tggagcagag gtgaaaaagc ccggggagtc tctgaagatc 60
tcctgtaagg gttctggata cagctttacc agctactgga tcggctgggt gcgccagatg 120
cccgggaaag gcctggagtg gatggggatc atctatcctg gtgactctga taccagatac 180
agcccgtcct tccaaggcca ggtcaccatc tcagccgaca agtccatcag caccgcctac 240
ctgcagtgga gcagcctgaa ggcctcggac accgccatgt attactgtgc gagactgggc 300
tacggtgtcc ccctgcctga gtacttcgat ctctggggcc gtggaaccct ggtcaccgtc 360
tcaagcgcct ccaccaaggg cccatcggtc ttccccctgg caccctcctc caagagcacc 420
tctgggggca cagcggccct gggctgcctg gtcaaggact acttccccga accggtgacg 480
gtgtcgtgga actcaggcgc cctgaccagc ggcgtccaca ccttcccggc tgtcctacag 540
tcctcaggac tctactccct cagcagcgta gtgaccgtgc cctccagcag cttgggcacc 600
cagacctaca tctgcaacgt gaatcacaag cccagcaaca ccaaggtgga caagaaagtt 660
gagcccaaat cttgt 675

<210> SEQ ID NO 192
<211> LENGTH: 216
<212> TYPE: PRT
<213> ORGANISM: Artificial Sequence
<220> FEATURE:
<223> OTHER INFORMATION: PFD3 Light chain VD

<400> SEQUENCE: 192

Gln Ala Val Val Ile Gln Glu Pro Ser Phe Ser Val Ser Pro Gly Gly
1 5 10 15

Thr Val Thr Leu Thr Cys Ala Leu Thr Ser Gly Ser Val Ser Thr Ser
20 25 30

Tyr Tyr Pro Ser Trp Tyr Gln Gln Thr Pro Gly Gln Pro Pro Arg Thr
35 40 45

Leu Ile Tyr Ser Thr Asn Leu Arg Ser Ser Gly Val Pro Asp Arg Phe
50 55 60

Ser Gly Ser Ile Leu Gly Asn Lys Ala Ala Leu Thr Ile Thr Gly Ala
65 70 75 80

Gln Ala Asp Asp Glu Ser Asp Tyr Tyr Cys Glu Leu Tyr Met Gly Ser
85 90 95

Gly Ile Ser Val Phe Gly Gly Gly Thr Lys Val Thr Val Leu Gly Gln
100 105 110

Pro Lys Ala Ala Pro Ser Val Thr Leu Phe Pro Pro Ser Ser Glu Glu
115 120 125

Leu Gln Ala Asn Lys Ala Thr Leu Val Cys Leu Ile Ser Asp Phe Tyr
130 135 140

Pro Gly Ala Val Thr Val Ala Trp Lys Ala Asp Ser Ser Pro Val Lys
145 150 155 160

Ala Gly Val Glu Thr Thr Thr Pro Ser Lys Gln Ser Asn Asn Lys Tyr
165 170 175

Ala Ala Ser Ser Tyr Leu Ser Leu Thr Pro Glu Gln Trp Lys Ser His
180 185 190

Lys Ser Tyr Ser Cys Gln Val Thr His Glu Gly Ser Thr Val Glu Lys
195 200 205

Thr Val Ala Pro Thr Glu Cys Ser
210 215

<210> SEQ ID NO 193
<211> LENGTH: 225
<212> TYPE: PRT
<213> ORGANISM: Artificial Sequence
<220> FEATURE:
<223> OTHER INFORMATION: PFD3 Heavy chain VD

<400> SEQUENCE: 193

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Ser Tyr
20 25 30

Trp Ile Gly Trp Val Arg Gln Met Pro Gly Lys Gly Leu Glu Trp Met
35 40 45

Gly Ile Ile Tyr Pro Gly Asp Ser Asp Thr Arg Tyr Ser Pro Ser Phe
50 55 60

Gln Gly Gln Val Thr Ile Ser Ala Asp Lys Ser Ile Ser Thr Ala Tyr
65 70 75 80

```
Leu Gln Trp Ser Ser Leu Lys Ala Ser Asp Thr Ala Met Tyr Tyr Cys
                85                  90                  95

Ala Arg Leu Gly Tyr Gly Val Pro Leu Pro Glu Tyr Phe Asp Leu Trp
            100                 105                 110

Gly Arg Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225


<210> SEQ ID NO 194
<211> LENGTH: 14
<212> TYPE: PRT
<213> ORGANISM: Artificial Sequence
<220> FEATURE:
<223> OTHER INFORMATION: PFD3 LC-CDR1

<400> SEQUENCE: 194

Ala Leu Thr Ser Gly Ser Val Ser Thr Ser Tyr Tyr Pro Ser
1               5                   10


<210> SEQ ID NO 195
<211> LENGTH: 7
<212> TYPE: PRT
<213> ORGANISM: Artificial Sequence
<220> FEATURE:
<223> OTHER INFORMATION: PFD3 LC-CDR2

<400> SEQUENCE: 195

Ser Thr Asn Leu Arg Ser Ser
1               5


<210> SEQ ID NO 196
<211> LENGTH: 10
<212> TYPE: PRT
<213> ORGANISM: Artificial Sequence
<220> FEATURE:
<223> OTHER INFORMATION: PFD3 LC-CDR3

<400> SEQUENCE: 196

Glu Leu Tyr Met Gly Ser Gly Ile Ser Val
1               5                   10


<210> SEQ ID NO 197
<211> LENGTH: 5
<212> TYPE: PRT
<213> ORGANISM: Artificial Sequence
<220> FEATURE:
<223> OTHER INFORMATION: PFD3 HC-CDR1

<400> SEQUENCE: 197
```

Ser Tyr Trp Ile Gly
1 5

<210> SEQ ID NO 198
<211> LENGTH: 17
<212> TYPE: PRT
<213> ORGANISM: Artificial Sequence
<220> FEATURE:
<223> OTHER INFORMATION: PFD3 HC-CDR2

<400> SEQUENCE: 198

Ile Ile Tyr Pro Gly Asp Ser Asp Thr Arg Tyr Ser Pro Ser Phe Gln
1 5 10 15

Gly

<210> SEQ ID NO 199
<211> LENGTH: 13
<212> TYPE: PRT
<213> ORGANISM: Artificial Sequence
<220> FEATURE:
<223> OTHER INFORMATION: PFD3 HC-CDR3

<400> SEQUENCE: 199

Leu Gly Tyr Gly Val Pro Leu Pro Glu Tyr Phe Asp Leu
1 5 10

<210> SEQ ID NO 200
<211> LENGTH: 657
<212> TYPE: DNA
<213> ORGANISM: Artificial Sequence
<220> FEATURE:
<223> OTHER INFORMATION: PFD4 Light chain nucleotide sequence

<400> SEQUENCE: 200
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggcca atctccaagg cgcctaattt ataaggtttc tgaccgggac 180
tctggggtcc cagacagatt cagcggcagt gggtcaggca ctgatttcac actgaaaatc 240
agcagggtgg aggctgagga tgttggggtt tattactgca tgcaaggcac acactggcct 300
cagacttttg gccaggggac caagctggag atcaaacgaa ctgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtt acaaagagct tcaacagggg agagtgt 657

<210> SEQ ID NO 201
<211> LENGTH: 663
<212> TYPE: DNA
<213> ORGANISM: Artificial Sequence
<220> FEATURE:
<223> OTHER INFORMATION: PFD4 Heavy chain nucleotide sequence

<400> SEQUENCE: 201
caggtgcagc tggtgcagtc tgggggaggc ttggtccagc ctggggggtc cctgagactc 60
tcctgttcag cctctggatt caccttcagt agctatgcta tgcactgggt ccgccaggct 120
ccagggaagg gactggaata tgtttcagct attagtagta atgggggtag cacatactac 180
gcagactccg tgaagggcag attcaccatc tccagagaca attccaagaa cacgctgtat 240
cttcaaatga gcagtctgag agctgaggac acggctgtgt attactgtgc gagaagtagg 300
ggctactacg gtatggacgt ctggggccaa gggaccacgg tcaccgtctc aagcgcctcc 360
accaagggcc catcggtctt cccccctggca ccctcctcca agagcacctc tgggggcaca 420
gcggccctgg gctgcctggt caaggactac ttccccgaac cggtgacggt gtcgtggaac 480
tcaggcgccc tgaccagcgg cgtccacacc ttcccggctg tcctacagtc ctcaggactc 540
tactccctca gcagcgtagt gaccgtgccc tccagcagct tgggcaccca gacctacatc 600
tgcaacgtga atcacaagcc cagcaacacc aaggtggaca agaaagttga gcccaaatct 660
tgt 663

<210> SEQ ID NO 202
<211> LENGTH: 219
<212> TYPE: PRT
<213> ORGANISM: Artificial Sequence
<220> FEATURE:
<223> OTHER INFORMATION: PFD4 Light chain VD

<400> SEQUENCE: 202

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Asn Trp Phe Gln Gln Arg Pro Gly Gln Ser
35 40 45

Pro Arg Arg Leu Ile Tyr Lys Val Ser Asp Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Gln Thr Phe Gly Gln Gly Thr Lys Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 203
<211> LENGTH: 221
<212> TYPE: PRT
<213> ORGANISM: Artificial Sequence
<220> FEATURE:
<223> OTHER INFORMATION: PFD4 Heavy chain VD

<400> SEQUENCE: 203

```
Gln Val Gln Leu Val Gln Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Ser Arg Gly Tyr Tyr Gly Met Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220


<210> SEQ ID NO 204
<211> LENGTH: 7
<212> TYPE: PRT
<213> ORGANISM: Artificial Sequence
<220> FEATURE:
<223> OTHER INFORMATION: PFD4 LC-CDR2

<400> SEQUENCE: 204

Lys Val Ser Asp Arg Asp Ser
1               5


<210> SEQ ID NO 205
<211> LENGTH: 9
<212> TYPE: PRT
<213> ORGANISM: Artificial Sequence
<220> FEATURE:
<223> OTHER INFORMATION: PFD4 LC-CDR3

<400> SEQUENCE: 205

Met Gln Gly Thr His Trp Pro Gln Thr
1               5


<210> SEQ ID NO 206
<211> LENGTH: 17
<212> TYPE: PRT
<213> ORGANISM: Artificial Sequence
<220> FEATURE:
<223> OTHER INFORMATION: PFD4 HC-CDR2 PFF3 HC-CDR2

<400> SEQUENCE: 206
```

Ala Ile Ser Ser Asn Gly Gly Ser Thr Tyr Tyr Ala Asp Ser Val Lys
1               5                   10                  15

Gly

<210> SEQ ID NO 207
<211> LENGTH: 657
<212> TYPE: DNA
<213> ORGANISM: Artificial Sequence
<220> FEATURE:
<223> OTHER INFORMATION: PFE1 Light chain nucleotide sequence

<400> SEQUENCE: 207
gatgttgtga tgactcagtc tccactctcc ctgcccgtca cccttggaca gccggcctcc 60
atctcctgca cgtctagtca aagcctcgta tacagtgatg gaaacaccta cttgaattgg 120
tttcagcaga ggccaggcca atctccaagg cgcctaattt ataaggtttc taagcgggac 180
tctggggtcc cagacagatt cagcggcagt gggtcaggca ctgatttcac actgaaaata 240
agcagggtgg aggctgagga tgttgcgatt tattactgca tgcaaggtac acactggcct 300
ctcactttcg gcggagggac caaggtggag atcaaacgaa ctgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaactcta cgcctgcgaa 600
gtcacccatc agggcctgag ctcgcccgtc acaaagagct tcaacagggg agagtgt 657

<210> SEQ ID NO 208
<211> LENGTH: 663
<212> TYPE: DNA
<213> ORGANISM: Artificial Sequence
<220> FEATURE:
<223> OTHER INFORMATION: PFE1 Heavy chain nucleotide sequence

<400> SEQUENCE: 208
gaggtccagc tggtgcagtc tggggggaggc gtggtccagc ctgggaggtc cctgagactc 60
tcctgtgcag cctctggatt caccttcagt agctatgcta tgcactgggt ccgccaggct 120
ccaggcaagg ggctggagtg ggtggcagtt atatcatatg atggaagtaa taaatactac 180
gcagactccg tgaagggccg attcaccatc tccagagaca attccaagaa cacgctgtat 240
ctgcaaatga acagcctgag agctgaggac acggctgtgt attactgtgc gaggagtcga 300
ggctactacg gtatggacgt ctggggccaa gggaccacgg tcaccgtctc aagcgcctcc 360
accaagggcc catcggtctt ccccctggca ccctcctcca agagcacctc tgggggcaca 420
gcggccctgg gctgcctggt caaggactac ttccccgaac cggtgacggt gtcgtggaac 480
tcaggcgccc tgaccagcgg cgtccacacc ttcccggctg tcctacagtc ctcaggactc 540
tactccctca gcagcgtagt gaccgtgccc tccagcagct tgggcaccca gacctacatc 600
tgcaacgtga atcacaagcc cagcaacacc aaggtggaca agaaagttga gcccaaatct 660
tgt 663

<210> SEQ ID NO 209
<211> LENGTH: 219
<212> TYPE: PRT
<213> ORGANISM: Artificial Sequence
<220> FEATURE:
<223> OTHER INFORMATION: PFE1 Light chain VD

<400> SEQUENCE: 209

```
Asp Val Val Met Thr Gln Ser Pro Leu Ser Leu Pro Val Thr Leu Gly
1               5                   10                  15

Gln Pro Ala Ser Ile Ser Cys Thr Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Lys Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Ala Ile Tyr Tyr Cys Met Gln Gly
                85                  90                  95

Thr His Trp Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 210
<211> LENGTH: 221
<212> TYPE: PRT
<213> ORGANISM: Artificial Sequence
<220> FEATURE:
<223> OTHER INFORMATION: PFE1 Heavy chain VD

<400> SEQUENCE: 210

```
Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Arg Gly Tyr Tyr Gly Met Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
```

```
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220


<210> SEQ ID NO 211
<211> LENGTH: 16
<212> TYPE: PRT
<213> ORGANISM: Artificial Sequence
<220> FEATURE:
<223> OTHER INFORMATION: PFE1 LC-CDR1

<400> SEQUENCE: 211

Thr Ser Ser Gln Ser Leu Val Tyr Ser Asp Gly Asn Thr Tyr Leu Asn
1               5                   10                  15


<210> SEQ ID NO 212
<211> LENGTH: 7
<212> TYPE: PRT
<213> ORGANISM: Artificial Sequence
<220> FEATURE:
<223> OTHER INFORMATION: PFE1 LC-CDR2

<400> SEQUENCE: 212

Lys Val Ser Lys Arg Asp Ser
1               5


<210> SEQ ID NO 213
<211> LENGTH: 717
<212> TYPE: DNA
<213> ORGANISM: Artificial Sequence
<220> FEATURE:
<223> OTHER INFORMATION: PFE2 Light chain nucleotide sequence

<400> SEQUENCE: 213

gtgaaaaaat tattattcgc aattccttta gttgttcctt tctattctca cagtgcactt      60

gatgttgtga tgactcagtc tccactctcc ctgcccgtca cccctggaga gccggcctcc     120

atctcctgca ggtctagtca gagcctcctg cgcagtgatg gatacaactt tgtggattgg     180

tacctgcaga aggcagggca gtctccacag ctcctgatcc atttgggttc tgatcgggcc     240

tccggggtcc ctgacaggtt cagtggcagt ggatcaggca cagattttac actgagaatc     300

agcagagtgg aggctgagga tgttggagtt tattactgca tgcaagctct acaaactcct     360

cggacgttcg gccaagggac caaggtggaa atcaaacgaa ctgtggctgc accatctgtc     420

ttcatcttcc cgccatctga tgagcagttg aaatctggaa ctgcctctgt tgtgtgcctg     480

ctgaataact tctatcccag agaggccaaa gtacagtgga aggtggataa cgccctccaa     540

tcgggtaact cccaggagag tgtcacagag caggacagca aggacagcac ctacagcctc     600

agcagcaccc tgacgctgag caaagcagac tacgagaaac acaaagtcta cgcctgcgaa     660

gtcacccatc agggcctgag ctcgcccgtc acaaagagct tcaacagggg agagtgt        717


<210> SEQ ID NO 214
```

<211> LENGTH: 690
<212> TYPE: DNA
<213> ORGANISM: Artificial Sequence
<220> FEATURE:
<223> OTHER INFORMATION: PFE2 Heavy chain nucleotide sequence

<400> SEQUENCE: 214
gaggtccagc tggtgcagtc tgggggaggc gtggtccagc ctgggaggtc cctgagactc 60
tcctgtgcag cctctggatt caccttcagt agctatgcta tgcactgggt ccgccaggct 120
ccaggcaagg ggctggagtg ggtggcagtt atatcatatg atgaaagcaa taaatactac 180
gcagactccg tgaagggccg attcaccatc tccagagaca attccaagaa cacgctgtat 240
ctgcaaatga acagcctgag agctgaggac acggctgtgt attactgtgc gagggagcca 300
agcggcagct ggtcgtacct ctactactac tactacggta tggacgtctg gggccaaggg 360
accacggtca ccgtctcaag cgcctccacc aagggcccat cggtcttccc cctggcaccc 420
tcctccaaga gcacctctgg gggcacagcg gccctgggct gcctggtcaa ggactacttc 480
cccgaaccgg tgacggtgtc gtggaactca ggcgccctga ccagcggcgt ccacaccttc 540
ccggctgtcc tacagtcctc aggactctac tccctcagca gcgtagtgac cgtgccctcc 600
agcagcttgg gcacccagac ctacatctgc aacgtgaatc acaagcccag caacaccaag 660
gtggacaaga aagttgagcc caaatcttgt 690

<210> SEQ ID NO 215
<211> LENGTH: 219
<212> TYPE: PRT
<213> ORGANISM: Artificial Sequence
<220> FEATURE:
<223> OTHER INFORMATION: PFE2 Light chain VD

<400> SEQUENCE: 215

Asp Val Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu Arg Ser
20 25 30

Asp Gly Tyr Asn Phe Val Asp Trp Tyr Leu Gln Lys Ala Gly Gln Ser
35 40 45

Pro Gln Leu Leu Ile His Leu Gly Ser Asp Arg Ala Ser Gly Val Pro
50 55 60

Asp Arg Phe Ser Gly Ser Gly Ser Gly Thr Asp Phe Thr Leu Arg Ile
65 70 75 80

Ser Arg Val Glu Ala Glu Asp Val Gly Val Tyr Tyr Cys Met Gln Ala
85 90 95

Leu Gln Thr Pro Arg Thr Phe Gly Gln Gly Thr Lys Val Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser 195 200 205

Pro Val Thr Lys Ser Phe Asn Arg Gly Glu Cys
210 215

<210> SEQ ID NO 216
<211> LENGTH: 230
<212> TYPE: PRT
<213> ORGANISM: Artificial Sequence
<220> FEATURE:
<223> OTHER INFORMATION: PFE2 Heavy chain VD

<400> SEQUENCE: 216

Glu Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Met His Trp Val Arg Gln Ala Pro Gly Lys Gly Leu Glu Trp Val
35 40 45

Ala Val Ile Ser Tyr Asp Glu Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Glu Pro Ser Gly Ser Trp Ser Tyr Leu Tyr Tyr Tyr Tyr Tyr
100 105 110

Gly Met Asp Val Trp Gly Gln Gly Thr Thr Val Thr Val Ser Ser Ala
115 120 125

Ser Thr Lys Gly Pro Ser Val Phe Pro Leu Ala Pro Ser Ser Lys Ser
130 135 140

Thr Ser Gly Gly Thr Ala Ala Leu Gly Cys Leu Val Lys Asp Tyr Phe
145 150 155 160

Pro Glu Pro Val Thr Val Ser Trp Asn Ser Gly Ala Leu Thr Ser Gly
165 170 175

Val His Thr Phe Pro Ala Val Leu Gln Ser Ser Gly Leu Tyr Ser Leu
180 185 190

Ser Ser Val Val Thr Val Pro Ser Ser Ser Leu Gly Thr Gln Thr Tyr
195 200 205

Ile Cys Asn Val Asn His Lys Pro Ser Asn Thr Lys Val Asp Lys Lys
210 215 220

Val Glu Pro Lys Ser Cys
225 230

<210> SEQ ID NO 217
<211> LENGTH: 16
<212> TYPE: PRT
<213> ORGANISM: Artificial Sequence
<220> FEATURE:
<223> OTHER INFORMATION: PFE2 LC-CDR1

<400> SEQUENCE: 217

Arg Ser Ser Gln Ser Leu Leu Arg Ser Asp Gly Tyr Asn Phe Val Asp
1 5 10 15

<210> SEQ ID NO 218
<211> LENGTH: 7
<212> TYPE: PRT
<213> ORGANISM: Artificial Sequence
<220> FEATURE:

<223> OTHER INFORMATION: PFE2 LC-CDR2

<400> SEQUENCE: 218

Leu Gly Ser Asp Arg Ala Ser
1 5

<210> SEQ ID NO 219
<211> LENGTH: 9
<212> TYPE: PRT
<213> ORGANISM: Artificial Sequence
<220> FEATURE:
<223> OTHER INFORMATION: PFE2 LC-CDR3

<400> SEQUENCE: 219

Met Gln Ala Leu Gln Thr Pro Arg Thr
1 5

<210> SEQ ID NO 220
<211> LENGTH: 17
<212> TYPE: PRT
<213> ORGANISM: Artificial Sequence
<220> FEATURE:
<223> OTHER INFORMATION: PFE2 HC-CDR2

<400> SEQUENCE: 220

Val Ile Ser Tyr Asp Glu Ser Asn Lys Tyr Tyr Ala Asp Ser Val Lys
1 5 10 15

Gly

<210> SEQ ID NO 221
<211> LENGTH: 18
<212> TYPE: PRT
<213> ORGANISM: Artificial Sequence
<220> FEATURE:
<223> OTHER INFORMATION: PFE2 HC-CDR3

<400> SEQUENCE: 221

Glu Pro Ser Gly Ser Trp Ser Tyr Leu Tyr Tyr Tyr Tyr Tyr Gly Met
1 5 10 15

Asp Val

<210> SEQ ID NO 222
<211> LENGTH: 642
<212> TYPE: DNA
<213> ORGANISM: Artificial Sequence
<220> FEATURE:
<223> OTHER INFORMATION: PFE5 Light chain nucleotide sequence

<400> SEQUENCE: 222
gacatccaga tgacccagtc tccatcctcc ctgtctgcat ctgtaggaga cagagtcacc 60
atcacttgtc gggcgagtca gggtattagc agctggttag cctggtatca gcagaaacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttacta ttgtcaacag gctaacagtt tccctcccac tttcggccct 300
gggaccaaag tggatatcaa acgaactgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 223
<211> LENGTH: 663
<212> TYPE: DNA
<213> ORGANISM: Artificial Sequence
<220> FEATURE:
<223> OTHER INFORMATION: PFE5 Heavy chain nucleotide sequence

<400> SEQUENCE: 223
gaggtccagc tggtgcagtc tgggggaggc gtggtccagc ctgggaggtc cctgagactc 60
tcctgtgcag cctctggatt caccttcagt agctatgcta tgcactgggt ccgccaggct 120
ccaggcaagg ggctggagtg ggtggcagtt atatcatatg atggaagtaa taaatactac 180
gcagactccg tgaagggccg attcaccatc tccagagaca attccaagaa cacgctgtat 240
ctgcaaatga acagcctgag agctgaggac acggctgtgt attactgtgc gaggagtcga 300
ggctactacg gtatggacgt ctggggccaa gggaccacgg tcaccgtctc aagcgcctcc 360
accaagggcc catcggtctt ccccctggca ccctcctcca agagcacctc tgggggcaca 420
gcggccctgg gctgcctggt caaggactac ttccccgaac cggtgacggt gtcgtggaac 480
tcaggcgccc tgaccagcgg cgtccacacc ttcccggctg tcctacagtc ctcaggactc 540
tactccctca gcagcgtagt gaccgtgccc tccagcagct tgggcaccca gacctacatc 600
tgcaacgtga atcacaagcc cagcaacacc aaggtggaca agaaagttga gcccaaatct 660
tgt 663

<210> SEQ ID NO 224
<211> LENGTH: 214
<212> TYPE: PRT
<213> ORGANISM: Artificial Sequence
<220> FEATURE:
<223> OTHER INFORMATION: PFE5 Light chain VD

<400> SEQUENCE: 224

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 225
<211> LENGTH: 221
<212> TYPE: PRT
<213> ORGANISM: Artificial Sequence
<220> FEATURE:
<223> OTHER INFORMATION: PFE5 Heavy chain VD

<400> SEQUENCE: 225

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Arg Gly Tyr Tyr Gly Met Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220


<210> SEQ ID NO 226
<211> LENGTH: 11
<212> TYPE: PRT
<213> ORGANISM: Artificial Sequence
<220> FEATURE:
<223> OTHER INFORMATION: PFE5 LC-CDR1

<400> SEQUENCE: 226

Arg Ala Ser Gln Gly Ile Ser Ser Trp Leu Ala
1               5                   10


<210> SEQ ID NO 227
<211> LENGTH: 7
<212> TYPE: PRT
```

<213> ORGANISM: Artificial Sequence
<220> FEATURE:
<223> OTHER INFORMATION: PFE5 LC-CDR2

<400> SEQUENCE: 227

Ala Ala Ser Ser Leu Gln Ser
1 5

<210> SEQ ID NO 228
<211> LENGTH: 9
<212> TYPE: PRT
<213> ORGANISM: Artificial Sequence
<220> FEATURE:
<223> OTHER INFORMATION: PFE5 LC-CDR3

<400> SEQUENCE: 228

Gln Gln Ala Asn Ser Phe Pro Pro Thr
1 5

<210> SEQ ID NO 229
<211> LENGTH: 642
<212> TYPE: DNA
<213> ORGANISM: Artificial Sequence
<220> FEATURE:
<223> OTHER INFORMATION: PFF2 Light chain nucleotide sequence

<400> SEQUENCE: 229
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcctccgc tttcggccct 300
gggaccaaag tggatatcaa acgaactgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 230
<211> LENGTH: 675
<212> TYPE: DNA
<213> ORGANISM: Artificial Sequence
<220> FEATURE:
<223> OTHER INFORMATION: PFF2 Heavy chain nucleotide sequence

<400> SEQUENCE: 230
cagatgcagc tggtgcagtc tgggggaggc gtggtccagc ctgggaggtc actgagactc 60
tcctgtgcag cctctggatt cagtttcaaa aattatggca tgcactgggt ccgccaggct 120
ccaggcaagg ggctggagtg ggtggcattt atctcatatg atggaactaa taaatactat 180
gcagactccg tgaagggccg attcaccatc tccagagaca attccaagaa cacgctgtat 240
ctgcaaatga acagcctgag agccgaggac acggccgtat attactgtgc gaagcactac 300
ggtgactact actactacta cggtatggac gtctggggcc aagggaccac ggtcaccgtc 360
tcaagcgcct ccaccaaggg cccatcggtc ttccccctgg caccctcctc caagagcacc 420
tctgggggca cagcggccct gggctgcctg gtcaaggact acttccccga accggtgacg 480

```
gtgtcgtgga actcaggcgc cctgaccagc ggcgtccaca ccttcccggc tgtcctacag    540

tcctcaggac tctactccct cagcagcgta gtgaccgtgc cctccagcag cttgggcacc    600

cagacctaca tctgcaacgt gaatcacaag cccagcaaca ccaaggtgga caagaaagtt    660

gagcccaaat cttgt                                                     675


<210> SEQ ID NO 231
<211> LENGTH: 214
<212> TYPE: PRT
<213> ORGANISM: Artificial Sequence
<220> FEATURE:
<223> OTHER INFORMATION: PFF2 Light chain VD

<400> SEQUENCE: 231

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Ser
                85                  90                  95

Ala Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 232
<211> LENGTH: 225
<212> TYPE: PRT
<213> ORGANISM: Artificial Sequence
<220> FEATURE:
<223> OTHER INFORMATION: PFF2 Heavy chain VD

<400> SEQUENCE: 232

Gln Met Gln Leu Val Gln Ser Gly Gly Gly Val Val Gln Pro Gly Arg
1               5                   10                  15

Ser Leu Arg Leu Ser Cys Ala Ala Ser Gly Phe Ser Phe Lys Asn Tyr
            20                  25                  30

Gly Met His Trp Val Arg Gln Ala Pro Gly Lys Gly Leu Glu Trp Val
        35                  40                  45
```

```
Ala Phe Ile Ser Tyr Asp Gly Thr Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Tyr Gly Asp Tyr Tyr Tyr Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225
```

<210> SEQ ID NO 233
<211> LENGTH: 8
<212> TYPE: PRT
<213> ORGANISM: Artificial Sequence
<220> FEATURE:
<223> OTHER INFORMATION: PFF2 LC-CDR3

<400> SEQUENCE: 233

```
Gln Gln Tyr Gly Ser Ser Ser Ala
1               5
```

<210> SEQ ID NO 234
<211> LENGTH: 5
<212> TYPE: PRT
<213> ORGANISM: Artificial Sequence
<220> FEATURE:
<223> OTHER INFORMATION: PFF2 HC-CDR1

<400> SEQUENCE: 234

```
Asn Tyr Gly Met His
1               5
```

<210> SEQ ID NO 235
<211> LENGTH: 17
<212> TYPE: PRT
<213> ORGANISM: Artificial Sequence
<220> FEATURE:
<223> OTHER INFORMATION: PFF2 HC-CDR2

<400> SEQUENCE: 235

```
Phe Ile Ser Tyr Asp Gly Thr Asn Lys Tyr Tyr Ala Asp Ser Val Lys
1               5                   10                  15

Gly
```

<210> SEQ ID NO 236
<211> LENGTH: 13
<212> TYPE: PRT
<213> ORGANISM: Artificial Sequence
<220> FEATURE:
<223> OTHER INFORMATION: PFF2 HC-CDR3

<400> SEQUENCE: 236

His Tyr Gly Asp Tyr Tyr Tyr Tyr Tyr Gly Met Asp Val
1 5 10

<210> SEQ ID NO 237
<211> LENGTH: 657
<212> TYPE: DNA
<213> ORGANISM: Artificial Sequence
<220> FEATURE:
<223> OTHER INFORMATION: PFF3 Light chain nucleotide sequence

<400> SEQUENCE: 237
gatgttgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatct acttgggttc taatcgggcc 180
tccggggtcc ctgacaggct cagtggcagt ggatcaggca cagattttac actgaaaatc 240
agcagagtgg aggctgagga tgttggggtt tattactgca tgcaaggtac acactggcca 300
gggacgttcg gccaagggac caaggtggaa atcaaacgaa ctgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtc acaaagagct tcaacagggg agagtgt 657

<210> SEQ ID NO 238
<211> LENGTH: 675
<212> TYPE: DNA
<213> ORGANISM: Artificial Sequence
<220> FEATURE:
<223> OTHER INFORMATION: PFF3 Heavy chain nucleotide sequence

<400> SEQUENCE: 238
caggtccagc tggtacagtc tgggggaggc ttggtccagc ctggggggtc cctgagactc 60
tcctgttcag cctctggatt caccttcagt agctatgcta tccactgggt ccgccaggct 120
ccagggaagg gactggaata tgtttcagct attagtagta atgggggtag cacatactac 180
gcagactccg tgaagggcag attcaccatc tccagagaca attccaagaa cacgctgtat 240
cttcaaatga acagcctgag agccgaggac acggctgtgt attactgtgc gagagtctat 300
ggatatggtc tccactacta cggtatggac gtctggggcc aagggaccac ggtcaccgtc 360
tcaagcgcct ccaccaaggg cccatcggtc ttccccctgg caccctcctc caagagcacc 420
tctgggggca cagcggccct gggctgcctg gtcaaggact acttccccga accggtgacg 480
gtgtcgtgga actcaggcgc cctgaccagc ggcgtccaca ccttcccggc tgtcctacag 540
tcctcaggac tctactccct cagcagcgta gtgaccgtgc cctccagcag cttgggcacc 600
cagacctaca tctgcaacgt gaatcacaag cccagcaaca ccaaggtgga caagaaagtt 660
gagcccaaat cttgt 675

<210> SEQ ID NO 239
<211> LENGTH: 219
<212> TYPE: PRT
<213> ORGANISM: Artificial Sequence
<220> FEATURE:
<223> OTHER INFORMATION: PFF3 Light chain VD

<400> SEQUENCE: 239

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Leu Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Gly Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 240
<211> LENGTH: 225
<212> TYPE: PRT
<213> ORGANISM: Artificial Sequence
<220> FEATURE:
<223> OTHER INFORMATION: PFF3 Heavy chain VD

<400> SEQUENCE: 240

```
Gln Val Gln Leu Val Gln Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Ile His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Val Tyr Gly Tyr Gly Leu His Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225
```

<210> SEQ ID NO 241
<211> LENGTH: 5
<212> TYPE: PRT
<213> ORGANISM: Artificial Sequence
<220> FEATURE:
<223> OTHER INFORMATION: PFF3 HC-CDR1

<400> SEQUENCE: 241

```
Ser Tyr Ala Ile His
1               5
```

<210> SEQ ID NO 242
<211> LENGTH: 13
<212> TYPE: PRT
<213> ORGANISM: Artificial Sequence
<220> FEATURE:
<223> OTHER INFORMATION: PFF3 HC-CDR3

<400> SEQUENCE: 242

```
Val Tyr Gly Tyr Gly Leu His Tyr Tyr Gly Met Asp Val
1               5                   10
```

<210> SEQ ID NO 243
<211> LENGTH: 645
<212> TYPE: DNA
<213> ORGANISM: Artificial Sequence
<220> FEATURE:
<223> OTHER INFORMATION: PFF4 Light chain nucleotide sequence

<400> SEQUENCE: 243

```
gaaacgacac tcacgcagtc tccaggcacg ctgtctttgt ctccagggga aagagccacc      60

ctctcctgca gggccagtcg gagtgttggc aagtacttag cctggtacca gcagaaacct     120

ggccaggctc ccaccttagt catttatgat gcatcaacca gggcctccgg cattccagac     180

aggttcagtg ccagtggctc tgggactgac ttcactctca ccatcagcag tctggagcct     240

gaagattttg cagtgtattt ctgtcagcac tatggtacct cacctccgtt catttttggc     300

caagggacac gactggagat taaacgaact gtggctgcac catctgtctt catcttcccg     360

ccatctgatg agcagttgaa atctggaact gcctctgttg tgtgcctgct gaataacttc     420

tatcccagag aggccaaagt acagtggaag gtggataacg ccctccaatc gggtaactcc     480
```

-continued

```
caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgt                    645
```

<210> SEQ ID NO 244
<211> LENGTH: 672
<212> TYPE: DNA
<213> ORGANISM: Artificial Sequence
<220> FEATURE:
<223> OTHER INFORMATION: PFF4 Heavy chain nucleotide sequence

<400> SEQUENCE: 244

```
gaagtgcagc tggtgcagtc tggggctgag gtgaagaagc ctgggtcctc ggtgaaggtc     60

tcctgcaagg cttctggagg caccttcagc agctatgcta tcagctgggt gcgacaggcc    120

cctggacaag ggcttgagtg gatgggaggg atcatcccta tctttggtac ggcaaactac    180

gcacagaagt tccagggcag agtcacgatt accgcggacg aatccacgag cacagcctac    240

atggagctga gcagcctgag atctgaggac acggccgtgt attactgtgc gagatcctat    300

gatagtagtg gttattacta ctttgactac tggggccagg gaaccctggt caccgtctca    360

agcgcctcca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtccacacct tcccggctgt cctacagtcc    540

tcaggactct actccctcag cagcgtagtg accgtgccct ccagcagctt gggcacccag    600

acctacatct gcaacgtgaa tcacaagccc agcaacacca aggtggacaa gaaagttgag    660

cccaaatctt gt                                                        672
```

<210> SEQ ID NO 245
<211> LENGTH: 215
<212> TYPE: PRT
<213> ORGANISM: Artificial Sequence
<220> FEATURE:
<223> OTHER INFORMATION: PFF4 Light chain VD

<400> SEQUENCE: 245

```
Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Arg Ser Val Gly Lys Tyr
            20                  25                  30

Leu Ala Trp Tyr Gln Gln Lys Pro Gly Gln Ala Pro Thr Leu Val Ile
        35                  40                  45

Tyr Asp Ala Ser Thr Arg Ala Ser Gly Ile Pro Asp Arg Phe Ser Ala
    50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln His Tyr Gly Thr Ser Pro Pro
                85                  90                  95

Phe Ile Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160
```

```
Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 246
<211> LENGTH: 224
<212> TYPE: PRT
<213> ORGANISM: Artificial Sequence
<220> FEATURE:
<223> OTHER INFORMATION: PFF4 Heavy chain VD

<400> SEQUENCE: 246

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Asp Ser Ser Gly Tyr Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220


<210> SEQ ID NO 247
<211> LENGTH: 11
<212> TYPE: PRT
<213> ORGANISM: Artificial Sequence
<220> FEATURE:
<223> OTHER INFORMATION: PFF4 LC-CDR1

<400> SEQUENCE: 247

Arg Ala Ser Arg Ser Val Gly Lys Tyr Leu Ala
1               5                   10
```

<210> SEQ ID NO 248
<211> LENGTH: 7
<212> TYPE: PRT
<213> ORGANISM: Artificial Sequence
<220> FEATURE:
<223> OTHER INFORMATION: PFF4 LC-CDR2

<400> SEQUENCE: 248

Asp Ala Ser Thr Arg Ala Ser
1               5

<210> SEQ ID NO 249
<211> LENGTH: 10
<212> TYPE: PRT
<213> ORGANISM: Artificial Sequence
<220> FEATURE:
<223> OTHER INFORMATION: PFF4 LC-CDR3

<400> SEQUENCE: 249

Gln His Tyr Gly Thr Ser Pro Pro Phe Ile
1               5                   10

<210> SEQ ID NO 250
<211> LENGTH: 12
<212> TYPE: PRT
<213> ORGANISM: Artificial Sequence
<220> FEATURE:
<223> OTHER INFORMATION: PFF4 HC-CDR3

<400> SEQUENCE: 250

Ser Tyr Asp Ser Ser Gly Tyr Tyr Tyr Phe Asp Tyr
1               5                   10

<210> SEQ ID NO 251
<211> LENGTH: 648
<212> TYPE: DNA
<213> ORGANISM: Artificial Sequence
<220> FEATURE:
<223> OTHER INFORMATION: PFF5 Light chain nucleotide sequence

<400> SEQUENCE: 251
caggctgtgg tgatccagga gccatcgttc tcagtgtccc ctggagggac agtcacactc     60
acttgtggct tgagctctgg ctcagtctct actacttact accccagctg gtaccagcag    120
accccaggcc aggctccacg cacgctcatc tacagcacaa acactcgctc ttctggggtc    180
cctgatcgct tctctggctc catccttggg aacaaagctg ccctcaccat cacgggggcc    240
caggcagatg atgaatctga ttattactgt gtgctgtata tgggtaatgg catttcggtg    300
ttcggcggag ggaccaagct gaccgtccta ggtcagccca aggctgcccc ctcggtcact    360
ctgttcccgc cctcctctga ggagcttcaa gccaacaagg ccacactggt gtgtctcata    420
agtgacttct acccgggagc cgtgacagtg gcctggaagg cagatagcag ccccgtcaag    480
gcgggagtgg agaccaccac accctccaaa caaagcaaca acaagtacgc ggccagcagc    540
tacctgagcc tgacgcctga gcagtggaag tcccacaaaa gctacagctg ccaggtcacg    600
catgaaggga gcaccgtgga gaagacagtg gcccctgcag aatgctct                 648

<210> SEQ ID NO 252
<211> LENGTH: 681
<212> TYPE: DNA
<213> ORGANISM: Artificial Sequence
<220> FEATURE:
<223> OTHER INFORMATION: PFF5 Heavy chain nucleotide sequence

<400> SEQUENCE: 252

```
caggtgcagc tgcaggagtc gggcccagga ctggtgaagc cttcggagac cctgtccctc     60

acctgcactg tctctggtgg ctccatcagc agtagtagtt actactgggg ctggatccgc    120

cagcccccag ggaaggggct ggagtggatt gggagtatct attatagtgg gagcacctac    180

tacaacccgt ccctcaagag tcgagtcacc atatccgtag acacgtccaa gaaccagttc    240

tccctgaggc tgagctctgt gagcgccgca gacacggccg tgtattactg tgcgagatac    300

gcgcctgata gtagtggtta cctggtggct tttgatatct ggggccaagg gacaatggtc    360

accgtctcaa gcgcctccac caagggccca tcggtcttcc ccctggcacc ctcctccaag    420

agcacctctg ggggcacagc ggccctgggc tgcctggtca aggactactt ccccgaaccg    480

gtgacggtgt cgtggaactc aggcgccctg accagcggcg tccacacctt cccggctgtc    540

ctacagtcct caggactcta ctccctcagc agcgtagtga ccgtgccctc cagcagcttg    600

ggcacccaga cctacatctg caacgtgaat cacaagccca gcaacaccaa ggtggacaag    660

aaagttgagc ccaaatcttg t                                              681
```

```
<210> SEQ ID NO 253
<211> LENGTH: 216
<212> TYPE: PRT
<213> ORGANISM: Artificial Sequence
<220> FEATURE:
<223> OTHER INFORMATION: PFF5 Light chain VD

<400> SEQUENCE: 253

Gln Ala Val Val Ile Gln Glu Pro Ser Phe Ser Val Ser Pro Gly Gly
1               5                   10                  15

Thr Val Thr Leu Thr Cys Gly Leu Ser Ser Gly Ser Val Ser Thr Thr
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Asn
                85                  90                  95

Gly Ile Ser Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Ala Glu Cys Ser
    210                 215

<210> SEQ ID NO 254
```

<211> LENGTH: 227
<212> TYPE: PRT
<213> ORGANISM: Artificial Sequence
<220> FEATURE:
<223> OTHER INFORMATION: PFF5 Heavy chain VD

<400> SEQUENCE: 254

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Arg Leu Ser Ser Val Ser Ala Ala Asp Thr Ala Val Tyr Tyr
                85                  90                  95

Cys Ala Arg Tyr Ala Pro Asp Ser Ser Gly Tyr Leu Val Ala Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225
```

<210> SEQ ID NO 255
<211> LENGTH: 14
<212> TYPE: PRT
<213> ORGANISM: Artificial Sequence
<220> FEATURE:
<223> OTHER INFORMATION: PFF5 LC-CDR1

<400> SEQUENCE: 255

```
Gly Leu Ser Ser Gly Ser Val Ser Thr Thr Tyr Tyr Pro Ser
1               5                   10
```

<210> SEQ ID NO 256
<211> LENGTH: 10
<212> TYPE: PRT
<213> ORGANISM: Artificial Sequence
<220> FEATURE:
<223> OTHER INFORMATION: PFF5 LC-CDR3

<400> SEQUENCE: 256

```
Val Leu Tyr Met Gly Asn Gly Ile Ser Val
1               5                   10
```

<210> SEQ ID NO 257
<211> LENGTH: 663
<212> TYPE: DNA
<213> ORGANISM: Artificial Sequence
<220> FEATURE:
<223> OTHER INFORMATION: PFG1 Light chain nucleotide sequence

<400> SEQUENCE: 257
caggctgtgc tgactcagcc gtcttccctc tctgcatctc ctggagcatc agccagtctc 60
acctgcacct tgcgcagtgg catcaatgtt ggtacctaca ggatatactg gtaccagcag 120
aagccaggga gtcctcccca gtatctcctg aggtacaaat cagactcaga taagcagcag 180
ggctctggag tccccagccg cttctctgga tccaaagatg cttcggccaa tgcagggatt 240
ttactcatct ctgggctcca gtctgaggat gaggctgact attactgtat gatttggcac 300
agcagcgctt gggtgttcgg cggagggacc aagctgaccg tcctaggtca gcccaaggct 360
gccccctcgg tcactctgtt cccaccctcc tctgaggagc ttcaagccaa caaggccaca 420
ctggtgtgtc tcataagtga cttctacccg ggagccgtga cagtggcctg gaaggcagat 480
agcagccccg tcaaggcggg agtggagacc accacaccct ccaaacaaag caacaacaag 540
tacgcggcca gcagctacct gagcctgacg cctgagcagt ggaagtccca caaaagctac 600
agctgccagg tcacgcatga agggagcacc gtggagaaga cagtggcccc tgcagaatgc 660
tct 663

<210> SEQ ID NO 258
<211> LENGTH: 654
<212> TYPE: DNA
<213> ORGANISM: Artificial Sequence
<220> FEATURE:
<223> OTHER INFORMATION: PFG1 Heavy chain nucleotide sequence

<400> SEQUENCE: 258
gaggtccagc tggtacagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatggtatg atggaagtaa taaatactat 180
gcagactccg tgaagggccg attcaccatc tccagagaca attccaagaa cacgctgtat 240
ctgcaaatga acagcctgag agctgaggac acggctgtat attactgtgc cacaatgact 300
actgaggact actggggcca gggcaccctg gtcaccgtct caagcgcctc caccaagggc 360
ccatcggtct tccccctggc accctcctcc aagagcacct ctgggggcac agcggccctg 420
ggctgcctgg tcaaggacta cttccccgaa ccggtgacgg tgtcgtggaa ctcaggcgcc 480
ctgaccagcg gcgtccacac cttcccggct gtcctacagt cctcaggact ctactccctc 540
agcagcgtag tgaccgtgcc ctccagcagc ttgggcaccc agacctacat ctgcaacgtg 600
aatcacaagc ccagcaacac caaggtggac aagaaagttg agcccaaatc ttgt 654

<210> SEQ ID NO 259
<211> LENGTH: 221
<212> TYPE: PRT
<213> ORGANISM: Artificial Sequence
<220> FEATURE:
<223> OTHER INFORMATION: PFG1 Light chain VD

<400> SEQUENCE: 259

Gln Ala Val Leu Thr Gln Pro Ser Ser Leu Ser Ala Ser Pro Gly Ala
1 5 10 15

-continued

```
Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Trp Val Phe Gly Gly Gly Thr Lys Leu
            100                 105                 110

Thr Val Leu Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
    130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Lys Ser Tyr Ser Cys Gln Val Thr His Glu Gly
        195                 200                 205

Ser Thr Val Glu Lys Thr Val Ala Pro Ala Glu Cys Ser
    210                 215                 220


<210> SEQ ID NO 260
<211> LENGTH: 218
<212> TYPE: PRT
<213> ORGANISM: Artificial Sequence
<220> FEATURE:
<223> OTHER INFORMATION: PFG1 Heavy chain VD

<400> SEQUENCE: 260

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Met Thr Thr Glu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160
```

```
Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys
    210                 215


<210> SEQ ID NO 261
<211> LENGTH: 14
<212> TYPE: PRT
<213> ORGANISM: Artificial Sequence
<220> FEATURE:
<223> OTHER INFORMATION: PFG1 LC-CDR1

<400> SEQUENCE: 261

Thr Leu Arg Ser Gly Ile Asn Val Gly Thr Tyr Arg Ile Tyr
1               5                   10


<210> SEQ ID NO 262
<211> LENGTH: 11
<212> TYPE: PRT
<213> ORGANISM: Artificial Sequence
<220> FEATURE:
<223> OTHER INFORMATION: PFG1 LC-CDR2

<400> SEQUENCE: 262

Tyr Lys Ser Asp Ser Asp Lys Gln Gln Gly Ser
1               5                   10


<210> SEQ ID NO 263
<211> LENGTH: 9
<212> TYPE: PRT
<213> ORGANISM: Artificial Sequence
<220> FEATURE:
<223> OTHER INFORMATION: PFG1 LC-CDR3

<400> SEQUENCE: 263

Met Ile Trp His Ser Ser Ala Trp Val
1               5


<210> SEQ ID NO 264
<211> LENGTH: 17
<212> TYPE: PRT
<213> ORGANISM: Artificial Sequence
<220> FEATURE:
<223> OTHER INFORMATION: PFG1 HC-CDR2

<400> SEQUENCE: 264

Val Ile Trp Tyr Asp Gly Ser Asn Lys Tyr Tyr Ala Asp Ser Val Lys
1               5                   10                  15

Gly


<210> SEQ ID NO 265
<211> LENGTH: 6
<212> TYPE: PRT
<213> ORGANISM: Artificial Sequence
<220> FEATURE:
<223> OTHER INFORMATION: PFG1 HC-CDR3

<400> SEQUENCE: 265

Met Thr Thr Glu Asp Tyr
1               5
```

-continued

<210> SEQ ID NO 266
<211> LENGTH: 642
<212> TYPE: DNA
<213> ORGANISM: Artificial Sequence
<220> FEATURE:
<223> OTHER INFORMATION: PFG2 Light chain nucleotide sequence

<400> SEQUENCE: 266
gaaattgtgt tgacgcagtc tccagccacc ctgtctttgt ctccagggga aagagccacc 60
ctctcctgca gggccagtca gagtgttagc agctacttag cctggtacca acagaaacct 120
ggccaggctc ccaggctcct catctatgat gcgtccaaca gggccactgg catcccagcc 180
aggttcagtg gcagtgggtc tgggacagac ttcactctca ccatcagcag cctagagcct 240
gaagattttg cagtttatta ctgtcagcag cgtagcaact ggccgctcac tttcggcgga 300
gggaccaagg tggagatcaa acgaactgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 267
<211> LENGTH: 663
<212> TYPE: DNA
<213> ORGANISM: Artificial Sequence
<220> FEATURE:
<223> OTHER INFORMATION: PFG2 Heavy chain nucleotide sequence

<400> SEQUENCE: 267
gaagtgcagc tggtgcagtc tgggggaggc ttggtacagc ctggggggtc cctgagactc 60
tcctgtgcag cctctggatt cacctttagc agctatgcca tgagctgggt ccgccaggct 120
ccagggaagg ggctggagtg ggtctcatcc attagtagta gtagtagtta catatactac 180
gcagactcgg tgaagggccg attcaccatc tccagagaca acgccaagaa ttcactgtat 240
ctgcaaatga acagcctgag ggccgaggac acggctgtct attactgtgc gagagatggc 300
agtgcctggt cacgacccta ctggggccag ggaaccctgg tcaccgtctc aagcgcctcc 360
accaagggcc catcggtctt ccccctggca ccctcctcca agagcacctc tgggggcaca 420
gcggccctgg gctgcctggt caaggactac ttccccgaac cggtgacggt gtcgtggaac 480
tcaggcgccc tgaccagcgg cgtccacacc ttcccggctg tcctacagtc ctcaggactc 540
tactccctca gcagcgtagt gaccgtgccc tccagcagct tgggcaccca gacctacatc 600
tgcaacgtga atcacaagcc cagcaacacc aaggtggaca agaaagttga gcccaaatct 660
tgt 663

<210> SEQ ID NO 268
<211> LENGTH: 214
<212> TYPE: PRT
<213> ORGANISM: Artificial Sequence
<220> FEATURE:
<223> OTHER INFORMATION: PFG2 Light chain VD

<400> SEQUENCE: 268

Glu Ile Val Leu Thr Gln Ser Pro Ala Thr Leu Ser Leu Ser Pro Gly
1               5                   10                  15

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 269
<211> LENGTH: 221
<212> TYPE: PRT
<213> ORGANISM: Artificial Sequence
<220> FEATURE:
<223> OTHER INFORMATION: PFG2 Heavy chain VD

<400> SEQUENCE: 269

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ala Trp Ser Arg Pro Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

```
Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220


<210> SEQ ID NO 270
<211> LENGTH: 11
<212> TYPE: PRT
<213> ORGANISM: Artificial Sequence
<220> FEATURE:
<223> OTHER INFORMATION: PFG2 LC-CDR1

<400> SEQUENCE: 270

Arg Ala Ser Gln Ser Val Ser Ser Tyr Leu Ala
1               5                   10


<210> SEQ ID NO 271
<211> LENGTH: 7
<212> TYPE: PRT
<213> ORGANISM: Artificial Sequence
<220> FEATURE:
<223> OTHER INFORMATION: PFG2 LC-CDR2

<400> SEQUENCE: 271

Asp Ala Ser Asn Arg Ala Thr
1               5


<210> SEQ ID NO 272
<211> LENGTH: 9
<212> TYPE: PRT
<213> ORGANISM: Artificial Sequence
<220> FEATURE:
<223> OTHER INFORMATION: PFG2 LC-CDR3

<400> SEQUENCE: 272

Gln Gln Arg Ser Asn Trp Pro Leu Thr
1               5


<210> SEQ ID NO 273
<211> LENGTH: 17
<212> TYPE: PRT
<213> ORGANISM: Artificial Sequence
<220> FEATURE:
<223> OTHER INFORMATION: PFG2 HC-CDR2

<400> SEQUENCE: 273

Ser Ile Ser Ser Ser Ser Ser Tyr Ile Tyr Tyr Ala Asp Ser Val Lys
1               5                   10                  15

Gly


<210> SEQ ID NO 274
<211> LENGTH: 9
<212> TYPE: PRT
<213> ORGANISM: Artificial Sequence
<220> FEATURE:
<223> OTHER INFORMATION: PFG2 HC-CDR3

<400> SEQUENCE: 274

Asp Gly Ser Ala Trp Ser Arg Pro Tyr
1               5
```

<210> SEQ ID NO 275
<211> LENGTH: 648
<212> TYPE: DNA
<213> ORGANISM: Artificial Sequence
<220> FEATURE:
<223> OTHER INFORMATION: PFG3 Light chain nucleotide sequence

<400> SEQUENCE: 275
caggctgtgg tgctccagga gccatcgttc tcagtgtccc ctggagggac agtcacactc 60
acttgtggct tgacctctgg cgcagtctcc agttcttact accccagctg gtaccagcag 120
accccaggcc aggctcctcg cactctcatt tataacacag acattcgctt ttctggggtc 180
cctgatcgct tctctggctc catccttggg aacaaagctg ccctcaccat cacgggggcc 240
caggcagatg atgaatctga ttattactgt gtactatata tgggtagtgg catttcggtg 300
ttcggcggag ggaccaaact gaccgtccta ggtcagccca aggctgcccc ctcggtcact 360
ctgttcccac cctcctctga ggagcttcaa gccaacaagg ccacactggt gtgtctcata 420
agtgacttct acccgggagc cgtgacagtg gcctggaagg cagatagcag ccccgtcaag 480
gcgggagtgg agaccaccac accctccaaa caaagcaaca acaagtacgc ggccagcagc 540
tacctgagcc tgacgcctga gcagtggaag tcccacaaaa gctacagctg ccaggtcacg 600
catgaaggga gcaccgtgga gaaaacagtg gcccctgcag aatgctct 648

<210> SEQ ID NO 276
<211> LENGTH: 672
<212> TYPE: DNA
<213> ORGANISM: Artificial Sequence
<220> FEATURE:
<223> OTHER INFORMATION: PFG3 Heavy chain nucleotide sequence

<400> SEQUENCE: 276
gaagtgcagc tggtgcagtc tggggctgag gtgaagaagc ctgggacctc agtgacagtc 60
tcctgcaggg cttctggatt caccttcagc gactactata tacactgggt gcgacaggcc 120
cctggacaag ggcttgagtg gatgggatgg gtcagcgctt acaatggtga cacaaactat 180
gcgcagaagt tccagggcag agtcaccgtg accacagaca catccacgag cacagcctac 240
atggagctga ggagcctgag atctgacgac acggccgtgt atttctgtgc gagagagatt 300
gcctcctata gtgggagcta ctacgactac tggggccagg gcaccctggt caccgtctca 360
agcgcctcca ccaagggccc atcggtcttc cccctggcac cctcctccaa gagcacctct 420
gggggcacag cggccctggg ctgcctggtc aaggactact tccccgaacc ggtgacggtg 480
tcgtggaact caggcgccct gaccagcggc gtccacacct tcccggctgt cctacagtcc 540
tcaggactct actccctcag cagcgtagtg accgtgccct ccagcagctt gggcacccag 600
acctacatct gcaacgtgaa tcacaagccc agcaacacca aggtggacaa gaaagttgag 660
cccaaatctt gt 672

<210> SEQ ID NO 277
<211> LENGTH: 216
<212> TYPE: PRT
<213> ORGANISM: Artificial Sequence
<220> FEATURE:
<223> OTHER INFORMATION: PFG3 Light chain VD

<400> SEQUENCE: 277

Gln Ala Val Val Leu Gln Glu Pro Ser Phe Ser Val Ser Pro Gly Gly
1 5 10 15

```
Thr Val Thr Leu Thr Cys Gly Leu Thr Ser Gly Ala Val Ser Ser Ser
            20                  25                  30

Tyr Tyr Pro Ser Trp Tyr Gln Gln Thr Pro Gly Gln Ala Pro Arg Thr
        35                  40                  45

Leu Ile Tyr Asn Thr Asp Ile Arg Phe Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile Ser Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Ala Glu Cys Ser
    210                 215
```

<210> SEQ ID NO 278
<211> LENGTH: 224
<212> TYPE: PRT
<213> ORGANISM: Artificial Sequence
<220> FEATURE:
<223> OTHER INFORMATION: PFG3 Heavy chain VD

<400> SEQUENCE: 278

```
Glu Val Gln Leu Val Gln Ser Gly Ala Glu Val Lys Lys Pro Gly Thr
1               5                   10                  15

Ser Val Thr Val Ser Cys Arg Ala Ser Gly Phe Thr Phe Ser Asp Tyr
            20                  25                  30

Tyr Ile His Trp Val Arg Gln Ala Pro Gly Gln Gly Leu Glu Trp Met
        35                  40                  45

Gly Trp Val Ser Ala Tyr Asn Gly Asp Thr Asn Tyr Ala Gln Lys Phe
    50                  55                  60

Gln Gly Arg Val Thr Val Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Glu Ile Ala Ser Tyr Ser Gly Ser Tyr Tyr Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
210                 215                 220


<210> SEQ ID NO 279
<211> LENGTH: 14
<212> TYPE: PRT
<213> ORGANISM: Artificial Sequence
<220> FEATURE:
<223> OTHER INFORMATION: PFG3 LC-CDR1

<400> SEQUENCE: 279

Gly Leu Thr Ser Gly Ala Val Ser Ser Ser Tyr Tyr Pro Ser
1               5                   10


<210> SEQ ID NO 280
<211> LENGTH: 7
<212> TYPE: PRT
<213> ORGANISM: Artificial Sequence
<220> FEATURE:
<223> OTHER INFORMATION: PFG3 LC-CDR2

<400> SEQUENCE: 280

Asn Thr Asp Ile Arg Phe Ser
1               5


<210> SEQ ID NO 281
<211> LENGTH: 5
<212> TYPE: PRT
<213> ORGANISM: Artificial Sequence
<220> FEATURE:
<223> OTHER INFORMATION: PFG3 HC-CDR1

<400> SEQUENCE: 281

Asp Tyr Tyr Ile His
1               5


<210> SEQ ID NO 282
<211> LENGTH: 17
<212> TYPE: PRT
<213> ORGANISM: Artificial Sequence
<220> FEATURE:
<223> OTHER INFORMATION: PFG3 HC-CDR2

<400> SEQUENCE: 282

Trp Val Ser Ala Tyr Asn Gly Asp Thr Asn Tyr Ala Gln Lys Phe Gln
1               5                   10                  15

Gly


<210> SEQ ID NO 283
<211> LENGTH: 648
<212> TYPE: DNA
<213> ORGANISM: Artificial Sequence
<220> FEATURE:
<223> OTHER INFORMATION: PFG4 Light chain nucleotide sequence

<400> SEQUENCE: 283

cagtctgtgc tgactcagcc accctcggtg tccaaggcct tgagacagac cgccaccctc      60

acctgcacgg ggaacaacaa caatgttggc ttcgcaggag cagcttggtt tctgcagcac     120
```

```
cagggccacc ctcccaagct cctggcctac aggaataacg accggccctc agggatctca    180

gagagatttt ctgcttccag gtcaggcaat actgcctccc tgaccattac tggactccag    240

cctgaggacg aggctgatta ttactgctca gcatgggaca gcagtctcaa agttcaggtg    300

ttcggcggag ggaccaagct gaccgtccta ggtcagccca aggctgcccc ctcggtcact    360

ctgttcccac cctcctctga ggagcttcaa gccaacaagg ccacactggt gtgtctcata    420

agtgacttct acccgggagc cgtgacagtg gcctggaagg cagatagcag ccccgtcaag    480

gcgggagtgg agaccaccac accctccaaa caaagcaaca acaagtacgc ggccagcagc    540

tacctgagcc tgacgcctga gcagtggaag tcccacaaaa gctacagctg ccaggtcacg    600

catgaaggga gcaccgtgga gaagacagtg gcccctacag aatgttca                 648
```

<210> SEQ ID NO 284
<211> LENGTH: 660
<212> TYPE: DNA
<213> ORGANISM: Artificial Sequence
<220> FEATURE:
<223> OTHER INFORMATION: PFG4 Heavy chain nucleotide sequence

<400> SEQUENCE: 284

```
caggtacagc tgcagcagtc aggggctgag gtgaagaagc ctgggtcctc ggtgaaggtc     60

tcctgcaagg cttctggagg caccttcagc agctatgcta tcagctgggt gcgacaggcc    120

cctggacaag ggcttgagtg gatgggaggg atcatcccta tctttggtac agcaaactac    180

gcacagaagt tccagggcag agtcacgatt accgcggaca aatccacgag cacagcctac    240

atggagctga gcagcctgag atctgaggac acggccgtgt attactgtgc gagaggtgcc    300

gactggaaca gtgactactg gggccaggga accctggtca ccgtctcaag cgcctccacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt ccacaccttc ccggctgtcc tacagtcctc aggactctac    540

tccctcagca gcgtagtgac cgtgccctcc agcagcttgg gcacccagac ctacatctgc    600

aacgtgaatc acaagcccag caacaccaag gtggacaaga aagttgagcc caaatcttgt    660
```

<210> SEQ ID NO 285
<211> LENGTH: 216
<212> TYPE: PRT
<213> ORGANISM: Artificial Sequence
<220> FEATURE:
<223> OTHER INFORMATION: PFG4 Light chain VD

<400> SEQUENCE: 285

```
Gln Ser Val Leu Thr Gln Pro Pro Ser Val Ser Lys Ala Leu Arg Gln
1               5                   10                  15

Thr Ala Thr Leu Thr Cys Thr Gly Asn Asn Asn Asn Val Gly Phe Ala
            20                  25                  30

Gly Ala Ala Trp Phe Leu Gln His Gln Gly His Pro Pro Lys Leu Leu
        35                  40                  45

Ala Tyr Arg Asn Asn Asp Arg Pro Ser Gly Ile Ser Glu Arg Phe Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
                85                  90                  95
```

```
Lys Val Gln Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 286
<211> LENGTH: 220
<212> TYPE: PRT
<213> ORGANISM: Artificial Sequence
<220> FEATURE:
<223> OTHER INFORMATION: PFG4 Heavy chain VD

<400> SEQUENCE: 286

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Asp Trp Asn Ser Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
    210                 215                 220


<210> SEQ ID NO 287
<211> LENGTH: 13
```

<212> TYPE: PRT
<213> ORGANISM: Artificial Sequence
<220> FEATURE:
<223> OTHER INFORMATION: PFG4 LC-CDR1

<400> SEQUENCE: 287

Thr Gly Asn Asn Asn Asn Val Gly Phe Ala Gly Ala Ala
1               5                   10

<210> SEQ ID NO 288
<211> LENGTH: 7
<212> TYPE: PRT
<213> ORGANISM: Artificial Sequence
<220> FEATURE:
<223> OTHER INFORMATION: PFG4 LC-CDR2

<400> SEQUENCE: 288

Arg Asn Asn Asp Arg Pro Ser
1               5

<210> SEQ ID NO 289
<211> LENGTH: 11
<212> TYPE: PRT
<213> ORGANISM: Artificial Sequence
<220> FEATURE:
<223> OTHER INFORMATION: PFG4 LC-CDR3

<400> SEQUENCE: 289

Ser Ala Trp Asp Ser Ser Leu Lys Val Gln Val
1               5                   10

<210> SEQ ID NO 290
<211> LENGTH: 8
<212> TYPE: PRT
<213> ORGANISM: Artificial Sequence
<220> FEATURE:
<223> OTHER INFORMATION: PFG4 HC-CDR3

<400> SEQUENCE: 290

Gly Ala Asp Trp Asn Ser Asp Tyr
1               5

<210> SEQ ID NO 291
<211> LENGTH: 657
<212> TYPE: DNA
<213> ORGANISM: Artificial Sequence
<220> FEATURE:
<223> OTHER INFORMATION: PFG5 Light chain nucleotide sequence

<400> SEQUENCE: 291
gatgttgtga tgactcagtc tccactctcc ctgcccgtca cccctggaga gccggcctcc      60
atctcctgca ggtctagtca gagcctcctg catagtaatg gatacaacta tttggattgg     120
tacctgcaga agccagggca gtctccacag ctcctgatct acttgggttc taatcgggcc     180
cccggggtcc ctgacaggtt cagtggcagt ggatcaggca cagattttac actgaaaatc     240
agcagagtgg aggctgagga tgttggggtt tattactgca tgcaaggtac acactggcct     300
ctcactttcg gcggagggac caaggtggag atcaaacgaa ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt 657

<210> SEQ ID NO 292
<211> LENGTH: 678
<212> TYPE: DNA
<213> ORGANISM: Artificial Sequence
<220> FEATURE:
<223> OTHER INFORMATION: PFG5 Heavy chain nucleotide sequence

<400> SEQUENCE: 292
gaagtgcagc tggtgcagtc tgggggaggc gtggtccagc ctgggaggtc cctgagactc 60
tcctgtgcag cctctggatt caccttcagt agctatgcta tgcactgggt ccgccaggct 120
ccaggcaagg ggctggagtg ggtggcagtt atatcatatg atggaagcaa taaatactac 180
gcagactccg tgaagggccg attcaccatc tccagagaca attccaagaa cacgctgtat 240
ctgcaaatga acagcctgag agctgaggac acggctgtgt attactgtgc gagatcgtat 300
ggttcgggga gttataggtc ccatgctttt gatatctggg gccaagggac aatggtcacc 360
gtctcaagcg cctccaccaa gggcccatcg gtcttccccc tggcaccctc ctccaagagc 420
acctctgggg gcacagcggc cctgggctgc ctggtcaagg actacttccc cgaaccggtg 480
acggtgtcgt ggaactcagg cgccctgacc agcggcgtcc acaccttccc ggctgtccta 540
cagtcctcag gactctactc cctcagcagc gtagtgaccg tgccctccag cagcttgggc 600
acccagacct acatctgcaa cgtgaatcac aagcccagca acaccaaggt ggacaagaaa 660
gttgagccca aatcttgt 678

<210> SEQ ID NO 293
<211> LENGTH: 219
<212> TYPE: PRT
<213> ORGANISM: Artificial Sequence
<220> FEATURE:
<223> OTHER INFORMATION: PFG5 Light chain VD

<400> SEQUENCE: 293

Asp Val Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Pro Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Leu Thr Phe Gly Gly Gly Thr Lys Val Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

-continued

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 294
<211> LENGTH: 226
<212> TYPE: PRT
<213> ORGANISM: Artificial Sequence
<220> FEATURE:
<223> OTHER INFORMATION: PFG5 Heavy chain VD

<400> SEQUENCE: 294

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Gly Ser Gly Ser Tyr Arg Ser His Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225
```